(12) United States Patent
Sommadossi et al.

(10) Patent No.: US 7,163,929 B2
(45) Date of Patent: *Jan. 16, 2007

(54) METHODS AND COMPOSITIONS FOR TREATING FLAVIVIRUSES AND PESTIVIRUSES

(75) Inventors: Jean-Pierre Sommadossi, Birmingham, AL (US); Paulo LaColla, Cagliari (IT)

(73) Assignees: Idenix Pharmaceuticals, Inc., Cambridge, MA (US); Universita Degli Studi Di Cagliari, Cagliari (IT)

( * ) Notice: Subject to any disclaimer, the term of this patent is extended or adjusted under 35 U.S.C. 154(b) by 316 days.

This patent is subject to a terminal disclaimer.

(21) Appl. No.: 10/602,135

(22) Filed: Jun. 20, 2003

(65) Prior Publication Data

US 2006/0166865 A1    Jul. 27, 2006

Related U.S. Application Data

(63) Continuation of application No. 09/863,816, filed on May 23, 2001, now Pat. No. 6,812,219.

(60) Provisional application No. 60/283,276, filed on Apr. 11, 2001, provisional application No. 60/207,674, filed on May 26, 2000.

(51) Int. Cl.
*A61K 31/70* (2006.01)
*C07H 19/00* (2006.01)

(52) U.S. Cl. .............................. 514/49; 514/25; 514/44; 514/50; 536/27.1; 536/28.1; 536/28.2

(58) Field of Classification Search .................. 514/42, 514/43, 44, 49, 50; 536/22.1, 28.1, 28.2, 536/28.4, 28.5, 28.53
See application file for complete search history.

(56) References Cited

U.S. PATENT DOCUMENTS

| | | | |
|---|---|---|---|
| 3,480,613 | A | 11/1969 | Walton et al. |
| 5,977,061 | A | 11/1999 | De Clercq |
| 6,063,628 | A * | 5/2000 | Loeb et al. ................. 435/442 |
| 6,340,690 | B1 | 1/2002 | Bachand et al. |
| 6,348,587 | B1 | 2/2002 | Schinazi et al. |
| 6,395,716 | B1 | 5/2002 | Gosselin et al. |
| 6,444,652 | B1 | 9/2002 | Gosselin et al. |
| 6,455,508 | B1 | 9/2002 | Ramasamy et al. |
| 6,495,677 | B1 | 12/2002 | Ramasamy et al. |
| 6,566,344 | B1 | 5/2003 | Gosselin et al. |
| 6,566,365 | B1 | 5/2003 | Storer |
| 6,569,837 | B1 | 5/2003 | Gosselin et al. |
| 6,573,248 | B1 | 6/2003 | Ramasamy et al. |
| 6,605,614 | B1 | 8/2003 | Bachand et al. |
| 6,660,721 | B1 | 12/2003 | Devos et al. |
| 6,748,161 | B1 | 6/2004 | Ko et al. |
| 6,777,395 | B1 * | 8/2004 | Bhat et al. .................... 514/43 |
| 6,784,166 | B1 | 8/2004 | Devos et al. |
| 6,787,526 | B1 * | 9/2004 | Bryant et al. ................. 514/45 |
| 6,812,219 | B1 | 11/2004 | LaColla et al. |
| 6,815,542 | B1 | 11/2004 | Hong et al. |
| 6,831,069 | B1 | 12/2004 | Tam et al. |
| 6,908,924 | B1 | 6/2005 | Watanabe et al. |
| 6,911,424 | B1 | 6/2005 | Schinazi et al. |
| 6,914,054 | B1 | 7/2005 | LaColla et al. |
| 2002/0019363 | A1 | 2/2002 | Ismaili et al. |
| 2002/0055483 | A1 | 5/2002 | Watanabe et al. |
| 2002/0099072 | A1 | 7/2002 | Bachand et al. |
| 2002/0147160 | A1 | 10/2002 | Bhat et al. |
| 2002/0156030 | A1 | 10/2002 | Ramasamy et al. |
| 2003/0008841 | A1 | 1/2003 | Devos et al. |
| 2003/0028013 | A1 | 2/2003 | Wang et al. |
| 2003/0050229 | A1 | 3/2003 | Sommadossi et al. |
| 2003/0060400 | A1 | 3/2003 | LaColla et al. |
| 2003/0083307 | A1 | 5/2003 | Devos et al. |
| 2003/0087873 | A1 | 5/2003 | Stuyver et al. |
| 2003/0220290 | A1 | 11/2003 | Gosselin et al. |
| 2003/0225028 | A1 | 12/2003 | Gosselin et al. |
| 2003/0225037 | A1 | 12/2003 | Storer |
| 2003/0236216 | A1 | 12/2003 | Devos et al. |
| 2004/0002476 | A1 | 1/2004 | Stuyver et al. |
| 2004/0002596 | A1 | 1/2004 | Hong et al. |
| 2004/0023921 | A1 | 2/2004 | Hong et al. |
| 2004/0059104 | A1 | 3/2004 | Cook et al. |
| 2004/0063622 | A1 | 4/2004 | LaColla et al. |
| 2004/0063658 | A1 | 4/2004 | Roberts et al. |

(Continued)

FOREIGN PATENT DOCUMENTS

FR     1521076 A     4/1968

(Continued)

OTHER PUBLICATIONS

Altmann et al, "The synthesis of 1'-methyl carbocyclic thymidine and its effect on nucleic acid duplex stability," *Synlett*, Thieme Verlag, Stuttgart, De, 10:853-855 (1994).

(Continued)

*Primary Examiner*—James O. Wilson
*Assistant Examiner*—Traviss C. McIntosh, III
(74) *Attorney, Agent, or Firm*—Sherry M. Knowles, Esq.; King & Spalding LLP

(57) ABSTRACT

A method and composition for treating a host infected with flavivirus or pestivirus comprising administering an effective flavivirus or pestivirus treatment amount of a described 1', 2' or 3'-modified nucleoside or a pharmaceutically acceptable salt or prodrug thereof, is provided.

31 Claims, 8 Drawing Sheets

U.S. PATENT DOCUMENTS

| | | |
|---|---|---|
| 2004/0067901 A1 | 4/2004 | Bhat et al. |
| 2004/0072788 A1 | 4/2004 | Bhat et al. |
| 2004/0097461 A1 | 5/2004 | Sommadossi et al. |
| 2004/0097462 A1 | 5/2004 | LaColla et al. |
| 2004/0101535 A1 | 5/2004 | Sommadossi et al. |
| 2004/0102414 A1 | 5/2004 | Sommadossi et al. |
| 2004/0110717 A1 | 6/2004 | Carroll et al. |
| 2004/0110718 A1 | 6/2004 | Devos et al. |
| 2004/0147464 A1 | 7/2004 | Roberts et al. |
| 2004/0248844 A1 | 12/2004 | Ismaili et al. |
| 2005/0009737 A1 | 1/2005 | Clark et al. |
| 2005/0090463 A1 | 4/2005 | Roberts et al. |
| 2005/0101550 A1 | 5/2005 | Roberts et al. |
| 2005/0107312 A1 | 5/2005 | Keicher et al. |
| 2005/0119200 A1 | 6/2005 | Roberts et al. |
| 2005/0124532 A1 | 6/2005 | Sommadossi et al. |
| 2005/0137161 A1 | 6/2005 | Sommadossi et al. |

FOREIGN PATENT DOCUMENTS

| | | |
|---|---|---|
| FR | 1581628 A | 9/1969 |
| FR | 2662165 A | 11/1991 |
| FR | 2662165 A1 | 11/1991 |
| GB | 1163103 A | 9/1969 |
| GB | 1209654 A | 10/1970 |
| JP | 63-215694 A | 9/1988 |
| JP | 63-215694 A2 | 9/1988 |
| JP | 06-228186 A | 8/1994 |
| JP | 06-228186 A2 | 8/1994 |
| WO | WO 98/16184 A2 | 4/1998 |
| WO | WO 99/43691 A1 | 2/1999 |
| WO | WO 00/09531 A2 | 2/2000 |
| WO | WO 01/32153 A2 | 5/2001 |
| WO | WO 01/91737 A2 | 6/2001 |
| WO | WO 01/92282 A2 | 6/2001 |
| WO | WO 01/60315 A2 | 8/2001 |
| WO | WO 01/68663 A1 | 9/2001 |
| WO | WO 01/79246 A2 | 10/2001 |
| WO | WO 01/90121 A2 | 11/2001 |
| WO | WO 01/96353 A2 | 12/2001 |
| WO | WO 02/03997 A1 | 1/2002 |
| WO | WO 02/18404 A2 | 3/2002 |
| WO | WO 02/32920 A2 | 4/2002 |
| WO | WO 02/48165 A2 | 6/2002 |
| WO | WO 02/057287 A2 | 7/2002 |
| WO | WO 02/057425 A2 | 7/2002 |
| WO | WO 02/070533 A2 | 9/2002 |
| WO | WO 02/094289 A1 | 11/2002 |
| WO | WO 02/100415 A2 | 12/2002 |
| WO | WO 03/026589 A2 | 4/2003 |
| WO | WO 03/026675 A1 | 4/2003 |
| WO | WO 03/051899 A1 | 6/2003 |
| WO | WO 03/061385 A1 | 7/2003 |
| WO | WO 03/061576 A2 | 7/2003 |
| WO | WO 03/062255 A2 | 7/2003 |
| WO | WO 03/062256 A1 | 7/2003 |
| WO | WO 03/062257 A1 | 7/2003 |
| WO | WO 03/063771 A2 | 8/2003 |
| WO | WO 03/068162 A2 | 8/2003 |
| WO | WO 03/072757 A2 | 9/2003 |
| WO | WO 03/093290 A2 | 11/2003 |
| WO | WO 04/002422 A2 | 1/2004 |
| WO | WO 04/002999 A2 | 1/2004 |

OTHER PUBLICATIONS

Baginski, S. G, et al., "Mechanism of action of a pestivirus antiviral compound," *PNAS USA*, 97(14):7981-7986 (2000).

Beigelman, L.N., et al, "Epimerization during the acetolysis of 3-O-acetyl-5-O-benzoyl-1,2-O-isopropylidene-3-C-methyl-α,D-ribofuranose. Synthesis of 3'-C-methylnucleosides with the β-D-ribo- and α-D-arabino configurations," *Carbohydrate Research*, 181:77-88 (1988).

Beigelman, L.N., et al, "A general method for synthesis of 3'-C-alkylnucleosides," *Nucleic Acids Symp. Ser.*, 9:115-118 (1981).

Berenguer, M., et al, "Hepatitis B and C viruses: Molecular identification and targeted antiviral therapies," *Proceedings of the Association of American Physicians*, 110(2), 98-112 (1998).

Carroll, S.S., et al., "Inhibition of hepatitis C virus RNA replication by 2'-modified nucleoside analogs," *The Journal of Biological Chemistry*, 278(14):11979-11984 (2003).

Czernecki, S., et al, "Synthesis of various 3'-branched 2',3'-unsaturated pyrimidine nucleosides as potential anti-HIV agents," *J. Org. Chem.*, 57:7325-7328 (1992).

De Francesco, R., et al., "Approaching a new era for hepatitis C virus therapy: Inhibitors of the NS3-4A serine protease and the NS5B RNA-dependent RNA polymerase," *Antiviral Research*, 58:1-16 (2003).

Faivre-Buet, V., et al, "Synthesis of 1'-deoxypsicofuranosyl-deoxynucleosides as potential anti-HIV agents," *Nucleosides & Nucleotides*, 11(7):1411-1424 (1992).

Farkas, J., et al., "Nucleic acid components and their analogues. XCIV. Synthesis of 6-amino-9-(1-deoxy-β-D-psicofuranosyl)purine", *Collect. Czech. Chem. Commun.* 32:2663-2667 (1967).

Farkas, J., et al., "Nucleic acid components and their analogues. LXXIX. Synthesis of methyl I-deoxy-D-psicofurnanosides substituted at $C_{(1)}$ with halo atoms or a mercapto group," *Collect. Czech. Chem. Commun.*, 31:1535-1543 (1996).

Fedorov, I.I., et al., "3'-C-Branched 2'-deoxy-5-methyluridines: Synthesis, enzyme inhibition, and antiviral properties," *J. Med. Chem.*, 35(24):4567-4575 (1992).

Franchetti, P., et al., "2'-C-Methyl analogues of selective adenosine receptor agonists: synthesis and binding studies," *J. Med. Chem.*, 41(10):1708-1715 (1998).

Grouiller, A., et al., "Novel p-toluenesulfonylation and thionocarbonylation of unprotected thymine nucleosides," *Synlett*, 1993, 221-222 (Mar. 1993).

Haraguchi, K., et al., "Preparation and reactions of 2'- and 3'- vinyl bromides of uracil nucleosides: Versatile synthons for anti-HIV agents," *Tetrahedron Letters*, 32(28):3391-3394 (1991).

Haraguchi, K., et al., "Stereoselective synthesis of 1'-C-branched uracil nucleosides from uridine," *Nucleosides & Nucleotides*, 14(3-5):417-420 (1995).

Harry-O'Kuru, R.E., et al., "A short, flexible route toward 2'-C-branched ribonucleosides", *J.Org. Chem.*, 62:1754-1759 (1997). (Scheme 11).

Harry-O'Kuru, R.E., et al., "2'-C-Alkylribonucleosides: Design, synthesis, and conformation," *Nucleosides & Nucleotides*, 16(7-9):1457-1460 (1997). ["Rogers" in #2; correct name in #7].

Hattori, H., et al, "Nucleosides and nucleotides. 175. Structural requirements of the sugar moiety for the antitumor activities of new nucleoside antimetabolites, 1-(3-C-ethynyl-b-D-ribo-pentofuranosyl)cytosine and -uracil," *J. Med. Chem.*, 41:2892-2902 (1998).

Hrebabecky, H., et al., "Nucleic acid components and their analogues. CXLIX. Synthesis of pyrimidine nucleosides derived from 1-deoxy-D-psicose," *Collect. Czech. Chem. Commun.*, 37:2059-2065 (1972).

Hrebabecky, H., et al., "Synthesis of 7- and 9β-D-psicofuranosylguanine and their 1'-deoxy derivatives," *Collect. Czech. Chem. Commun.*, 39:2115-2123 (1974).

Iino, T., et al., "Nucleosides and nucleotides. 139. Stereoselective synthesis of (2'S)-2'-C-alkyl-2'-deoxyuridines," *Nucleosides and Nucleotides*, 15(1-3):169-181 (1996).

Itoh, Y., et al, "Diverrgent and stereocontrolled approach to the synthesis of uracil nucleosides branched at the anomeric position," *J. Org. Chem.*, 60(3):656-662 (1995).

Johnson, C.R., et al, "3'-C-Trifluoromethyl ribonucleosides," *Nucleosides & Nucleotides*, 14(1&2):185-194 (1995).

Kawana, M., et al., "The deoxygenation of tosylated adenosine derivatives with Grignard reagents," *Nucleic Acids Symp. Ser.*, 17:37-40 (1986).

Lavaire, S., et al., "3'-Deoxy-3'-C-trifluoromethyl nucleosides: Synthesis and antiviral evaluation," *Nucleosides & Nucleotides*, 17(12):2267-2280 (1998).

Leyssen, P. et al., "Perspectives for the treatment of infections with *Flaviviridae*," *Clinical Microbiology Reviews* (Washington, D.C.), 13(1):67-82 (Jan. 2000).

Martin, X., et al., "Intramolecular hydrogen bonding in primary hydroxyl of thymine 1-(1-deoxy-β-D-psicofuranosyl) nucleoside," *Tetrahedron*, 50(22):6689-6694 (1994).

Matsuda, A., et al., "Radical deoxygenation of tert-alcohols in 2'-branched-chain sugar pyrimidine nucleosides: Synthesis and antileukemic activity of 2'-deoxy-2'(S)-methylcytidine," *Chem. Pharm. Bull.*, 35(9):3967-3970 (1987).

Matsuda, A., et al., "Alkyl addition reaction of pyrimidine 2'-ketonucleosides: Synthesis of 2'-branched-chain sugar pyrimidine nucleosides (Nucleosides and Nucleotides. LXXXI)," *Chem. Pharm. Bull.*, 36(3):945-953 (1988).

Matsuda, A., et al., Nucleosides and Nucleotides. 94. Radical deoxygenation of tert-alcohols in 1-(2-C-alkylpentofuranosyl)pyrimidines: Synthesis of (2'S)-2'-deoxy-2'-C-methylcytidine, an antileukemic nucleoside, *J. Med. Chem.*, 34:234-239 (1991).

Matsuda, A., et al., "Nucleosides and Nucleotides. 104. Radical and palladium-catalyzed deoxygenation of the allylic alcohol systems in the sugar moiety of pyrimidine nucleosides," *Nucleosides & Nucleotides*, 11(2/4):197-226 (1992).

Mikhailov, S,N., et al., "Synthesis and properties of 3'C-methylnucleosides and their phosphoric esters," *Carbohydrate Research*, 124:75-96 (1983).

Mikhailov, S,N., et al., "Substrate properties of C'methylnucleoside and C'-methyl-2'-deoxynucleoside 5'-triphosphates in RNA and DNA synthesis reactions catalysed by RNA and DNA polymerases," *Nucleoside & Nucleotides*, 10(1-3):339-343 (1991).

Mikhailov, S.N., et al., "Hydrolysis of 2'- and 3'-C-methyluridine 2'c3'-cyclic monophosphates and interconversion and dephosphorylation of the resulting 2'-and 3'-monophosphates: Comparison with the reactions of uridine monophosphates," *J. Org. Chem.*, 57(15):4122-4126 (1992).

Nutt, R.F., et al., "Branched-chain suger nucleosides. III. 3'-C-methyladenine", *J.Org. Chem.*, 33:1789-1795 (1968).

Oivanen, M., et al, "Additional evidence for the exceptional mechanism of the acid-catalyzed hydrolysis of 4-oxopyrimidine nucleosides: Hydrolysis of 1-(1-alkoxyalkyl)uracils, seconucleosides, 3'-C-alkyl nucleosides and nucleoside 3',5'-cyclic monophosphates," *J. Chem. Soc. Perkin Trans. 2*, 1994:309-314 (1994).

Ong, S.P., et al., "Synthesis of 3'-C-methyladenosine and 3'-C-methyluridine diphosphates and their interaction with the ribonucleoside diphosphate reductase from *Corynebacterium nephridii*," *Biochemistry*, 31(45):11210-11215 (1992).

Oral Session V, Hepatitis C Virus, Flaviviridae; 16th International Conference on Antiviral Research (Apr. 27, 2003, Savannah, Ga.) p. A75-77.

Pan-Zhou, X-R, et al., "Differential effects of antiretroviral nucleoside analogs on mitochondrial function in HepG2 cells," *Antimicrob. Agents Chemother.*, 44:496-503 (2000).

Rosenthal, A., et al., Branched-chain sugar nucleosides. Synthesis of 3'-C-ethyl (and 3'-C-butyl)uridine *Carbohydrate Research*, 79:235-242 (1980).

Samano, V., et al., "Synthesis and radical-induced ring-opening reactions of 2'-deoxyadenosine-2'-spirocyclopropane and its uridine analogue. Mechanistic probe for ribonucleotide reductases," *J. Am. Chem. Soc.*, 114:4007-4008 (1992).

Samano, V., et al., "Nucleic acid related compounds. 77. 2',3'-Didehydro-2',3'-dideoxy-2'(and 3')-methylnucleosides via [3,3]-sigmatropic rearrangements of 2'(and 3')-methylene-3'(and 2')-O-thiocarbonyl derivatives and radical reduction of a 2'-chloro-3'-methylene analogue," *Can. J. Chem.*, 71:186-191 (1993).

Schmit, C., et al, "The effects of 2'- and 3'-alkyl substituents on oligonucleotide hybridization and stability," *Biorganic & Medicinal Chemistry Letters*, 4(16):1969-1974 (1994). ["Altmann"].

Serafinowski, P.J., et al., "New method for the preparation of some 2'- and 3'-trifluoromethyl-2', 3'-dideoxyuridine derivatives," *Tetrahedron* (Elsevier Science Publishers), 56(2):333-339 (1999).

Sharma, P.K., et al., "Synthesis of 3'-trifluoromethyl nucleosides as potential antiviral agents," *Nucleosides, Nucleotides and Nucleic Acids*, 19(4):757-774 (2000).

Sommadossi J-P, et al., "Comparison of cytotoxicity of the (−)- and (+)-enatiomer of 2',3'-dideoxy-3'-thiacytidine in normal human bone marrow progenitor cells" *Biochemical Pharmacology*, 44:1921-1925 (1992).

Sommadossi J-P, et al., "Toxicity of 3'-azido-3'-deoxythymidine and 9-(1,3-dihydroxy-2-propoxymethyl)guanine for normal human hematopoietic progenitor cells in vitro" *Antimicrobial Agents and Chemotherapy*, 31:452-454 (1987).

Tritsch, D., et al., "3'-β-ethynyl and 2'-deoxy-3'-β-ethynyl adenosines: First 3'-β-branched adenosines substrates of adenosine deaminase," *Bioorganic & Medicinal Chemistry Letters*, 10:139-141 (2000).

Tunitskaya, V.L., et al., "Substrate properties of C'-methyl UTP derivatives in T7 RNA polymerase reactions. Evidence for N-type NTP conformation," *FEBS Letters*, 400:263-266 (1997).

Usui, H., et al., "Synthesis of 2'-deoxy-8,2'-ethanoadenosine and 3'-deoxy-8,3'-ethanoadenosine (Nucleosides and Nucleotides. LXIV)," *Chem. Pharm. Bull.*, 34(1):15-23 (1986).

Walczak, K., et al., "Synthesis of 1-(3-alkyl-2,3-dideoxy-D-pentofuranosyl)uracils with potential anti-HIV activity," *Acta Chemica Scand.*, 45:930-934 (1991).

Walton, E., et al., "Branched-chain sugar nucleosides. V. Synthesis and antiviral properties of several branched-chain sugar nucleotides," *J. Med. Chem.*, 12:306-309 (1969).

Wolfe, M.S., et al., "A concise synthesis of 2'-C-methylribonucleosides," *Tetrahedron Letters*, 36(42):7611-7614 (1995).

Wu, J.-C., et al., A new stereospecific synthesis of [3.1.0] bicyclic cyclopropano analog of 2',3'-dideoxyuridine, *Tetrahedron*, 46(7):2587-2592 (1990).

\* cited by examiner

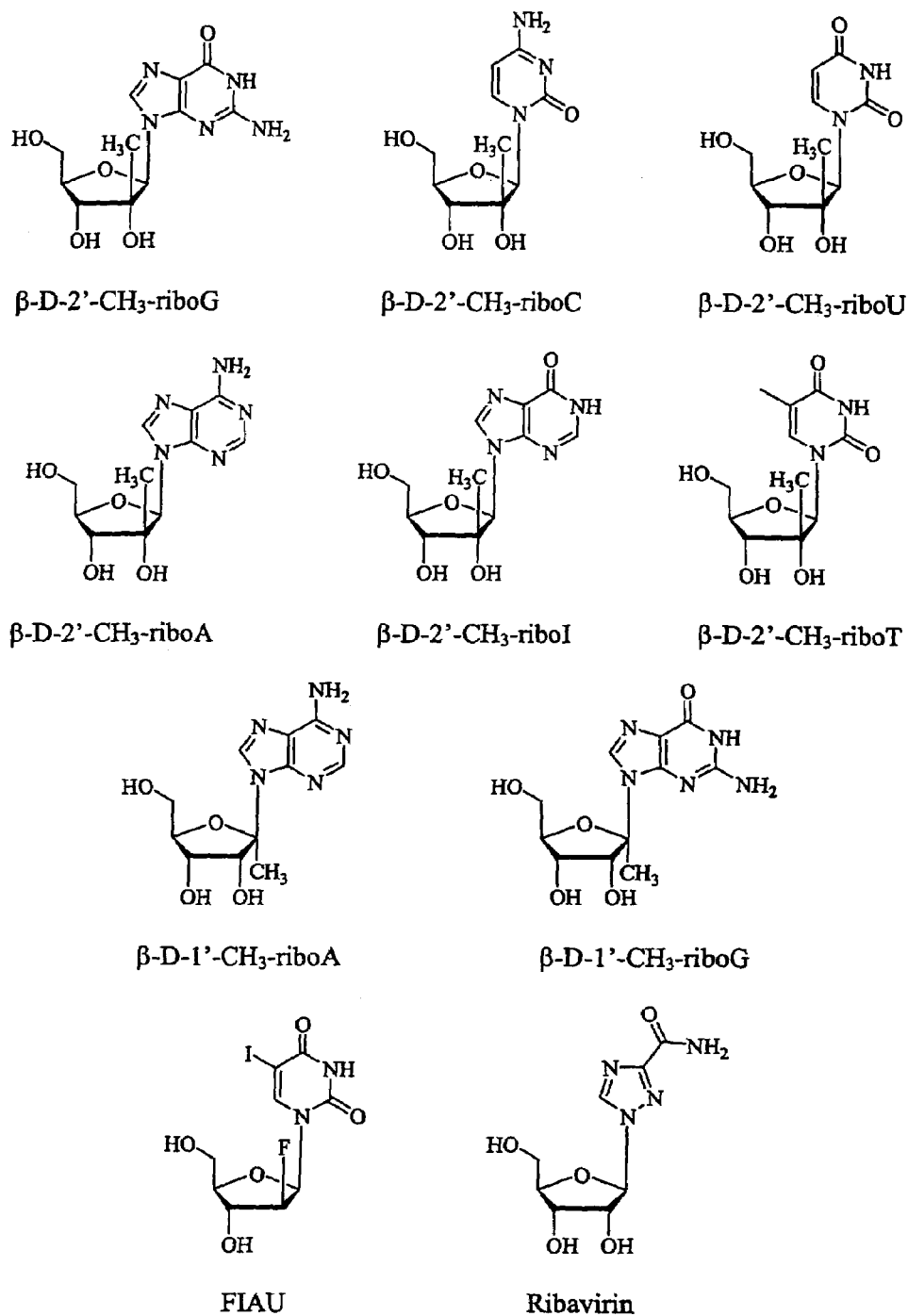
Figure 1: Chemical Structures of Illustrative Nucleosides

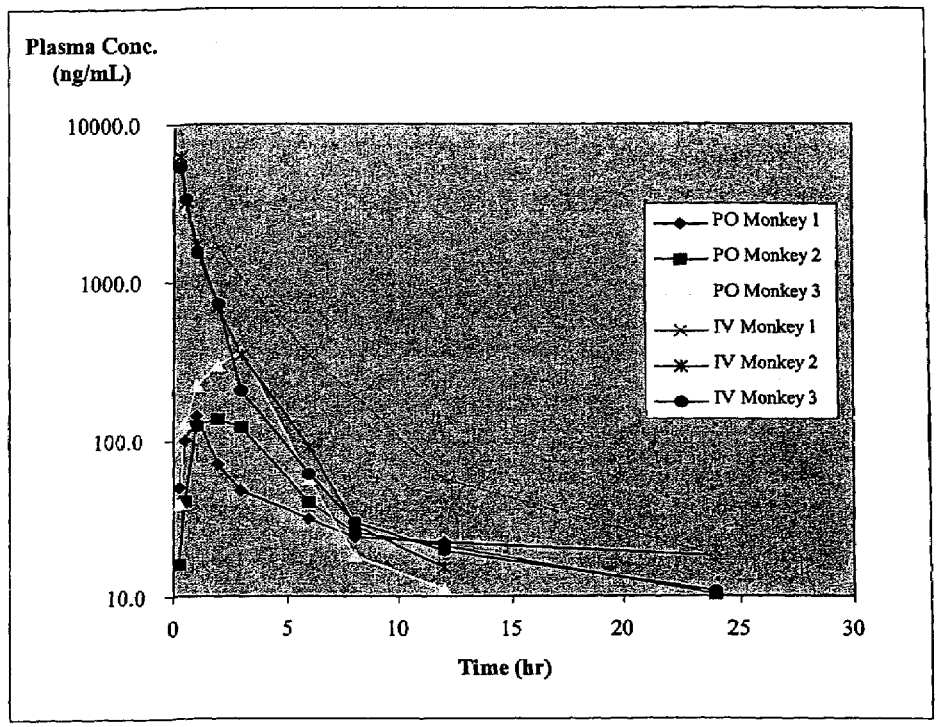
Figure 2: Screening Phamacokinetics of β-D-2'-CH$_3$-riboG in Cynomolgus Monkeys Figure 3: Phamacokinetics of β-D-2'-CH₃-riboG in Cynomolgus Monkeys Figure 4: BVDV Cell Protection Assay (CPA) Of β-D-2'-CH₃-riboG
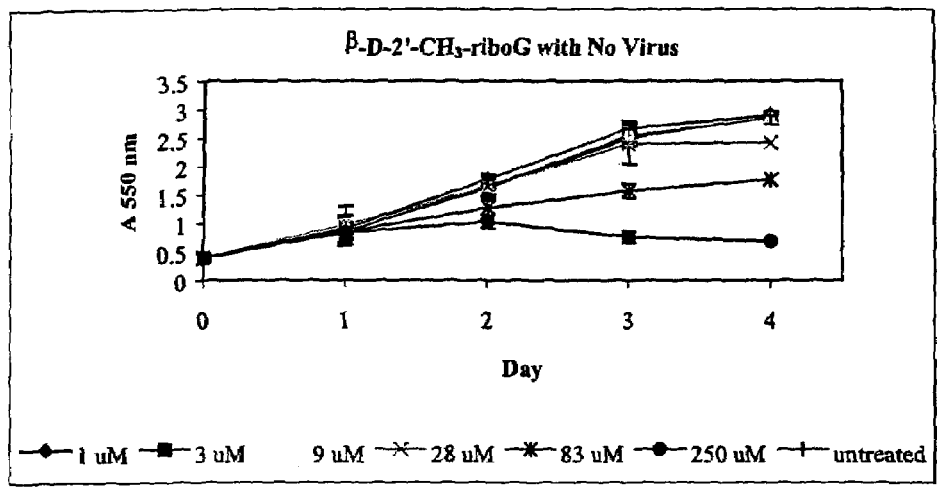
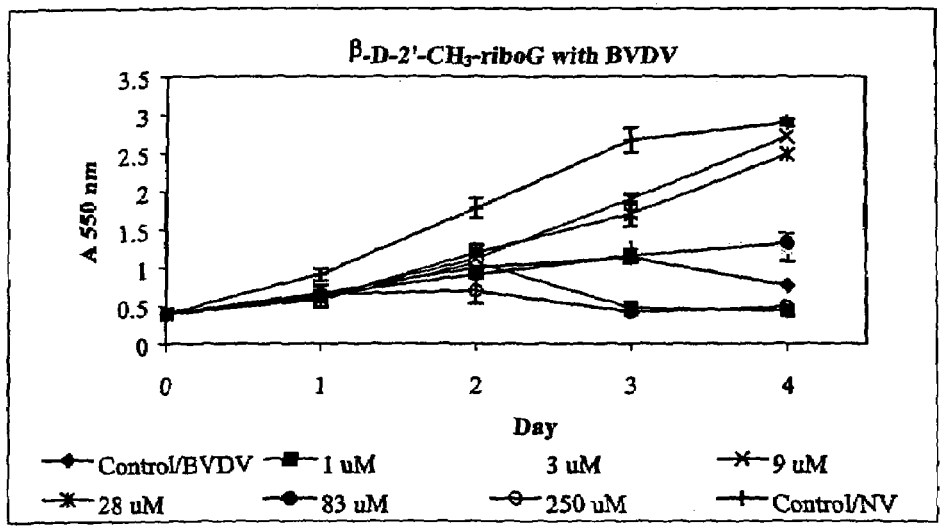

Figure 5: BVDV Cell Protection Assay (CPA) of Ribavirin
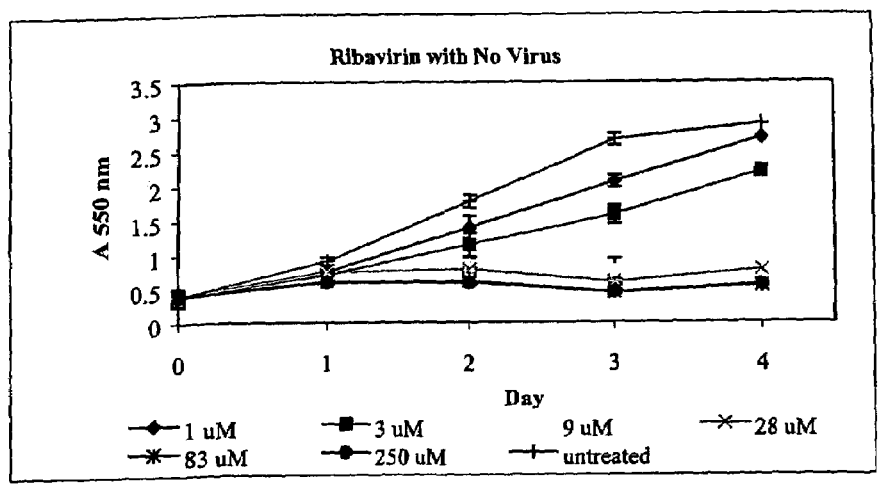
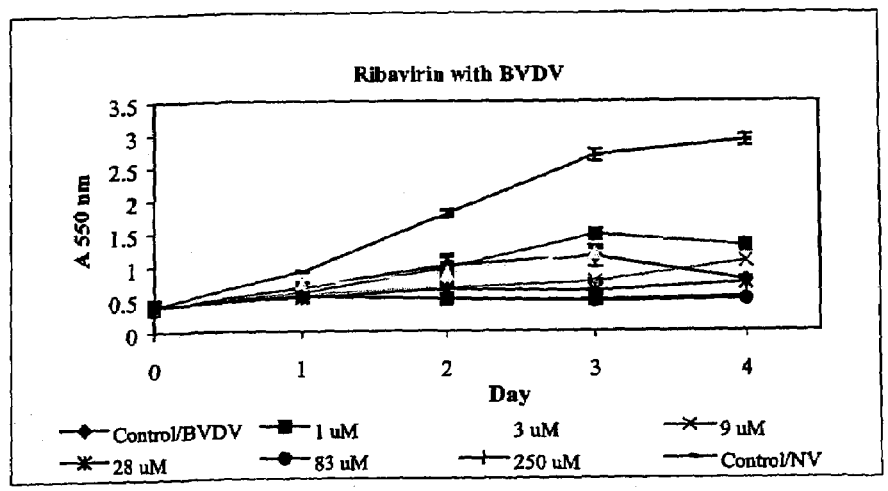
Cell Protection Assay
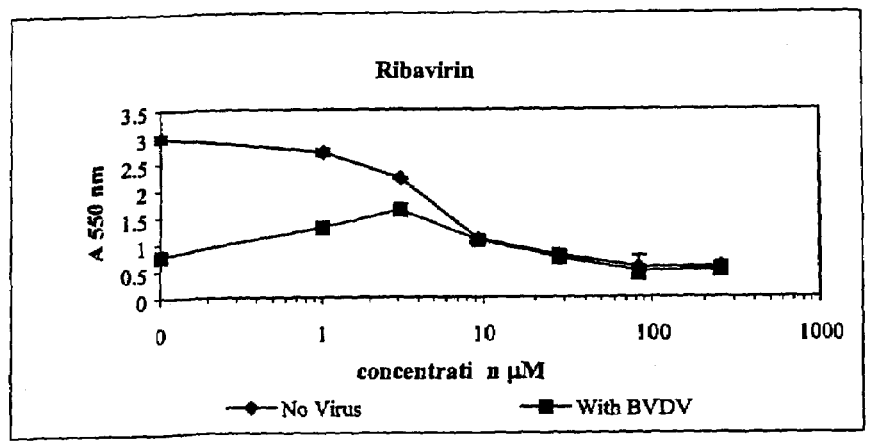

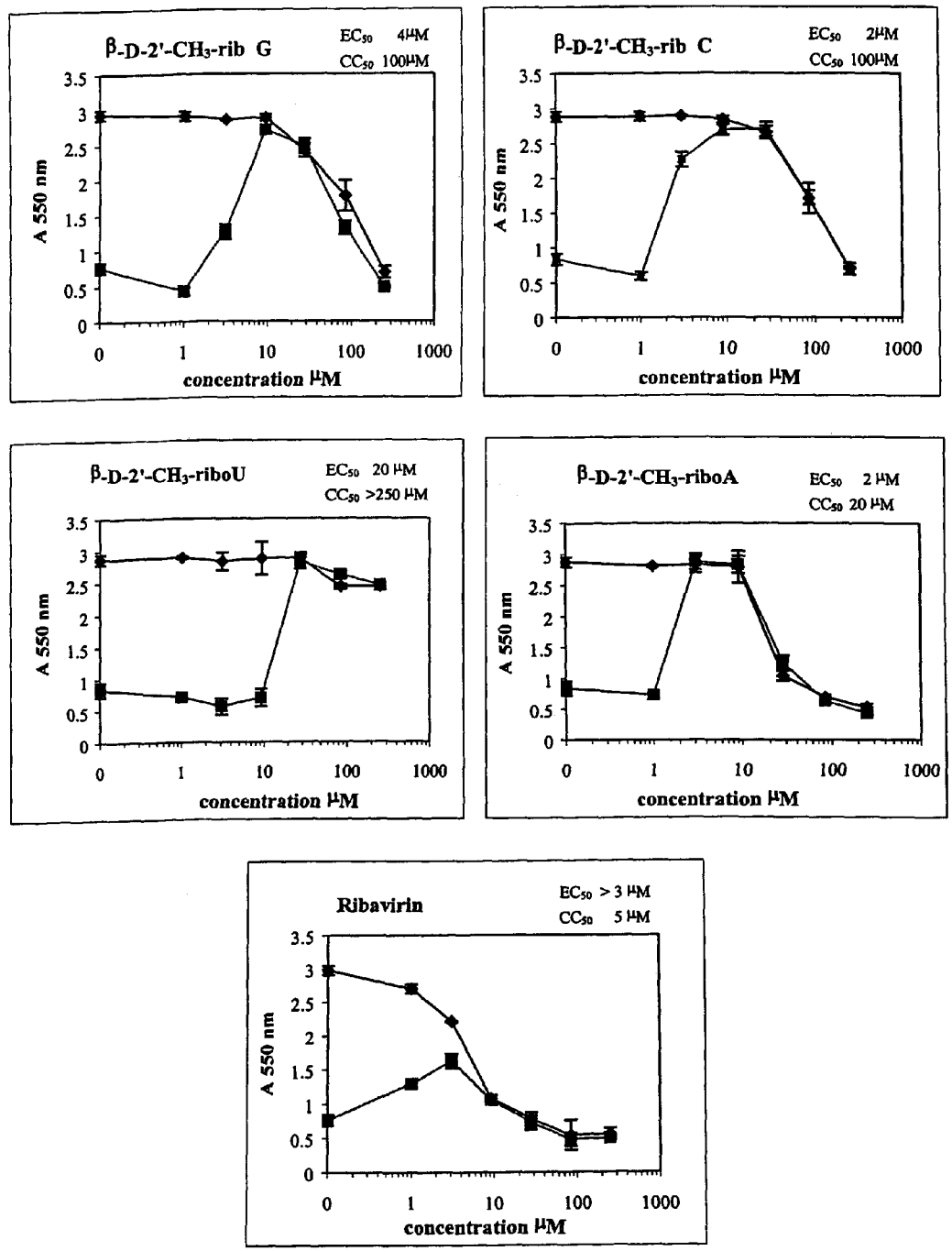
Figure 6: BVDV Cell Protection Assays

Figure 7: Plaque Purified BVDV

No Virus
BVDV
BVDV plaque purified

Figure 8: BVDV Plaque Assay of β-D-2'-CH₃-riboU

0 μM    0 μM    3 μM    9 μM    27 μM    81 μM

Figure 9: Yield Reduction Assay of β-D-2'-CH₃-riboG
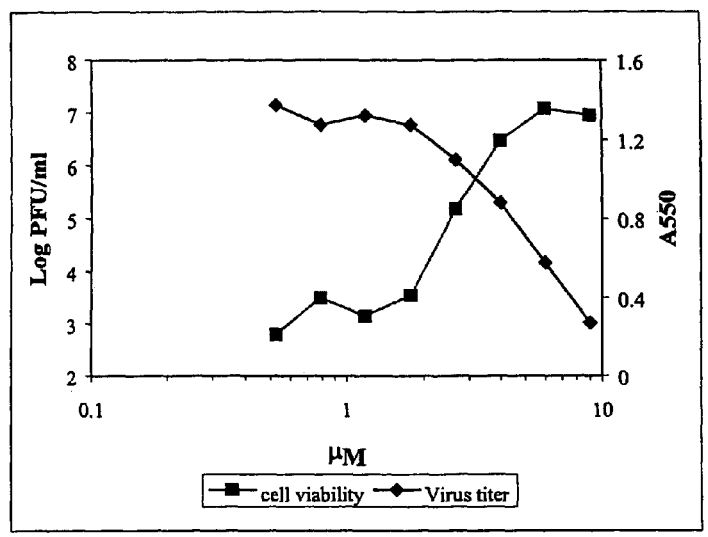
4-log virus reduction at 9 μM
Figure 10: BVDV Yield Reduction Assay for β-D-2'-CH₃-riboC
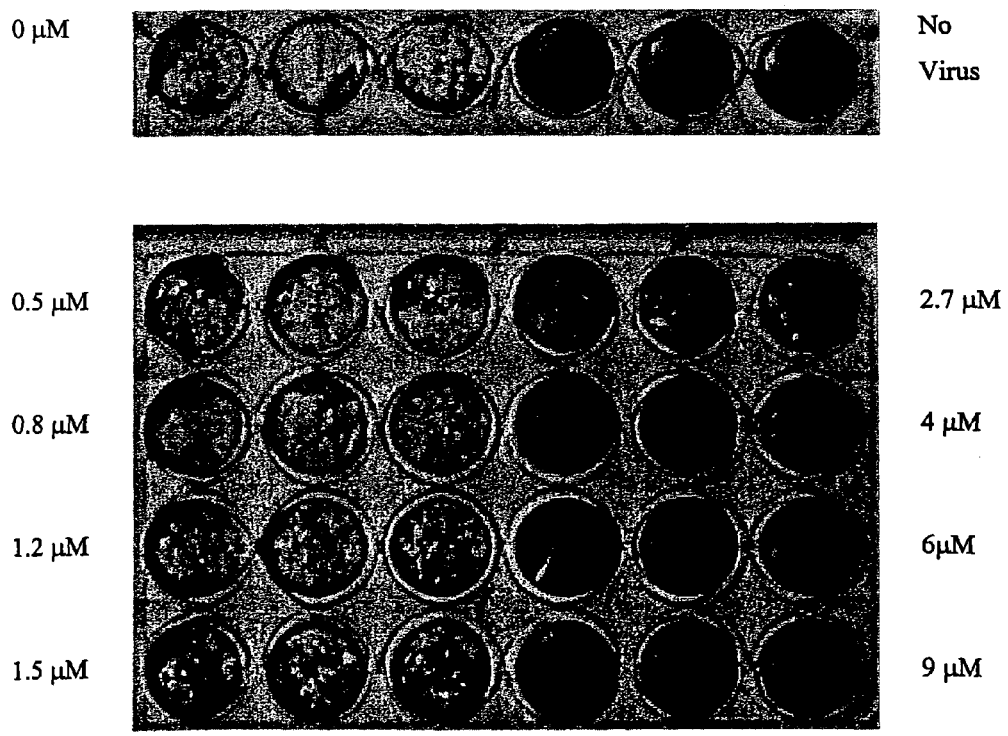

METHODS AND COMPOSITIONS FOR TREATING FLAVIVIRUSES AND PESTIVIRUSES

FIELD OF THE INVENTION

This invention is in the area of pharmaceutical chemistry, and in particular, is a compound, method and composition for the treatment of flaviviruses and pestiviruses. This application is a continuation of U.S. application Ser. No. 09/863,816, filed on May 23, 2001, now U.S. Pat. No. 6,812,219, which claims priority to U.S. provisional application No. 60/207,674, filed on May 26, 2000 and U.S. provisional application No. 60/283,276, filed on Apr. 11, 2001, the disclosures of which are incorporated herein by reference.

BACKGROUND OF THE INVENTION

Pestiviruses and flaviviruses belong to the Flaviviridae family of viruses along with hepatitis C virus. The pestivirus genus includes bovine viral diarrhea virus (BVDV), classical swine fever virus (CSFV, also called hog cholera virus) and border disease virus (BDV) of sheep (Moennig, V. et al. *Adv. Vir. Res.* 1992, 41, 53–98). Pestivirus infections of domesticated livestock (cattle, pigs and sheep) cause significant economic losses worldwide. BVDV causes mucosal disease in cattle and is of significant economic importance to the livestock industry (Meyers, G. and Thiel, H.-J., *Advances in Virus Research*, 1996, 47, 53–118; Moennig V., et al, *Adv. Vir. Res.* 1992, 41, 53–98).

Human pestiviruses have not been as extensively characterized as the animal pestiviruses. However, serological surveys indicate considerable pestivirus exposure in humans. Pestivirus infections in man have been implicated in several diseases including congenital brain injury, infantile gastroenteritis and chronic diarrhea in human immunodeficiency virus (HIV) positive patients. M. Giangaspero et al., *Arch. Virol. Suppl.,* 1993, 7, 53–62; M. Giangaspero et al., *Int. J. Std. Aids,* 1993, 4 (5): 300–302.

The flavivirus genus includes more than 68 members separated into groups on the basis of serological relatedness (Calisher et al., *J. Gen. Virol,* 1993, 70, 37–43). Clinical symptoms vary and include fever, encephalitis and hemorrhagic fever. *Fields Virology*, Editors: Fields, B. N., Knipe, D. M., and Howley, P. M., Lippincott-Raven Publishers, Philadelphia, Pa., 1996, Chapter 31, 931–959. Flaviviruses of global concern that are associated with human disease include the dengue hemorrhagic fever viruses (DHF), yellow fever virus, shock syndrome and Japanese encephalitis virus. Halstead, S. B., *Rev. Infect. Dis.,* 1984, 6, 251–264; Halstead, S. B., *Science,* 239:476–481, 1988; Monath, T. P., *New Eng. J. Med.,* 1988, 319, 641–643.

Examples of antiviral agents that have been identified as active against the flavivirus or pestiviruses include:

(1) interferon and ribavirin (Battaglia, A. M. et al., *Ann. Pharmacother,* 2000, 34, 487–494); Berenguer, M. et al. *Antivir. Ther.,* 1998, 3 (Suppl. 3), 125–136);

(2) Substrate-based NS3 protease inhibitors (Attwood et al., Antiviral peptide derivatives, PCT WO 98/22496, 1998; Attwood et al., *Antiviral Chemistry and Chemotherapy* 1999, 10, 259–273; Attwood et al., Preparation and use of amino acid derivatives as anti-viral agents, German Patent Pub. DE 19914474; Tung et al. Inhibitors of serine proteases, particularly hepatitis C virus NS3 protease, PCT WO 98/17679), including alphaketoamides and hydrazinoureas, and inhibitors that terminate in an electrophile such as a boronic acid or phosphonate (Llinas-Brunet et al, Hepatitis C inhibitor peptide analogues, PCT WO 99/07734).

(3) Non-substrate-based inhibitors such as 2,4,6-trihydroxy-3-nitro-benzamide derivatives (Sudo K. et al., *Biochemical and Biophysical Research Communications,* 1997, 238, 643–647; Sudo K. et al. *Antiviral Chemistry and Chemotherapy,* 1998, 9, 186), including RD3-4082 and RD3-4078, the former substituted on the amide with a 14 carbon chain and the latter processing a para-phenoxyphenyl group;

(4) Thiazolidine derivatives which show relevant inhibition in a reverse-phase HPLC assay with an NS3/4A fusion protein and NS5A/5B substrate (Sudo K. et al., *Antiviral Research,* 1996, 32, 9–18), especially compound RD-1-6250, possessing a fused cinnamoyl moiety substituted with a long alkyl chain, RD4 6205 and RD4 6193;

(5) Thiazolidines and benzanilides identified in Kakiuchi N. et al. *J. EBS Letters* 421, 217–220; Takeshita N. et al. *Analytical Biochemistry,* 1997, 247, 242–246;

(6) A phenan-threnequinone possessing activity against protease in a SDS-PAGE and autoradiography assay isolated from the fermentation culture broth of *Streptomyces* sp., Sch 68631 (Chu M. et al., *Tetrahedron Letters,* 1996, 37, 7229–7232), and Sch 351633, isolated from the fungus *Penicillium griscofuluum*, which demonstrates activity in a scintillation proximity assay (Chu M. et al., *Bioorganic and Medicinal Chemistry Letters* 9, 1949–1952);

(7) Selective NS3 inhibitors based on the macromolecule elgin c, isolated from leech (Qasim M. A. et al., *Biochemistry,* 1997, 36, 1598–1607);

(8) Helicase inhibitors (Diana G. D. et al., Compounds, compositions and methods for treatment of hepatitis C, U.S. Pat. No. 5,633,358; Diana G. D. et al., Piperidine derivatives, pharmaceutical compositions thereof and their use in the treatment of hepatitis C, PCT WO 97/36554);

(9) Polymerase inhibitors such as nucleotide analogues, gliotoxin (Ferrari R. et al. *Journal of Virology,* 1999, 73, 1649–1654), and the natural product cerulenin (Lohmann V. et al., *Virology,* 1998, 249, 108–118);

(10) Antisense phosphorothioate oligodeoxynucleotides (S-ODN) complementary to sequence stretches in the 5' non-coding region (NCR) of the virus (Alt M. et al., *Hepatology,* 1995, 22, 707–717), or nucleotides 326–348 comprising the 3' end of the NCR and nucleotides 371–388 located in the core coding region of the IICV RNA (Alt M. et al., *Archives of Virology,* 1997, 142, 589–599; Galderisi U. et al., *Journal of Cellular Physiology,* 1999, 181, 251–257);

(11) Inhibitors of IRES-dependent translation (Ikeda N et al., Agent for the prevention and treatment of hepatitis C, Japanese Patent Pub. JP-08268890; Kai Y. et al. Prevention and treatment of viral diseases, Japanese Patent Pub. JP-10101591);

(12) Nuclease-resistant ribozymes (Maccjak, D. J. et al., *Hepatology* 1999, 30, abstract 995); and

(13) Other miscellaneous compounds including 1-aminoalkylcyclohexanes (U.S. Pat. No. 6,034,134 to Gold et al.), alkyl lipids (U.S. Pat. No. 5,922,757 to Chojkier et al.), vitamin E and other antioxidants (U.S. Pat. No. 5,922,757 to Chojkier et al.), squalene, amantadine, bile acids (U.S. Pat. No. 5,846,964 to Ozeki et al.), N-(phosphonoacetyl)-L-aspartic acid, (U.S. Pat. No. 5,830,905 to Diana et al.), benzenedicarboxamides (U.S. Pat. No. 5,633,388 to Diana et al.), polyadenylic acid derivatives (U.S. Pat. No. 5,496,546 to Wang et al.), 2',3'-dideoxyinosine (U.S. Pat. No. 5,026,687 to Yarchoan et al.), and benzimidazoles (U.S. Pat. No. 5,891,874 to Colacino et al.).

In view of the severity of diseases associated with pestiviruses and flaviviruses, and their pervasiveness in animal and man, it is an object of the present invention to provide a compound, method and composition for the treatment of a host infected with flavivirus or pestivirus.

SUMMARY OF THE INVENTION

Compounds, methods and compositions for the treatment of a host infected with a flavivirus or pestivirus infection are described that includes an effective treatment amount of a β-D- or β-L-nucleoside of the Formulas (I)–(XVIII), or a pharmaceutically acceptable salt or prodrug thereof.

In a first principal embodiment, a compound of Formula I, or a pharmaceutically acceptable salt or prodrug thereof, is provided:

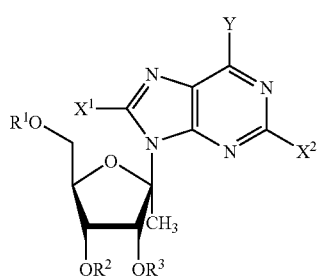

(I)

wherein:

$R^1$, $R^2$ and $R^3$ are independently H, phosphate (including mono-, di- or triphosphate and a stabilized phosphate prodrug); acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; a cholesterol; or other pharmaceutically acceptable leaving group which when administered in vivo is capable of providing a compound wherein $R^1$, $R^2$ or $R^3$ is independently H or phosphate;

Y is hydrogen, bromo, chloro, fluoro, iodo, $OR^4$, $NR^4R^5$ or $SR^4$;

$X^1$ and $X^2$ are independently selected from the group consisting of H, straight chained, branched or cyclic alkyl, CO-alkyl, CO-aryl, CO-alkoxyalkyl, chloro, bromo, fluoro, iodo, $OR^4$, $NR^4NR^5$ or $SR^5$; and $R^4$ and $R^5$ are independently hydrogen, acyl (including lower acyl), or alkyl (including but not limited to methyl, ethyl, propyl and cyclopropyl).

In a second principal embodiment, a compound of Formula II, or a pharmaceutically acceptable salt or prodrug thereof, is provided:

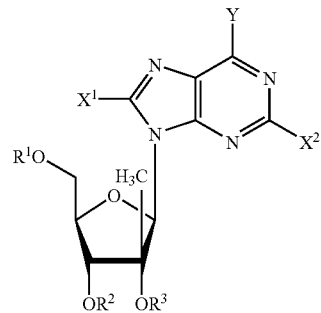

(II)

wherein:

$R^1$, $R^2$ and $R^3$ are independently H; phosphate (including monophosphate, diphosphate, triphosphate, or a stabilized phosphate prodrug); acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; a cholesterol; or other pharmaceutically acceptable leaving group which when administered in vivo is capable of providing a compound wherein $R^1$, $R^2$ or $R^3$ is independently H or phosphate; and Y is hydrogen, bromo, chloro, fluoro, iodo, $OR^4$, $NR^4R^5$ or $SR^4$;

$X^1$ and $X^2$ are independently selected from the group consisting of H, straight chained, branched or cyclic alkyl, CO-alkyl, CO-aryl, CO-alkoxyalkyl, chloro, bromo, fluoro, iodo, $OR^4$, $NR^4NR^5$ or $SR^5$; and $R^4$ and $R^5$ are independently hydrogen, acyl (including lower acyl), or alkyl (including but not limited to methyl, ethyl, propyl and cyclopropyl).

In a third principal embodiment, a compound of Formula III, or a pharmaceutically acceptable salt or prodrug thereof, is provided:

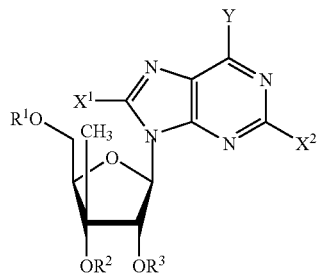

(III)

wherein:

$R^1$, $R^2$ and $R^3$ are independently H; phosphate (including monophosphate, diphosphate, triphosphate, or a stabilized phosphate prodrug); acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; a cholesterol; or other pharmaceutically acceptable leaving group which when administered in vivo is capable of providing a compound wherein $R^1$, $R^2$ or $R^3$ is independently H or phosphate; and Y is hydrogen, bromo, chloro, fluoro, iodo, $OR^4$, $NR^4R^5$ or $SR^4$;

$X^1$ and $X^2$ are independently selected from the group consisting of H, straight chained, branched or cyclic alkyl, CO-alkyl, CO-aryl, CO-alkoxyalkyl, chloro, bromo, fluoro, iodo, $OR^4$, $NR^4NR^5$ or $SR^5$; and $R^4$ and $R^5$ are independently hydrogen, acyl (including lower acyl), or alkyl (including but not limited to methyl, ethyl, propyl and cyclopropyl).

In a fourth principal embodiment, a compound of Formula IV, or a pharmaceutically acceptable salt or prodrug thereof, is provided:

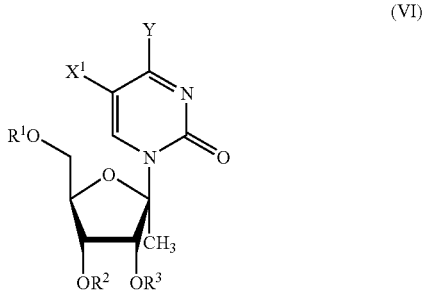

(VI)

wherein:

$R^1$, $R^2$ and $R^3$ are independently H, phosphate (including mono-, di- or triphosphate and a stabilized phosphate prodrug); acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; a cholesterol; or other pharmaceutically acceptable leaving group which when administered in vivo is capable of providing a compound wherein $R^1$, $R^2$ or $R^3$ is independently H or phosphate;

Y is hydrogen, bromo, chloro, fluoro, iodo, $OR^4$, $NR^4R^5$ or $SR^4$;

$X^1$ is selected from the group consisting of H, straight chained, branched or cyclic alkyl, CO-alkyl, CO-aryl, CO-alkoxyalkyl, chloro, bromo, fluoro, iodo, $OR^4$, $NR^4NR^5$ or $SR^5$; and $R^4$ and $R^5$ are independently hydrogen, acyl (including lower acyl), or alkyl (including but not limited to methyl, ethyl, propyl and cyclopropyl).

In a fifth principal embodiment, a compound of Formula V, or a pharmaceutically acceptable salt or prodrug thereof, is provided:

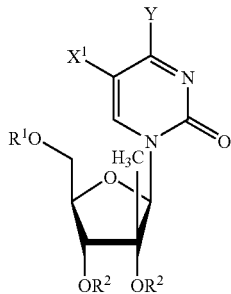

(V)

wherein:

$R^1$, $R^2$ and $R^3$ are independently H; phosphate (including monophosphate, diphosphate, triphosphate, or a stabilized phosphate prodrug); acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; a cholesterol; or other pharmaceutically acceptable leaving group which when administered in vivo is capable of providing a compound wherein $R^1$, $R^2$ or $R^3$ is independently H or phosphate; and Y is hydrogen, bromo, chloro, fluoro, iodo, $OR^4$, $NR^4R^5$ or $SR^4$;

$X^1$ is selected from the group consisting of H, straight chained, branched or cyclic alkyl, CO-alkyl, CO-aryl, CO-alkoxyalkyl, chloro, bromo, fluoro, iodo, $OR^4$, $NR^4NR^5$ or $SR^5$; and $R^4$ and $R^5$ are independently hydrogen, acyl (including lower acyl), or alkyl (including but not limited to methyl, ethyl, propyl and cyclopropyl).

In a sixth principal embodiment, a compound of Formula VI, or a pharmaceutically acceptable salt or prodrug thereof, is provided:

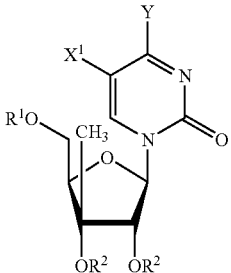

(VI)

wherein:

$R^1$, $R^2$ and $R^3$ are independently H; phosphate (including monophosphate, diphosphate, triphosphate, or a stabilized phosphate prodrug); acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; a cholesterol; or other pharmaceutically acceptable leaving group which when administered in vivo is capable of providing a compound wherein $R^1$, $R^2$ or $R^3$ is independently H or phosphate; and Y is hydrogen, bromo, chloro, fluoro, iodo, $OR^4$, $NR^4R^5$ or $SR^4$;

$X^1$ is selected from the group consisting of H, straight chained, branched or cyclic alkyl, CO-alkyl, CO-aryl, CO-alkoxyalkyl, chloro, bromo, fluoro, iodo, $OR^4$, $NR^4NR^5$ or $SR^5$; and $R^4$ and $R^5$ are independently hydrogen, acyl (including lower acyl), or alkyl (including but not limited to methyl, ethyl, propyl and cyclopropyl).

In a seventh principal embodiment, a compound selected from Formulas VII, VIII and IX, or a pharmaceutically acceptable salt or prodrug thereof, is provided:

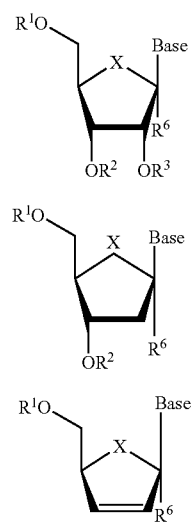

(VII)

(VIII)

(IX)

wherein:

Base is a purine or pyrimidine base as defined herein;

$R^1$, $R^2$ and $R^3$ are independently H; phosphate (including monophosphate, diphosphate, triphosphate, or a stabilized phosphate prodrug); acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; a cholesterol; or other pharmaceutically acceptable leaving group which when administered in vivo is capable of providing a compound wherein $R^1$, $R^2$ or $R^3$ is independently H or phosphate;

$R^6$ is hydrogen, hydroxy, alkyl (including lower alkyl), azido, cyano, alkenyl, alkynyl, Br-vinyl, 2-Br-ethyl, —C(O)O(alkyl), —C(O)O(lower alkyl), —O(acyl), —O(lower acyl), —O(alkyl), —O(lower alkyl), —O(alkenyl), $CF_3$, chloro, bromo, fluoro, iodo, $NO_2$, $NH_2$, —NH(lower alkyl), —NH(acyl), —N(lower alkyl)$_2$, —N(acyl)$_2$; and X is O, S, $SO_2$ or $CH_2$.

In a eighth principal embodiment, a compound of Formulas X, XI and XII, or a pharmaceutically acceptable salt or prodrug thereof, is provided:

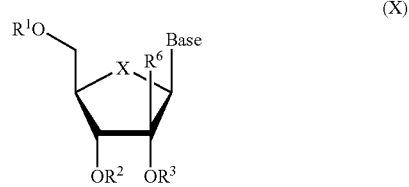

(X)

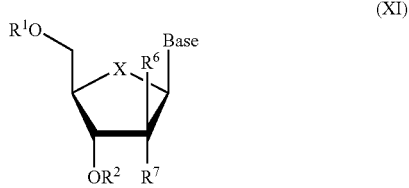

(XI)

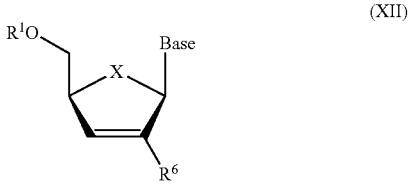

(XII)

wherein:

Base is a purine or pyrimidine base as defined herein;

$R^1$, $R^2$ and $R^3$ are independently H; phosphate (including monophosphate, diphosphate, triphosphate, or a stabilized phosphate prodrug); acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; a cholesterol; or other pharmaceutically acceptable leaving group which when administered in vivo is capable of providing a compound wherein $R^1$, $R^2$ or $R^3$ is independently H or phosphate;

$R^6$ is hydrogen, hydroxy, alkyl (including lower alkyl), azido, cyano, alkenyl, alkynyl, Br-vinyl, —C(O)O(alkyl), —C(O)O(lower alkyl), —O(acyl), —O(lower acyl), —O(alkyl), —O(lower alkyl), —O(alkenyl), chloro, bromo, fluoro, iodo, $NO_2$, $NH_2$, —NH(lower alkyl), —NH(acyl), —N(lower alkyl)$_2$, —N(acyl)$_2$;

$R^7$ is hydrogen, $OR^3$, hydroxy, alkyl (including lower alkyl), azido, cyano, alkenyl, alkynyl, Br-vinyl, —C(O)O(alkyl), —C(O)O(lower alkyl), —O(acyl), —O(lower acyl), —O(alkyl), —O(lower alkyl), —O(alkenyl), chlorine, bromine, iodine, $NO_2$, $NH_2$, —NH(lower alkyl), —NH(acyl), —N(lower alkyl)$_2$, —N(acyl)$_2$; and X is O, S, $SO_2$ or $CH_2$.

In a ninth principal embodiment a compound selected from Formulas XIII, XIV and XV, or a pharmaceutically acceptable salt or prodrug thereof, is provided:

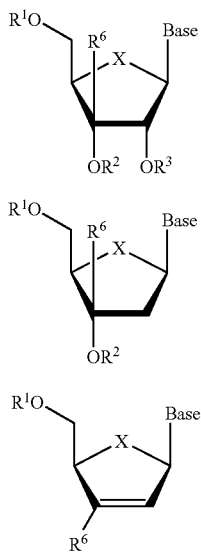

(XIII)

(XIV)

(XV)

wherein:

Base is a purine or pyrimidine base as defined herein;

$R^1$, $R^2$ and $R^3$ are independently H; phosphate (including monophosphate, diphosphate, triphosphate, or a stabilized phosphate prodrug); acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; a cholesterol; or other pharmaceutically acceptable leaving group which when administered in vivo is capable of providing a compound wherein $R^1$, $R^2$ or $R^3$ is independently H or phosphate;

$R^6$ is hydrogen, hydroxy, alkyl (including lower alkyl), azido, cyano, alkenyl, alkynyl, Br-vinyl, —C(O)O(alkyl), —C(O)O(lower alkyl), —O(acyl), —O(lower acyl), —O(alkyl), —O(lower alkyl), —O(alkenyl), chloro, bromo, fluoro, iodo, $NO_2$, $NH_2$, —NH(lower alkyl), —NH(acyl), —N(lower alkyl)$_2$, —N(acyl)$_2$; and X is O, S, $SO_2$, or $CH_2$.

In a tenth principal embodiment the invention provides a compound of Formula XVI, or a pharmaceutically acceptable salt or prodrug thereof:

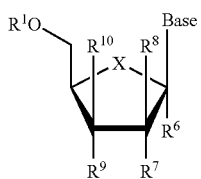

(XVI)

wherein:

Base is a purine or pyrimidine base as defined herein;

$R^1$ and $R^2$ are independently H; phosphate (including monophosphate, diphosphate, triphosphate, or a stabilized phosphate prodrug); acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; a cholesterol; or other pharmaceutically acceptable leaving group which when administered in vivo is capable of providing a compound wherein $R^1$ or $R^2$ is independently H or phosphate;

$R^6$ is hydrogen, hydroxy, alkyl (including lower alkyl), azido, cyano, alkenyl, alkynyl, Br-vinyl, —C(O)O(alkyl), —C(O)O(lower alkyl), —O(acyl), —O(lower acyl), —O(alkyl), —O(lower alkyl), —O(alkenyl), chloro, bromo, fluoro, iodo, $NO_2$, $NH_2$, —NH(lower alkyl), —NH(acyl), —N(lower alkyl)$_2$, —N(acyl)$_2$;

$R^7$ and $R^9$ are independently hydrogen, $OR^2$, hydroxy, alkyl (including lower alkyl), azido, cyano, alkenyl, alkynyl, Br-vinyl, —C(O)O(alkyl), —C(O)O(lower alkyl), —O(acyl), —O(lower acyl), —O(alkyl), —O(lower alkyl), —O(alkenyl), chlorine, bromine, iodine, $NO_2$, $NH_2$, —NH(lower alkyl), —NH(acyl), —N(lower alkyl)$_2$, —N(acyl)$_2$;

$R^8$ and $R^{10}$ are independently H, alkyl (including lower alkyl), chlorine, bromine or iodine; alternatively, $R^7$ and $R^9$, $R^7$ and $R^{10}$, $R^8$ and $R^9$, or $R^8$ and $R^{10}$ can come together to form a pi bond; and X is O, S, $SO_2$ or $CH_2$.

In a eleventh principal embodiment the invention provides a compound of Formula XVII, or a pharmaceutically acceptable salt or prodrug thereof:

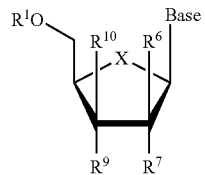

(XVII)

wherein:

Base is a purine or pyrimidine base as defined herein;

$R^1$ and $R^2$ are independently H; phosphate (including monophosphate, diphosphate, triphosphate, or a stabilized phosphate prodrug); acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; a cholesterol; or other pharmaceutically acceptable leaving group which when administered in vivo is capable of providing a compound wherein $R^1$ or $R^2$ is independently H or phosphate;

$R^6$ is hydrogen, hydroxy, alkyl (including lower alkyl), azido, cyano, alkenyl, alkynyl, Br-vinyl, —C(O)O(alkyl), —C(O)O(lower alkyl), —O(acyl), —O(lower acyl), —O(alkyl), —O(lower alkyl), —O(alkenyl), chloro, bromo, fluoro, iodo, $NO_2$, $NH_2$, —NH(lower alkyl), —NH(acyl), —N(lower alkyl)$_2$, —N(acyl)$_2$;

$R^7$ and $R^9$ are independently hydrogen, $OR^2$, hydroxy, alkyl (including lower alkyl), azido, cyano, alkenyl, alkynyl, Br-vinyl, —C(O)O(alkyl), —C(O)O(lower alkyl), —O(acyl), —O(lower acyl), —O(alkyl), —O(lower alkyl), —O(alkenyl), chlorine, bromine, iodine, $NO_2$, $NH_2$, —NH(lower alkyl), —NH(acyl), —N(lower alkyl)$_2$, —N(acyl)$_2$;

$R^{10}$ is H, alkyl (including lower alkyl), chlorine, bromine or iodine;

alternatively, $R^7$ and $R^9$, or $R^7$ and $R^{10}$ can come together to form a pi bond; and X is O, S, $SO_2$ or $CH_2$.

In an twelfth principal embodiment, the invention provides a compound of Formula XVIII, or a pharmaceutically acceptable salt or prodrug thereof:

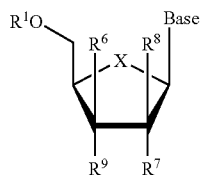

(XVIII)

wherein:

Base is a purine or pyrimidine base as defined herein;

$R^1$ and $R^2$ independently H; phosphate (including monophosphate, diphosphate, triphosphate, or a stabilized phosphate prodrug); acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; a cholesterol; or other pharmaceutically acceptable leaving group which when administered in vivo is capable of providing a compound wherein $R^1$ or $R^2$ is independently H or phosphate;

$R^6$ is hydrogen, hydroxy, alkyl (including lower alkyl), azido, cyano, alkenyl, alkynyl, Br-vinyl, —C(O)O(alkyl), —C(O)O(lower alkyl), —O(acyl), —O(lower acyl), —O(alkyl), —O(lower alkyl), —O(alkenyl), chloro, bromo, fluoro, iodo, $NO_2$, $NH_2$, —NH(lower alkyl), —NH(acyl), —N(lower alkyl)$_2$, —N(acyl)$_2$;

$R^7$ and $R^9$ are independently hydrogen, $OR^2$, alkyl (including lower alkyl), alkenyl, alkynyl, Br-vinyl, O-alkenyl, chlorine, bromine, iodine, $NO_2$, amino, loweralkylamino or di(lower-alkyl)amino;

$R^8$ is H, alkyl (including lower alkyl), chlorine, bromine or iodine;

alternatively, $R^7$ and $R^9$, or $R^8$ and $R^9$ can come together to form a pi bond;

X is O, S, $SO_2$ or $CH_2$.

The β-D- and β-L-nucleosides of this invention may inhibit flavivirus or pestivirus polymerase activity. These nucleosides can be assessed for their ability to inhibit flavivirus or pestivirus polymerase activity in vitro according to standard screening methods.

In one embodiment the efficacy of the anti-flavivirus or pestivirus compound is measured according to the concentration of compound necessary to reduce the plaque number of the virus in vitro, according to methods set forth more particularly herein, by 50% (i.e. the compound's $EC_{50}$). In preferred embodiments the compound exhibits an $EC_{50}$ of less than 15 or preferably, less than 10 micromolar in vitro.

In another embodiment, the active compound can be administered in combination or alternation with another anti-flavivirus or pestivirus agent. In combination therapy, effective dosages of two or more agents are administered together, whereas during alternation therapy an effective dosage of each agent is administered serially. The dosages will depend on absorption, inactivation and excretion rates of the drug as well as other factors known to those of skill in the art. It is to be noted that dosage values will also vary with the severity of the condition to be alleviated. It is to be further understood that for any particular subject, specific dosage regimens and schedules should be adjusted over time according to the individual need and the professional judgment of the person administering or supervising the administration of the compositions.

HCV is a member of the Flaviviridae family; however, now, HCV has been placed in a new monotypic genus, hepacivirus. Therefore, in one embodiment, the flavivirus or pestivirus is not HCV.

Nonlimiting examples of antiviral agents that can be used in combination with the compounds disclosed herein include:

(1) an interferon and/or ribavirin (Battaglia, A. M. et al., *Ann. Pharmacother.* 34:487–494, 2000); Berenguer, M. et al. *Antivir. Ther.* 3(Suppl. 3):125–136, 1998);

(2) Substrate-based NS3 protease inhibitors (Attwood et al., Antiviral peptide derivatives, PCT WO 98/22496, 1998; Attwood et al., *Antiviral Chemistry and Chemotherapy* 10.259–273, 1999; Attwood et al, Preparation and use of amino acid derivatives as anti-viral agents, German Patent Publication DE 19914474; Tung et al. Inhibitors of serine proteases, particularly hepatitis C virus NS3 protease, PCT WO 98/17679), including alphaketoamides and hydrazinoureas, and inhibitors that terminate in an electrophile such as a boronic acid or phosphonate. Llinas-Brunet et al, Hepatitis C inhibitor peptide analogues, PCT WO 99/07734.

(3) Non-substrate-based inhibitors such as 2,4,6-trihydroxy-3-nitro-benzamide derivatives (Sudo K. et al., *Biochemical and Biophysical Research Communications,* 238: 643–647, 1997; Sudo K. et al. *Antiviral Chemistry and Chemotherapy* 9:186, 1998), including RD3-4082 and RD3-4078, the former substituted on the amide with a 14 carbon chain and the latter processing a para-phenoxyphenyl group;

(4) Thiazolidine derivatives which show relevant inhibition in a reverse-phase HPLC assay with an NS3/4A fusion protein and NS5A/5B substrate (Sudo K. et al., *Antiviral Research* 32:9–18, 1996), especially compound RD-1-6250, possessing a fused cinnamoyl moiety substituted with a long alkyl chain, RD4 6205 and RD4 6193;

(5) Thiazolidines and benzanilides identified in Kakiuchi N. et al. *J. EBS Letters* 421:217–220; Takeshita N. et al. *Analytical Biochemistry* 247:242–246, 1997;

(6) A phenan-threnequinone possessing activity against protease in a SDS-PAGE and autoradiography assay isolated from the fermentation culture broth of *Streptomyces* sp., Sch 68631 (Chu M. et al., *Tetrahedron Letters* 37:7229–7232, 1996), and Sch 351633, isolated from the fungus *Penicillium griscofuluum*, which demonstrates activity in a scintillation proximity assay (Chu M. et al., *Bioorganic and Medicinal Chemistry Letters* 9:1949–1952);

(7) Selective NS3 inhibitors based on the macromolecule elgin c, isolated from leech (Qasim M. A. et al., *Biochemistry* 36:1598–1607, 1997);

(8) Helicase inhibitors (Diana G. D. et al., Compounds, compositions and methods for treatment of hepatitis C, U.S.

Pat. No. 5,633,358; Diana G. D. et al., Piperidine derivatives, pharmaceutical compositions thereof and their use in the treatment of hepatitis C, PCT WO 97/36554);

(9) Polymerase inhibitors such as nucleotide analogues, gliotoxin (Ferrari R. et al. *Journal of Virology* 73:1649–1654, 1999), and the natural product cerulenin (Lohmann V. et al., *Virology* 249:108–118, 1998);

(10) Antisense phosphorothioate oligodeoxynucleotides (S-ODN) complementary to sequence stretches in the 5' non-coding region (NCR) of the virus (Alt M. et al., *Hepatology* 22:707–717, 1995), or nucleotides 326–348 comprising the 3' end of the NCR and nucleotides 371–388 located in the core coding region of the IICV RNA (Alt M. et al., *Archives of Virology* 142:589–599, 1997; Galderisi U. et al., *Journal of Cellular Physiology* 181:251–257, 1999);

(11) Inhibitors of IRES-dependent translation (Ikeda N et al., Agent for the prevention and treatment of hepatitis C, Japanese Patent Publication JP-08268890; Kai Y. et al. Prevention and treatment of viral diseases, Japanese Patent Publication JP-10101591);

(12) Nuclease-resistant ribozymes. (Maccjak D. J. et al., *Hepatology* 30 abstract 995, 1999); and

(13) Other miscellaneous compounds including 1-aminoalkylcyclohexanes (U.S. Pat. No. 6,034,134 to Gold et al.), alkyl lipids (U.S. Pat. No. 5,922,757 to Chojkier et al.), vitamin E and other antioxidants (U.S. Pat. No. 5,922,757 to Chojkier et al.), squalene, amantadine, bile acids (U.S. Pat. No. 5,846,964 to Ozeki et al.), N-(phosphonoacetyl)-L-aspartic acid, (U.S. Pat. No. 5,830,905 to Diana et al.), benzenedicarboxamides (U.S. Pat. No. 5,633,388 to Diana et al.), polyadenylic acid derivatives (U.S. Pat. No. 5,496,546 to Wang et al.), 2',3'-dideoxyinosine (U.S. Pat. No. 5,026,687 to Yarchoan et al.), and benzimidazoles (U.S. Pat. No. 5,891,874 to Colacino et al.).

BRIEF DESCRIPTION OF THE FIGURES

FIG. 1 provides the structure of various non-limiting examples of nucleosides of the present invention, as well as other known nucleosides, FIAU and Ribavirin, which are used as comparative examples in the text.

FIG. 2 is a line graph of the pharmacokinetics (plasma concentrations) of β-D-2'-CH$_3$-riboG administered to Cynomolgus Monkeys over time after administration.

FIG. 4 depicts line graphs of the results of the cell protection assay of β-D-2'-CH$_3$-riboG against BVDV.

FIG. 5 depicts line graphs of the results of the cell protection assay of ribavirin against BVDV.

FIG. 6 are line graphs of the cell protection assay of β-D-2'-CH$_3$-riboG, β-D-2'-CH$_3$-riboC, β-D-2'-CH$_3$-riboU, β-D-2'-CH$_3$-riboA and ribavirin.

FIG. 7 are line graphs of the results of the plaque reduction assay for β-D-2'-CH$_3$-riboU, β-D-2'-CH$_3$-riboC and β-D-2'-CH$_3$-riboG.

FIG. 8 is an illustration of plaque reduction based on increasing concentrations of β-D-2'-CH$_3$-riboU.

FIG. 9 is a line graph of the results of the yield reduction assay for β-D-2'-CH$_3$-riboG, depicting a 4 log reduction at 9 μM.

FIG. 10 is an illustration of the yield reduction based on increasing concentrations of β-D-2'-CH$_3$-riboC.

DETAILED DESCRIPTION OF THE INVENTION

Figure 3A:
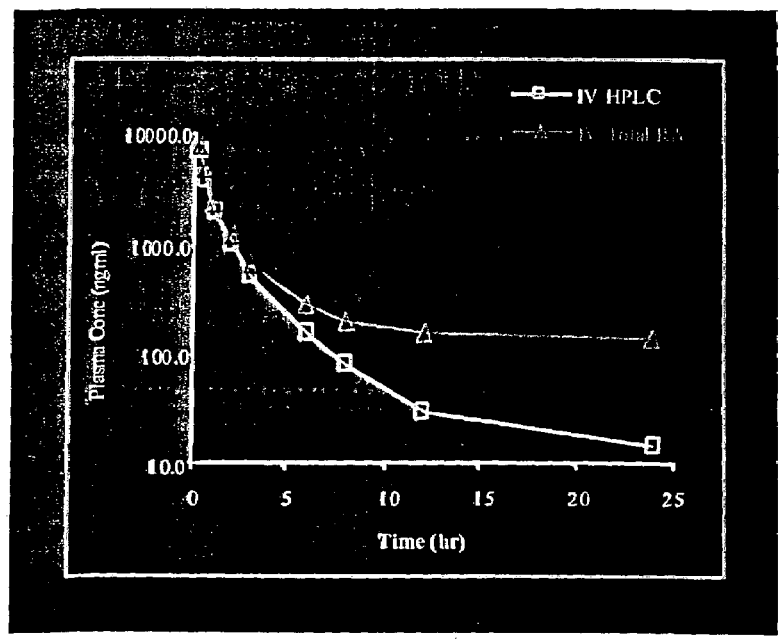
FIGS. 3a and 3b are line graphs of the pharmacokinetics (plasma concentrations) of β-D-2'-CH$_3$-riboG administered to Cynomolgus Monkeys either intravenously (3a) or orally (3b) over time after administration.

The invention as disclosed herein is a compound, method and composition for the treatment of pestiviruses and flaviviruses in humans and other host animals, that includes the administration of an effective flavivirus or pestivirus treatment amount of an β-D- or β-L-nucleoside as described herein or a pharmaceutically acceptable salt or prodrug thereof, optionally in a pharmaceutically acceptable carrier. The compounds of this invention either possess antiviral (i.e., anti-flavivirus or pestivirus) activity, or are metabolized to a compound that exhibits such activity.

In summary, the present invention includes the following features:

(a) β-D- and β-L-nucleosides, as described herein, and pharmaceutically acceptable salts and prodrugs thereof;

(b) β-D- and β-L-nucleosides as described herein, and pharmaceutically acceptable salts and prodrugs thereof for use in the treatment or prophylaxis of a flavivirus or pestivirus infection, especially in individuals diagnosed as having a flavivirus or pestivirus infection or being at risk for becoming infected by flavivirus or pestivirus;

(c) use of these β-D- and β-L-nucleosides, and pharmaceutically acceptable salts and prodrugs thereof in the manufacture of a medicament for treatment of a flavivirus or pestivirus infection;

(d) pharmaceutical formulations comprising the β-D- and β-L-nucleosides or pharmaceutically acceptable salts or prodrugs thereof together with a pharmaceutically acceptable carrier or diluent;

(e) β-D- and β-L-nucleosides as described herein substantially in the absence of enantiomers of the described nucleoside, or substantially isolated from other chemical entities;

(f) processes for the preparation of β-D- and β-L-nucleosides, as described in more detail below; and (g) processes for the preparation of β-D- and β-L-nucleosides substantially in the absence of enantiomers of the described nucleoside, or substantially isolated from other chemical entities.

Flaviviruses included within the scope of this invention are discussed generally in *Fields Virology*, Editors: Fields, B. N., Knipe, D. M., and Howley, P. M., Lippincott-Raven Publishers, Philadelphia, Pa., Chapter 31, 1996. Specific flaviviruses include, without limitation: Absettarov, Alfuy, Apoi, Aroa, Bagaza, Banzi, Bouboui, Bussuquara, Cacipacore, Carey Island, Dakar bat, Dengue 1, Dengue 2, Dengue 3, Dengue 4, Edge Hill, Entebbe bat, Gadgets Gully, Hanzalova, Hypr, Ilheus, Israel turkey meningoencephalitis, Japanese encephalitis, Jugra, Jutiapa, Kadam, Karshi, Kedougou, Kokobera, Koutango, Kumlinge, Kunjin, Kyasanur Forest disease, Langat, Louping ill, Meaban, Modoc, Montana myotis leukoencephalitis, Murray valley encephalitis, Naranjal, Negishi, Ntaya, Omsk hemorrhagic fever, Phnom-Penh bat, Powassan, Rio Bravo, Rocio, Royal Farm, Russian spring-summer encephalitis, Saboya, St. Louis encephalitis, Sal Vieja, San Perlita, Saumarez Reef, Sepik, Sokuluk, Spondweni, Stratford, Tembusu, Tyuleniy, Uganda S, Usutu, Wesselsbron, West Nile, Yaounde, Yellow fever, and Zika.

Pestiviruses included within the scope of this invention are discussed generally in *Fields Virology*, Editors: Fields, B. N., Knipe, D. M., and Howley, P. M., Lippincott-Raven Publishers, Philadelphia, Pa., Chapter 33, 1996. Specific pestiviruses include, without limitation: bovine viral diarrhea virus ("BVDV"), classical swine fever virus ("CSFV," also called hog cholera virus), and border disease virus ("BDV").

I. Active Compound, and Physiologically Acceptable Salts and Prodrugs Thereof

In a first principal embodiment, a compound of Formula I, or a pharmaceutically acceptable salt or prodrug thereof, is provided:

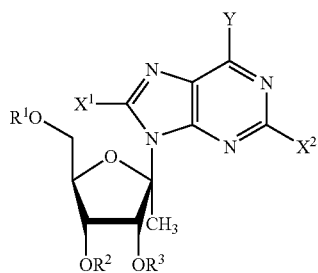

(I)

wherein:

$R^1$, $R^2$ and $R^3$ are independently H, phosphate (including mono-, di- or triphosphate and a stabilized phosphate prodrug); acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; a cholesterol; or other pharmaceutically acceptable leaving group which when administered in vivo is capable of providing a compound wherein $R^1$, $R^2$ or $R^3$ is independently H or phosphate;

Y is hydrogen, bromo, chloro, fluoro, iodo, $OR^4$, $NR^4R^5$ or $SR^4$;

$X^1$ and $X^2$ are independently selected from the group consisting of H, straight chained, branched or cyclic alkyl, CO-alkyl, CO-aryl, CO-alkoxyalkyl, chloro, bromo, fluoro, iodo, $OR^4$, $NR^4NR^5$ or $SR^5$; and $R^4$ and $R^5$ are independently hydrogen, acyl (including lower acyl), or alkyl (including but not limited to methyl, ethyl, propyl and cyclopropyl).

In a preferred subembodiment, a compound of Formula I, or a pharmaceutically acceptable salt or prodrug thereof, is provided wherein:

$R^1$, $R^2$ and $R^3$ are independently H or phosphate (preferably H);

$X^1$ is H;

$X^2$ is H or $NH_2$; and

Y is hydrogen, bromo, chloro, fluoro, iodo, $NH_2$ or OH.

In a second principal embodiment, a compound of Formula II, or a pharmaceutically acceptable salt or prodrug thereof, is provided:

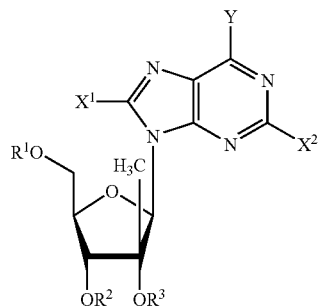

(II)

wherein:

$R^1$, $R^2$ and $R^3$ are independently H; phosphate (including monophosphate, diphosphate, triphosphate, or a stabilized phosphate prodrug); acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; a cholesterol; or other pharmaceutically acceptable leaving group which when administered in vivo is capable of providing a compound wherein $R^1$, $R^2$ or $R^3$ is independently H or phosphate; and Y is hydrogen, bromo, chloro, fluoro, iodo, $OR^4$, $NR^4R^5$ or $SR^4$;

$X^1$ and $X^2$ are independently selected from the group consisting of H, straight chained, branched or cyclic alkyl, CO-alkyl, CO-aryl, CO-alkoxyalkyl, chloro, bromo, fluoro, iodo, $OR^4$, $NR^4NR^5$ or $SR^5$; and $R^4$ and $R^5$ are independently hydrogen, acyl (including lower acyl), or alkyl (including but not limited to methyl, ethyl, propyl and cyclopropyl).

In a preferred subembodiment, a compound of Formula II, or a pharmaceutically acceptable salt or prodrug thereof, is provided wherein:

$R^1$, $R^2$ and $R^3$ are independently H or phosphate (preferably H);

$X^1$ is H;

$X^2$ is H or $NH_2$; and

Y is hydrogen, bromo, chloro, fluoro, iodo, $NH_2$ or OH.

In a third principal embodiment, a compound of Formula III, or a pharmaceutically acceptable salt or prodrug thereof, is provided:

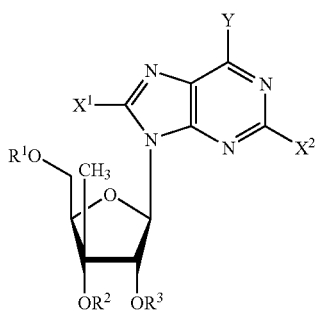

(III)

wherein:

R¹, R² and R³ are independently H; phosphate (including monophosphate, diphosphate, triphosphate, or a stabilized phosphate prodrug); acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; a cholesterol; or other pharmaceutically acceptable leaving group which when administered in vivo is capable of providing a compound wherein R¹, R² or R³ is independently H or phosphate; and Y is hydrogen, bromo, chloro, fluoro, iodo, OR⁴, NR⁴R⁵ or SR⁴;

X¹ and X² are independently selected from the group consisting of H, straight chained, branched or cyclic alkyl, CO-alkyl, CO-aryl, CO-alkoxyalkyl, chloro, bromo, fluoro, iodo, OR⁴, NR⁴NR⁵ or SR⁵; and R⁴ and R⁵ are independently hydrogen, acyl (including lower acyl), or alkyl (including but not limited to methyl, ethyl, propyl and cyclopropyl).

In a preferred subembodiment, a compound of Formula III, or a pharmaceutically acceptable salt or prodrug thereof, is provided wherein:

R¹, R² and R³ are independently H or phosphate (preferably H);

X¹ is H;

X² is H or NH₂; and

Y is hydrogen, bromo, chloro, fluoro, iodo, NH₂ or OH.

In a fourth principal embodiment, a compound of Formula IV, or a pharmaceutically acceptable salt or prodrug thereof, is provided:

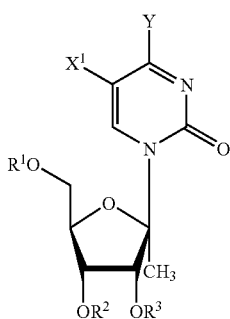

(IV)

wherein:

R¹, R² and R³ are independently H, phosphate (including mono-, di- or triphosphate and a stabilized phosphate prodrug); acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; a cholesterol; or other pharmaceutically acceptable leaving group which when administered in vivo is capable of providing a compound wherein R¹, R² or R³ is independently H or phosphate;

Y is hydrogen, bromo, chloro, fluoro, iodo, OR⁴, NR⁴R⁵ or SR⁴;

X¹ is selected from the group consisting of H, straight chained, branched or cyclic alkyl, CO-alkyl, CO-aryl, CO-alkoxyalkyl, chloro, bromo, fluoro, iodo, OR⁴, NR⁴NR⁵ or SR⁵; and R⁴ and R⁵ are independently hydrogen, acyl (including lower acyl), or alkyl (including but not limited to methyl, ethyl, propyl and cyclopropyl).

In a preferred subembodiment, a compound of Formula IV, or a pharmaceutically acceptable salt or prodrug thereof, is provided wherein:

R¹, R² and R³ are independently H or phosphate (preferably H);

X¹ is H or CH₃; and

Y is hydrogen, bromo, chloro, fluoro, iodo, NH₂ or OH.

In a fifth principal embodiment, a compound of Formula V, or a pharmaceutically acceptable salt or prodrug thereof, is provided:

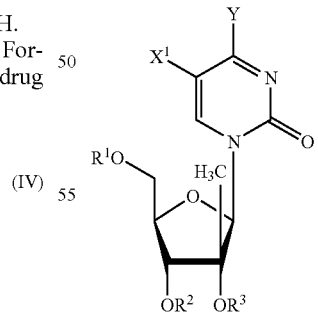

(V)

wherein:

R¹, R² and R³ are independently H; phosphate (including monophosphate, diphosphate, triphosphate, or a stabilized phosphate prodrug); acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; a cholesterol; or other pharmaceutically acceptable leaving group which when administered in vivo is capable of providing a compound wherein $R^1$, $R^2$ or $R^3$ is independently H or phosphate; and Y is hydrogen, bromo, chloro, fluoro, iodo, $OR^4$, $NR^4R^5$ or $SR^4$;

$X^1$ is selected from the group consisting of H, straight chained, branched or cyclic alkyl, CO-alkyl, CO-aryl, CO-alkoxyalkyl, chloro, bromo, fluoro, iodo, $OR^4$, $NR^4NR^5$ or $SR^5$; and $R^4$ and $R^5$ are independently hydrogen, acyl (including lower acyl), or alkyl (including but not limited to methyl, ethyl, propyl and cyclopropyl).

In a preferred subembodiment, a compound of Formula V, or a pharmaceutically acceptable salt or prodrug thereof, is provided wherein:

$R^1$, $R^2$ and $R^3$ are independently H or phosphate (preferably H);

$X^1$ is H or $CH_3$; and

Y is hydrogen, bromo, chloro, fluoro, iodo, $NH_2$ or OH.

In a sixth principal embodiment, a compound of Formula VI, or a pharmaceutically acceptable salt or prodrug thereof, is provided:

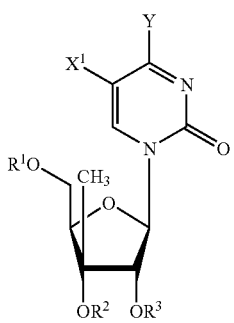

(VI)

wherein:

$R^1$, $R^2$ and $R^3$ are independently H; phosphate (including monophosphate, diphosphate, triphosphate, or a stabilized phosphate prodrug); acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; a cholesterol; or other pharmaceutically acceptable leaving group which when administered in vivo is capable of providing a compound wherein $R^1$, $R^2$ or $R^3$ is independently H or phosphate; and Y is hydrogen, bromo, chloro, fluoro, iodo, $OR^4$, $NR^4R^5$ or $SR^4$;

$X^1$ is selected from the group consisting of H, straight chained, branched or cyclic alkyl, CO-alkyl, CO-aryl, CO-alkoxyalkyl, chloro, bromo, fluoro, iodo, $OR^4$, $NR^4NR^5$ or $SR^5$; and $R^4$ and $R^5$ are independently hydrogen, acyl (including lower acyl), or alkyl (including but not limited to methyl, ethyl, propyl and cyclopropyl).

In a preferred subembodiment, a compound of Formula VI, or a pharmaceutically acceptable salt or prodrug thereof, is provided wherein:

$R^1$, $R^2$ and $R^3$ are independently H or phosphate (preferably H);

$X^1$ is H or $CH_3$; and

Y is hydrogen, bromo, chloro, fluoro, iodo, $NH_2$ or OH.

In a seventh principal embodiment, a compound selected from Formulas VII, VIII and IX, or a pharmaceutically acceptable salt or prodrug thereof, is provided:

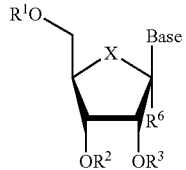

(VII)

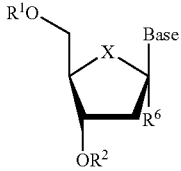

(VIII)

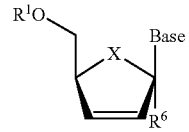

(IX)

wherein:

Base is a purine or pyrimidine base as defined herein;

$R^1$, $R^2$ and $R^3$ are independently H; phosphate (including monophosphate, diphosphate, triphosphate, or a stabilized phosphate prodrug); acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; a cholesterol; or other pharmaceutically acceptable leaving group which when administered in vivo is capable of providing a compound wherein $R^1$, $R^2$ or $R^3$ is independently H or phosphate;

$R^6$ is hydrogen, hydroxy, alkyl (including lower alkyl), azido, cyano, alkenyl, alkynyl, Br-vinyl, 2-Br-ethyl, —C(O)O(alkyl), —C(O)O(lower alkyl), —O(acyl), —O(lower acyl), —O(alkyl), —O(lower alkyl), —O(alkenyl), $CF_3$, chloro, bromo, fluoro, iodo, $NO_2$, $NH_2$, —NH(lower alkyl), —NH(acyl), —N(lower alkyl)$_2$, —N(acyl)$_2$; and X is O, S, SO$_2$, or CH$_2$.

In a first preferred subembodiment, a compound of Formula VII, VIII or IX, or a pharmaceutically acceptable salt or prodrug thereof, is provided wherein:

Base is a purine or pyrimidine base as defined herein;

R$^1$, R$^2$ and R$^3$ are independently hydrogen or phosphate;

R$^6$ is alkyl; and

X is O, S, SO$_2$ or CH$_2$.

In a second preferred subembodiment, a compound of Formula VII, VIII or IX, or a pharmaceutically acceptable salt or prodrug thereof, is provided wherein:

Base is a purine or pyrimidine base as defined herein;

R$^1$, R$^2$ and R$^3$ are hydrogens;

R$^6$ is alkyl; and

X is O, S, SO$_2$ Or CH$_2$.

In a third preferred subembodiment, a compound of Formula VII, VIII or IX, or a pharmaceutically acceptable salt or prodrug thereof, is provided wherein:

Base is a purine or pyrimidine base as defined herein;

R$^1$, R$^2$ and R$^3$ are independently hydrogen or phosphate;

R$^6$ is alkyl; and

X is O.

In a eighth principal embodiment, a compound of Formula X, XI or XII, or a pharmaceutically acceptable salt or prodrug thereof, is provided:

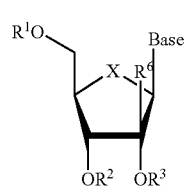
(X)

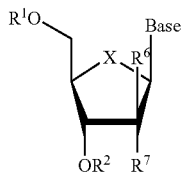
(XI)

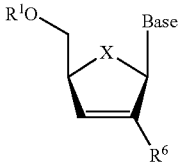
(XII)

wherein:

Base is a purine or pyrimidine base as defined herein;

R$^1$, R$^2$ and R$^3$ are independently H; phosphate (including monophosphate, diphosphate, triphosphate, or a stabilized phosphate prodrug); acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; a cholesterol; or other pharmaceutically acceptable leaving group which when administered in vivo is capable of providing a compound wherein R$^1$, R$^2$ or R$^3$ is independently H or phosphate;

R$^6$ is hydrogen, hydroxy, alkyl (including lower alkyl), azido, cyano, alkenyl, alkynyl, Br-vinyl, —C(O)O(alkyl), —C(O)O(lower alkyl), —O(acyl), —O(lower acyl), —O(alkyl), —O(lower alkyl), —O(alkenyl), chloro, bromo, fluoro, iodo, NO$_2$, NH$_2$, —NH(lower alkyl), —NH(acyl), —N(lower alkyl)$_2$, —N(acyl)$_2$;

R$^7$ is hydrogen, OR$^3$, hydroxy, alkyl (including lower alkyl), azido, cyano, alkenyl, alkynyl, Br-vinyl, —C(O)O(alkyl), —C(O)O(lower alkyl), —O(acyl), —O(lower acyl), —O(alkyl), —O(lower alkyl), —O(alkenyl), chlorine, bromine, iodine, NO$_2$, NH$_2$, —NH(lower alkyl), —NH(acyl), —N(loweralkyl)$_2$, —N(acyl)$_2$; and X is O, S, SO$_2$ or CH$_2$.

In a first preferred subembodiment, a compound of Formula X, XI or XII, or a pharmaceutically acceptable salt or prodrug thereof, is provided wherein:

Base is a purine or pyrimidine base as defined herein;

R$^1$, R$^2$ and R$^3$ are independently hydrogen or phosphate;

R$^6$ is alkyl; and

X is O, S, SO$_2$ or CH$_2$.

In a second preferred subembodiment, a compound of Formula X, XI or XII, or a pharmaceutically acceptable salt or prodrug thereof, is provided wherein:

Base is a purine or pyrimidine base as defined herein;

R$^1$, R$^2$ and R$^3$ are hydrogens;

R$^6$ is alkyl; and

X is O, S, SO$_2$ or CH$_2$.

In a third preferred subembodiment, a compound of Formula X, XI or XII, or a pharmaceutically acceptable salt or prodrug thereof, is provided wherein:

Base is a purine or pyrimidine base as defined herein;

R$^1$, R$^2$ and R$^3$ are independently H or phosphate;

R$^6$ is alkyl; and

X is O.

In even more preferred subembodiments, a compound of Formula XI, or its pharmaceutically acceptable salt or prodrug, is provided:

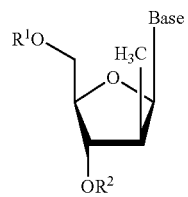
(XI)

wherein:

Base is a purine or pyrimidine base as defined herein; optionally substituted with an amine or cyclopropyl (e.g., 2-amino, 2,6-diamino or cyclopropyl guanosine); and R¹ and R² are independently H; phosphate (including monophosphate, diphosphate, triphosphate, or a stabilized phosphate prodrug); acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; a cholesterol; or other pharmaceutically acceptable leaving group which when administered in vivo is capable of providing a compound wherein R¹ or R² is independently H or phosphate.

In a ninth principal embodiment a compound selected from Formula XIII, XIV or XV, or a pharmaceutically acceptable salt or prodrug thereof, is provided:

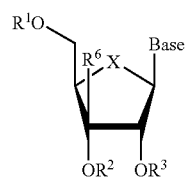
(XIII)

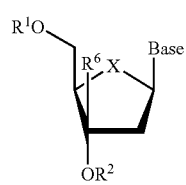
(XIV)

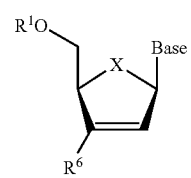
(XV)

wherein:

Base is a purine or pyrimidine base as defined herein;

R¹, R² and R³ are independently H; phosphate (including monophosphate, diphosphate, triphosphate, or a stabilized phosphate prodrug); acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; a cholesterol; or other pharmaceutically acceptable leaving group which when administered in vivo is capable of providing a compound wherein R¹, R² or R³ is independently H or phosphate;

R⁶ is hydrogen, hydroxy, alkyl (including lower alkyl), azido, cyano, alkenyl, alkynyl, Br-vinyl, —C(O)O(alkyl), —C(O)O(lower alkyl), —O(acyl), —O(lower acyl), —O(alkyl), —O(lower alkyl), —O(alkenyl), chloro, bromo, fluoro, iodo, NO₂, NH₂, —NH(lower alkyl), —NH(acyl), —N(lower alkyl)₂, —N(acyl)₂; and X is O, S, SO₂ or CH₂.

In a first preferred subembodiment, a compound of Formula XIII, XIV or XV, or a pharmaceutically acceptable salt or prodrug thereof, is provided wherein:

Base is a purine or pyrimidine base as defined herein;

R¹, R² and R³ are independently hydrogen or phosphate;

R⁶ is alkyl; and

X is O, S, SO₂ or CH₂.

In a second preferred subembodiment, a compound of Formula XIII, XIV or XV, or a pharmaceutically acceptable salt or prodrug thereof, is provided wherein:

Base is a purine or pyrimidine base as defined herein;

R¹, R² and R³ are hydrogens;

R⁶ is alkyl; and

X is O, S, SO₂ or CH₂.

In a third preferred subembodiment, a compound of Formula XIII, XIV or XV, or a pharmaceutically acceptable salt or prodrug thereof, is provided wherein:

Base is a purine or pyrimidine base as defined herein;

R¹, R² and R³ are independently hydrogen or phosphate;

R⁶ is alkyl; and

X is O.

In a tenth principal embodiment the invention provides a compound of Formula XVI, or a pharmaceutically acceptable salt or prodrug thereof:

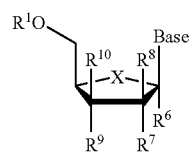
(XVI)

wherein:

Base is a purine or pyrimidine base as defined herein;

R¹ and R² are independently H; phosphate (including monophosphate, diphosphate, triphosphate, or a stabilized phosphate prodrug); acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; a cholesterol; or other pharmaceutically acceptable leaving group which when administered in vivo is capable of providing a compound wherein R¹ and R² are independently H or phosphate;

R⁶ is hydrogen, hydroxy, alkyl (including lower alkyl), azido, cyano, alkenyl, alkynyl, Br-vinyl, —C(O)O(alkyl), —C(O)O(lower alkyl), —O(acyl), —O(lower acyl), —O(alkyl), —O(lower alkyl), —O(alkenyl), chloro, bromo, fluoro, iodo, NO₂, NH₂, —NH(lower alkyl), —NH(acyl), —N(lower alkyl)₂, —N(acyl)₂;

R⁷ and R⁹ are independently hydrogen, OR², hydroxy, alkyl (including lower alkyl), azido, cyano, alkenyl, alkynyl, Br-vinyl, —C(O)O(alkyl), —C(O)O(lower alkyl), —O(acyl), —O(lower acyl), —O(alkyl), —O(lower alkyl), —O(alkenyl), chlorine, bromine, iodine, NO₂, NH₂, —NH (lower alkyl), —NH(acyl), —N(lower alkyl)₂, —N(acyl)₂;

$R^8$ and $R^{10}$ are independently H, alkyl (including lower alkyl), chlorine, bromine or iodine; alternatively, $R^7$ and $R^9$, $R^7$ and $R^{10}$, $R^8$ and $R^9$, or $R^8$ and $R^{10}$ can come together to form a pi bond; and X is O, S, $SO_2$ or $CH_2$.

In a first preferred subembodiment, a compound of Formula XVI, or its pharmaceutically acceptable salt or prodrug, is provided in which: (1) Base is a purine or pyrimidine base as defined herein; (2) $R^1$ is independently H or phosphate (including monophosphate, diphosphate, triphosphate, or a stabilized phosphate prodrug); acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; a cholesterol; or other pharmaceutically acceptable leaving group which when administered in vivo is capable of providing a compound wherein $R^1$ is independently H or phosphate; (3) $R^6$ is alkyl; (4) $R^7$ and $R^9$ are independently $OR^2$, alkyl, alkenyl, alkynyl, Br-vinyl, O-alkenyl, chlorine, bromine, iodine, $NO_2$, amino, loweralkylamino or di(loweralkyl)amino; (5) $R^8$ and $R^{10}$ are independently H, alkyl (including lower alkyl), chlorine, bromine, or iodine; and (6) X is O, S, $SO_2$ or $CH_2$.

In a second preferred subembodiment, a compound of Formula XVI, or its pharmaceutically acceptable salt or prodrug, is provided in which: (1) Base is a purine or pyrimidine base as defined herein; (2) $R^1$ is independently H or phosphate (including monophosphate, diphosphate, triphosphate, or a stabilized phosphate prodrug); acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; a cholesterol; or other pharmaceutically acceptable leaving group which when administered in vivo is capable of providing a compound wherein $R^1$ is independently H or phosphate; (3) $R^6$ is alkyl, alkenyl, alkynyl, Br-vinyl, hydroxy, O-alkyl, O-alkenyl, chloro, bromo, fluoro, iodo, $NO_2$, amino, loweralkylamino, or di(loweralkyl)amino; (4) $R^7$ and $R^9$ are independently $OR^2$; (5) $R^8$ and $R^{10}$ are independently H, alkyl (including lower alkyl), chlorine, bromine, or iodine; and (6) X is O, S, $SO_2$ or $CH_2$.

In a third preferred subembodiment, a compound of Formula XVI, or its pharmaceutically acceptable salt or prodrug, is provided in which: (1) Base is a purine or pyrimidine base as defined herein; (2) $R^1$ is independently H or phosphate (including monophosphate, diphosphate, triphosphate, or a stabilized phosphate prodrug); acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; a cholesterol; or other pharmaceutically acceptable leaving group which when administered in vivo is capable of providing a compound wherein $R^1$ is independently H or phosphate; (3) $R^6$ is alkyl, alkenyl, alkynyl, Br-vinyl, hydroxy, O-alkyl, O-alkenyl, chloro, bromo, fluoro, iodo, $NO_2$, amino, loweralkylamino or di(loweralkyl)amino; (4) $R^7$ and $R^9$ are independently $OR^2$, alkyl, alkenyl, alkynyl, Br-vinyl, O-alkenyl, chlorine, bromine, iodine, $NO_2$, amino, loweralkylamino or di(loweralkyl)amino; (5) $R^8$ and $R^{10}$ are H; and (6) X is O, S, $SO_2$ or $CH_2$.

In a fourth preferred subembodiment, a compound of Formula XVI, or its pharmaceutically acceptable salt or prodrug, is provided in which: (1) Base is a purine or pyrimidine base as defined herein; (2) $R^1$ is independently H or phosphate (including monophosphate, diphosphate, triphosphate, or a stabilized phosphate prodrug); acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; a cholesterol; or other pharmaceutically acceptable leaving group which when administered in vivo is capable of providing a compound wherein $R^1$ is independently H or phosphate; (3) $R^6$ is alkyl, alkenyl, alkynyl, Br-vinyl, hydroxy, O-alkyl, O-alkenyl, chloro, bromo, fluoro, iodo, $NO_2$, amino, loweralkylamino, or di(loweralkyl)amino; (4) $R^7$ and $R^9$ are independently $OR^2$, alkyl, alkenyl, alkynyl, Br-vinyl, O-alkenyl, chlorine, bromine, iodine, $NO_2$, amino, loweralkylamino, or di(loweralkyl)amino; (5) $R^8$ and $R^{10}$ are independently H, alkyl (including lower alkyl), chlorine, bromine, or iodine; and (6) X is O.

In a fifth preferred subembodiment, a compound of Formula XVI, or its pharmaceutically acceptable salt or prodrug, is provided in which: (1) Base is a purine or pyrimidine base as defined herein; (2) $R^1$ is independently H or phosphate (including monophosphate, diphosphate, triphosphate, or a stabilized phosphate prodrug); acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; a cholesterol; or other pharmaceutically acceptable leaving group which when administered in vivo is capable of providing a compound wherein $R^1$ is independently H or phosphate; (3) $R^6$ is alkyl; (4) $R^7$ and $R^9$ are independently $OR^1$; (5) $R^8$ and $R^{10}$ are independently H, alkyl (including lower alkyl), chlorine, bromine or iodine; and (6) X is O, S, $SO_2$ or $CH_2$.

In a sixth preferred subembodiment, a compound of Formula XVI, or its pharmaceutically acceptable salt or prodrug, is provided in which: (1) Base is a purine or pyrimidine base as defined herein; (2) $R^1$ is independently H or phosphate (including monophosphate, diphosphate, triphosphate, or a stabilized phosphate prodrug); acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; a cholesterol; or other pharmaceutically acceptable leaving group which when administered in vivo is capable of providing a compound wherein $R^1$ is independently H or phosphate; (3) $R^6$ is alkyl; (4) $R^7$ and $R^9$ are independently $OR^2$, alkyl (including lower alkyl), alkenyl, alkynyl, Br-vinyl, O-alkenyl, chlorine, bromine, iodine, $NO_2$, amino, loweralkylamino, or di(loweralkyl)amino; (5) $R^8$ and $R^{10}$ are H; and (6) X is O, S, $SO_2$, or $CH_2$.

In a seventh preferred subembodiment, a compound of Formula XVI, or its pharmaceutically acceptable salt or prodrug, is provided in which: (1) Base is a purine or pyrimidine base as defined herein; (2) $R^1$ is independently H or phosphate (including monophosphate, diphosphate, triphosphate, or a stabilized phosphate prodrug); acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; a cholesterol; or other pharmaceutically acceptable leaving group which when administered in vivo is capable of providing a compound wherein $R^1$ is independently H or phosphate; (3) $R^6$ is alkyl; (4) $R^7$ and $R^9$ are independently $OR^2$, alkyl (including lower alkyl), alkenyl, alkynyl, Br-vinyl, O-alkenyl, chlorine, bromine, iodine, $NO_2$, amino, loweralkylamino or di(loweralkyl)amino; (5) $R^8$ and $R^{10}$ are independently H, alkyl (including lower alkyl), chlorine, bromine or iodine; and (6) X is O.

In a eighth preferred subembodiment, a compound of Formula XVI, or its pharmaceutically acceptable salt or prodrug, is provided in which: (1) Base is a purine or pyrimidine base as defined herein; (2) $R^1$ is independently H or phosphate (including monophosphate, diphosphate, triphosphate, or a stabilized phosphate prodrug); acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; a cholesterol; or other pharmaceutically acceptable leaving group which when administered in vivo is capable of providing a compound wherein $R^1$ is independently H or phosphate; (3) $R^6$ is alkyl (including lower alkyl), alkenyl, alkynyl, Br-vinyl, hydroxy, O-alkyl, O-alkenyl, chloro, bromo, fluoro, iodo, $NO_2$, amino, loweralkylamino or di(loweralkyl)amino; (4) $R^7$ and $R^9$ are independently $OR^2$; (5) $R^8$ and $R^{10}$ are hydrogen; and (6) X is O, S, $SO_2$ or $CH_2$.

In a ninth preferred subembodiment, a compound of Formula XVI, or its pharmaceutically acceptable salt or prodrug, is provided in which: (1) Base is a purine or pyrimidine base as defined herein; (2) $R^1$ is independently H or phosphate (including monophosphate, diphosphate, triphosphate, or a stabilized phosphate prodrug); acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; a cholesterol; or other pharmaceutically acceptable leaving group which when administered in vivo is capable of providing a compound wherein $R^1$ is independently H or phosphate; (3) $R^6$ is alkyl (including lower alkyl), alkenyl, alkynyl, Br-vinyl, hydroxy, O-alkyl, O-alkenyl, chloro, bromo, fluoro, iodo, $NO_2$, amino, loweralkylamino or di(loweralkyl)amino; (4) $R^7$ and $R^9$ are independently $OR^2$; (5) $R^8$ and $R^{10}$ are independently H, alkyl (including lower alkyl), chlorine, bromine or iodine; and (6) X is O.

In a tenth preferred subembodiment, a compound of Formula XVI, or its pharmaceutically acceptable salt or prodrug, is provided in which: (1) Base is a purine or pyrimidine base as defined herein; (2) $R^1$ is independently H or phosphate (including monophosphate, diphosphate, triphosphate, or a stabilized phosphate prodrug); acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; a cholesterol; or other pharmaceutically acceptable leaving group which when administered in vivo is capable of providing a compound wherein $R^1$ is independently H or phosphate; (3) $R^6$ is alkyl (including lower alkyl), alkenyl, alkynyl, Br-vinyl, hydroxy, O-alkyl, O-alkenyl, chloro, bromo, fluoro, iodo, $NO_2$, amino, loweralkylamino or di(loweralkyl)amino; (4) $R^7$ and $R^9$ are independently $OR^2$, alkyl (including lower alkyl), alkenyl, alkynyl, Br-vinyl, O-alkenyl, chlorine, bromine, iodine, $NO_2$, amino, loweralkylamino, or di(loweralkyl)amino; (5) $R^8$ and $R^{10}$ are hydrogen; and (6) X is O.

In an eleventh preferred subembodiment, a compound of Formula XVI, or its pharmaceutically acceptable salt or prodrug, is provided in which: (1) Base is a purine or pyrimidine base as defined herein; (2) $R^1$ is independently H or phosphate; (3) $R^6$ is alkyl (including lower alkyl), alkenyl, alkynyl, Br-vinyl, hydroxy, O-alkyl, O-alkenyl, chloro, bromo, fluoro, iodo, $NO_2$, amino, loweralkylamino or di(loweralkyl)amino; (4) $R^7$ and $R^9$ are independently $OR^2$; (5) $R^8$ and $R^{10}$ are hydrogen; and (6) X is O, S, $SO_2$ or $CH_2$.

In a twelfth preferred subembodiment, a compound of Formula XVI, or its pharmaceutically acceptable salt or prodrug, is provided in which: (1) Base is a purine or pyrimidine base as defined herein; (2) $R^1$ is independently H or phosphate; (3) $R^6$ is alkyl; (4) $R^7$ and $R^9$ are independently $OR^2$; (5) $R^8$ and $R^{10}$ are hydrogen; and (6) X is O, S, $SO_2$, or $CH_2$.

In a thirteenth preferred subembodiment, a compound of Formula XVI, or its pharmaceutically acceptable salt or prodrug, is provided in which: (1) Base is a purine or pyrimidine base as defined herein; (2) $R^1$ is independently H or phosphate; (3) $R^6$ is alkyl; (4) $R^7$ and $R^9$ are independently $OR^2$; (S)$R^8$ and $R^{10}$ are independently H, alkyl (including lower alkyl), chlorine, bromine, or iodine; and (6) X is O.

In a fourteenth preferred subembodiment, a compound of Formula XVI, or its pharmaceutically acceptable salt or prodrug, is provided in which: (1) Base is a purine or pyrimidine base as defined herein; (2) $R^1$ is independently H or phosphate; (3) $R^6$ is alkyl; (4) $R^7$ and $R^9$ are independently $OR^2$, alkyl (including lower alkyl), alkenyl, alkynyl, Br-vinyl, O-alkenyl, chlorine, bromine, iodine, $NO_2$, amino, loweralkylamino or di(loweralkyl)amino; (5) $R^8$ and $R^{10}$ are hydrogen; and (6) X is O.

In even more preferred subembodiments, a compound of Formula XVI, or its pharmaceutically acceptable salt or prodrug, is provided in which:

(1) Base is adenine; (2) $R^1$ is hydrogen; (3) $R^6$ is methyl; (4) $R^7$ and $R^9$ are hydroxyl; (5) $R^8$ and $R^{10}$ are hydrogen; and (6) X is O;

(1) Base is guanine; (2) $R^1$ is hydrogen; (3) $R^6$ is methyl; (4) $R^7$ and $R^9$ are hydroxyl; (5) $R^8$ and $R^{10}$ are hydrogen; and (6) X is O;

(1) Base is cytosine; (2) $R^1$ is hydrogen; (3) $R^6$ is methyl; (4) $R^7$ and $R^9$ are hydroxyl; (5) $R^8$ and $R^{10}$ are hydrogen; and (6) X is O;

(1) Base is thymine; (2) $R^1$ is hydrogen; (3) $R^6$ is methyl; (4) $R^7$ and $R^9$ are hydroxyl; (5) $R^8$ and $R^{10}$ are hydrogen; and (6) X is O;

(1) Base is uracil; (2) $R^1$ is hydrogen; (3) $R^6$ is methyl; (4) $R^7$ and $R^9$ are hydroxyl; (5) $R^8$ and $R^{10}$ are hydrogen; and (6) X is O;

(1) Base is adenine; (2) $R^1$ is phosphate; (3) $R^6$ is methyl; (4) $R^7$ and $R^9$ are hydroxyl; (5) $R^8$ and $R^{10}$ are hydrogen; and (6) X is O;

(1) Base is adenine; (2) $R^1$ is hydrogen; (3) $R^6$ is ethyl; (4) $R^7$ and $R^9$ are hydroxyl; (5) $R^8$ and $R^{10}$ are hydrogen; and (6) X is O;

(1) Base is adenine; (2) $R^1$ is hydrogen; (3) $R^6$ is propyl; (4) $R^7$ and $R^9$ are hydroxyl; (5) $R^8$ and $R^{10}$ are hydrogen; and (6) X is O;

(1) Base is adenine; (2) $R^1$ is hydrogen; (3) $R^6$ is butyl; (4) $R^7$ and $R^9$ are hydroxyl; (5) $R^8$ and $R^{10}$ are hydrogen; and (6) X is O;

(1) Base is adenine; (2) $R^1$ is hydrogen; (3) $R^6$ is methyl; (4) $R^7$ is hydrogen and $R^9$ is hydroxyl; (5) $R^8$ and $R^{10}$ are hydrogen; and (6) X is O;

(1) Base is adenine; (2) $R^1$ is hydrogen; (3) $R^6$ is methyl; (4) $R^7$ and $R^9$ are hydroxyl; (5) $R^8$ and $R^{10}$ are hydrogen; and (6) X is S;

(1) Base is adenine; (2) $R^1$ is hydrogen; (3) $R^6$ is methyl; (4) $R^7$ and $R^9$ are hydroxyl; (5) $R^8$ and $R^{10}$ are hydrogen; and (6) X is $SO_2$;

(1) Base is adenine; (2) $R^1$ is hydrogen; (3) $R^6$ is methyl; (4) $R^7$ and $R^9$ are hydroxyl; (5) $R^8$ and $R^{10}$ are hydrogen; and (6) X is $CH_2$;

In a eleventh principal embodiment the invention provides a compound of Formula XVII, or a pharmaceutically acceptable salt or prodrug thereof:

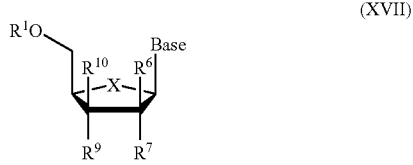

(XVII)

wherein:

Base is a purine or pyrimidine base as defined herein;

$R^1$ is H; phosphate (including monophosphate, diphosphate, triphosphate, or a stabilized phosphate prodrug); acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; a cholesterol; or other pharmaceutically acceptable leaving group which when administered in vivo is capable of providing a compound wherein $R^1$ is independently H or phosphate;

$R^6$ is hydrogen, hydroxy, alkyl (including lower alkyl), azido, cyano, alkenyl, alkynyl, Br-vinyl, —C(O)O(alkyl), —C(O)O(lower alkyl), —O(acyl), —O(lower acyl), —O(alkyl), —O(lower alkyl), —O(alkenyl), chloro, bromo, fluoro, iodo, $NO_2$, $NH_2$, —NH(lower alkyl), —NH(acyl), —N(lower alkyl)$_2$, —N(acyl)$_2$;

$R^7$ and $R^9$ are independently hydrogen, $OR^2$, hydroxy, alkyl (including lower alkyl), azido, cyano, alkenyl, alkynyl, Br-vinyl, —C(O)O(alkyl), —C(O)O(lower alkyl), —O(acyl), —O(lower acyl), —O(alkyl), —O(lower alkyl), —O(alkenyl), chlorine, bromine, iodine, $NO_2$, $NH_2$, —NH (lower alkyl), —NH(acyl), —N(lower alkyl)$_2$, —N(acyl)$_2$;

$R^{10}$ is H, alkyl (including lower alkyl), chlorine, bromine, or iodine;

alternatively, $R^7$ and $R^9$, or $R^7$ and $R^{10}$ can come together to form a pi bond; and X is O, S, $SO_2$ or $CH_2$.

In a first preferred subembodiment, a compound of Formula XVII, or its pharmaceutically acceptable salt or prodrug, is provided in which: (1) Base is a purine or pyrimidine base as defined herein; (2) $R^1$ is independently H; phosphate (including monophosphate, diphosphate, triphosphate, or a stabilized phosphate prodrug); acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; a cholesterol; or other pharmaceutically acceptable leaving group which when administered in vivo is capable of providing a compound wherein $R^1$ is independently H or phosphate; (3) $R^6$ is alkyl (including lower alkyl), alkenyl, alkynyl, Br-vinyl, hydroxy, O-alkyl, O-alkenyl, chloro, bromo, fluoro, iodo, $NO_2$, amino, loweralkylamino, or di(loweralkyl)amino; (4) $R^7$ and $R^9$ are independently hydrogen, $OR^2$, alkyl (including lower alkyl), alkenyl, alkynyl, Br-vinyl, O-alkenyl, chlorine, bromine, iodine, $NO_2$, amino, loweralkylamino or di(loweralkyl)-amino; (5) $R^{10}$ is H; and (6) X is O, S, $SO_2$, or $CH_2$.

In a second preferred subembodiment, a compound of Formula XVII, or its pharmaceutically acceptable salt or prodrug, is provided in which: (1) Base is a purine or pyrimidine base as defined herein; (2) $R^1$ is independently H; phosphate (including monophosphate, diphosphate, triphosphate, or a stabilized phosphate prodrug); acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; a cholesterol; or other pharmaceutically acceptable leaving group which when administered in vivo is capable of providing a compound wherein $R^1$ is independently H or phosphate; (3) $R^6$ is alkyl (including lower alkyl), alkenyl, alkynyl, Br-vinyl, hydroxy, O-alkyl, O-alkenyl, chloro, bromo, fluoro, iodo, $NO_2$, amino, loweralkylamino or di(loweralkyl)amino; (4) $R^7$ and $R^9$ are independently $OR^2$; (5) $R^{10}$ is H, alkyl (including lower alkyl), chlorine, bromine, or iodine; and (6) X is O, S, $SO_2$ or $CH_2$.

In a third preferred subembodiment, a compound of Formula XVII, or its pharmaceutically acceptable salt or prodrug, is provided in which: (1) Base is a purine or pyrimidine base as defined herein; (2) $R^1$ is independently H; phosphate (including monophosphate, diphosphate, triphosphate, or a stabilized phosphate prodrug); acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; a cholesterol; or other pharmaceutically acceptable leaving group which when administered in vivo is capable of providing a compound wherein $R^1$ is independently H or phosphate; (3) $R^6$ is alkyl (including lower alkyl), alkenyl, alkynyl, Br-vinyl, hydroxy, O-alkyl, O-alkenyl, chloro, bromo, fluoro, iodo, $NO_2$, amino, loweralkylamino, or di(loweralkyl)amino; (4) $R^7$ and $R^9$ are independently hydrogen, $OR^2$, alkyl (including lower alkyl), alkenyl, alkynyl, Br-vinyl, O-alkenyl, chlorine, bromine, iodine, $NO_2$, amino, loweralkylamino or di(loweralkyl)-amino; (5) $R^{10}$ is H, alkyl (including lower alkyl), chlorine, bromine or iodine; and (6) X is O.

In a fourth preferred subembodiment, a compound of Formula XVII, or its pharmaceutically acceptable salt or prodrug, is provided in which: (1) Base is a purine or pyrimidine base as defined herein; (2) $R^1$ is independently H; phosphate (including monophosphate, diphosphate, triphosphate, or a stabilized phosphate prodrug); acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; a cholesterol; or other pharmaceutically acceptable leaving group which when administered in vivo is capable of providing a compound wherein $R^1$ is independently H or phosphate; (3) $R^6$ is alkyl (including lower alkyl), alkenyl, alkynyl, Br-vinyl, hydroxy, O-alkyl, O-alkenyl, chloro, bromo, fluoro, iodo, $NO_2$, amino, loweralkylamino or di(loweralkyl)amino; (4) $R^7$ and $R^9$ are independently $OR^2$; (5) $R^{10}$ is H; and (6) X is O, S, $SO_2$ or $CH_2$.

In a fifth preferred subembodiment, a compound of Formula XVII, or its pharmaceutically acceptable salt or prodrug, is provided in which: (1) Base is a purine or pyrimidine base as defined herein; (2) $R^1$ is independently H; phosphate (including monophosphate, diphosphate, triphosphate, or a stabilized phosphate prodrug); acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; a cholesterol; or other pharmaceutically acceptable leaving group which when administered in vivo is capable of providing a compound wherein $R^1$ is independently H or phosphate; (3) $R^6$ is alkyl (including lower alkyl), alkenyl, alkynyl, Br-vinyl, hydroxy, O-alkyl, O-alkenyl, chloro, bromo, fluoro, iodo, $NO_2$, amino, loweralkylamino or di(loweralkyl)amino; (4) $R^7$ and $R^9$ are independently $OR^2$; (5) $R^{10}$ is H, alkyl (including lower alkyl), chlorine, bromine or iodine; and (6) X is O.

In a sixth preferred subembodiment, a compound of Formula XVII, or its pharmaceutically acceptable salt or prodrug, is provided in which: (1) Base is a purine or pyrimidine base as defined herein; (2) $R^1$ is independently H; phosphate (including monophosphate, diphosphate, triphosphate, or a stabilized phosphate prodrug); acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; a cholesterol; or other pharmaceutically acceptable leaving group which when administered in vivo is capable of providing a compound wherein $R^1$ is independently H or phosphate; (3) $R^6$ is alkyl (including lower alkyl), alkenyl, alkynyl, Br-vinyl, hydroxy, O-alkyl, O-alkenyl, chloro, bromo, fluoro, iodo, $NO_2$, amino, loweralkylamino, or di(loweralkyl)amino; (4) $R^7$ and $R^9$ are independently hydrogen, $OR^2$, alkyl (including lower alkyl), alkenyl, alkynyl, Br-vinyl, O-alkenyl, chlorine, bromine, iodine, $NO_2$, amino, loweralkylamino, or di(loweralkyl)amino; (5) $R^{10}$ is H; and (6) X is O.

In a seventh preferred subembodiment, a compound of Formula XVII, or its pharmaceutically acceptable salt or prodrug, is provided in which: (1) Base is a purine or pyrimidine base as defined herein; (2) $R^1$ is independently H; phosphate (including monophosphate, diphosphate, triphosphate, or a stabilized phosphate prodrug); acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; a cholesterol; or other pharmaceutically acceptable leaving group which when administered in vivo is capable of providing a compound wherein $R^1$ is independently H or phosphate; (3) $R^6$ is alkyl (including lower alkyl), alkenyl, alkynyl, Br-vinyl, hydroxy, O-alkyl, O-alkenyl, chloro, bromo, fluoro, iodo, $NO_2$, amino, loweralkylamino, or di(loweralkyl)amino; (4) $R^7$ and $R^9$ are independently $OR^2$; (5) $R^{10}$ is H; and (6) X is O.

In an eighth preferred subembodiment, a compound of Formula XVII, or its pharmaceutically acceptable salt or prodrug, is provided in which: (1) Base is a purine or pyrimidine base as defined herein; (2) $R^1$ is independently H or phosphate; (3) $R^6$ is alkyl; (4) $R^7$ and $R^9$ are independently hydrogen, $OR^2$, alkyl (including lower alkyl), alkenyl, alkynyl, Br-vinyl, O-alkenyl, chlorine, bromine, iodine, $NO_2$, amino, loweralkylamino or di(loweralkyl)-amino; (5) $R^{10}$ is H, alkyl (including lower alkyl), chlorine, bromine or iodine; and (6) X is O, S, $SO_2$, or $CH_2$.

In a ninth preferred subembodiment, a compound of Formula XVII, or its pharmaceutically acceptable salt or prodrug, is provided in which: (1) Base is a purine or pyrimidine base as defined herein; (2) $R^1$ is independently H or phosphate; (3) $R^6$ is alkyl (including lower alkyl), alkenyl, alkynyl, Br-vinyl, hydroxy, O-alkyl, O-alkenyl, chloro, bromo, fluoro, iodo, $NO_2$, amino, loweralkylamino, or di(loweralkyl)amino; (4) $R^7$ and $R^9$ are independently $OR^2$; (5) $R^{10}$ is H; and (6) X is O, S, $SO_2$, or $CH_2$.

In a tenth preferred subembodiment, a compound of Formula XVII, or its pharmaceutically acceptable salt or prodrug, is provided in which: (1) Base is a purine or pyrimidine base as defined herein; (2) $R^1$ is independently H or phosphate; (3) $R^6$ is alkyl; (4) $R^7$ and $R^9$ are independently $OR^2$; (5) $R^{10}$ is H; and (6) X is O, S, $SO_2$, or $CH_2$.

In even more preferred subembodiments, a compound of Formula XVII, or its pharmaceutically acceptable salt or prodrug, is provided in which:

(1) Base is adenine; (2) $R^1$ is hydrogen; (3) $R^6$ is methyl; (4) $R^7$ and $R^9$ are hydroxyl; (5) $R^{10}$ is hydrogen; and (6) X is O;

(1) Base is guanine; (2) $R^1$ is hydrogen; (3) $R^6$ is methyl; (4) $R^7$ and $R^9$ are hydroxyl; (5) $R^{10}$ is hydrogen; and (6) X is O;

(1) Base is cytosine; (2) $R^1$ is hydrogen; (3) $R^6$ is methyl; (4) $R^7$ and $R^9$ are hydroxyl; (5) $R^{10}$ is hydrogen; and (6) X is O;

(1) Base is thymine; (2) $R^1$ is hydrogen; (3) $R^6$ is methyl; (4) $R^7$ and $R^9$ are hydroxyl; (5) $R^{10}$ is hydrogen; and (6) X is O;

(1) Base is uracil; (2) $R^1$ is hydrogen; (3) $R^6$ is methyl; (4) $R^7$ and $R^9$ are hydroxyl; (5) $R^{10}$ is hydrogen; and (6) X is O;

(1) Base is adenine; (2) $R^1$ is phosphate; (3) $R^6$ is methyl; (4) $R^7$ and $R^9$ are hydroxyl; (5) $R^{10}$ is hydrogen; and (6) X is O;

(1) Base is adenine; (2) $R^1$ is hydrogen; (3) $R^6$ is ethyl; (4) $R^7$ and $R^9$ are hydroxyl; (5) $R^{10}$ is hydrogen; and (6) X is O;

(1) Base is adenine; (2) $R^1$ is hydrogen; (3) $R^6$ is propyl; (4) $R^7$ and $R^9$ are hydroxyl; (5) $R^{10}$ is hydrogen; and (6) X is O;

(1) Base is adenine; (2) $R^1$ is hydrogen; (3) $R^6$ is butyl; (4) $R^7$ and $R^9$ are hydroxyl; (5) $R^{10}$ is hydrogen; and (6) X is O;

(1) Base is adenine; (2) $R^1$ is hydrogen; (3) $R^6$ is methyl; (4) $R^7$ and $R^9$ are hydroxyl; (5) $R^{10}$ is hydrogen; and (6) X is S;

(1) Base is adenine; (2) $R^1$ is hydrogen; (3) $R^6$ is methyl; (4) $R^7$ and $R^9$ are hydroxyl; (5) $R^{10}$ is hydrogen; and (6) X is $SO_2$; or (1) Base is adenine; (2) $R^1$ is hydrogen; (3) $R^6$ is methyl; (4) $R^7$ and $R^9$ are hydroxyl; (5) $R^{10}$ is hydrogen; and (6) X is $CH_2$.

In an twelfth principal embodiment the invention provides a compound of Formula XVIII, or a pharmaceutically acceptable salt or prodrug thereof:

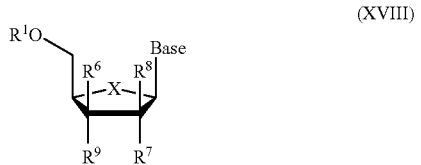

(XVIII)

wherein:

Base is a purine or pyrimidine base as defined herein;

$R^1$ is independently H; phosphate (including monophosphate, diphosphate, triphosphate, or a stabilized phosphate prodrug); acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; a cholesterol; or other pharmaceutically acceptable leaving group which when administered in vivo is capable of providing a compound wherein $R^1$ is independently H or phosphate;

$R^6$ is hydrogen, hydroxy, alkyl (including lower alkyl), azido, cyano, alkenyl, alkynyl, Br-vinyl, —C(O)O(alkyl), —C(O)O(lower alkyl), —O(acyl), —O(lower acyl), —O(alkyl), —O(lower alkyl), —O(alkenyl), chloro, bromo, fluoro, iodo, $NO_2$, $NH_2$, —NH(lower alkyl), —NH(acyl), —N(lower alkyl)$_2$, —N(acyl)$_2$;

$R^7$ and $R^9$ are independently hydrogen, $OR^2$, alkyl (including lower alkyl), alkenyl, alkynyl, Br-vinyl, O-alkenyl, chlorine, bromine, iodine, $NO_2$, amino, lower alkylamino, or di(loweralkyl)amino;

$R^8$ is H, alkyl (including lower alkyl), chlorine, bromine or iodine;

alternatively, $R^7$ and $R^9$, or $R^8$ and $R^9$ can come together to form a pi bond;

X is O, S, $SO_2$ or $CH_2$.

In a first preferred subembodiment, a compound of Formula XVIII, or its pharmaceutically acceptable salt or prodrug, is provided in which: (1) Base is a purine or pyrimidine base as defined herein; (2) $R^1$ is independently H; phosphate (including monophosphate, diphosphate, triphosphate, or a stabilized phosphate prodrug); acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; a cholesterol; or other pharmaceutically acceptable leaving group which when administered in vivo is capable of providing a compound wherein $R^1$ is independently H or phosphate; (3) $R^6$ is alkyl; (4) $R^7$ and $R^9$ are independently hydrogen, $OR^2$, alkyl (including lower alkyl), alkenyl, alkynyl, Br-vinyl, O-alkenyl, chlorine, bromine, iodine, $NO_2$, amino, loweralkylamino or di(loweralkyl)amino; (5) $R^8$ is H, alkyl (including lower alkyl), chlorine, bromine or iodine; and (6) X is O, S, $SO_2$ or $CH_2$.

In a second preferred subembodiment, a compound of Formula XVIII, or its pharmaceutically acceptable salt or prodrug, is provided in which: (1) Base is a purine or pyrimidine base as defined herein; (2) $R^1$ is independently H; phosphate (including monophosphate, diphosphate, triphosphate, or a stabilized phosphate prodrug); acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; a cholesterol; or other pharmaceutically acceptable leaving group which when administered in vivo is capable of providing a compound wherein $R^1$ is independently H or phosphate; (3) $R^6$ is alkyl (including lower alkyl), alkenyl, alkynyl, Br-vinyl, hydroxy, O-alkyl, O-alkenyl, chloro, bromo, fluoro, iodo, $NO_2$, amino, loweralkylamino or di(loweralkyl)amino; (4) $R^7$ and $R^9$ are independently $OR^2$; (5) $R^8$ is H, alkyl (including lower alkyl), chlorine, bromine, or iodine; and (6) X is O, S, $SO_2$ or $CH_2$.

In a third preferred subembodiment, a compound of Formula XVIII, or its pharmaceutically acceptable salt or prodrug, is provided in which: (1) Base is a purine or pyrimidine base as defined herein; (2) $R^1$ is independently H; phosphate (including monophosphate, diphosphate, triphosphate, or a stabilized phosphate prodrug); acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; a cholesterol; or other pharmaceutically acceptable leaving group which when administered in vivo is capable of providing a compound wherein $R^1$ is independently H or phosphate; (3) $R^6$ is alkyl (including lower alkyl), alkenyl, alkynyl, Br-vinyl, hydroxy, O-alkyl, O-alkenyl, chloro, bromo, fluoro, iodo, $NO_2$, amino, loweralkylamino, or di(lower-alkyl)amino; (4) $R^7$ and $R^9$ are independently hydrogen, $OR^2$, alkyl (including lower alkyl), alkenyl, alkynyl, Br-vinyl, O-alkenyl, chlorine, bromine, iodine, $NO_2$, amino, loweralkylamino, or di(loweralkyl)amino; (5) $R^8$ is H; and (6) X is O, S, $SO_2$ or $CH_2$.

In a fourth preferred subembodiment, a compound of Formula XVIII, or its pharmaceutically acceptable salt or prodrug, is provided in which: (1) Base is a purine or pyrimidine base as defined herein; (2) $R^1$ is independently H; phosphate (including monophosphate, diphosphate, triphosphate, or a stabilized phosphate prodrug); acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; a cholesterol; or other pharmaceutically acceptable leaving group which when administered in vivo is capable of providing a compound wherein $R^1$ is independently H or phosphate; (3) $R^6$ is alkyl (including lower alkyl), alkenyl, alkynyl, Br-vinyl, hydroxy, O-alkyl, O-alkenyl, chloro, bromo, fluoro, iodo, $NO_2$, amino, loweralkylamino, or di(loweralkyl)amino; (4) $R^7$ and $R^9$ are independently hydrogen, $OR^2$, alkyl (including lower alkyl), alkenyl, alkynyl, Br-vinyl, O-alkenyl, chlorine, bromine, iodine, $NO_2$, amino, loweralkylamino, or di(loweralkyl)amino; (5) $R^8$ is H, alkyl (including lower alkyl), chlorine, bromine, or iodine; and (6) X is O.

In a fifth preferred subembodiment, a compound of Formula XVIII, or its pharmaceutically acceptable salt or prodrug, is provided in which: (1) Base is a purine or pyrimidine base as defined herein; (2) $R^1$ is independently H; phosphate (including monophosphate, diphosphate, triphosphate, or a stabilized phosphate prodrug); acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; a cholesterol; or other pharmaceutically acceptable leaving group which when administered in vivo is capable of providing a compound wherein $R^1$ is independently H or phosphate; (3) $R^6$ is alkyl (including lower alkyl), alkenyl, alkynyl, Br-vinyl, hydroxy, O-alkyl, O-alkenyl, chloro, bromo, fluoro, iodo, $NO_2$, amino, loweralkylamino, or di(loweralkyl)amino; (4) $R^7$ and $R^9$ are independently $OR^2$; (5) $R^8$ is H; and (6) X is O, S, $SO_2$, or $CH_2$.

In a sixth preferred subembodiment, a compound of Formula XVIII, or its pharmaceutically acceptable salt or prodrug, is provided in which: (1) Base is a purine or pyrimidine base as defined herein; (2) $R^1$ is independently H; phosphate (including monophosphate, diphosphate, triphosphate, or a stabilized phosphate prodrug); acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; a cholesterol; or other pharmaceutically acceptable leaving group which when administered in vivo is capable of providing a compound wherein $R^1$ is independently H or phosphate; (3) $R^6$ is alkyl (including lower alkyl), alkenyl, alkynyl, Br-vinyl, hydroxy, O-alkyl, O-alkenyl, chloro, bromo, fluoro, iodo, $NO_2$, amino, loweralkylamino, or di(loweralkyl)amino; (4) $R^7$ and $R^9$ are independently $OR^2$; (5) $R^8$ is H, alkyl (including lower alkyl), chlorine, bromine, or iodine; and (6) X is O.

In a seventh preferred subembodiment, a compound of Formula XVIII, or its pharmaceutically acceptable salt or prodrug, is provided in which: (1) Base is a purine or pyrimidine base as defined herein; (2) $R^1$ is independently H; phosphate (including monophosphate, diphosphate, triphosphate, or a stabilized phosphate prodrug); acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; a cholesterol; or other pharmaceutically acceptable leaving group which when administered in vivo is capable of providing a compound wherein $R^1$ is independently H or phosphate; (3) $R^6$ is alkyl (including lower alkyl), alkenyl, alkynyl, Br-vinyl, hydroxy, O-alkyl, O-alkenyl, chloro, bromo, fluoro, iodo, $NO_2$, amino, loweralkylamino, or di(loweralkyl)amino; (4) $R^7$ and $R^9$ are independently hydrogen, $OR^2$, alkyl (including lower alkyl), alkenyl, alkynyl, Br-vinyl, O-alkenyl, chlorine, bromine, iodine, $NO_2$, amino, loweralkylamino, or di(loweralkyl)amino; (5) $R^8$ is H; and (6) X is O.

In an eighth preferred subembodiment, a compound of Formula XVIII, or its pharmaceutically acceptable salt or prodrug, is provided in which: (1) Base is a purine or pyrimidine base as defined herein; (2) $R^1$ is independently H or phosphate; (3) $R^6$ is alkyl (including lower alkyl), alkenyl, alkynyl, Br-vinyl, hydroxy, O-alkyl, O-alkenyl, chloro, bromo, fluoro, iodo, $NO_2$, amino, loweralkylamino or di(loweralkyl)amino; (4) $R^7$ and $R^9$ are independently $OR^2$; (5) $R^8$ is H; and (6) X is O, S, $SO_2$ or $CH_2$.

In a ninth preferred subembodiment, a compound of Formula XVIII, or its pharmaceutically acceptable salt or prodrug, is provided in which: (1) Base is a purine or pyrimidine base as defined herein; (2) $R^1$ is independently H or phosphate; (3) $R^6$ is alkyl; (4) $R^7$ and $R^9$ are independently $OR^2$; (5) $R^8$ is H; and (6) X is O, S, $SO_2$, or $CH_2$.

In a tenth preferred subembodiment, a compound of Formula XVIII, or its pharmaceutically acceptable salt or prodrug, is provided in which: (1) Base is a purine or pyrimidine base as defined herein; (2) $R^1$ is independently H or phosphate; (3) $R^6$ is alkyl; (4) $R^7$ and $R^9$ are independently $OR^2$; (5) $R^8$ is H; and (6) X is O.

In even more preferred subembodiments, a compound of Formula XVIII, or its pharmaceutically acceptable salt or prodrug, is provided in which:

(1) Base is adenine; (2) $R^1$ is hydrogen; (3) $R^6$ is methyl; (4) $R^7$ and $R^9$ are hydroxyl; (5) $R^8$ is hydrogen; and (6) X is O;

(1) Base is guanine; (2) $R^1$ is hydrogen; (3) $R^6$ is methyl; (4) $R^7$ and $R^9$ are hydroxyl; (5) $R^8$ is hydrogen; and (6) X is O;

(1) Base is cytosine; (2) $R^1$ is hydrogen; (3) $R^6$ is methyl; (4) $R^7$ and $R^9$ are hydroxyl; (5) $R^8$ is hydrogen; and (6) X is O;

(1) Base is thymine; (2) $R^1$ is hydrogen; (3) $R^6$ is methyl; (4) $R^7$ and $R^9$ are hydroxyl; (5) $R^8$ is hydrogen; and (6) X is O;

(1) Base is uracil; (2) $R^1$ is hydrogen; (3) $R^6$ is methyl; (4) $R^7$ and $R^9$ are hydroxyl; (5) $R^8$ is hydrogen; and (6) X is O;

(1) Base is adenine; (2) $R^1$ is phosphate; (3) $R^6$ is methyl; (4) $R^7$ and $R^9$ are hydroxyl; (5) $R^8$ is hydrogen; and (6) X is O;

(1) Base is adenine; (2) $R^1$ is hydrogen; (3) $R^6$ is ethyl; (4) $R^7$ and $R^9$ are hydroxyl; (5) $R^8$ is hydrogen; and (6) X is O;

(1) Base is adenine; (2) $R^1$ is hydrogen; (3) $R^6$ is propyl; (4) $R^7$ and $R^9$ are hydroxyl; (5) $R^8$ is hydrogen; and (6) X is O;

(1) Base is adenine; (2) $R^1$ is hydrogen; (3) $R^6$ is butyl; (4) $R^7$ and $R^9$ are hydroxyl; (5) $R^8$ is hydrogen; and (6) X is O;

(1) Base is adenine; (2) $R^1$ is hydrogen; (3) $R^6$ is methyl; (4) $R^7$ and $R^9$ are hydroxyl; (5) $R^8$ is hydrogen; and (6) X is S;

(1) Base is adenine; (2) $R^1$ is hydrogen; (3) $R^6$ is methyl; (4) $R^7$ and $R^9$ are hydroxyl; (5) $R^8$ is hydrogen; and (6) X is $SO_2$; or (1) Base is adenine; (2) $R^1$ is hydrogen; (3) $R^6$ is methyl; (4) $R^7$ and $R^9$ are hydroxyl; (5) $R^8$ is hydrogen; and (6) X is $CH_2$.

The β-D- and β-L-nucleosides of this invention belong to a class of anti-flavivirus or pestivirus agents that may inhibit flavivirus or pestivirus polymerase activity. Nucleosides can be screened for their ability to inhibit flavivirus or pestivirus polymerase activity in vitro according to screening methods set forth more particularly herein. One can readily determine the spectrum of activity by evaluating the compound in the assays described herein or with another confirmatory assay.

In one embodiment the efficacy of the anti-flavivirus or pestivirus compound is measured according to the concentration of compound necessary to reduce the plaque number of the virus in vitro, according to methods set forth more particularly herein, by 50% (i.e. the compound's $EC_{50}$). In preferred embodiments the compound exhibits an $EC_{50}$ of less than 15 or 10 micromolar.

HCV is a member of the Flaviviridae family; however, now, HCV has been placed in a new monotypic genus, hepacivirus. Therefore, in one embodiment, the flavivirus or pestivirus is not HCV.

The active compound can be administered as any salt or prodrug that upon administration to the recipient is capable of providing directly or indirectly the parent compound, or that exhibits activity itself. Nonlimiting examples are the pharmaceutically acceptable salts (alternatively referred to as "physiologically acceptable salts"), and a compound, which has been alkylated or acylated at the 5'-position, or on the purine or pyrimidine base (a type of "pharmaceutically acceptable prodrug"). Further, the modifications can affect the biological activity of the compound, in some cases increasing the activity over the parent compound. This can easily be assessed by preparing the salt or prodrug and testing its antiviral activity according to the methods described herein, or other methods known to those skilled in the art.

II. Definitions

The term alkyl, as used herein, unless otherwise specified, refers to a saturated straight, branched, or cyclic, primary, secondary, or tertiary hydrocarbon of typically $C_1$ to $C_{10}$, and specifically includes methyl, trifluoromethyl, ethyl, propyl, isopropyl, cyclopropyl, butyl, isobutyl, t-butyl, pentyl, cyclopentyl, isopentyl, neopentyl, hexyl, isohexyl, cyclohexyl, cyclohexylmethyl, 3-methylpentyl, 2,2-dimethylbutyl, and 2,3-dimethylbutyl. The term includes both substituted and unsubstituted alkyl groups. Moieties with which the alkyl group can be substituted are selected from the group consisting of hydroxyl, amino, alkylamino, arylamino, alkoxy, aryloxy, nitro, cyano, sulfonic acid, sulfate, phosphonic acid, phosphate, or phosphonate, either unprotected, or protected as necessary, as known to those skilled in the art, for example, as taught in Greene, et al., *Protective Groups in Organic Synthesis*, John Wiley and Sons, Second Edition, 1991, hereby incorporated by reference.

The term lower alkyl, as used herein, and unless otherwise specified, refers to a $C_1$ to $C_4$ saturated straight, branched, or if appropriate, a cyclic (for example, cyclopropyl) alkyl group, including both substituted and unsubstituted forms. Unless otherwise specifically stated in this application, when alkyl is a suitable moiety, lower alkyl is preferred. Similarly, when alkyl or lower alkyl is a suitable moiety, unsubstituted alkyl or lower alkyl is preferred.

The term alkylamino or arylamino refers to an amino group that has one or two alkyl or aryl substituents, respectively.

The term "protected" as used herein and unless otherwise defined refers to a group that is added to an oxygen, nitrogen, or phosphorus atom to prevent its further reaction or for other purposes. A wide variety of oxygen and nitrogen protecting groups are known to those skilled in the art of organic synthesis.

The term aryl, as used herein, and unless otherwise specified, refers to phenyl, biphenyl, or naphthyl, and preferably phenyl. The term includes both substituted and unsubstituted moieties. The aryl group can be substituted with one or more moieties selected from the group consisting of hydroxyl, amino, alkylamino, arylamino, alkoxy, aryloxy, nitro, cyano, sulfonic acid, sulfate, phosphonic acid, phosphate, or phosphonate, either unprotected, or protected as necessary, as known to those skilled in the art, for example, as taught in Greene, et al., *Protective Groups in Organic Synthesis*, John Wiley and Sons, Second Edition, 1991.

The term alkaryl or alkylaryl refers to an alkyl group with an aryl substituent. The term aralkyl or arylalkyl refers to an aryl group with an alkyl substituent.

The term halo, as used herein, includes chloro, bromo, iodo, and fluoro.

The term purine or pyrimidine base includes, but is not limited to, adenine, $N^6$-alkylpurines, $N^6$-acylpurines (wherein acyl is C(O)(alkyl, aryl, alkylaryl, or arylalkyl), $N^6$-benzylpurine, $N^6$-halopurine, $N^6$-vinylpurine, $N^6$-acetylenic purine, $N^6$-acyl purine, $N^6$-hydroxyalkyl purine, $N^6$-thioalkyl purine, $N^2$-alkylpurines, $N^2$-alkyl-6-thiopurines, thymine, cytosine, 5-fluorocytosine, 5-methylcytosine, 6-azapyrimidine, including 6-azacytosine, 2- and/or 4-mercaptopyrmidine, uracil, 5-halouracil, including 5-fluorouracil, $C^5$-alkylpyrimidines, $C^5$-benzylpyrimidines, $C^5$-halopyrimidines, $C^5$-vinylpyrimidine, $C^5$-acetylenic pyrimidine, $C^5$-acyl pyrimidine, $C^5$-hydroxyalkyl purine, $C^5$-amidopyrimidine, $C^5$-cyanopyrimidine, $C^5$-nitropyrimidine, $C^5$-aminopyrimidine, $N^2$-alkylpurines, $N^2$-alkyl-6-thiopurines, 5-azacytidinyl, 5-azauracilyl, triazolopyridinyl, imidazolopyridinyl, pyrrolopyrimidinyl, and pyrazolo-pyrimidinyl. Purine bases include, but are not limited to, guanine, adenine, hypoxanthine, 2,6-diaminopurine, and 6-chloropurine. Functional oxygen and nitrogen groups on the base can be protected as necessary or desired. Suitable protecting groups are well known to those skilled in the art, and include trimethylsilyl, dimethylhexylsilyl, t-butyldimethylsilyl and t-butyldiphenylsilyl, trityl, alkyl groups, and acyl groups such as acetyl and propionyl, methanesulfonyl, and p-toluenesulfonyl. Alternatively, the purine or pyrimidine base can optionally substituted such that it forms a viable prodrug, which can be cleaved in vivo. Examples of appropriate substituents include acyl moiety, an amine or cyclopropyl (e.g., 2-amino, 2,6-diamino or cyclopropyl guanosine).

The term acyl refers to a carboxylic acid ester in which the non-carbonyl moiety of the ester group is selected from straight, branched, or cyclic alkyl or lower alkyl, alkoxyalkyl including methoxymethyl, aralkyl including benzyl, aryloxyalkyl such as phenoxymethyl, aryl including phenyl optionally substituted with halogen, $C_1$ to $C_4$ alkyl or $C_1$ to $C_4$ alkoxy, sulfonate esters such as alkyl or aralkyl sulphonyl including methanesulfonyl, the mono, di or triphosphate ester, trityl or monomethoxytrityl, substituted benzyl, trialkylsilyl (e.g. dimethyl-t-butylsilyl) or diphenylmethylsilyl. Aryl groups in the esters optimally comprise a phenyl group. The term "lower acyl" refers to an acyl group in which the non-carbonyl moiety is lower alkyl.

As used herein, the term "substantially free of" or "substantially in the absence of" refers to a nucleoside composition that includes at least 85 or 90% by weight, preferably 95% to 98% by weight, and even more preferably 99% to 100% by weight, of the designated enantiomer of that nucleoside. In a preferred embodiment, in the methods and compounds of this invention, the compounds are substantially free of enantiomers.

Similarly, the term "isolated" refers to a nucleoside composition that includes at least 85 or 90% by weight, preferably 95% to 98% by weight, and even more preferably 99% to 100% by weight, of the nucleoside, the remainder comprising other chemical species or enantiomers.

The term "independently" is used herein to indicate that the variable, which is independently applied, varies independently from application to application. Thus, in a compound such as R"XYR", wherein R" is "independently carbon or nitrogen," both R" can be carbon, both R" can be nitrogen, or one R" can be carbon and the other R" nitrogen.

The term host, as used herein, refers to an unicellular or multicellular organism in which the virus can replicate, including cell lines and animals, and preferably a human. Alternatively, the host can be carrying a part of the flavivirus or pestivirus genome, whose replication or function can be altered by the compounds of the present invention. The term host specifically refers to infected cells, cells transfected with all or part of the flavivirus or pestivirus genome and animals, in particular, primates (including chimpanzees) and humans. In most animal applications of the present invention, the host is a human patient. Veterinary applications, in certain indications, however, are clearly anticipated by the present invention (such as chimpanzees).

The term "pharmaceutically acceptable salt or prodrug" is used throughout the specification to describe any pharmaceutically acceptable form (such as an ester, phosphate ester, salt of an ester or a related group) of a nucleoside compound which, upon administration to a patient, provides the nucleoside compound. Pharmaceutically acceptable salts include those derived from pharmaceutically acceptable inorganic or organic bases and acids. Suitable salts include those derived from alkali metals such as potassium and sodium, alkaline earth metals such as calcium and magnesium, among numerous other acids well known in the pharmaceutical art. Pharmaceutically acceptable prodrugs refer to a compound that is metabolized, for example hydrolyzed or oxidized, in the host to form the compound of the present invention. Typical examples of prodrugs include compounds that have biologically labile protecting groups on a functional moiety of the active compound. Prodrugs include compounds that can be oxidized, reduced, aminated, deaminated, hydroxylated, dehydroxylated, hydrolyzed, dehydrolyzed, alkylated, dealkylated, acylated, deacylated, phosphorylated, dephosphorylated to produce the active compound. The compounds of this invention possess antiviral activity against flavivirus or pestivirus, or are metabolized to a compound that exhibits such activity.

III. Nucleotide Salt or Prodrug Formulations

In cases where compounds are sufficiently basic or acidic to form stable nontoxic acid or base salts, administration of the compound as a pharmaceutically acceptable salt may be appropriate. Examples of pharmaceutically acceptable salts are organic acid addition salts formed with acids, which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

Any of the nucleosides described herein can be administered as a nucleotide prodrug to increase the activity, bioavailability, stability or otherwise alter the properties of the nucleoside. A number of nucleotide prodrug ligands are known. In general, alkylation, acylation or other lipophilic modification of the mono, di or triphosphate of the nucleoside will increase the stability of the nucleotide. Examples of substituent groups that can replace one or more hydrogens on the phosphate moiety are alkyl, aryl, steroids, carbohydrates, including sugars, 1,2-diacylglycerol and alcohols. Many are described in R. Jones and N. Bischofberger, *Antiviral Research*, 27 (1995) 1–17. Any of these can be used in combination with the disclosed nucleosides to achieve a desired effect.

The active nucleoside can also be provided as a 5'-phosphoether lipid or a 5'-ether lipid, as disclosed in the following references, which are incorporated by reference herein: Kucera, L. S., N. Iyer, E. Leake, A. Raben, Modest E. K., D. L. W., and C. Piantadosi, "Novel membrane-interactive ether lipid analogs that inhibit infectious HIV-1 production and induce defective virus formation," *AIDS Res. Hum. Retro Viruses*, 1990, 6, 491–501; Piantadosi, C., J. Marasco C. J., S. L. Morris-Natschke, K. L. Meyer, F. Gumus, J. R. Surles, K. S. Ishaq, L. S. Kucera, N. Iyer, C. A. Wallen, S. Piantadosi, and E. J. Modest, "Synthesis and evaluation of novel ether lipid nucleoside conjugates for anti-HIV activity," *J. Med. Chem.*, 1991, 34, 1408–1414; Hostetler, K. Y., D. D. Richman, D. A. Carson, L. M. Stuhmiller, G. M. T. van Wijk, and H. van den Bosch, "Greatly enhanced inhibition of human immunodeficiency virus type 1 replication in CEM and HT4-6C cells by 3'-deoxythymidine diphosphate dimyristoylglycerol, a lipid prodrug of 3,-deoxythymidine," *Antimicrob. Agents Chemother.*, 1992, 36, 2025–2029; Hosetler, K. Y., L. M. Stuhmiller, H. B. Lenting, H. van den Bosch, and D. D. Richman, "Synthesis and antiretroviral activity of phospholipid analogs of azidothymidine and other antiviral nucleosides." *J. Biol. Chem.*, 1990, 265, 61127.

Nonlimiting examples of U.S. patents that disclose suitable lipophilic substituents that can be covalently incorporated into the nucleoside, preferably at the 5'-OH position of the nucleoside or lipophilic preparations, include U.S. Pat. No. 5,149,794 (Sep. 22, 1992, Yatvin et al.); U.S. Pat. No. 5,194,654 (Mar. 16, 1993, Hostetler et al., U.S. Pat. No. 5,223,263 (Jun. 29, 1993, Hostetler et al.); U.S. Pat. No. 5,256,641 (Oct. 26, 1993, Yatvin et al.); U.S. Pat. No. 5,411,947 (May 2, 1995, Hostetler et al.); U.S. Pat. No. 5,463,092 (Oct. 31, 1995, Hostetler et al.); U.S. Pat. No. 5,543,389 (Aug. 6, 1996, Yatvin et al.); U.S. Pat. No. 5,543,390 (Aug. 6, 1996, Yatvin et al.); U.S. Pat. No. 5,543,391 (Aug. 6, 1996, Yatvin et al.); and U.S. Pat. No. 5,554,728 (Sep. 10, 1996; Basava et al.), all of which are incorporated herein by reference. Foreign patent applications that disclose lipophilic substituents that can be attached to the nucleosides of the present invention, or lipophilic preparations, include WO 89/02733, WO 90/00555, WO 91/16920, WO 91/18914, WO 93/00910, WO 94/26273, WO 96/15132, EP 0 350 287, EP 93917054.4, and WO 91/19721.

IV. Combination and Alternation Therapy

It has been recognized that drug-resistant variants of viruses can emerge after prolonged treatment with an antiviral agent. Drug resistance most typically occurs by mutation of a gene that encodes for an enzyme used in viral replication. The efficacy of a drug against flavivirus or pestivirus infection can be prolonged, augmented, or restored by administering the compound in combination or alternation with a second, and perhaps third, antiviral compound that induces a different mutation from that caused by the principle drug. Alternatively, the pharmacokinetics, biodistribution or other parameter of the drug can be altered by such combination or alternation therapy. In general, combination therapy is typically preferred over alternation therapy because it induces multiple simultaneous stresses on the virus.

Nonlimiting examples of antiviral agents that can be used in combination or alternation with the compounds disclosed herein include:

(1) an interferon and/or ribavirin (Battaglia, A. M. et al., *Ann. Pharmacother.* 34:487–494, 2000); Berenguer, M. et al. *Antivir. Ther.* 3(Suppl. 3):125–136, 1998);

(2) Substrate-based NS3 protease inhibitors (Attwood et al., Antiviral peptide derivatives, PCT WO 98/22496, 1998; Attwood et al., *Antiviral Chemistry and Chemotherapy* 10.259–273, 1999; Attwood et al., Preparation and use of amino acid derivatives as anti-viral agents, German Patent Publication DE 19914474; Tung et al. Inhibitors of serine proteases, particularly hepatitis C virus NS3 protease, PCT WO 98/17679), including alphaketoamides and hydrazinoureas, and inhibitors that terminate in an electrophile such as a boronic acid or phosphonate. Llinas-Brunet et al, Hepatitis C inhibitor peptide analogues, PCT WO 99/07734.

(3) Non-substrate-based inhibitors such as 2,4,6-trihydroxy-3-nitro-benzamide derivatives (Sudo K. et al., *Biochemical and Biophysical Research Communications*, 238: 643–647, 1997; Sudo K. et al. *Antiviral Chemistry and Chemotherapy* 9:186, 1998), including RD3-4082 and RD3-4078, the former substituted on the amide with a 14 carbon chain and the latter processing a para-phenoxyphenyl group;

(4) Thiazolidine derivatives which show relevant inhibition in a reverse-phase HPLC assay with an NS3/4A fusion protein and NS5A/5B substrate (Sudo K. et al., *Antiviral Research* 32:9–18, 1996), especially compound RD-1-6250, possessing a fused cinnamoyl moiety substituted with a long alkyl chain, RD4 6205 and RD4 6193;

(5) Thiazolidines and benzanilides identified in Kakiuchi N. et al. *J EBS Letters* 421:217–220; Takeshita N. et al. *Analytical Biochemistry* 247:242–246, 1997;

(6) A phenan-threnequinone possessing activity against protease in a SDS-PAGE and autoradiography assay isolated from the fermentation culture broth of *Streptomyces* sp., Sch 68631 (Chu M. et al., *Tetrahedron Letters* 37:7229–7232, 1996), and Sch 351633, isolated from the fungus *Penicillium griscofuluum*, which demonstrates activity in a scintillation proximity assay (Chu M. et al., *Bioorganic and Medicinal Chemistry Letters* 9:1949–1952);

(7) Selective NS3 inhibitors based on the macromolecule elgin c, isolated from leech (Qasim M. A. et al., *Biochemistry* 36:1598–1607, 1997);

(8) Helicase inhibitors (Diana G. D. et al., Compounds, compositions and methods for treatment of hepatitis C, U.S. Pat. No. 5,633,358; Diana G. D. et al., Piperidine derivatives, pharmaceutical compositions thereof and their use in the treatment of hepatitis C, PCT WO 97/36554);

(9) Polymerase inhibitors such as nucleotide analogues, gliotoxin (Ferrari R. et al. *Journal of Virology* 73:1649–1654, 1999), and the natural product cerulenin (Lohmann V. et al., *Virology* 249:108–118, 1998);

(10) Antisense phosphorothioate oligodeoxynucleotides (S-ODN) complementary to sequence stretches in the 5' non-coding region (NCR) of the virus (Alt M. et al., *Hepatology* 22:707–717, 1995), or nucleotides 326–348 comprising the 3' end of the NCR and nucleotides 371–388 located in the core coding region of the IICV RNA (Alt M. et al., *Archives of Virology* 142:589–599, 1997; Galderisi U. et al., *Journal of Cellular Physiology* 181:251–257, 1999);

(11) Inhibitors of IRES-dependent translation (Ikeda N et al., Agent for the prevention and treatment of hepatitis C, Japanese Patent Publication JP-08268890; Kai Y. et al. Prevention and treatment of viral diseases, Japanese Patent Publication JP-10101591);

(12) Nuclease-resistant ribozymes. (Maccjak D. J. et al., *Hepatology* 30 abstract 995, 1999); and

(13) Other miscellaneous compounds including 1-aminoalkylcyclohexanes (U.S. Pat. No. 6,034,134 to Gold et al.), alkyl lipids (U.S. Pat. No. 5,922,757 to Chojkier et al.), vitamin E and other antioxidants (U.S. Pat. No. 5,922,757 to Chojkier et al.), squalene, amantadine, bile acids (U.S. Pat. No. 5,846,964 to Ozeki et al.), N-(phosphonoacetyl)-L-aspartic acid, (U.S. Pat. No. 5,830,905 to Diana et al.), benzenedicarboxamides (U.S. Pat. No. 5,633,388 to Diana et al.), polyadenylic acid derivatives (U.S. Pat. No. 5,496,546 to Wang et al.), 2',3'-dideoxyinosine (U.S. Pat. No. 5,026,687 to Yarchoan et al.), and benzimidazoles (U.S. Pat. No. 5,891,874 to Colacino et al.).

V. Pharmaceutical Compositions

Host, including humans, infected with flavivirus or pestivirus, or a gene fragment thereof can be treated by administering to the patient an effective amount of the active compound or a pharmaceutically acceptable prodrug or salt thereof in the presence of a pharmaceutically acceptable carrier or diluent. The active materials can be administered by any appropriate route, for example, orally, parenterally, intravenously, intradermally, subcutaneously, or topically, in liquid or solid form.

A preferred dose of the compound for flavivirus or pestivirus infection will be in the range from about 1 to 50 mg/kg, preferably 1 to 20 mg/kg, of body weight per day, more generally 0.1 to about 100 mg per kilogram body weight of the recipient per day. The effective dosage range of the pharmaceutically acceptable salts and prodrugs can be calculated based on the weight of the parent nucleoside to be delivered. If the salt or prodrug exhibits activity in itself, the effective dosage can be estimated as above using the weight of the salt or prodrug, or by other means known to those skilled in the art.

The compound is conveniently administered in unit any suitable dosage form, including but not limited to one containing 7 to 3000 mg, preferably 70 to 1400 mg of active ingredient per unit dosage form. A oral dosage of 50–1000 mg is usually convenient.

Ideally the active ingredient should be administered to achieve peak plasma concentrations of the active compound of from about 0.2 to 70 $\mu$M, preferably about 1.0 to 10 $\mu$M. This may be achieved, for example, by the intravenous injection of a 0.1 to 5% solution of the active ingredient, optionally in saline, or administered as a bolus of the active ingredient.

The concentration of active compound in the drug composition will depend on absorption, inactivation, and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The active ingredient may be administered at once, or may be divided into a number of smaller doses to be administered at varying intervals of time.

A preferred mode of administration of the active compound is oral. Oral compositions will generally include an inert diluent or an edible carrier. They may be enclosed in gelatin capsules or compressed into tablets. For the purpose of oral therapeutic administration, the active compound can be incorporated with excipients and used in the form of tablets, troches or capsules. Pharmaceutically compatible binding agents, and/or adjuvant materials can be included as part of the composition.

The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or other enteric agents.

The compound can be administered as a component of an elixir, suspension, syrup, wafer, chewing gum or the like. A syrup may contain, in addition to the active compounds, sucrose as a sweetening agent and certain preservatives, dyes and colorings and flavors.

The compound or a pharmaceutically acceptable prodrug or salts thereof can also be mixed with other active materials that do not impair the desired action, or with materials that supplement the desired action, such as antibiotics, antifungals, anti-inflammatories, or other antivirals, including other nucleoside compounds. Solutions or suspensions used for parenteral, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parental preparation can be enclosed in ampoules, disposable syringes or multiple dose vials made of glass or plastic.

If administered intravenously, preferred carriers are physiological saline or phosphate buffered saline (PBS).

In a preferred embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters and polylactic acid. Methods for preparation of such formulations will be apparent to those skilled in the art. The materials can also be obtained commercially from Alza Corporation.

Liposomal suspensions (including liposomes targeted to infected cells with monoclonal antibodies to viral antigens) are also preferred as pharmaceutically acceptable carriers. These may be prepared according to methods known to those skilled in the art, for example, as described in U.S. Pat. No. 4,522,811 (which is incorporated herein by reference in its entirety). For example, liposome formulations may be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the active compound or its monophosphate, diphosphate, and/or triphosphate derivatives is then introduced into the container. The container is then swirled by hand to free lipid material from the sides of the container and to disperse lipid aggregates, thereby forming the liposomal suspension.

VI. Processes for the Preparation of Active Compounds

The nucleosides of the present invention can be synthesized by any means known in the art. In particular, the synthesis of the present nucleosides can be achieved by either alkylating the appropriately modified sugar, followed by glycosylation or glycosylation followed by alkylation of the nucleoside. The following non-limiting embodiments illustrate some general methodology to obtain the nucleosides of the present invention.

A. General Synthesis of 1'-C-Branched Nucleosides

1'-C-Branched ribonucleosides of the following structure:

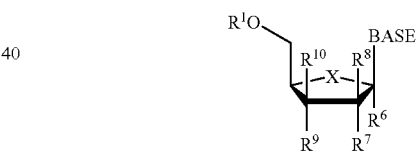

wherein BASE is a purine or pyrimidine base as defined herein;

$R^7$ and $R^9$ are independently hydrogen, $OR^2$, hydroxy, alkyl (including lower alkyl), azido, cyano, alkenyl, alkynyl, Br-vinyl, —C(O)O(alkyl), —C(O)O(lower alkyl), —O(acyl), —O(lower acyl), —O(alkyl), —O(lower alkyl), —O(alkenyl), chlorine, bromine, iodine, $NO_2$, $NH_2$, —NH(lower alkyl), —NH(acyl), —N(lower alkyl)$_2$, —N(acyl)$_2$;

$R^8$ and $R^{10}$ are independently H, alkyl (including lower alkyl), chlorine, bromine or iodine; alternatively, $R^7$ and $R^9$, $R^7$ and $R^{10}$, $R^8$ and $R^9$, or $R^8$ and $R^{10}$ can come together to form a pi bond;

$R^1$ and $R^2$ are independently H; phosphate (including monophosphate, diphosphate, triphosphate, or a stabilized phosphate prodrug); acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; a cholesterol; or other pharmaceutically acceptable leaving group which when administered in vivo is capable of providing a compound wherein $R^1$ is independently H or phosphate;

$R^6$ is an alkyl, halogeno-alkyl (i.e. $CF_3$), alkenyl, or alkynyl (i.e. allyl); and X is O, S, $SO_2$ or $CH_2$ can be prepared by one of the following general methods.

1) Modification from the Lactone

The key starting material for this process is an appropriately substituted lactone. The lactone can be purchased or Subsequently, the nucleoside can be deprotected by methods well known to those skilled in the art, as taught by Greene et al. *Protective Groups in Organic Synthesis*, John Wiley and Sons, Second Edition, 1991.

In a particular embodiment, the 1'-C-branched ribonucleoside is desired. The synthesis of a ribonucleoside is shown in Scheme 1. Alternatively, deoxyribo-nucleoside is desired. To obtain these nucleosides, the formed ribonucleoside can optionally be protected by methods well known to those skilled in the art, as taught by Greene et al. *Protective Groups in Organic Synthesis*, John Wiley and Sons, Second Edition, 1991, and then the 2'-OH can be reduced with a suitable reducing agent. Optionally, the 2'-hydroxyl can be activated to facilitate reduction; i.e. via the Barton reduction.

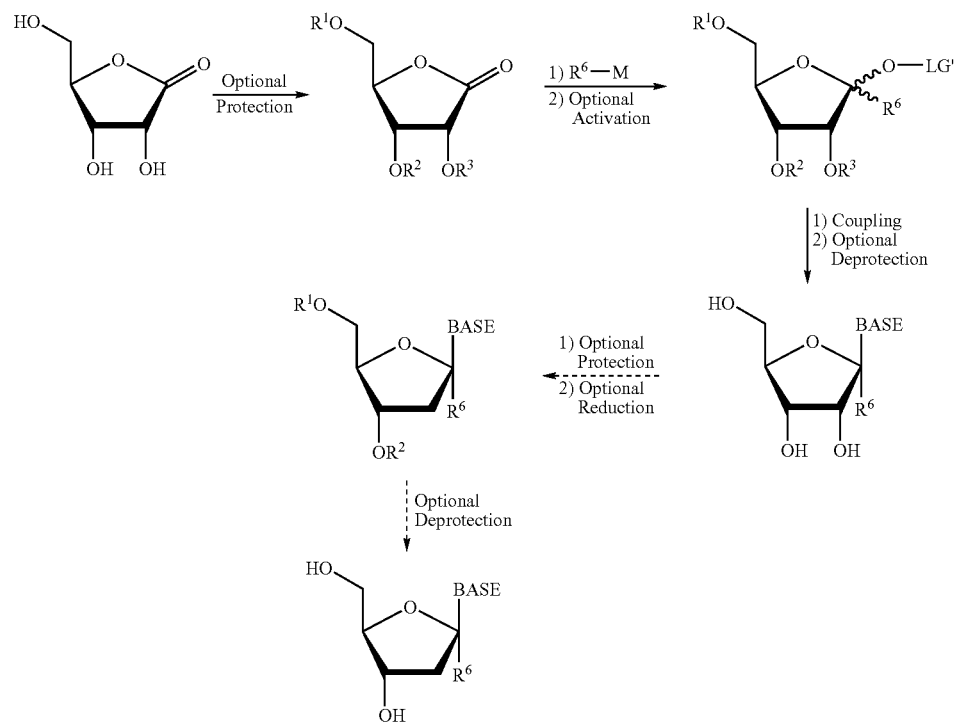

Scheme 1 can be prepared by any known means including standard epimerization, substitution and cyclization techniques. The lactone can be optionally protected with a suitable protecting group, preferably with an acyl or silyl group, by methods well known to those skilled in the art, as taught by Greene et al. *Protective Groups in Organic Synthesis*, John Wiley and Sons, Second Edition, 1991. The protected lactone can then be coupled with a suitable coupling agent, such as an organometallic carbon nucleophile, such as a Grignard reagent, an organolithium, lithium dialkylcopper or $R_6$-$SiMe_3$ in TBAF with the appropriate non-protic solvent at a suitable temperature, to give the 1'-alkylated sugar.

The optionally activated sugar can then be coupled to the BASE by methods well known to those skilled in the art, as taught by Townsend *Chemistry of Nucleosides and Nucleotides*, Plenum Press, 1994. For example, an acylated sugar can be coupled to a silylated base with a lewis acid, such as tin tetrachloride, titanium tetrachloride or trimethylsilyltriflate in the appropriate solvent at a suitable temperature.

2. Alternative Method for the Preparation of 1'-C-Branched Nucleosides

The key starting material for this process is an appropriately substituted hexose. The hexose can be purchased or can be prepared by any known means including standard epimerization (e.g. via alkaline treatment), substitution and coupling techniques. The hexose can be selectively protected to give the appropriate hexa-furanose, as taught by Townsend *Chemistry of Nucleosides and Nucleotides*, Plenum Press, 1994.

The 1'-hydroxyl can be optionally activated to a suitable leaving group such as an acyl group or a halogen via acylation or halogenation, respectively. The optionally activated sugar can then be coupled to the BASE by methods well known to those skilled in the art, as taught by Townsend *Chemistry of Nucleosides and Nucleotides*, Plenum Press, 1994. For example, an acylated sugar can be coupled to a silylated base with a lewis acid, such as tin tetrachloride, titanium tetrachloride or trimethylsilyltriflate in the appropriate solvent at a suitable temperature. Alternatively, a halo-sugar can be coupled to a silylated base with the presence of trimethylsilyltriflate.

The 1'-CH$_2$—OH, if protected, can be selectively deprotected by methods well known in the art. The resultant primary hydroxyl can be functionalized to yield various C-branched nucleosides. For example, the primary hydroxyl can be reduced to give the methyl, using a suitable reducing agent. Alternatively, the hydroxyl can be activated prior to reduction to facilitate the reaction; i.e. via the Barton reduction. In an alternate embodiment, the primary hydroxyl can be oxidized to the aldehyde, then coupled with a carbon nucleophile, such as a Grignard reagent, an organolithium, lithium dialkylcopper or R$^6$-SiMe$_3$ in TBAF with the appropriate non-protic solvent at a suitable temperature.

In a particular embodiment, the 1'-C-branched ribonucleoside is desired. The synthesis of a ribonucleoside is shown in Scheme 2. Alternatively, deoxyribo-nucleoside is desired. To obtain these nucleosides, the formed ribonucleoside can optionally be protected by methods well known to those skilled in the art, as taught by Greene et al. *Protective Groups in Organic Synthesis*, John Wiley and Sons, Second Edition, 1991, and then the 2'-OH can be reduced with a suitable reducing agent. Optionally, the 2'-hydroxyl can be activated to facilitate reduction; i.e. via the Barton reduction.

—O(acyl), —O(lower acyl), —O(alkyl), —O(lower alkyl), —O(alkenyl), chlorine, bromine, iodine, NO$_2$, NH$_2$, —NH (lower alkyl), —NH(acyl), —N(lower alkyl)$_2$, —N(acyl)$_2$;

R$^{10}$ is H, alkyl (including lower alkyl), chlorine, bromine or iodine;

alternatively, R$^7$ and R$^9$, or R$^7$ and R$^{10}$ can come together to form a pi bond;

R$^1$ and R$^2$ are independently H; phosphate (including monophosphate, diphosphate, triphosphate, or a stabilized phosphate prodrug); acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; a cholesterol; or other pharmaceutically acceptable leaving group which when administered in vivo is capable of providing a compound wherein R$^1$ is independently H or phosphate;

R$^6$ is an alkyl, halogeno-alkyl (i.e. CF$_3$), alkenyl, or alkynyl (i.e. allyl); and X is O, S SO$_2$ or CH$_2$

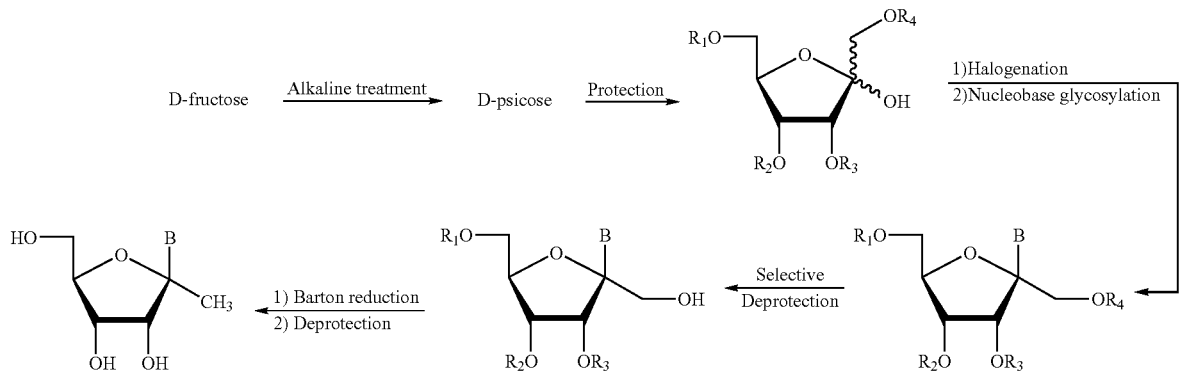

Scheme 2

In addition, the L-enantiomers corresponding to the compounds of the invention can be prepared following the same general methods (1 or 2), beginning with the corresponding L-sugar or nucleoside L-enantiomer as starting material.

B. General Synthesis of 2'-C-Branched Nucleosides

2'-C-Branched ribonucleosides of the following structure:

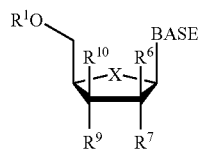

wherein BASE is a purine or pyrimidine base as defined herein;

R$^7$ and R$^9$ are independently hydrogen, OR$^2$, hydroxy, alkyl (including lower alkyl), azido, cyano, alkenyl, alkynyl, Br-vinyl, —C(O)O(alkyl), —C(O)O(lower alkyl), can be prepared by one of the following general methods.

1. Glycosylation of the Nucleobase with an Appropriately Modified Sugar

The key starting material for this process is an appropriately substituted sugar with a 2'-OH and 2'-H, with the appropriate leaving group (LG), for example an acyl group or a halogen. The sugar can be purchased or can be prepared by any known means including standard epimerization, substitution, oxidation and reduction techniques. The substituted sugar can then be oxidized with the appropriate oxidizing agent in a compatible solvent at a suitable temperature to yield the 2'-modified sugar. Possible oxidizing agents are Jones reagent (a mixture of chromic acid and sulfuric acid), Collins's reagent (dipyridine Cr(VI) oxide, Corey's reagent (pyridinium chlorochromate), pyridinium dichromate, acid dichromate, potassium permanganate, MnO$_2$, ruthenium tetroxide, phase transfer catalysts such as chromic acid or permanganate supported on a polymer, Cl$_2$-pyridine, H$_2$O$_2$-ammonium molybdate, NaBrO$_2$—CAN, NaOCl in HOAc, copper chromite, copper oxide, Raney nickel, palladium acetate, Meerwin-Pondorf-Verley reagent (aluminum t-butoxide with another ketone) and N-bromosuccinimide.

side can optionally be protected by methods well known to those skilled in the art, as taught by Greene et al. *Protective Groups in Organic Synthesis*, John Wiley and Sons, Second Edition, 1991, and then the 2'-OH can be reduced with a suitable reducing agent. Optionally, the 2'-hydroxyl can be activated to facilitate reduction; i.e. via the Barton reduction.

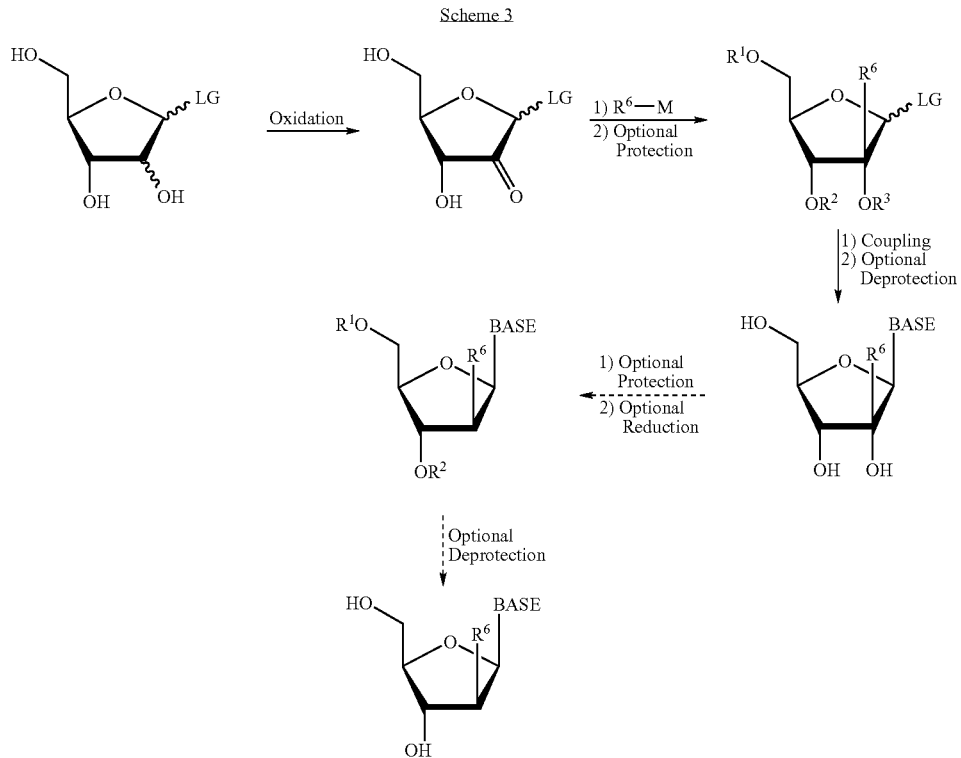

Scheme 3

Then coupling of an organometallic carbon nucleophile, such as a Grignard reagent, an organolithium, lithium dialkylcopper or R$^6$-SiMe$_3$ in TBAF with the ketone with the appropriate non-protic solvent at a suitable temperature, yields the 2'-alkylated sugar. The alkylated sugar can be optionally protected with a suitable protecting group, preferably with an acyl or silyl group, by methods well known to those skilled in the art, as taught by Greene et al. *Protective Groups in Organic Synthesis*, John Wiley and Sons, Second Edition, 1991.

The optionally protected sugar can then be coupled to the BASE by methods well known to those skilled in the art, as taught by Townsend *Chemistry of Nucleosides and Nucleotides*, Plenum Press, 1994. For example, an acylated sugar can be coupled to a silylated base with a lewis acid, such as tin tetrachloride, titanium tetrachloride or trimethylsilyltriflate in the appropriate solvent at a suitable temperature. Alternatively, a halo-sugar can be coupled to a silylated base with the presence of trimethylsilyltriflate.

Subsequently, the nucleoside can be deprotected by methods well known to those skilled in the art, as taught by Greene et al. *Protective Groups in Organic Synthesis*, John Wiley and Sons, Second Edition, 1991.

In a particular embodiment, the 2'-C-branched ribonucleoside is desired. The synthesis of a ribonucleoside is shown in Scheme 3. Alternatively, deoxyribo-nucleoside is desired. To obtain these nucleosides, the formed ribonucleo- 2. Modification of a Pre-Formed Nucleoside The key starting material for this process is an appropriately substituted nucleoside with a 2'-OH and 2'-H. The nucleoside can be purchased or can be prepared by any known means including standard coupling techniques. The nucleoside can be optionally protected with suitable protecting groups, preferably with acyl or silyl groups, by methods well known to those skilled in the art, as taught by Greene et al. *Protective Groups in Organic Synthesis*, John Wiley and Sons, Second Edition, 1991.

The appropriately protected nucleoside can then be oxidized with the appropriate oxidizing agent in a compatible solvent at a suitable temperature to yield the 2'-modified sugar. Possible oxidizing agents are Jones reagent (a mixture of chromic acid and sulfric acid), Collins's reagent (dipyridine Cr(VI) oxide, Corey's reagent (pyridinium chlorochromate), pyridinium dichromate, acid dichromate, potassium permanganate, MnO$_2$, ruthenium tetroxide, phase transfer catalysts such as chromic acid or permanganate supported on a polymer, Cl$_2$-pyridine, H$_2$O$_2$-ammonium molybdate, NaBrO$_2$—CAN, NaOCl in HOAc, copper chromite, copper oxide, Raney nickel, palladium acetate, Meerwin-Pondorf-Verley reagent (aluminum t-butoxide with another ketone) and N-bromosuccinimide.

Subsequently, the nucleoside can be deprotected by methods well known to those skilled in the art, as taught by GreeneGreene et al. *Protective Groups in Organic Synthesis*, John Wiley and Sons, Second Edition, 1991.

In a particular embodiment, the 2'-C-branched ribonucleoside is desired. The synthesis of a ribonucleoside is shown in Scheme 4. Alternatively, deoxyribo-nucleoside is desired. To obtain these nucleosides, the formed ribonucleoside can optionally be protected by methods well known to those skilled in the art, as taught by Greene et al. *Protective Groups in Organic Synthesis*, John Wiley and Sons, Second Edition, 1991, and then the 2'-OH can be reduced with a suitable reducing agent. Optionally, the 2'-hydroxyl can be activated to facilitate reduction; i.e. via the Barton reduction.

Br-vinyl, —C(O)O(alkyl), —C(O)O(lower alkyl), —O(acyl), —O(lower acyl), —O(alkyl), —O(lower alkyl), —O(alkenyl), chlorine, bromine, iodine, $NO_2$, $NH_2$, —NH(lower alkyl), —NH(acyl), —N(lower alkyl)$_2$, —N(acyl)$_2$;

$R^8$ is H, alkyl (including lower alkyl), chlorine, bromine or iodine;

alternatively, $R^7$ and $R^9$, or $R^8$ and $R^9$ can come together to form a pi bond;

$R^1$ and $R^2$ are independently H; phosphate (including monophosphate, diphosphate, triphosphate, or a stabilized phos- Scheme 4

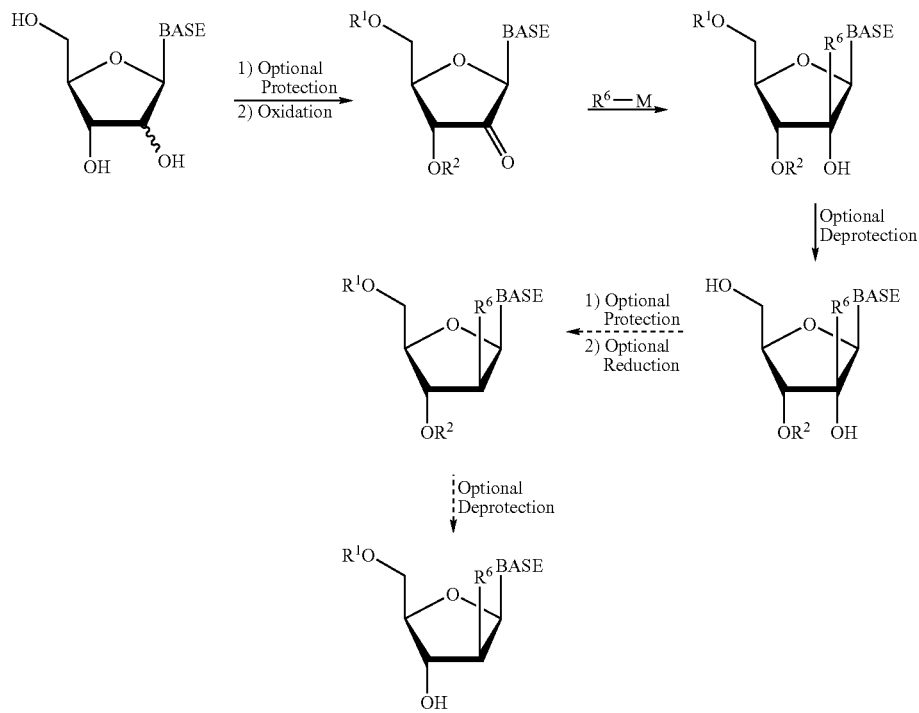

In another embodiment of the invention, the L-enantiomers are desired. Therefore, the L-enantiomers can be corresponding to the compounds of the invention can be prepared following the same foregoing general methods, beginning with the corresponding L-sugar or nucleoside L-enantiomer as starting material.

C. General Synthesis of 3'-C-Branched Nucleosides

3'-C-Branched ribonucleosides of the following structure:

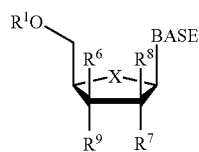

wherein BASE is a purine or pyrimidine base as defined herein;

$R^7$ and $R^9$ are independently hydrogen, $OR^2$, hydroxy, alkyl (including lower alkyl), azido, cyano, alkenyl, alkynyl, phate prodrug); acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; a cholesterol; or other pharmaceutically acceptable leaving group which when administered in vivo is capable of providing a compound wherein $R^1$ is independently H or phosphate;

$R^6$ is an alkyl, halogeno-alkyl (i.e. $CF_3$), alkenyl, or alkynyl (i.e. allyl); and X is O, S, $SO_2$ or $CH_2$ can be prepared by one of the following general methods.

1 Glycosylation of the Nucleobase with an Appropriately Modified Sugar

The key starting material for this process is an appropriately substituted sugar with a 3'-OH and 3'-H, with the appropriate leaving group (LG), for example an acyl group or a halogen. The sugar can be purchased or can be prepared by any known means including standard epimerization, substitution, oxidation and reduction techniques. The substituted sugar can then be oxidized with the appropriate oxidizing agent in a compatible solvent at a suitable temperature to yield the 3'-modified sugar. Possible oxidizing agents are Jones reagent (a mixture of chromic acid and sulfuric acid), Collins's reagent (dipyridine Cr(VI) oxide, Corey's reagent (pyridinium chlorochromate), pyridinium dichromate, acid dichromate, potassium permanganate, $MnO_2$, ruthenium tetroxide, phase transfer catalysts such as chromic acid or permanganate supported on a polymer, $Cl_2$-pyridine, $H_2O_2$-ammonium molybdate, $NaBrO_2$—CAN, NaOCl in HOAc, copper chromite, copper oxide, Raney nickel, palladium acetate, Meerwin-Pondorf-Verley reagent (aluminum t-butoxide with another ketone) and N-bromosuccinimide.

flate in the appropriate solvent at a suitable temperature. Alternatively, a halo-sugar can be coupled to a sylated base with the presence of trimethylsilyltriflate.

Subsequently, the nucleoside can be deprotected by methods well known to those skilled in the art, as taught by Greene et al. *Protective Groups in Organic Synthesis*, John Wiley and Sons, Second Edition, 1991.

In a particular embodiment, the 3'-C-branched ribonucleoside is desired. The synthesis of a ribonucleoside is shown in Scheme 5. Alternatively, deoxyribo-nucleoside is desired. To obtain these nucleosides, the formed ribonucleoside can optionally be protected by methods well known to those skilled in the art, as taught by Greene et al. *Protective Groups in Organic Synthesis*, John Wiley and Sons, Second Edition, 1991, and then the 2'-OH can be reduced with a suitable reducing agent. Optionally, the 2'-hydroxyl can be activated to facilitate reduction; i.e. via the Barton reduction.

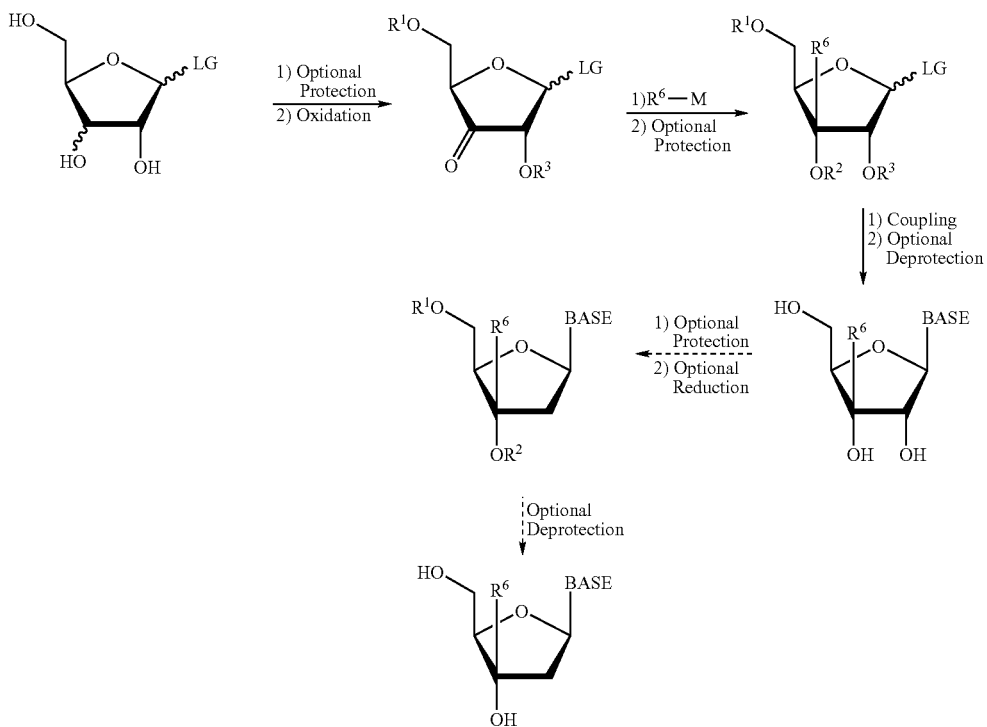

Then coupling of an organometallic carbon nucleophile, such as a Grignard reagent, an organolithium, lithium dialkylcopper or $R^6$-$SiMe_3$ in TBAF with the ketone with the appropriate non-protic solvent at a suitable temperature, yields the 3'-C-branched sugar. The 3'-C-branched sugar can be optionally protected with a suitable protecting group, preferably with an acyl or silyl group, by methods well known to those skilled in the art, as taught by Greene et al. *Protective Groups in Organic Synthesis*, John Wiley and Sons, Second Edition, 1991.

The optionally protected sugar can then be coupled to the BASE by methods well known to those skilled in the art, as taught by Townsend *Chemistry of Nucleosides and Nucleotides*, Plenum Press, 1994. For example, an acylated sugar can be coupled to a sylated base with a lewis acid, such as tin tetrachloride, titanium tetrachloride or trimethylsilyltri- 2. Modification of a Pre-Formed Nucleoside The key starting material for this process is an appropriately substituted nucleoside with a 3'-OH and 3'-H. The nucleoside can be purchased or can be prepared by any known means including standard coupling techniques. The nucleoside can be optionally protected with suitable protecting groups, preferably with acyl or silyl groups, by methods well known to those skilled in the art, as taught by Greene et al. *Protective Groups in Organic Synthesis*, John Wiley and Sons, Second Edition, 1991.

The appropriately protected nucleoside can then be oxidized with the appropriate oxidizing agent in a compatible solvent at a suitable temperature to yield the 2'-modified sugar. Possible oxidizing agents are Jones reagent (a mixture of chromic acid and sulfluric acid), Collins's reagent (dipyridine Cr(VI) oxide, Corey's reagent (pyridinium chlorochromate), pyridinium dichromate, acid dichromate, potassium permanganate, MnO$_2$, ruthenium tetroxide, phase transfer catalysts such as chromic acid or permanganate supported on a polymer, Cl$_2$-pyridine, H$_2$O$_2$-ammonium molybdate, NaBrO$_2$—CAN, NaOCl in HOAc, copper chromite, copper oxide, Raney nickel, palladium acetate, Meerwin-Pondorf-Verley reagent (aluminum t-butoxide with another ketone) and N-bromosuccinimide.

Subsequently, the nucleoside can be deprotected by methods well known to those skilled in the art, as taught by Greene et al. *Protective Groups in Organic Synthesis*, John Wiley and Sons, Second Edition, 1991.

In a particular embodiment, the 3'-C-branched ribonucleoside is desired. The synthesis of a ribonucleoside is shown in Scheme 6. Alternatively, deoxyribo-nucleoside is desired. To obtain these nucleosides, the formed ribonucleoside can optionally be protected by methods well known to those skilled in the art, as taught by Greene et al. *Protective Groups in Organic Synthesis*, John Wiley and Sons, Second Edition, 1991, and then the 2'-OH can be reduced with a suitable reducing agent. Optionally, the 2'-hydroxyl can be activated to facilitate reduction; i.e. via the Barton reduction.

Scheme 6

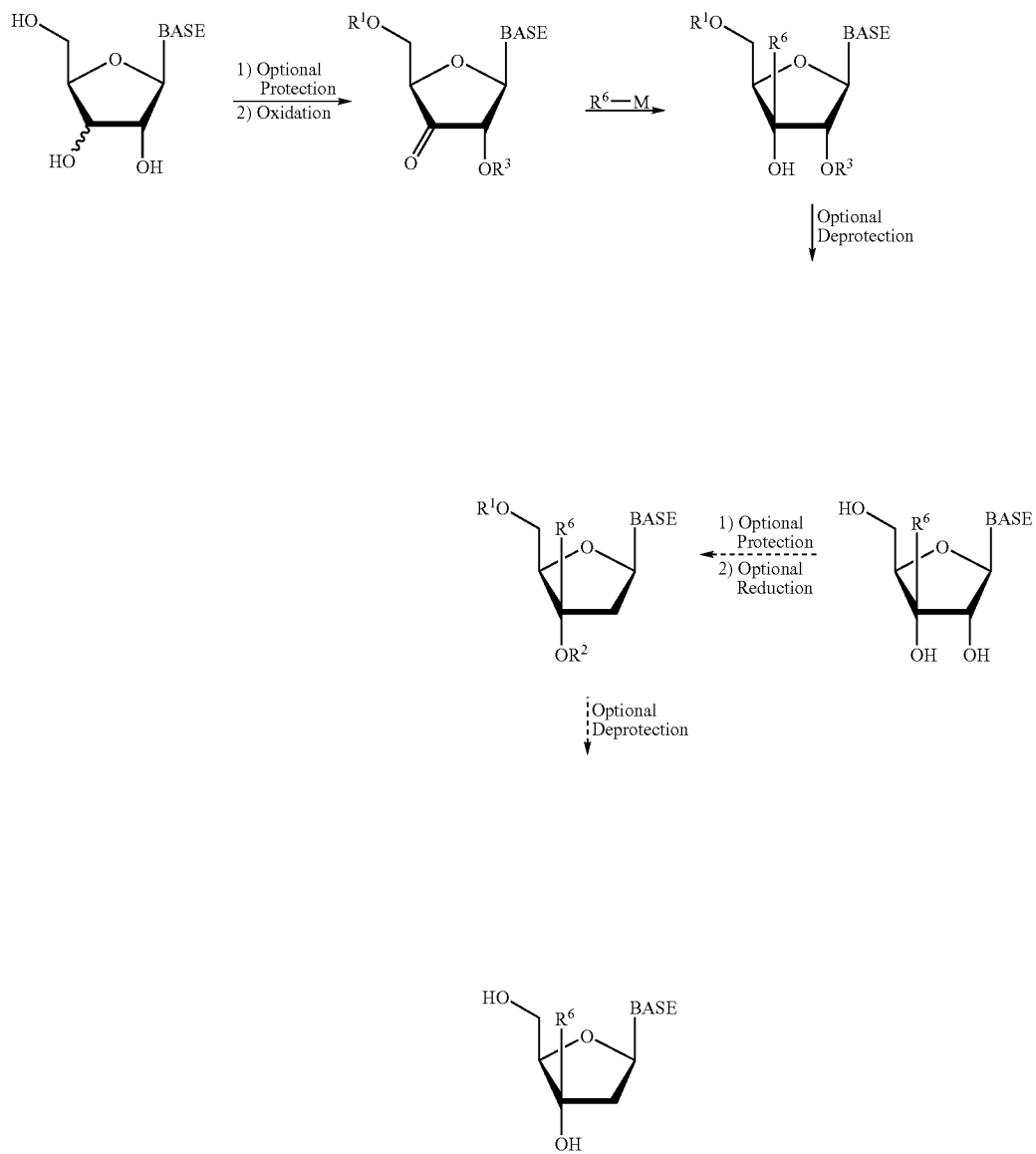

In another embodiment of the invention, the L-enantiomers are desired. Therefore, the L-enantiomers can be corresponding to the compounds of the invention can be prepared following the same foregoing general methods, beginning with the corresponding L-sugar or nucleoside L-enantiomer as starting material.

EXAMPLES

Example 1

Preparation of 1'-C-methylriboadenine via 6-amino-9-(1-deoxy-β-D-psicofuranosyl)purine The title compound could also be prepared according to a published procedure (J. Farkas, and F. Sorm, "Nucleic acid components and their analogues. XCIV. Synthesis of 6-amino-9-(1-deoxy-β-D-psicofuranosyl)purine" *Collect. Czech. Chem. Commun.* 1967, 32, 2663–2667; J. Farkas", *Collect. Czech. Chem. Commun.* 1966, 31, 1535) (Scheme 7).

In a similar manner, but using the appropriate sugar and pyrimidine or purine bases, the following nucleosides of Formula I are prepared.

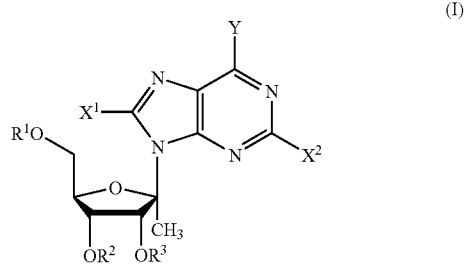

wherein:

| $R^1$ | $R^2$ | $R^3$ | $X^1$ | $X^2$ | Y |
|---|---|---|---|---|---|
| H | H | H | H | H | H |
| H | H | H | H | H | $NH_2$ |
| H | H | H | H | H | NH-cyclopropyl |

Scheme 7

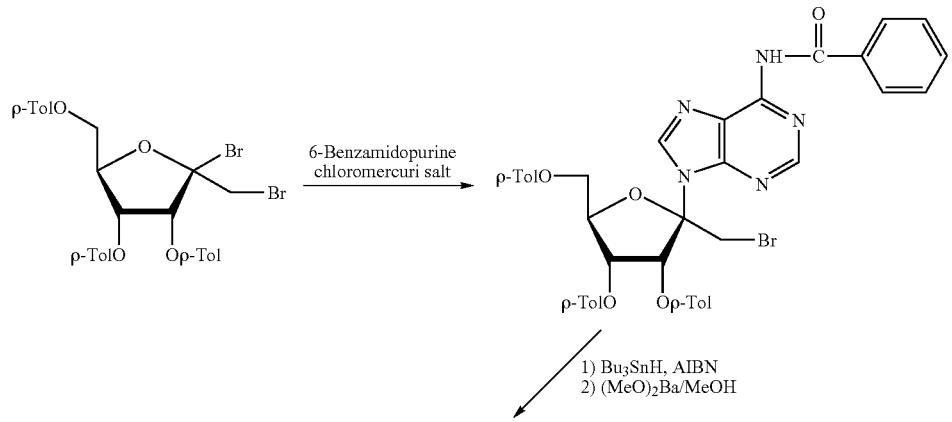

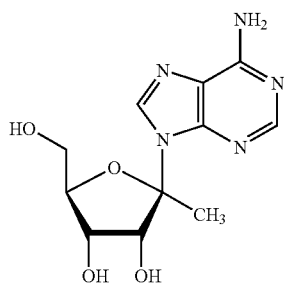

| R¹ | R² | R³ | X¹ | X² | Y |
|---|---|---|---|---|---|
| H | H | H | H | H | NH-methyl |
| H | H | H | H | H | NH-ethyl |
| H | H | H | H | H | NH-acetyl |
| H | H | H | H | H | OH |
| H | H | H | H | H | OMe |
| H | H | H | H | H | OEt |
| H | H | H | H | H | O-cyclopropyl |
| H | H | H | H | H | O-acetyl |
| H | H | H | H | H | SH |
| H | H | H | H | H | SMe |
| H | H | H | H | H | SEt |
| H | H | H | H | H | S-cyclopropyl |
| H | H | H | H | H | F |
| H | H | H | H | H | Cl |
| H | H | H | H | H | Br |
| H | H | H | H | H | I |
| monophosphate | H | H | H | H | NH₂ |
| monophosphate | H | H | H | H | NH-acetyl |
| monophosphate | H | H | H | H | NH-cyclopropyl |
| monophosphate | H | H | H | H | NH-methyl |
| monophosphate | H | H | H | H | NH-ethyl |
| monophosphate | H | H | H | H | OH |
| monophosphate | H | H | H | H | O-acetyl |
| monophosphate | H | H | H | H | OMe |
| monophosphate | H | H | H | H | OEt |
| monophosphate | H | H | H | H | O-cyclopropyl |
| monophosphate | H | H | H | H | SH |
| monophosphate | H | H | H | H | SMe |
| monophosphate | H | H | H | H | SEt |
| monophosphate | H | H | H | H | S-cyclopropyl |
| monophosphate | H | H | H | H | F |
| monophosphate | H | H | H | H | Cl |
| monophosphate | H | H | H | H | Br |
| monophosphate | H | H | H | H | I |
| diphosphate | H | H | H | H | NH₂ |
| diphosphate | H | H | H | H | NH-acetyl |
| diphosphate | H | H | H | H | NH-cyclopropyl |
| diphosphate | H | H | H | H | NH-methyl |
| diphosphate | H | H | H | H | NH-ethyl |
| diphosphate | H | H | H | H | OH |
| diphosphate | H | H | H | H | O-acetyl |
| diphosphate | H | H | H | H | OMe |
| diphosphate | H | H | H | H | OEt |
| diphosphate | H | H | H | H | O-cyclopropyl |
| diphosphate | H | H | H | H | SH |
| diphosphate | H | H | H | H | SMe |
| diphosphate | H | H | H | H | SEt |
| diphosphate | H | H | H | H | S-cyclopropyl |
| diphosphate | H | H | H | H | F |
| diphosphate | H | H | H | H | Cl |
| diphosphate | H | H | H | H | Br |
| diphosphate | H | H | H | H | I |
| triphosphate | H | H | H | H | NH₂ |
| triphosphate | H | H | H | H | NH-acetyl |
| triphosphate | H | H | H | H | NH-cyclopropyl |
| triphosphate | H | H | H | H | NH-methyl |
| triphosphate | H | H | H | H | NH-ethyl |
| triphosphate | H | H | H | H | OH |
| triphosphate | H | H | H | H | OMe |
| triphosphate | H | H | H | H | OEt |
| triphosphate | H | H | H | H | O-cyclopropyl |
| triphosphate | H | H | H | H | O-acetyl |
| triphosphate | H | H | H | H | SH |
| triphosphate | H | H | H | H | SMe |
| triphosphate | H | H | H | H | SEt |
| triphosphate | H | H | H | H | S-cyclopropyl |
| triphosphate | H | H | H | H | F |
| triphosphate | H | H | H | H | Cl |
| triphosphate | H | H | H | H | Br |
| triphosphate | H | H | H | H | I |
| monophosphate | monophosphate | monophosphate | H | H | NH₂ |
| monophosphate | monophosphate | monophosphate | H | H | NH-cyclopropyl |
| monophosphate | monophosphate | monophosphate | H | H | OH |
| monophosphate | monophosphate | monophosphate | H | H | F |
| monophosphate | monophosphate | monophosphate | H | H | Cl |
| diphosphate | diphosphate | diphosphate | H | H | NH₂ |
| diphosphate | diphosphate | diphosphate | H | H | NH-cyclopropyl |
| diphosphate | diphosphate | diphosphate | H | H | OH |
| diphosphate | diphosphate | diphosphate | H | H | F |
| diphosphate | diphosphate | diphosphate | H | H | Cl |
| triphosphate | triphosphate | triphosphate | H | H | NH₂ |
| triphosphate | triphosphate | triphosphate | H | H | NH-cyclopropyl |
| triphosphate | triphosphate | triphosphate | H | H | OH |
| triphosphate | triphosphate | triphosphate | H | H | F |
| triphosphate | triphosphate | triphosphate | H | H | Cl |
| H | H | H | F | H | NH₂ |
| H | H | H | F | H | NH-cyclopropyl |
| H | H | H | F | H | OH |
| H | H | H | F | H | F |
| H | H | H | F | H | Cl |
| H | H | H | Cl | H | NH₂ |
| H | H | H | Cl | H | NH-cyclopropyl |
| H | H | H | Cl | H | OH |
| H | H | H | Cl | H | F |
| H | H | H | Cl | H | Cl |
| H | H | H | Br | H | NH₂ |
| H | H | H | Br | H | NH-cyclopropyl |
| H | H | H | Br | H | OH |
| H | H | H | Br | H | F |
| H | H | H | Br | H | Cl |
| H | H | H | NH₂ | H | NH₂ |
| H | H | H | NH₂ | H | NH-cyclopropyl |
| H | H | H | NH₂ | H | OH |
| H | H | H | NH₂ | H | F |
| H | H | H | NH₂ | H | Cl |
| H | H | H | SH | H | NH₂ |
| H | H | H | SH | H | NH-cyclopropyl |
| H | H | H | SH | H | OH |
| H | H | H | SH | H | F |
| H | H | H | SH | H | Cl |
| acetyl | H | H | H | H | NH₂ |
| acetyl | H | H | H | H | NH-cyclopropyl |
| acetyl | H | H | H | H | OH |
| acetyl | H | H | H | H | F |
| acetyl | H | H | H | H | Cl |
| acetyl | H | H | F | H | NH₂ |
| acetyl | H | H | F | H | NH-cyclopropyl |
| acetyl | H | H | F | H | OH |
| acetyl | H | H | F | H | F |
| acetyl | H | H | F | H | Cl |
| H | acetyl | acetyl | H | H | NH₂ |
| H | acetyl | acetyl | H | H | NH-cyclopropyl |
| H | acetyl | acetyl | H | H | OH |
| H | acetyl | acetyl | H | H | F |
| H | acetyl | acetyl | H | H | Cl |
| acetyl | acetyl | acetyl | H | H | NH₂ |
| acetyl | acetyl | acetyl | H | H | NH-cyclopropyl |
| acetyl | acetyl | acetyl | H | H | OH |
| acetyl | acetyl | acetyl | H | H | F |
| acetyl | acetyl | acetyl | H | H | Cl |
| monophosphate | acetyl | acetyl | H | H | NH₂ |
| monophosphate | acetyl | acetyl | H | H | NH-cyclopropyl |
| monophosphate | acetyl | acetyl | H | H | OH |
| monophosphate | acetyl | acetyl | H | H | F |
| monophosphate | acetyl | acetyl | H | H | Cl |
| diphosphate | acetyl | acetyl | H | H | NH₂ |
| diphosphate | acetyl | acetyl | H | H | NH-cyclopropyl |
| diphosphate | acetyl | acetyl | H | H | OH |

| R¹ | R² | R³ | X¹ | X² | Y |
|---|---|---|---|---|---|
| diphosphate | acetyl | acetyl | H | H | F |
| diphosphate | acetyl | acetyl | H | H | Cl |
| triphosphate | acetyl | acetyl | H | H | NH₂ |
| triphosphate | acetyl | acetyl | H | H | NH-cyclopropyl |
| triphosphate | acetyl | acetyl | H | H | OH |
| triphosphate | acetyl | acetyl | H | H | F |
| triphosphate | acetyl | acetyl | H | H | Cl |
| H | H | H | H | NH₂ | H |
| H | H | H | H | NH₂ | NH₂ |
| H | H | H | H | NH₂ | NH-cyclopropyl |
| H | H | H | H | NH₂ | NH-methyl |
| H | H | H | H | NH₂ | NH-ethyl |
| H | H | H | H | NH₂ | NH-acetyl |
| H | H | H | H | NH₂ | OH |
| H | H | H | H | NH₂ | OMe |
| H | H | H | H | NH₂ | OEt |
| H | H | H | H | NH₂ | O-cyclopropyl |
| H | H | H | H | NH₂ | O-acetyl |
| H | H | H | H | NH₂ | SH |
| H | H | H | H | NH₂ | SMe |
| H | H | H | H | NH₂ | SEt |
| H | H | H | H | NH₂ | S-cyclopropyl |
| H | H | H | H | NH₂ | F |
| H | H | H | H | NH₂ | Cl |
| H | H | H | H | NH₂ | Br |
| H | H | H | H | NH₂ | I |
| monophosphate | H | H | H | NH₂ | NH₂ |
| monophosphate | H | H | H | NH₂ | NH-acetyl |
| monophosphate | H | H | H | NH₂ | NH-cyclopropyl |
| monophosphate | H | H | H | NH₂ | NH-methyl |
| monophosphate | H | H | H | NH₂ | NH-ethyl |
| monophosphate | H | H | H | NH₂ | OH |
| monophosphate | H | H | H | NH₂ | O-acetyl |
| monophosphate | H | H | H | NH₂ | OMe |
| monophosphate | H | H | H | NH₂ | OEt |
| monophosphate | H | H | H | NH₂ | O-cyclopropyl |
| monophosphate | H | H | H | NH₂ | SH |
| monophosphate | H | H | H | NH₂ | SMe |
| monophosphate | H | H | H | NH₂ | SEt |
| monophosphate | H | H | H | NH₂ | S-cyclopropyl |
| monophosphate | H | H | H | NH₂ | F |
| monophosphate | H | H | H | NH₂ | Cl |
| monophosphate | H | H | H | NH₂ | Br |
| monophosphate | H | H | H | NH₂ | I |
| diphosphate | H | H | H | NH₂ | NH₂ |
| diphosphate | H | H | H | NH₂ | NH-acetyl |
| diphosphate | H | H | H | NH₂ | NH-cyclopropyl |
| diphosphate | H | H | H | NH₂ | NH-methyl |
| diphosphate | H | H | H | NH₂ | NH-ethyl |
| diphosphate | H | H | H | NH₂ | OH |
| diphosphate | H | H | H | NH₂ | O-acetyl |
| diphosphate | H | H | H | NH₂ | OMe |
| diphosphate | H | H | H | NH₂ | OEt |
| diphosphate | H | H | H | NH₂ | O-cyclopropyl |
| diphosphate | H | H | H | NH₂ | SH |
| diphosphate | H | H | H | NH₂ | SMe |
| diphosphate | H | H | H | NH₂ | SEt |
| diphosphate | H | H | H | NH₂ | S-cyclopropyl |
| diphosphate | H | H | H | NH₂ | F |
| diphosphate | H | H | H | NH₂ | Cl |
| diphosphate | H | H | H | NH₂ | Br |
| diphosphate | H | H | H | NH₂ | I |
| triphosphate | H | H | H | NH₂ | NH₂ |
| triphosphate | H | H | H | NH₂ | NH-acetyl |
| triphosphate | H | H | H | NH₂ | NH-cyclopropyl |
| triphosphate | H | H | H | NH₂ | NH-methyl |
| triphosphate | H | H | H | NH₂ | NH-ethyl |
| triphosphate | H | H | H | NH₂ | OH |
| triphosphate | H | H | H | NH₂ | OMe |
| triphosphate | H | H | H | NH₂ | OEt |
| triphosphate | H | H | H | NH₂ | O-cyclopropyl |
| triphosphate | H | H | H | NH₂ | O-acetyl |
| triphosphate | H | H | H | NH₂ | SH |
| triphosphate | H | H | H | NH₂ | SMe |
| triphosphate | H | H | H | NH₂ | SEt |
| triphosphate | H | H | H | NH₂ | S-cyclopropyl |
| triphosphate | H | H | H | NH₂ | F |
| triphosphate | H | H | H | NH₂ | Cl |
| triphosphate | H | H | H | NH₂ | Br |
| triphosphate | H | H | H | NH₂ | I |
| monophosphate | mono-phosphate | mono-phosphate | H | NH₂ | NH₂ |
| monophosphate | mono-phosphate | mono-phosphate | H | NH₂ | NH-cyclopropyl |
| monophosphate | mono-phosphate | mono-phosphate | H | NH₂ | OH |
| monophosphate | mono-phosphate | mono-phosphate | H | NH₂ | F |
| monophosphate | mono-phosphate | mono-phosphate | H | NH₂ | Cl |
| diphosphate | di-phosphate | di-phosphate | H | NH₂ | NH₂ |
| diphosphate | di-phosphate | di-phosphate | H | NH₂ | NH-cyclopropyl |
| diphosphate | di-phosphate | di-phosphate | H | NH₂ | OH |
| diphosphate | di-phosphate | di-phosphate | H | NH₂ | F |
| diphosphate | di-phosphate | di-phosphate | H | NH₂ | Cl |
| triphosphate | tri-phosphate | tri-phosphate | H | NH₂ | NH₂ |
| triphosphate | tri-phosphate | tri-phosphate | H | NH₂ | NH-cyclopropyl |
| triphosphate | tri-phosphate | tri-phosphate | H | NH₂ | OH |
| triphosphate | tri-phosphate | tri-phosphate | H | NH₂ | F |
| triphosphate | tri-phosphate | tri-phosphate | H | NH₂ | Cl |
| H | H | H | F | NH₂ | NH₂ |
| H | H | H | F | NH₂ | NH-cyclopropyl |
| H | H | H | F | NH₂ | OH |
| H | H | H | F | NH₂ | F |
| H | H | H | F | NH₂ | Cl |
| H | H | H | Cl | NH₂ | NH₂ |
| H | H | H | Cl | NH₂ | NH-cyclopropyl |
| H | H | H | Cl | NH₂ | OH |
| H | H | H | Cl | NH₂ | F |
| H | H | H | Cl | NH₂ | Cl |
| H | H | H | Br | NH₂ | NH₂ |
| H | H | H | Br | NH₂ | NH-cyclopropyl |
| H | H | H | Br | NH₂ | OH |
| H | H | H | Br | NH₂ | F |
| H | H | H | Br | NH₂ | Cl |
| H | H | H | NH₂ | NH₂ | NH₂ |
| H | H | H | NH₂ | NH₂ | NH-cyclopropyl |
| H | H | H | NH₂ | NH₂ | OH |
| H | H | H | NH₂ | NH₂ | F |
| H | H | H | NH₂ | NH₂ | Cl |
| H | H | H | SH | NH₂ | NH₂ |
| H | H | H | SH | NH₂ | NH-cyclopropyl |
| H | H | H | SH | NH₂ | OH |
| H | H | H | SH | NH₂ | F |
| H | H | H | SH | NH₂ | Cl |
| acetyl | H | H | H | NH₂ | NH₂ |
| acetyl | H | H | H | NH₂ | NH-cyclopropyl |
| acetyl | H | H | H | NH₂ | OH |
| acetyl | H | H | H | NH₂ | F |
| acetyl | H | H | H | NH₂ | Cl |
| acetyl | H | H | F | NH₂ | NH₂ |
| acetyl | H | H | F | NH₂ | NH-cyclopropyl |
| acetyl | H | H | F | NH₂ | OH |
| acetyl | H | H | F | NH₂ | F |
| acetyl | H | H | F | NH₂ | Cl |
| H | acetyl | acetyl | H | NH₂ | NH₂ |
| H | acetyl | acetyl | H | NH₂ | NH-cyclopropyl |
| H | acetyl | acetyl | H | NH₂ | OH |
| H | acetyl | acetyl | H | NH₂ | F |
| H | acetyl | acetyl | H | NH₂ | Cl |
| acetyl | acetyl | acetyl | H | NH₂ | NH₂ |
| acetyl | acetyl | acetyl | H | NH₂ | NH-cyclopropyl |
| acetyl | acetyl | acetyl | H | NH₂ | OH |
| acetyl | acetyl | acetyl | H | NH₂ | F |

-continued

| R¹ | R² | R³ | X¹ | X² | Y |
|---|---|---|---|---|---|
| acetyl | acetyl | acetyl | H | NH₂ | Cl |
| monophosphate | acetyl | acetyl | H | NH₂ | NH₂ |
| monophosphate | acetyl | acetyl | H | NH₂ | NH-cyclopropyl |
| monophosphate | acetyl | acetyl | H | NH₂ | OH |
| monophosphate | acetyl | acetyl | H | NH₂ | F |
| monophosphate | acetyl | acetyl | H | NH₂ | Cl |
| diphosphate | acetyl | acetyl | H | NH₂ | NH₂ |
| diphosphate | acetyl | acetyl | H | NH₂ | NH-cyclopropyl |
| diphosphate | acetyl | acetyl | H | NH₂ | OH |
| diphosphate | acetyl | acetyl | H | NH₂ | F |
| diphosphate | acetyl | acetyl | H | NH₂ | Cl |
| triphosphate | acetyl | acetyl | H | NH₂ | NH₂ |
| triphosphate | acetyl | acetyl | H | NH₂ | NH-cyclopropyl |
| triphosphate | acetyl | acetyl | H | NH₂ | OH |
| triphosphate | acetyl | acetyl | H | NH₂ | F |
| triphosphate | acetyl | acetyl | H | NH₂ | Cl |
| H | H | H | H | Cl | H |
| H | H | H | H | Cl | H |
| H | H | H | H | Cl | NH₂ |
| H | H | H | H | Cl | NH-cyclopropyl |
| H | H | H | H | Cl | NH-methyl |
| H | H | H | H | Cl | NH-ethyl |
| H | H | H | H | Cl | NH-acetyl |
| H | H | H | H | Cl | OH |
| H | H | H | H | Cl | OMe |
| H | H | H | H | Cl | OEt |
| H | H | H | H | Cl | O-cyclopropyl |
| H | H | H | H | Cl | O-acetyl |
| H | H | H | H | Cl | SH |
| H | H | H | H | Cl | SMe |
| H | H | H | H | Cl | SEt |
| H | H | H | H | Cl | S-cyclopropyl |
| monophosphate | H | H | H | Cl | NH₂ |
| monophosphate | H | H | H | Cl | NH-acetyl |
| monophosphate | H | H | H | Cl | NH-cyclopropyl |
| monophosphate | H | H | H | Cl | NH-methyl |
| monophosphate | H | H | H | Cl | NH-ethyl |
| monophosphate | H | H | H | Cl | OH |
| monophosphate | H | H | H | Cl | O-acetyl |
| monophosphate | H | H | H | Cl | OMe |
| monophosphate | H | H | H | Cl | OEt |
| monophosphate | H | H | H | Cl | O-cyclopropyl |
| monophosphate | H | H | H | Cl | SH |
| monophosphate | H | H | H | Cl | SMe |
| monophosphate | H | H | H | Cl | SEt |
| monophosphate | H | H | H | Cl | S-cyclopropyl |
| diphosphate | H | H | H | Cl | NH₂ |
| diphosphate | H | H | H | Cl | NH-acetyl |
| diphosphate | H | H | H | Cl | NH-cyclopropyl |
| diphosphate | H | H | H | Cl | NH-methyl |
| diphosphate | H | H | H | Cl | NH-ethyl |
| diphosphate | H | H | H | Cl | OH |
| diphosphate | H | H | H | Cl | O-acetyl |
| diphosphate | H | H | H | Cl | OMe |
| diphosphate | H | H | H | Cl | OEt |
| diphosphate | H | H | H | Cl | O-cyclopropyl |
| diphosphate | H | H | H | Cl | SH |
| diphosphate | H | H | H | Cl | SMe |
| diphosphate | H | H | H | Cl | SEt |
| diphosphate | H | H | H | Cl | S-cyclopropyl |
| triphosphate | H | H | H | Cl | NH₂ |
| triphosphate | H | H | H | Cl | NH-acetyl |
| triphosphate | H | H | H | Cl | NH-cyclopropyl |
| triphosphate | H | H | H | Cl | NH-methyl |
| triphosphate | H | H | H | Cl | NH-ethyl |
| triphosphate | H | H | H | Cl | OH |
| triphosphate | H | H | H | Cl | OMe |
| triphosphate | H | H | H | Cl | OEt |
| triphosphate | H | H | H | Cl | O-cyclopropyl |
| triphosphate | H | H | H | Cl | O-acetyl |
| triphosphate | H | H | H | Cl | SH |
| triphosphate | H | H | H | Cl | SMe |
| triphosphate | H | H | H | Cl | SEt |
| triphosphate | H | H | H | Cl | S-cyclopropyl |
| monophosphate | monophosphate | monophosphate | H | Cl | NH₂ |
| monophosphate | monophosphate | monophosphate | H | Cl | NH-cyclopropyl |
| monophosphate | monophosphate | monophosphate | H | Cl | OH |
| diphosphate | diphosphate | diphosphate | H | Cl | NH₂ |
| diphosphate | diphosphate | diphosphate | H | Cl | NH-cyclopropyl |
| diphosphate | diphosphate | diphosphate | H | Cl | OH |
| triphosphate | triphosphate | triphosphate | H | Cl | NH₂ |
| triphosphate | triphosphate | triphosphate | H | Cl | NH-cyclopropyl |
| triphosphate | triphosphate | triphosphate | H | Cl | OH |
| H | H | H | F | Cl | NH₂ |
| H | H | H | F | Cl | NH-cyclopropyl |
| H | H | H | F | Cl | OH |
| H | H | H | Cl | Cl | NH₂ |
| H | H | H | Cl | Cl | NH-cyclopropyl |
| H | H | H | Cl | Cl | OH |
| H | H | H | Br | Cl | NH₂ |
| H | H | H | Br | Cl | NH-cyclopropyl |
| H | H | H | Br | Cl | OH |
| H | H | H | NH₂ | Cl | NH₂ |
| H | H | H | NH₂ | Cl | NH-cyclopropyl |
| H | H | H | NH₂ | Cl | OH |
| H | H | H | SH | Cl | NH₂ |
| H | H | H | SH | Cl | NH-cyclopropyl |
| H | H | H | SH | Cl | OH |
| acetyl | H | H | H | Cl | NH₂ |
| acetyl | H | H | H | Cl | NH-cyclopropyl |
| acetyl | H | H | H | Cl | OH |
| acetyl | H | H | F | Cl | NH₂ |
| acetyl | H | H | F | Cl | NH-cyclopropyl |
| acetyl | H | H | F | Cl | OH |
| H | acetyl | acetyl | H | Cl | NH₂ |
| H | acetyl | acetyl | H | Cl | NH-cyclopropyl |
| H | acetyl | acetyl | H | Cl | OH |
| acetyl | acetyl | acetyl | H | Cl | NH₂ |
| acetyl | acetyl | acetyl | H | Cl | NH-cyclopropyl |
| acetyl | acetyl | acetyl | H | Cl | OH |
| monophosphate | acetyl | acetyl | H | Cl | NH₂ |
| monophosphate | acetyl | acetyl | H | Cl | NH-cyclopropyl |
| monophosphate | acetyl | acetyl | H | Cl | OH |
| diphosphate | acetyl | acetyl | H | Cl | NH₂ |
| diphosphate | acetyl | acetyl | H | Cl | NH-cyclopropyl |
| diphosphate | acetyl | acetyl | H | Cl | OH |
| triphosphate | acetyl | acetyl | H | Cl | NH₂ |
| triphosphate | acetyl | acetyl | H | Cl | NH-cyclopropyl |
| triphosphate | acetyl | acetyl | H | Cl | OH |
| H | H | H | H | Cl | NH₂ |
| H | H | H | H | Cl | NH-cyclopropyl |
| H | H | H | H | Cl | OH |
| H | H | H | H | Br | NH₂ |
| H | H | H | H | Br | NH-cyclopropyl |
| H | H | H | H | Br | OH |

Alternatively, the following nucleosides of Formula IV are prepared, using the appropriate sugar and pyrimidine or purine bases.

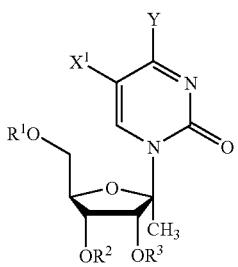

(IV)

wherein:

| R¹ | R² | R³ | X¹ | Y |
|---|---|---|---|---|
| H | H | H | H | H |
| H | H | H | H | NH₂ |
| H | H | H | H | NH-cyclopropyl |
| H | H | H | H | NH-methyl |
| H | H | H | H | NH-ethyl |
| H | H | H | H | NH-acetyl |
| H | H | H | H | OH |
| H | H | H | H | OMe |
| H | H | H | H | OEt |
| H | H | H | H | O-cyclopropyl |
| H | H | H | H | O-acetyl |
| H | H | H | H | SH |
| H | H | H | H | SMe |
| H | H | H | H | SEt |
| H | H | H | H | S-cyclopropyl |
| monophosphate | H | H | H | NH₂ |
| monophosphate | H | H | H | NH-acetyl |
| monophosphate | H | H | H | NH-cyclopropyl |
| monophosphate | H | H | H | NH-methyl |
| monophosphate | H | H | H | NH-ethyl |
| monophosphate | H | H | H | OH |
| monophosphate | H | H | H | O-acetyl |
| monophosphate | H | H | H | OMe |
| monophosphate | H | H | H | OEt |
| monophosphate | H | H | H | O-cyclopropyl |
| monophosphate | H | H | H | SH |
| monophosphate | H | H | H | SMe |
| monophosphate | H | H | H | SEt |
| monophosphate | H | H | H | S-cyclopropyl |
| diphosphate | H | H | H | NH₂ |
| diphosphate | H | H | H | NH-acetyl |
| diphosphate | H | H | H | NH-cyclopropyl |
| diphosphate | H | H | H | NH-methyl |
| diphosphate | H | H | H | NH-ethyl |
| diphosphate | H | H | H | OH |
| diphosphate | H | H | H | O-acetyl |
| diphosphate | H | H | H | OMe |
| diphosphate | H | H | H | OEt |
| diphosphate | H | H | H | O-cyclopropyl |
| diphosphate | H | H | H | SH |
| diphosphate | H | H | H | SMe |
| diphosphate | H | H | H | SEt |
| diphosphate | H | H | H | S-cyclopropyl |
| triphosphate | H | H | H | NH₂ |
| triphosphate | H | H | H | NH-acetyl |
| triphosphate | H | H | H | NH-cyclopropyl |
| triphosphate | H | H | H | NH-methyl |
| triphosphate | H | H | H | NH-ethyl |
| triphosphate | H | H | H | OH |
| triphosphate | H | H | H | OMe |
| triphosphate | H | H | H | OEt |
| triphosphate | H | H | H | O-cyclopropyl |
| triphosphate | H | H | H | O-acetyl |
| triphosphate | H | H | H | SH |
| triphosphate | H | H | H | SMe |
| triphosphate | H | H | H | SEt |
| triphosphate | H | H | H | S-cyclopropyl |
| monophosphate | monophosphate | monophosphate | H | NH₂ |
| monophosphate | monophosphate | monophosphate | H | NH-cyclopropyl |
| monophosphate | monophosphate | monophosphate | H | OH |
| diphosphate | diphosphate | diphosphate | H | NH₂ |
| diphosphate | diphosphate | diphosphate | H | NH-cyclopropyl |
| diphosphate | diphosphate | diphosphate | H | OH |
| triphosphate | triphosphate | triphosphate | H | NH₂ |
| triphosphate | triphosphate | triphosphate | H | NH-cyclopropyl |
| triphosphate | triphosphate | triphosphate | H | OH |
| H | H | H | F | NH₂ |
| H | H | H | F | NH-cyclopropyl |
| H | H | H | F | OH |
| H | H | H | Cl | NH₂ |
| H | H | H | Cl | NH-cyclopropyl |
| H | H | H | Cl | OH |
| H | H | H | Br | NH₂ |
| H | H | H | Br | NH-cyclopropyl |
| H | H | H | Br | OH |
| H | H | H | NH₂ | NH₂ |
| H | H | H | NH₂ | NH-cyclopropyl |
| H | H | H | NH₂ | OH |
| H | H | H | SH | NH₂ |
| H | H | H | SH | NH-cyclopropyl |
| H | H | H | SH | OH |
| acetyl | H | H | H | NH₂ |
| acetyl | H | H | H | NH-cyclopropyl |
| acetyl | H | H | H | OH |
| acetyl | H | H | F | NH₂ |
| acetyl | H | H | F | NH-cyclopropyl |
| acetyl | H | H | F | OH |
| H | acetyl | acetyl | H | NH₂ |
| H | acetyl | acetyl | H | NH-cyclopropyl |
| H | acetyl | acetyl | H | OH |
| acetyl | acetyl | acetyl | H | NH₂ |
| acetyl | acetyl | acetyl | H | NH-cyclopropyl |
| acetyl | acetyl | acetyl | H | OH |
| monophosphate | acetyl | acetyl | H | NH₂ |
| monophosphate | acetyl | acetyl | H | NH-cyclopropyl |
| monophosphate | acetyl | acetyl | H | OH |
| diphosphate | acetyl | acetyl | H | NH₂ |
| diphosphate | acetyl | acetyl | H | NH-cyclopropyl |
| diphosphate | acetyl | acetyl | H | OH |
| triphosphate | acetyl | acetyl | H | NH₂ |
| triphosphate | acetyl | acetyl | H | NH-cyclopropyl |
| triphosphate | acetyl | acetyl | H | OH |

Alternatively, the following nucleosides of Formula VII are prepared, using the appropriate sugar and pyrimidine or purine bases.

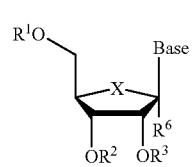

(VII)

wherein:

| R¹ | R² | R³ | R⁶ | X | Base |
|---|---|---|---|---|---|
| H | H | H | CH₃ | O | 2,4-O-Diacetyluracil |
| H | H | H | CH₃ | O | Hypoxanthine |
| H | H | H | CH₃ | O | 2,4-O-Diacetylthymine |
| H | H | H | CH₃ | O | Thymine |
| H | H | H | CH₃ | O | Cytosine |
| H | H | H | CH₃ | O | 4-(N-mono-acetyl)cytosine |
| H | H | H | CH₃ | O | 4-(N,N-diacetyl)cytosine |
| H | H | H | CH₃ | O | Uracil |
| H | H | H | CH₃ | O | 5-Fluorouracil |
| H | H | H | CH₃ | S | 2,4-O-Diacetyluraci |
| H | H | H | CH₃ | S | Hypoxanthine |
| H | H | H | CH₃ | S | 2,4-O-Diacetylthymine |
| H | H | H | CH₃ | S | Thymine |
| H | H | H | CH₃ | S | Cytosine |
| H | H | H | CH₃ | S | 4-(N-mono-acetyl)cytosine |
| H | H | H | CH₃ | S | 4-(N,N-diacetyl)cytosine |
| H | H | H | CH₃ | S | Uracil |
| H | H | H | CH₃ | S | 5-Fluorouracil |
| monophosphate | H | H | CH₃ | O | 2,4-O-Diacetyluracil |
| monophosphate | H | H | CH₃ | O | Hypoxanthine |
| monophosphate | H | H | CH₃ | O | 2,4-O-Diacetylthym |
| monophosphate | H | H | CH₃ | O | Thymine |
| monophosphate | H | H | CH₃ | O | Cytosine |
| monophosphate | H | H | CH₃ | O | 4-(N-mono-acetyl)cytosine |
| monophosphate | H | H | CH₃ | O | 4-(N,N-diacetyl)cytosine |
| monophosphate | H | H | CH₃ | O | Uracil |
| monophosphate | H | H | CH₃ | O | 5-Fluorouracil |
| monophosphate | H | H | CH₃ | S | 2,4-O-Diacetyluracil |
| monophosphate | H | H | CH₃ | S | Hypoxanthine |
| monophosphate | H | H | CH₃ | S | 2,4-O-Diacetylthym |
| monophosphate | H | H | CH₃ | S | Thymine |
| monophosphate | H | H | CH₃ | S | Cytosine |
| monophosphate | H | H | CH₃ | S | 4-(N-mono-acetyl)cytosine |
| monophosphate | H | H | CH₃ | S | 4-(N,N-diacetyl)cytosine |
| monophosphate | H | H | CH₃ | S | Uracil |
| monophosphate | H | H | CH₃ | S | 5-Fluorouracil |
| diphosphate | H | H | CH₃ | O | 2,4-O-Diacetyluracil |
| diphosphate | H | H | CH₃ | O | Hypoxanthine |
| diphosphate | H | H | CH₃ | O | 2,4-O-Diacetylthymine |
| diphosphate | H | H | CH₃ | O | Thymine |
| diphosphate | H | H | CH₃ | O | Cytosine |
| diphosphate | H | H | CH₃ | O | 4-(N-mono-acetyl)cytosine |
| diphosphate | H | H | CH₃ | O | 4-(N,N-diacetyl)cytosine |
| diphosphate | H | H | CH₃ | O | Uracil |
| diphosphate | H | H | CH₃ | O | 5-Fluorouracil |
| diphosphate | H | H | CH₃ | S | 2,4-O-Diacetyluracil |
| diphosphate | H | H | CH₃ | S | Hypoxanthine |
| diphosphate | H | H | CH₃ | S | 2,4-O-Diacetylthym |
| diphosphate | H | H | CH₃ | S | Thymine |
| diphosphate | H | H | CH₃ | S | Cytosine |
| triphosphate | H | H | CH₃ | O | 2,4-O-Diacetyluracil |

-continued

| R¹ | R² | R³ | R⁶ | X | Base |
|---|---|---|---|---|---|
| triphosphate | H | H | CH₃ | O | Hypoxanthine |
| triphosphate | H | H | CH₃ | O | 2,4-O-Diacetylthymine |
| triphosphate | H | H | CH₃ | O | Thymine |
| triphosphate | H | H | CH₃ | O | Cytosine |
| triphosphate | H | H | CH₃ | O | 4-(N-mono-acetyl)cytosine |
| triphosphate | H | H | CH₃ | O | 4-(N,N-diacetyl)cytosine |
| triphosphate | H | H | CH₃ | O | Uracil |
| triphosphate | H | H | CH₃ | O | 5-Fluorouracil |
| triphosphate | H | H | CH₃ | S | 2,4-O-Diacetyluracil |
| triphosphate | H | H | CH₃ | S | Hypoxanthine |
| triphosphate | H | H | CH₃ | S | 2,4-O-Diacetylthymine |
| triphosphate | H | H | CH₃ | S | Thymine |
| triphosphate | H | H | CH₃ | S | Cytosine |
| monophosphate | monophosphate | monophosphate | CF₃ | O | 2,4-O-Diacetyluracil |
| monophosphate | monophosphate | monophosphate | CF₃ | O | Hypoxanthine |
| monophosphate | monophosphate | monophosphate | CF₃ | O | 2,4-O-Diacetylthymine |
| monophosphate | monophosphate | monophosphate | CF₃ | O | Thymine |
| monophosphate | monophosphate | monophosphate | CF₃ | O | Cytosine |
| monophosphate | monophosphate | monophosphate | CF₃ | O | 4-(N-mono-acetyl)cytosine |
| monophosphate | monophosphate | monophosphate | CF₃ | O | 4-(N,N-diacetyl)cytosine |
| monophosphate | monophosphate | monophosphate | CF₃ | O | Uracil |
| monophosphate | monophosphate | monophosphate | CF₃ | O | 5-Fluorouracil |
| monophosphate | monophosphate | monophosphate | CF₃ | S | 2,4-O-Diacetyluracil |
| monophosphate | monophosphate | monophosphate | CF₃ | S | Hypoxanthine |
| monophosphate | monophosphate | monophosphate | CF₃ | S | 2,4-O-Diacetylthymine |
| monophosphate | monophosphate | monophosphate | CF₃ | S | Thymine |
| monophosphate | monophosphate | monophosphate | CF₃ | S | Cytosine |
| monophosphate | monophosphate | monophosphate | CF₃ | S | 4-(N-mono-acetyl)cytosine |
| monophosphate | monophosphate | monophosphate | CF₃ | S | 4-(N,N-diacetyl)cytosine |
| monophosphate | monophosphate | monophosphate | CF₃ | S | Uracil |
| monophosphate | monophosphate | monophosphate | CF₃ | S | 5-Fluorouracil |
| acetyl | acetyl | acetyl | CF₃ | O | 4-(N,N-diacetyl)cytosine |
| acetyl | acetyl | acetyl | CF₃ | S | 4-(N,N-diacetyl)cytosine |
| acetyl | acetyl | acetyl | 2-bromo-vinyl | O | 4-(N,N-diacetyl)cytosine |
| acetyl | acetyl | acetyl | 2-bromo-vinyl | S | 4-(N,N-diacetyl)cytosine |
| H | H | H | CH₃ | O | 2-(N,N-diacetyl)-guanine |
| H | H | H | CH₃ | O | 6-O-acetyl guanine |
| H | H | H | CH₃ | O | 8-fluoroguanine |
| H | H | H | CH₃ | O | guanine |
| H | H | H | CH₃ | O | 6-(N,N-diacetyl)-adenine |
| H | H | H | CH₃ | O | 2-fluoroadenine |
| H | H | H | CH₃ | O | 8-fluoroadenine |
| H | H | H | CH₃ | O | 2,8-difluoro-adenine |
| H | H | H | CH₃ | O | adenine |
| H | H | H | CH₃ | S | 2-(N,N-diacetyl)-guanine |
| H | H | H | CH₃ | S | 6-O-acetyl guanine |
| H | H | H | CH₃ | S | 8-fluoroguanine |
| H | H | H | CH₃ | S | guanine |
| H | H | H | CH₃ | S | 6-(N,N-diacetyl)-adenine |
| H | H | H | CH₃ | S | 2-fluoroadenine |
| H | H | H | CH₃ | S | 8-fluoroadenine |
| H | H | H | CH₃ | S | 2,8-difluoro-adenine |

-continued

| R¹ | R² | R³ | R⁶ | X | Base |
|---|---|---|---|---|---|
| H | H | H | CH₃ | S | adenine |
| monophosphate | H | H | CH₃ | O | 2-(N,N-diacetyl)-guanine |
| monophosphate | H | H | CH₃ | O | 6-O-acetyl guanine |
| monophosphate | H | H | CH₃ | O | 8-fluoroguanine |
| monophosphate | H | H | CH₃ | O | guanine |
| monophosphate | H | H | CH₃ | O | 6-(N,N-diacetyl)-adenine |
| monophosphate | H | H | CH₃ | O | 2-fluoroadenine |
| monophosphate | H | H | CH₃ | O | 8-fluoroadenine |
| monophosphate | H | H | CH₃ | O | 2,8-difluoro-adenine |
| monophosphate | H | H | CH₃ | O | adenine |
| monophosphate | H | H | CH₃ | S | 2-(N,N-diacetyl)-guanine |
| monophosphate | H | H | CH₃ | S | 6-O-acetyl guanine |
| monophosphate | H | H | CH₃ | S | 8-fluoroguanine |
| monophosphate | H | H | CH₃ | S | guanine |
| monophosphate | H | H | CH₃ | S | 6-(N,N-diacetyl)-adenine |
| monophosphate | H | H | CH₃ | S | 2-fluoroadenine |
| monophosphate | H | H | CH₃ | S | 8-fluoroadenine |
| monophosphate | H | H | CH₃ | S | 2,8-difluoro-adenine |
| monophosphate | H | H | CH₃ | S | adenine |
| diphosphate | H | H | CH₃ | O | 2-(N,N-diacetyl)-guanine |
| diphosphate | H | H | CH₃ | O | 6-O-acetyl guanine |
| diphosphate | H | H | CH₃ | O | 8-fluoroguanine |
| diphosphate | H | H | CH₃ | O | guanine |
| diphosphate | H | H | CH₃ | O | 6-(N,N-diacetyl)-adenine |
| diphosphate | H | H | CH₃ | O | 2-fluoroadenine |
| diphosphate | H | H | CH₃ | O | 8-fluoroadenine |
| diphosphate | H | H | CH₃ | O | 2,8-difluoro-adenine |
| diphosphate | H | H | CH₃ | O | adenine |
| diphosphate | H | H | CH₃ | S | 2-(N,N-diacetyl)-guanine |
| diphosphate | H | H | CH₃ | S | 6-O-acetyl guanine |
| diphosphate | H | H | CH₃ | S | 8-fluoroguanine |
| diphosphate | H | H | CH₃ | S | guanine |
| diphosphate | H | H | CH₃ | S | 6-(N,N-diacetyl)-adenine |
| diphosphate | H | H | CH₃ | S | 2-fluoroadenine |
| diphosphate | H | H | CH₃ | S | 8-fluoroadenine |
| diphosphate | H | H | CH₃ | S | 2,8-difluoro-adenine |
| diphosphate | H | H | CH₃ | S | adenine |
| triphosphate | H | H | CH₃ | O | 2-(N,N-diacetyl)-guanine |
| triphosphate | H | H | CH₃ | O | 6-O-acetyl guanine |
| triphosphate | H | H | CH₃ | O | 8-fluoroguanine |
| triphosphate | H | H | CH₃ | O | guanine |
| triphosphate | H | H | CH₃ | O | 6-(N,N-diacetyl)-adenine |
| triphosphate | H | H | CH₃ | O | 2-fluoroadenine |
| triphosphate | H | H | CH₃ | O | 8-fluoroadenine |
| triphosphate | H | H | CH₃ | O | 2,8-difluoro-adenine |
| triphosphate | H | H | CH₃ | O | 2-(N,N-diacetyl)-guanine |
| triphosphate | H | H | CH₃ | S | 6-O-acetyl guanine |
| triphosphate | H | H | CH₃ | S | 8-fluoroguanine |
| triphosphate | H | H | CH₃ | S | guanine |
| triphosphate | H | H | CH₃ | S | 6-(N,N-diacetyl)-adenine |
| triphosphate | H | H | CH₃ | S | 2-fluoroadenine |
| triphosphate | H | H | CH₃ | S | 8-fluoroadenine |
| triphosphate | H | H | CH₃ | S | 2,8-difluoro-adenine |

-continued

| R¹ | R² | R³ | R⁶ | X | Base |
|---|---|---|---|---|---|
| triphosphate | H | H | CH₃ | S | adenine |
| monophosphate | monophosphate | monophosphate | CF₃ | O | 2-(N,N-diacetyl)-guanine |
| monophosphate | monophosphate | monophosphate | CF₃ | O | 6-O-acetyl guanine |
| monophosphate | monophosphate | monophosphate | CF₃ | O | 8-fluoroguanine |
| monophosphate | monophosphate | monophosphate | CF₃ | O | guanine |
| monophosphate | monophosphate | monophosphate | CF₃ | O | 6-(N,N-diacetyl)-adenine |
| monophosphate | monophosphate | monophosphate | CF₃ | O | 2-fluoroadenine |
| monophosphate | monophosphate | monophosphate | CF₃ | O | 8-fluoroadenine |
| monophosphate | monophosphate | monophosphate | CF₃ | O | 2,8-difluoro-adenine |
| monophosphate | monophosphate | monophosphate | CF₃ | O | adenine |
| monophosphate | monophosphate | monophosphate | CF₃ | S | 2-(N,N-diacetyl)-guanine |
| monophosphate | monophosphate | monophosphate | CF₃ | S | 6-O-acetyl guanine |
| monophosphate | monophosphate | monophosphate | CF₃ | S | 8-fluoroguanine |
| monophosphate | monophosphate | monophosphate | CF₃ | S | guanine |
| monophosphate | monophosphate | monophosphate | CF₃ | S | 6-(N,N-diacetyl)-adenine |
| monophosphate | monophosphate | monophosphate | CF₃ | S | 2-fluoroadenine |
| monophosphate | monophosphate | monophosphate | CF₃ | S | 8-fluoroadenine |
| monophosphate | monophosphate | monophosphate | CF₃ | S | 2,8-difluoro-adenine |
| monophosphate | monophosphate | monophosphate | CF₃ | S | adenine |
| acetyl | acetyl | acetyl | CF₃ | O | guanine |
| acetyl | acetyl | acetyl | CF₃ | S | guanine |
| acetyl | acetyl | acetyl | 2-bromo-vinyl | O | guanine |
| acetyl | acetyl | acetyl | 2-bromo-vinyl | S | guanine |

Alternatively, the following nucleosides of Formula VIII are prepared, using the appropriate sugar and pyrimidine or purine bases.

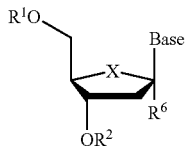

(VIII)

wherein

| R¹ | R² | R⁶ | X | Base |
|---|---|---|---|---|
| H | H | CH₃ | O | 2,4-O-Diacetyluracil |
| H | H | CH₃ | O | Hypoxanthine |
| H | H | CH₃ | O | 2,4-O-Diacetylthymine |
| H | H | CH₃ | O | Thymine |
| H | H | CH₃ | O | Cytosine |
| H | H | CH₃ | O | 4-(N-mono-acetyl)cytosine |
| H | H | CH₃ | O | 4-(N,N-diacetyl)cytosine |
| H | H | CH₃ | O | Uracil |
| H | H | CH₃ | O | 5-Fluorouracil |
| H | H | CH₃ | S | 2,4-O-Diacetyluracil |
| H | H | CH₃ | S | Hypoxanthine |
| H | H | CH₃ | S | 2,4-O-Diacetylthymine |
| H | H | CH₃ | S | Thymine |
| H | H | CH₃ | S | Cytosine |
| H | H | CH₃ | S | 4-(N-mono-acetyl)cytosine |
| H | H | CH₃ | S | 4-(N,N-diacetyl)cytosine |
| H | H | CH₃ | S | Uracil |
| H | H | CH₃ | S | 5-Fluorouracil |
| monophosphate | H | CH₃ | O | 2,4-O-Diacetyluracil |
| monophosphate | H | CH₃ | O | Hypoxanthine |
| monophosphate | H | CH₃ | O | 2,4-O-Diacetylthymine |
| monophosphate | H | CH₃ | O | Thymine |
| monophosphate | H | CH₃ | O | Cytosine |
| monophosphate | H | CH₃ | O | 4-(N-mono-acetyl)cytosine |
| monophosphate | H | CH₃ | O | 4-(N,N-diacetyl)cytosine |
| monophosphate | H | CH₃ | O | Uracil |
| monophosphate | H | CH₃ | O | 5-Fluorouracil |
| monophosphate | H | CH₃ | S | 2,4-O-Diacetyluracil |
| monophosphate | H | CH₃ | S | Hypoxanthine |
| monophosphate | H | CH₃ | S | 2,4-O-Diacetylthymine |
| monophosphate | H | CH₃ | S | Thymine |
| monophosphate | H | CH₃ | S | Cytosine |
| monophosphate | H | CH₃ | S | 4-(N-mono-acetyl)cytosine |
| monophosphate | H | CH₃ | S | 4-(N,N-diacetyl)cytosine |
| monophosphate | H | CH₃ | S | Uracil |
| monophosphate | H | CH₃ | S | 5-Fluorouracil |
| diphosphate | H | CH₃ | O | 2,4-O-Diacetyluracil |
| diphosphate | H | CH₃ | O | Hypoxanthine |
| diphosphate | H | CH₃ | O | 2,4-O-Diacetylthymine |
| diphosphate | H | CH₃ | O | Thymine |
| diphosphate | H | CH₃ | O | Cytosine |
| diphosphate | H | CH₃ | O | 4-(N-mono-acetyl)cytosine |
| diphosphate | H | CH₃ | O | 4-(N,N-diacetyl)cytosine |
| diphosphate | H | CH₃ | O | Uracil |
| diphosphate | H | CH₃ | O | 5-Fluorouracil |
| diphosphate | H | CH₃ | S | 2,4-O-Diacetyluracil |
| diphosphate | H | CH₃ | S | Hypoxanthine |
| diphosphate | H | CH₃ | S | 2,4-O-Diacetylthymine |
| diphosphate | H | CH₃ | S | Thymine |
| diphosphate | H | CH₃ | S | Cytosine |
| diphosphate | H | CH₃ | S | 4-(N-mono-acetyl)cytosine |
| diphosphate | H | CH₃ | S | 4-(N,N-diacetyl)cytosine |

-continued

| R¹ | R² | R⁶ | X | Base |
|---|---|---|---|---|
| diphosphate | H | CH₃ | S | Uracil |
| diphosphate | H | CH₃ | S | 5-Fluorouracil |
| triphosphate | H | CH₃ | O | 2,4-O-Diacetyluracil |
| triphosphate | H | CH₃ | O | Hypoxanthine |
| triphosphate | H | CH₃ | O | 2,4-O-diacethylthymine |
| triphosphate | H | CH₃ | O | Thymine |
| triphosphate | H | CH₃ | O | Cytosine |
| triphosphate | H | CH₃ | O | 4-(N-mono-acetyl)cytosine |
| triphosphate | H | CH₃ | O | 4-(N,N-diacetyl)cytosine |
| triphosphate | H | CH₃ | O | Uracil |
| triphosphate | H | CH₃ | O | 5-Fluorouracil |
| triphosphate | H | CH₃ | S | 2,4-O-Diacetyluracil |
| triphosphate | H | CH₃ | S | Hypoxanthine |
| triphosphate | H | CH₃ | S | 2,4-O-Diacetylthymine |
| triphosphate | H | CH₃ | S | Thymine |
| triphosphate | H | CH₃ | S | Cytosine |
| triphosphate | H | CH₃ | S | 4-(N-mono-acetyl)cytosine |
| triphosphate | H | CH₃ | S | 4-(N,N-diacetyl)cytosine |
| triphosphate | H | CH₃ | S | Uracil |
| triphosphate | H | CH₃ | S | 5-Fluorouracil |
| monophosphate | monophosphate | CF₃ | O | 2,4-O-Diacetyluracil |
| monophosphate | monophosphate | CF₃ | O | Hypoxanthine |
| monophosphate | monophosphate | CF₃ | O | 2,4-O-Diacetylthymine |
| monophosphate | monophosphate | CF₃ | O | Thymine |
| monophosphate | monophosphate | CF₃ | O | Cytosine |
| monophosphate | monophosphate | CF₃ | O | 4-(N-mono-acetyl)cytosine |
| monophosphate | monophosphate | CF₃ | O | 4-(N,N-diacetyl)cytosine |
| monophosphate | monophosphate | CF₃ | O | Uracil |
| monophosphate | monophosphate | CF₃ | O | 5-Fluorouracil |
| monophosphate | monophosphate | CF₃ | S | 2,4-O-Diacetyluracil |
| monophosphate | monophosphate | CF₃ | S | Hypoxanthine |
| monophosphate | monophosphate | CF₃ | S | 2,4-O-Diacetylthymine |
| monophosphate | monophosphate | CF₃ | S | Thymine |
| monophosphate | monophosphate | CF₃ | S | Cytosine |
| monophosphate | monophosphate | CF₃ | S | 4-(N-mono-acetyl)cytosine |
| monophosphate | monophosphate | CF₃ | S | 4-(N,N-diacetyl)cytosine |
| monophosphate | monophosphate | CF₃ | S | Uracil |
| monophosphate | monophosphate | CF₃ | S | 5-Fluorouracil |
| acetyl | acetyl | CF₃ | O | 4-(N,N-diacetyl)cytosine |
| acetyl | acetyl | CF₃ | S | 4-(N,N-diacetyl)cytosine |
| acetyl | acetyl | 2-bromo-vinyl | O | 4-(N,N-diacetyl)cytosine |
| acetyl | acetyl | 2-bromo-vinyl | S | 4-(N,N-diacetyl)cytosine |
| H | H | CH₃ | O | 2-(N,N-diacetyl)-guanine |
| H | H | CH₃ | O | 6-O-acetyl guanine |
| H | H | CH₃ | O | 8-fluoroguanine |
| H | H | CH₃ | O | guanine |
| H | H | CH₃ | O | 6-(N,N-diacetyl)-adenine |
| H | H | CH₃ | O | 2-fluoroadenine |
| H | H | CH₃ | O | 8-fluoroadenine |
| H | H | CH₃ | O | 2,8-difluoro-adenine |
| H | H | CH₃ | O | adenine |
| H | H | CH₃ | S | 2-(N,N-diacetyl)-guanine |
| H | H | CH₃ | S | 6-O-acetyl guanine |
| H | H | CH₃ | S | 8-fluoroguanine |
| H | H | CH₃ | S | guanine |
| H | H | CH₃ | S | 6-(N,N-diacetyl)-adenine |
| H | H | CH₃ | S | 2-fluoroadenine |
| H | H | CH₃ | S | 8-fluoroadenine |
| H | H | CH₃ | S | 2,8-difluoro-adenine |
| H | H | CH₃ | S | adenine |
| monophosphate | H | CH₃ | O | 2-(N,N-diacetyl)-guanine |
| monophosphate | H | CH₃ | O | 6-O-acetyl guanine |
| monophosphate | H | CH₃ | O | 8-fluoroguanine |
| monophosphate | H | CH₃ | O | guanine |
| monophosphate | H | CH₃ | O | 6-(N,N-diacetyl)-adenine |
| monophosphate | H | CH₃ | O | 2-fluoroadenine |
| monophosphate | H | CH₃ | O | 8-fluoroadenine |
| monophosphate | H | CH₃ | O | 2,8-difluoro-adenine |
| monophosphate | H | CH₃ | O | adenine |
| monophosphate | H | CH₃ | S | 2-(N,N-diacetyl)-guanine |
| monophosphate | H | CH₃ | S | 6-O-acetyl guanine |
| monophosphate | H | CH₃ | S | 8-fluoroguanine |
| monophosphate | H | CH₃ | S | guanine |
| monophosphate | H | CH₃ | S | 6-(N,N-diacetyl)-adenine |
| monophosphate | H | CH₃ | S | 2-fluoroadenine |
| monophosphate | H | CH₃ | S | 8-fluoroadenine |
| monophosphate | H | CH₃ | S | 2,8-difluoro-adenine |
| monophosphate | H | CH₃ | S | adenine |
| diphosphate | H | CH₃ | O | 2-(N,N-diacetyl)-guanine |
| diphosphate | H | CH₃ | O | 6-O-acetyl guanine |
| diphosphate | H | CH₃ | O | 8-fluoroguanine |
| diphosphate | H | CH₃ | O | guanine |
| diphosphate | H | CH₃ | O | 6-(N,N-diacetyl)-adenine |
| diphosphate | H | CH₃ | O | 2-fluoroadenine |
| diphosphate | H | CH₃ | O | 8-fluoroadenine |
| diphosphate | H | CH₃ | O | 2,8-difluoro-adenine |
| diphosphate | H | CH₃ | O | adenine |
| diphosphate | H | CH₃ | S | 2-(N,N-diacetyl)-guanine |
| diphosphate | H | CH₃ | S | 6-O-acetyl guanine |
| diphosphate | H | CH₃ | S | 8-fluoroguanine |
| diphosphate | H | CH₃ | S | guanine |
| diphosphate | H | CH₃ | S | 6-(N,N-diacetyl)-adenine |
| diphosphate | H | CH₃ | S | 2-fluoroadenine |
| diphosphate | H | CH₃ | S | 8-fluoroadenine |
| diphosphate | H | CH₃ | S | 2,8-difluoro-adenine |
| diphosphate | H | CH₃ | S | adenine |
| triphosphate | H | CH₃ | O | 2-(N,N-diacetyl)-guanine |
| triphosphate | H | CH₃ | O | 6-O-acetyl guanine |
| triphosphate | H | CH₃ | O | 8-fluoroguanine |
| triphosphate | H | CH₃ | O | guanine |
| triphosphate | H | CH₃ | O | 6-(N,N-diacetyl)-adenine |
| triphosphate | H | CH₃ | O | 2-fluoroadenine |
| triphosphate | H | CH₃ | O | 8-fluoroadenine |
| triphosphate | H | CH₃ | O | 2,8-difluoro-adenine |
| triphosphate | H | CH₃ | O | adenine |
| triphosphate | H | CH₃ | S | 2-(N,N-diacetyl)-guanine |
| triphosphate | H | CH₃ | S | 6-O-acetyl guanine |
| triphosphate | H | CH₃ | S | 8-fluoroguanine |
| triphosphate | H | CH₃ | S | guanine |
| triphosphate | H | CH₃ | S | 6-(N,N-diacetyl)-adenine |
| triphosphate | H | CH₃ | S | 2-fluoroadenine |
| triphosphate | H | CH₃ | S | 8-fluoroadenine |
| triphosphate | H | CH₃ | S | 2,8-difluoro-adenine |
| triphosphate | H | CH₃ | S | adenine |
| monophosphate | monophosphate | CF₃ | O | 2-(N,N-diacetyl)-guanine |
| monophosphate | monophosphate | CF₃ | O | 6-O-acetyl guanine |
| monophosphate | monophosphate | CF₃ | O | 8-fluoroguanine |
| monophosphate | monophosphate | CF₃ | O | guanine |
| monophosphate | monophosphate | CF₃ | O | 6-(N,N-diacetyl)-adenine |
| monophosphate | monophosphate | CF₃ | O | 2-fluoroadenine |
| monophosphate | monophosphate | CF₃ | O | 8-fluoroadenine |
| monophosphate | monophosphate | CF₃ | O | 2,8-difluoro-adenine |
| monophosphate | monophosphate | CF₃ | O | adenine |
| monophosphate | monophosphate | CF₃ | S | 2-(N,N-diacetyl)-guanine |
| monophosphate | monophosphate | CF₃ | S | 6-O-acetyl guanine |
| monophosphate | monophosphate | CF₃ | S | 8-fluoroguanine |
| monophosphate | monophosphate | CF₃ | S | guanine |
| monophosphate | monophosphate | CF₃ | S | 6-(N,N-diacetyl)-adenine |
| monophosphate | monophosphate | CF₃ | S | 2-fluoroadenine |
| monophosphate | monophosphate | CF₃ | S | 8-fluoroadenine |
| monophosphate | monophosphate | CF₃ | S | 2,8-difluoro-adenine |
| monophosphate | monophosphate | CF₃ | S | adenine |
| acetyl | acetyl | CF₃ | O | guanine |
| acetyl | acetyl | CF₃ | S | guanine |
| acetyl | acetyl | 2-bromo-vinyl | O | guanine |
| acetyl | acetyl | 2-bromo-vinyl | S | guanine |

Alternatively, the following nucleosides of Formula IX are prepared, using the appropriate sugar and pyrimidine or purine bases.

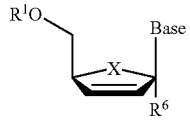

(IX)

wherein:

| R¹ | R⁶ | X | Base |
|---|---|---|---|
| H | CH₃ | O | 2,4-O-Diacetyluracil |
| H | CH₃ | O | Hypoxanthine |
| H | CH₃ | O | 2,4-O-Diacetylthymine |
| H | CH₃ | O | Thymine |
| H | CH₃ | O | Cytosine |
| H | CH₃ | O | 4-(N-mono-acetyl)cytosine |
| H | CH₃ | O | 4-(N,N-diacetyl)cytosine |
| H | CH₃ | O | Uracil |
| H | CH₃ | O | 5-Fluorouracil |
| H | CH₃ | S | 2,4-O-Diacetyluracil |
| H | CH₃ | S | Hypoxanthine |
| H | CH₃ | S | 2,4-O-Diacetylthymine |
| H | CH₃ | S | Thymine |
| H | CH₃ | S | Cytosine |
| H | CH₃ | S | 4-(N-mono-acetyl)cytosine |
| H | CH₃ | S | 4-(N,N-diacetyl)cytosine |
| H | CH₃ | S | Uracil |
| H | CH₃ | S | 5-Fluorouracil |
| monophosphate | CH₃ | O | 2,4-O-Diacetyluracil |
| monophosphate | CH₃ | O | Hypoxanthine |
| monophosphate | CH₃ | O | 2,4-O-Diacetylthymine |
| monophosphate | CH₃ | O | Thymine |
| monophosphate | CH₃ | O | Cytosine |
| monophosphate | CH₃ | O | 4-(N-mono-acetyl)cytosine |
| monophosphate | CH₃ | O | 4-(N,N-diacetyl)cytosine |
| monophosphate | CH₃ | O | Uracil |
| monophosphate | CH₃ | O | 5-Fluorouracil |
| monophosphate | CH₃ | S | 2,4-O-Diacetyluracil |
| monophosphate | CH₃ | S | Hypoxanthine |
| monophosphate | CH₃ | S | 2,4-O-Diacetylthymine |
| monophosphate | CH₃ | S | Thymine |
| monophosphate | CH₃ | S | Cytosine |
| monophosphate | CH₃ | S | 4-(N-mono-acetyl)cytosine |
| monophosphate | CH₃ | S | 4-(N,N-diacetyl)cytos |
| monophosphate | CH₃ | S | Uracil |
| monophosphate | CH₃ | S | 5-Fluorouracil |
| diphosphate | CH₃ | O | 2,4-O-Diacetyluracil |
| diphosphate | CH₃ | O | Hypoxanthine |
| diphosphate | CH₃ | O | 2,4-O-Diacetylthymine |
| diphosphate | CH₃ | O | Thymine |
| diphosphate | CH₃ | O | Cytosine |
| diphosphate | CH₃ | O | 4-(N-mono-acetyl)cytosine |
| diphosphate | CH₃ | O | 4-(N,N-diacetyl)cytosine |
| diphosphate | CH₃ | O | Uracil |
| diphosphate | CH₃ | O | 5-Fluorouracil |
| diphosphate | CH₃ | S | 2,4-O-Diacetyluracil |
| diphosphate | CH₃ | S | Hypoxanthine |
| diphosphate | CH₃ | S | 2,4-O-Diacetylthymine |
| diphosphate | CH₃ | S | Thymine |
| diphosphate | CH₃ | S | Cytosine |
| triphosphate | CH₃ | O | 2,4-O-Diacetyluracil |
| triphosphate | CH₃ | O | Hypoxanthine |
| triphosphate | CH₃ | O | 2,4-O-Diacetylthymine |
| triphosphate | CH₃ | O | Thymine |
| triphosphate | CH₃ | O | Cytosine |
| triphosphate | CH₃ | O | 4-(N-mono-acetyl)cytosine |
| triphosphate | CH₃ | O | 4-(N,N-diacetyl)cytosine |
| triphosphate | CH₃ | O | Uracil |
| triphosphate | CH₃ | O | 5-Fluorouracil |
| triphosphate | CH₃ | S | 2,4-O-Diacetyluracil |
| triphosphate | CH₃ | S | Hypoxanthine |
| triphospahate | CH₃ | S | 2,4-O-Diacetylthymine |
| triphospahate | CH₃ | S | Thymine |
| triphospahate | CH₃ | S | Cytosine |
| monophosphate | CF₃ | O | 2,4-O-Diacetyluracil |
| monophosphate | CF₃ | O | Hypoxanthine |
| monophosphate | CF₃ | O | 2,4-O-Diacetylthymine |
| monophosphate | CF₃ | O | Thymine |
| monophosphate | CF₃ | O | Cytosine |
| monophosphate | CF₃ | O | 4-(N-mono-acetyl)cytosine |
| monophosphate | CF₃ | O | 4-(N,N-diacetyl)cytos |
| monophosphate | CF₃ | O | Uracil |
| monophosphate | CF₃ | O | 5-Fluorouracil |
| monophosphate | CF₃ | S | 2,4-O-Diacetyluracil |
| monophosphate | CF₃ | S | Hypoxanthine |
| monophosphate | CF₃ | S | 2,4-O-Diacetylthymine |
| monophosphate | CF₃ | S | Thymine |
| monophosphate | CF₃ | S | Cytosine |
| monophosphate | CF₃ | S | 4-(N-mono-acetyl)cytosine |
| monophosphate | CF₃ | S | 4-(N,N-diacetyl)cytosine |
| monophosphate | CF₃ | S | Uracil |
| monophosphate | CF₃ | S | 5-Fluorouracil |
| acetyl | CF₃ | O | 4-(N,N-diacetyl)cytosine |
| acetyl | CF₃ | S | 4-(N,N-diacetyl)cytosine |
| acetyl | 2-bromo-vinyl | O | 4-(N,N-diacetyl)cytosine |
| acetyl | 2-bromo-vinyl | S | 4-(N,N-diacetyl)cytosine |

Alternatively, the following nucleosides of Formula XVI are prepared, using the appropriate sugar and pyrimidine or purine bases.

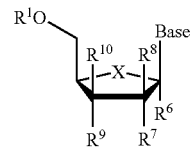

(XVI)

wherein:

| R¹ | R⁶ | R⁷ | R⁸ | X | Base | R¹⁰ | R⁹ |
|---|---|---|---|---|---|---|---|
| H | CH₃ | H | H | O | 2,4-O-Diacetyluracil | OH | Me |
| H | CH₃ | H | H | O | Hypoxanthine | OH | Me |
| H | CH₃ | H | H | O | 2,4-O-Diacetylthymine | OH | Me |
| H | CH₃ | H | H | O | Thymine | OH | Me |
| H | CH₃ | H | H | O | Cytosine | OH | Me |
| H | CH₃ | H | H | O | 4-(N-mono-acetyl)cytosine | OH | Me |
| H | CH₃ | H | H | O | 4-(N,N-diacetyl)cytosine | OH | Me |
| H | CH₃ | H | H | O | Uracil | OH | Me |
| H | CH₃ | H | H | O | 5-Fluorouracil | OH | Me |

-continued

| R¹ | R⁶ | R⁷ | R⁸ | X | Base | R¹⁰ | R⁹ |
|---|---|---|---|---|---|---|---|
| H | CH₃ | H | H | S | 2,4-O-Diacetyluracil | OH | Me |
| H | CH₃ | H | H | S | Hypoxanthine | OH | Me |
| H | CH₃ | H | H | S | 2,4-O-Diacetylthymine | OH | Me |
| H | CH₃ | H | H | S | Thymine | OH | Me |
| H | CH₃ | H | H | S | Cytosine | OH | Me |
| H | CH₃ | H | H | S | 4-(N-mono-acetyl)cytosine | OH | Me |
| H | CH₃ | H | H | S | 4-(N,N-diacetyl)cytosine | OH | Me |
| H | CH₃ | H | H | S | Uracil | OH | Me |
| H | CH₃ | H | H | S | 5-Fluorouracil | OH | Me |
| monophosphate | CH₃ | H | H | O | 2,4-O-Diacetyluracil | OH | Me |
| monophosphate | CH₃ | H | H | O | Hypoxanthine | OH | Me |
| monophosphate | CH₃ | H | H | O | 2,4-O-Diacetylthymine | OH | Me |
| monophosphate | CH₃ | H | H | O | Thymine | OH | Me |
| monophosphate | CH₃ | H | H | O | Cytosine | OH | Me |
| monophosphate | CH₃ | H | H | O | 4-(N-mono-acetyl)cytosine | OH | Me |
| monophosphate | CH₃ | H | H | O | 4-(N,N-diacetyl)cytosine | OH | Me |
| monophosphate | CH₃ | H | H | O | Uracil | OH | Me |
| monophosphate | CH₃ | H | H | O | 5-Fluorouracil | OH | Me |
| monophosphate | CH₃ | H | H | S | 2,4-O-Diacetyluracil | OH | Me |
| monophosphate | CH₃ | H | H | S | Hypoxanthine | OH | Me |
| monophosphate | CH₃ | H | H | S | 2,4-O-Diacetylthymine | OH | Me |
| monophosphate | CH₃ | H | H | S | Thymine | OH | Me |
| monophosphate | CH₃ | H | H | S | Cytosine | OH | Me |
| monophosphate | CH₃ | H | H | S | 4-(N-mono-acetyl)cytosine | OH | Me |
| monophosphate | CH₃ | H | H | S | 4-(N,N-diacetyl)cytosine | OH | Me |
| monophosphate | CH₃ | H | H | S | Uracil | OH | Me |
| monophosphate | CH₃ | H | H | S | 5-Fluorouracil | OH | Me |
| diphosphate | CH₃ | H | H | O | 2,4-O-Diacetyluracil | OH | Me |
| diphosphate | CH₃ | H | H | O | Hypoxanthine | OH | Me |
| diphosphate | CH₃ | H | H | O | 2,4-O-Diacetylthymine | OH | Me |
| diphosphate | CH₃ | H | H | O | Thymine | OH | Me |
| diphosphate | CH₃ | H | H | O | Cytosine | OH | Me |
| diphosphate | CH₃ | H | H | O | 4-(N-mono-acetyl)cytosine | OH | Me |
| diphosphate | CH₃ | H | H | O | 4-(N,N-diacetyl)cytosine | OH | Me |
| diphosphate | CH₃ | H | H | O | Uracil | OH | Me |
| diphosphate | CH₃ | H | H | O | 5-Fluorouracil | OH | Me |
| diphosphate | CH₃ | H | H | S | 2,4-O-Diacetyluracil | OH | Me |
| diphosphate | CH₃ | H | H | S | Hypoxanthine | OH | Me |
| diphosphate | CH₃ | H | H | S | 2,4-O-Diacetylthymine | OH | Me |
| diphosphate | CH₃ | H | H | S | Thymine | OH | Me |
| diphosphate | CH₃ | H | H | S | Cytosine | OH | Me |
| triphosphate | CH₃ | H | H | O | 2,4-O-Diacetyluracil | OH | Me |
| triphosphate | CH₃ | H | H | O | Hypoxanthine | OH | Me |
| triphosphate | CH₃ | H | H | O | 2,4-O-Diacetylthymine | OH | Me |
| triphosphate | CH₃ | H | H | O | Thymine | OH | Me |
| triphosphate | CH₃ | H | H | O | Cytosine | OH | Me |
| triphosphate | CH₃ | H | H | O | 4-(N-mono-acetyl)cytosine | OH | Me |
| triphosphate | CH₃ | H | H | O | 4-(N,N-diacetyl)cytosine | OH | Me |
| triphosphate | CH₃ | H | H | O | Uracil | OH | Me |
| triphosphate | CH₃ | H | H | O | 5-Fluorouracil | OH | Me |
| triphosphate | CH₃ | H | H | S | 2,4-O-Diacetyluracil | OH | Me |
| triphosphate | CH₃ | H | H | S | Hypoxanthine | OH | Me |
| triphosphate | CH₃ | H | H | S | 2,4-O-Diacetylthymine | OH | Me |
| triphosphate | CH₃ | H | H | S | Thymine | OH | Me |
| triphosphate | CH₃ | H | H | S | Cytosine | OH | Me |
| monophosphate | CF₃ | H | H | O | 2,4-O-Diacetyluracil | OH | Me |
| monophosphate | CF₃ | H | H | O | Hypoxanthine | OH | Me |
| monophosphate | CF₃ | H | H | O | 2,4-O-Diacetylthymine | OH | Me |
| monophosphate | CF₃ | H | H | O | Thymine | OH | Me |
| monophosphate | CF₃ | H | H | O | Cytosine | OH | Me |
| monophosphate | CF₃ | H | H | O | 4-(N-mono-acetyl)cytosine | OH | Me |
| monophosphate | CF₃ | H | H | O | 4-(N,N-diacetyl)cytosine | OH | Me |
| monophosphate | CF₃ | H | H | O | Uracil | OH | Me |
| monophosphate | CF₃ | H | H | O | 5-Fluorouracil | OH | Me |
| monophosphate | CF₃ | H | H | S | 2,4-O-Diacetyluracil | OH | Me |
| monophosphate | CF₃ | H | H | S | Hypoxanthine | OH | Me |
| monophosphate | CF₃ | H | H | S | 2,4-O-Diacetylthymine | OH | Me |
| monophosphate | CF₃ | H | H | S | Thymine | OH | Me |
| monophosphate | CF₃ | H | H | S | Cytosine | OH | Me |
| monophosphate | CF₃ | H | H | S | 4-(N-mono-acetyl)cytosine | OH | Me |
| monophosphate | CF₃ | H | H | S | 4-(N,N-diacetyl)cytosine | OH | Me |
| monophosphate | CF₃ | H | H | S | Uracil | OH | Me |
| monophosphate | CF₃ | H | H | S | 5-Fluorouracil | OH | Me |
| acetyl | CH₃ | H | H | O | 4-(N,N-diacetyl)cytosine | H | Br |
| acetyl | CH₃ | H | H | S | 4-(N,N-diacetyl)cytosine | H | Br |

-continued

| R¹ | R⁶ | R⁷ | R⁸ | X | Base | R¹⁰ | R⁹ |
|---|---|---|---|---|---|---|---|
| acetyl | CH₃ | OH | H | O | 4-(N,N-diacetyl)cytosine | H | Br |
| acetyl | CH₃ | OH | H | S | 4-(N,N-diacetyl)cytosine | H | Br |

Example 2

Preparation of 2'-C-methylriboadenine

The title compound was prepared according to a published procedure (R. E. Harry-O'kuru, J. M. Smith, and M. S. Wolfe, "A short, flexible route toward 2'-C-branched ribonucleosides", *J. Org. Chem.* 1997, 62, 1754–1759) (Scheme 8).

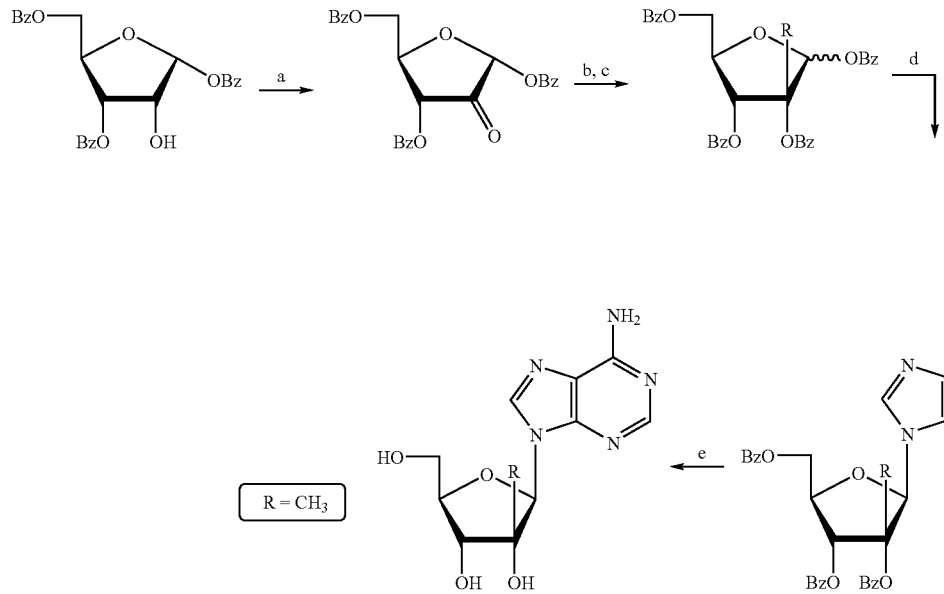

Scheme 8

(a) Dess-Martin periodinane; (b) MeMgBr/TiCl₄; (c) BzCl, DMAP, Et₃N; (d) bis(trimethylsilyl)acetamide, N⁶-benzoyl adenine, TMSOTf; (e) NH₃/MeOH In a similar manner, but using the appropriate sugar and pyrimidine or purine bases, the following nucleosides of Formula II are prepared.

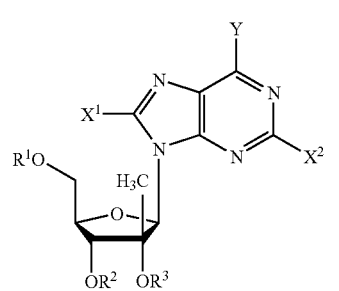

(II)

wherein:

| R¹ | R² | R³ | X¹ | X² | Y |
|---|---|---|---|---|---|
| H | H | H | H | H | H |
| H | H | H | H | H | NH₂ |
| H | H | H | H | H | NH-cyclopropyl |

-continued

| R¹ | R² | R³ | X¹ | X² | Y |
|---|---|---|---|---|---|
| H | H | H | H | H | NH-methyl |
| H | H | H | H | H | NH-ethyl |
| H | H | H | H | H | NH-acetyl |
| H | H | H | H | H | OH |
| H | H | H | H | H | OMe |
| H | H | H | H | H | OEt |
| H | H | H | H | H | O-cyclopropyl |
| H | H | H | H | H | O-acetyl |
| H | H | H | H | H | SH |
| H | H | H | H | H | SMe |
| H | H | H | H | H | SEt |
| H | H | H | H | H | S-cyclopropyl |
| H | H | H | H | H | F |
| H | H | H | H | H | Cl |
| H | H | H | H | H | Br |
| H | H | H | H | H | I |
| monophosphate | H | H | H | H | NH₂ |
| monophosphate | H | H | H | H | NH-acetyl |
| monophosphate | H | H | H | H | NH-cyclopropyl |

-continued

| R¹ | R² | R³ | X¹ | X² | Y |
|---|---|---|---|---|---|
| monophosphate | H | H | H | H | NH-methyl |
| monophosphate | H | H | H | H | NH-ethyl |
| monophosphate | H | H | H | H | OH |
| monophosphate | H | H | H | H | O-acetyl |
| monophosphate | H | H | H | H | OMe |
| monophosphate | H | H | H | H | OEt |
| monophosphate | H | H | H | H | O-cyclopropyl |
| monophosphate | H | H | H | H | SH |
| monophosphate | H | H | H | H | SMe |
| monophosphate | H | H | H | H | SEt |
| monophosphate | H | H | H | H | S-cyclopropyl |
| monophosphate | H | H | H | H | F |
| monophosphate | H | H | H | H | Cl |
| monophosphate | H | H | H | H | Br |
| monophosphate | H | H | H | H | I |
| diphosphate | H | H | H | H | NH₂ |
| diphosphate | H | H | H | H | NH-acetyl |
| diphosphate | H | H | H | H | NH-cyclopropyl |
| diphosphate | H | H | H | H | NH-methyl |
| diphosphate | H | H | H | H | NH-ethyl |
| diphosphate | H | H | H | H | OH |
| diphosphate | H | H | H | H | O-acetyl |
| diphosphate | H | H | H | H | OMe |
| diphosphate | H | H | H | H | OEt |
| diphosphate | H | H | H | H | O-cyclopropyl |
| diphosphate | H | H | H | H | SH |
| diphosphate | H | H | H | H | SMe |
| diphosphate | H | H | H | H | SEt |
| diphosphate | H | H | H | H | S-cyclopropyl |
| diphosphate | H | H | H | H | F |
| diphosphate | H | H | H | H | Cl |
| diphosphate | H | H | H | H | Br |
| diphosphate | H | H | H | H | I |
| triphosphate | H | H | H | H | NH₂ |
| triphosphate | H | H | H | H | NH-acetyl |
| triphosphate | H | H | H | H | NH-cyclopropyl |
| triphosphate | H | H | H | H | NH-methyl |
| triphosphate | H | H | H | H | NH-ethyl |
| triphosphate | H | H | H | H | OH |
| triphosphate | H | H | H | H | OMe |
| triphosphate | H | H | H | H | OEt |
| triphosphate | H | H | H | H | O-cyclopropyl |
| triphosphate | H | H | H | H | O-acetyl |
| triphosphate | H | H | H | H | SH |
| triphosphate | H | H | H | H | SMe |
| triphosphate | H | H | H | H | SEt |
| triphosphate | H | H | H | H | S-cyclopropyl |
| triphosphate | H | H | H | H | F |
| triphosphate | H | H | H | H | Cl |
| triphosphate | H | H | H | H | Br |
| triphosphate | H | H | H | H | I |
| monophosphate | monophosphate | monophosphate | H | H | NH₂ |
| monophosphate | monophosphate | monophosphate | H | H | NH-cyclopropyl |
| monophosphate | monophosphate | monophosphate | H | H | OH |
| monophosphate | monophosphate | monophosphate | H | H | F |
| monophosphate | monophosphate | monophosphate | H | H | Cl |
| diphosphate | diphosphate | diphosphate | H | H | NH₂ |
| diphosphate | diphosphate | diphosphate | H | H | NH-cyclopropyl |
| diphosphate | diphosphate | diphosphate | H | H | OH |
| diphosphate | diphosphate | diphosphate | H | H | F |
| diphosphate | diphosphate | diphosphate | H | H | Cl |
| triphosphate | triphosphate | triphosphate | H | H | NH₂ |
| triphosphate | triphosphate | triphosphate | H | H | NH-cyclopropyl |
| triphosphate | triphosphate | triphosphate | H | H | OH |
| triphosphate | triphosphate | triphosphate | H | H | F |
| triphosphate | triphosphate | triphosphate | H | H | Cl |
| H | H | H | F | H | NH₂ |
| H | H | H | F | H | NH-cyclopropyl |
| H | H | H | F | H | OH |
| H | H | H | F | H | F |
| H | H | H | F | H | Cl |
| H | H | H | Cl | H | NH₂ |
| H | H | H | Cl | H | NH-cyclopropyl |
| H | H | H | Cl | H | OH |
| H | H | H | Cl | H | F |
| H | H | H | Cl | H | Cl |
| H | H | H | Br | H | NH₂ |
| H | H | H | Br | H | NH-cyclopropyl |
| H | H | H | Br | H | OH |
| H | H | H | Br | H | F |
| H | H | H | Br | H | Cl |
| H | H | H | NH₂ | H | NH₂ |
| H | H | H | NH₂ | H | NH-cyclopropyl |
| H | H | H | NH₂ | H | OH |
| H | H | H | NH₂ | H | F |
| H | H | H | NH₂ | H | Cl |
| H | H | H | SH | H | NH₂ |
| H | H | H | SH | H | NH-cyclopropyl |
| H | H | H | SH | H | OH |
| H | H | H | SH | H | F |
| H | H | H | SH | H | Cl |
| acetyl | H | H | H | H | NH₂ |
| acetyl | H | H | H | H | NH-cyclopropyl |
| acetyl | H | H | H | H | OH |
| acetyl | H | H | H | H | F |
| acetyl | H | H | H | H | Cl |
| acetyl | H | H | F | H | NH₂ |
| acetyl | H | H | F | H | NH-cyclopropyl |
| acetyl | H | H | F | H | OH |
| acetyl | H | H | F | H | F |
| acetyl | H | H | F | H | Cl |
| H | acetyl | acetyl | H | H | NH₂ |
| H | acetyl | acetyl | H | H | NH-cyclopropyl |
| H | acetyl | acetyl | H | H | OH |
| H | acetyl | acetyl | H | H | F |
| H | acetyl | acetyl | H | H | Cl |
| acetyl | acetyl | acetyl | H | H | NH₂ |
| acetyl | acetyl | acetyl | H | H | NH-cyclopropyl |
| acetyl | acetyl | acetyl | H | H | OH |
| acetyl | acetyl | acetyl | H | H | F |
| acetyl | acetyl | acetyl | H | H | Cl |
| monophosphate | acetyl | acetyl | H | H | NH₂ |
| monophosphate | acetyl | acetyl | H | H | NH-cyclopropyl |
| monophosphate | acetyl | acetyl | H | H | OH |
| monophosphate | acetyl | acetyl | H | H | F |
| monophosphate | acetyl | acetyl | H | H | Cl |
| diphosphate | acetyl | acetyl | H | H | NH₂ |
| diphosphate | acetyl | acetyl | H | H | NH-cyclopropyl |
| diphosphate | acetyl | acetyl | H | H | OH |
| diphosphate | acetyl | acetyl | H | H | F |
| diphosphate | acetyl | acetyl | H | H | Cl |
| triphosphate | acetyl | acetyl | H | H | NH₂ |
| triphosphate | acetyl | acetyl | H | H | NH-cyclopropyl |
| triphosphate | acetyl | acetyl | H | H | OH |
| triphosphate | acetyl | acetyl | H | H | F |
| triphosphate | acetyl | acetyl | H | H | Cl |
| H | H | H | H | NH₂ | H |
| H | H | H | H | NH₂ | NH₂ |
| H | H | H | H | NH₂ | NH-cyclopropyl |
| H | H | H | H | NH₂ | NH-methyl |
| H | H | H | H | NH₂ | NH-ethyl |
| H | H | H | H | NH₂ | NH-acetyl |
| H | H | H | H | NH₂ | OH |
| H | H | H | H | NH₂ | OMe |
| H | H | H | H | NH₂ | OEt |
| H | H | H | H | NH₂ | O-cyclopropyl |
| H | H | H | H | NH₂ | O-acetyl |

-continued

| R¹ | R² | R³ | X¹ | X² | Y |
|---|---|---|---|---|---|
| H | H | H | H | NH₂ | SH |
| H | H | H | H | NH₂ | SMe |
| H | H | H | H | NH₂ | SEt |
| H | H | H | H | NH₂ | S-cyclopropyl |
| H | H | H | H | NH₂ | F |
| H | H | H | H | NH₂ | Cl |
| H | H | H | H | NH₂ | Br |
| H | H | H | H | NH₂ | I |
| monophosphate | H | H | H | NH₂ | NH₂ |
| monophosphate | H | H | H | NH₂ | NH-acetyl |
| monophosphate | H | H | H | NH₂ | NH-cyclopropyl |
| monophosphate | H | H | H | NH₂ | NH-methyl |
| monophosphate | H | H | H | NH₂ | NH-ethyl |
| monophosphate | H | H | H | NH₂ | OH |
| monophosphate | H | H | H | NH₂ | O-acetyl |
| monophosphate | H | H | H | NH₂ | OMe |
| monophosphate | H | H | H | NH₂ | OEt |
| monophosphate | H | H | H | NH₂ | O-cyclopropyl |
| monophosphate | H | H | H | NH₂ | SH |
| monophosphate | H | H | H | NH₂ | SMe |
| monophosphate | H | H | H | NH₂ | SEt |
| monophosphate | H | H | H | NH₂ | S-cyclopropyl |
| monophosphate | H | H | H | NH₂ | F |
| monophosphate | H | H | H | NH₂ | Cl |
| monophosphate | H | H | H | NH₂ | Br |
| monophosphate | H | H | H | NH₂ | I |
| diphosphate | H | H | H | NH₂ | NH₂ |
| diphosphate | H | H | H | NH₂ | NH-acetyl |
| diphosphate | H | H | H | NH₂ | NH-cyclopropyl |
| diphosphate | H | H | H | NH₂ | NH-methyl |
| diphosphate | H | H | H | NH₂ | NH-ethyl |
| diphosphate | H | H | H | NH₂ | OH |
| diphosphate | H | H | H | NH₂ | O-acetyl |
| diphosphate | H | H | H | NH₂ | OMe |
| diphosphate | H | H | H | NH₂ | OEt |
| diphosphate | H | H | H | NH₂ | O-cyclopropyl |
| diphosphate | H | H | H | NH₂ | SH |
| diphosphate | H | H | H | NH₂ | SMe |
| diphosphate | H | H | H | NH₂ | SEt |
| diphosphate | H | H | H | NH₂ | S-cyclopropyl |
| diphosphate | H | H | H | NH₂ | F |
| diphosphate | H | H | H | NH₂ | Cl |
| diphosphate | H | H | H | NH₂ | Br |
| diphosphate | H | H | H | NH₂ | I |
| triphosphate | H | H | H | NH₂ | NH₂ |
| triphosphate | H | H | H | NH₂ | NH-acetyl |
| triphosphate | H | H | H | NH₂ | NH-cyclopropyl |
| triphosphate | H | H | H | NH₂ | NH-methyl |
| triphosphate | H | H | H | NH₂ | NH-ethyl |
| triphosphate | H | H | H | NH₂ | OH |
| triphosphate | H | H | H | NH₂ | OMe |
| triphosphate | H | H | H | NH₂ | OEt |
| triphosphate | H | H | H | NH₂ | O-cyclopropyl |
| triphosphate | H | H | H | NH₂ | O-acetyl |
| triphosphate | H | H | H | NH₂ | SH |
| triphosphate | H | H | H | NH₂ | SMe |
| triphosphate | H | H | H | NH₂ | SEt |
| triphosphate | H | H | H | NH₂ | S-cyclopropyl |
| triphosphate | H | H | H | NH₂ | F |
| triphosphate | H | H | H | NH₂ | Cl |
| triphosphate | H | H | H | NH₂ | Br |
| triphosphate | H | H | H | NH₂ | I |
| monophosphate | monophosphate | monophosphate | H | NH₂ | NH₂ |
| monophosphate | monophosphate | monophosphate | H | NH₂ | NH-cyclopropyl |
| monophosphate | monophosphate | monophosphate | H | NH₂ | OH |
| monophosphate | monophosphate | monophosphate | H | NH₂ | F |
| monophosphate | monophosphate | monophosphate | H | NH₂ | Cl |
| diphosphate | diphosphate | diphosphate | H | NH₂ | NH₂ |
| diphosphate | diphosphate | diphosphate | H | NH₂ | NH-cyclopropyl |
| diphosphate | diphosphate | diphosphate | H | NH₂ | OH |
| diphosphate | diphosphate | diphosphate | H | NH₂ | F |
| diphosphate | diphosphate | diphosphate | H | NH₂ | Cl |
| triphosphate | triphosphate | triphosphate | H | NH₂ | NH₂ |
| triphosphate | triphosphate | triphosphate | H | NH₂ | NH-cyclopropyl |
| triphosphate | triphosphate | triphosphate | H | NH₂ | OH |
| triphosphate | triphosphate | triphosphate | H | NH₂ | F |
| triphosphate | triphosphate | triphosphate | H | NH₂ | Cl |
| H | H | H | F | NH₂ | NH₂ |
| H | H | H | F | NH₂ | NH-cyclopropyl |
| H | H | H | F | NH₂ | OH |
| H | H | H | F | NH₂ | F |
| H | H | H | F | NH₂ | Cl |
| H | H | H | Cl | NH₂ | NH₂ |
| H | H | H | Cl | NH₂ | NH-cyclopropyl |
| H | H | H | Cl | NH₂ | OH |
| H | H | H | Cl | NH₂ | F |
| H | H | H | Cl | NH₂ | Cl |
| H | H | H | Br | NH₂ | NH₂ |
| H | H | H | Br | NH₂ | NH-cyclopropyl |
| H | H | H | Br | NH₂ | OH |
| H | H | H | Br | NH₂ | F |
| H | H | H | Br | NH₂ | Cl |
| H | H | H | NH₂ | NH₂ | NH₂ |
| H | H | H | NH₂ | NH₂ | NH-cyclopropyl |
| H | H | H | NH₂ | NH₂ | OH |
| H | H | H | NH₂ | NH₂ | F |
| H | H | H | NH₂ | NH₂ | Cl |
| H | H | H | SH | NH₂ | NH₂ |
| H | H | H | SH | NH₂ | NH-cyclopropyl |
| H | H | H | SH | NH₂ | OH |
| H | H | H | SH | NH₂ | F |
| H | H | H | SH | NH₂ | Cl |
| acetyl | H | H | H | NH₂ | NH₂ |
| acetyl | H | H | H | NH₂ | NH-cyclopropyl |
| acetyl | H | H | H | NH₂ | OH |
| acetyl | H | H | H | NH₂ | F |
| acetyl | H | H | H | NH₂ | Cl |
| acetyl | H | H | F | NH₂ | NH₂ |
| acetyl | H | H | F | NH₂ | NH-cyclopropyl |
| acetyl | H | H | F | NH₂ | OH |
| acetyl | H | H | F | NH₂ | F |
| acetyl | H | H | F | NH₂ | Cl |
| H | acetyl | acetyl | H | NH₂ | NH₂ |
| H | acetyl | acetyl | H | NH₂ | NH-cyclopropyl |
| H | acetyl | acetyl | H | NH₂ | OH |
| H | acetyl | acetyl | H | NH₂ | F |
| H | acetyl | acetyl | H | NH₂ | Cl |
| acetyl | acetyl | acetyl | H | NH₂ | NH₂ |
| acetyl | acetyl | acetyl | H | NH₂ | NH-cyclopropyl |
| acetyl | acetyl | acetyl | H | NH₂ | OH |
| acetyl | acetyl | acetyl | H | NH₂ | F |
| acetyl | acetyl | acetyl | H | NH₂ | Cl |
| monophosphate | acetyl | acetyl | H | NH₂ | NH₂ |
| monophosphate | acetyl | acetyl | H | NH₂ | NH-cyclopropyl |
| monophosphate | acetyl | acetyl | H | NH₂ | OH |
| monophosphate | acetyl | acetyl | H | NH₂ | F |
| monophosphate | acetyl | acetyl | H | NH₂ | Cl |
| diphosphate | acetyl | acetyl | H | NH₂ | NH₂ |
| diphosphate | acetyl | acetyl | H | NH₂ | NH-cyclopropyl |
| diphosphate | acetyl | acetyl | H | NH₂ | OH |
| diphosphate | acetyl | acetyl | H | NH₂ | F |
| diphosphate | acetyl | acetyl | H | NH₂ | Cl |
| triphosphate | acetyl | acetyl | H | NH₂ | NH₂ |
| triphosphate | acetyl | acetyl | H | NH₂ | NH-cyclopropyl |
| triphosphate | acetyl | acetyl | H | NH₂ | OH |
| triphosphate | acetyl | acetyl | H | NH₂ | F |
| triphosphate | acetyl | acetyl | H | NH₂ | Cl |
| H | H | H | H | Cl | H |

-continued

| R¹ | R² | R³ | X¹ | X² | Y |
|---|---|---|---|---|---|
| H | H | H | H | Cl | H |
| H | H | H | H | Cl | NH₂ |
| H | H | H | H | Cl | NH-cyclopropyl |
| H | H | H | H | Cl | NH-methyl |
| H | H | H | H | Cl | NH-ethyl |
| H | H | H | H | Cl | NH-acetyl |
| H | H | H | H | Cl | OH |
| H | H | H | H | Cl | OMe |
| H | H | H | H | Cl | OEt |
| H | H | H | H | Cl | O-cyclopropyl |
| H | H | H | H | Cl | O-acetyl |
| H | H | H | H | Cl | SH |
| H | H | H | H | Cl | SMe |
| H | H | H | H | Cl | SEt |
| H | H | H | H | Cl | S-cyclopropyl |
| monophosphate | H | H | H | Cl | NH₂ |
| monophosphate | H | H | H | Cl | NH-acetyl |
| monophosphate | H | H | H | Cl | NH-cyclopropyl |
| monophosphate | H | H | H | Cl | NH-methyl |
| monophosphate | H | H | H | Cl | NH-ethyl |
| monophosphate | H | H | H | Cl | OH |
| monophosphate | H | H | H | Cl | O-acetyl |
| monophosphate | H | H | H | Cl | OMe |
| monophosphate | H | H | H | Cl | OEt |
| monophosphate | H | H | H | Cl | O-cyclopropyl |
| monophosphate | H | H | H | Cl | SH |
| monophosphate | H | H | H | Cl | SMe |
| monophosphate | H | H | H | Cl | SEt |
| monophosphate | H | H | H | Cl | S-cyclopropyl |
| diphosphate | H | H | H | Cl | NH₂ |
| diphosphate | H | H | H | Cl | NH-acetyl |
| diphosphate | H | H | H | Cl | NH-cyclopropyl |
| diphosphate | H | H | H | Cl | NH-methyl |
| diphosphate | H | H | H | Cl | NH-ethyl |
| diphosphate | H | H | H | Cl | OH |
| diphosphate | H | H | H | Cl | O-acetyl |
| diphosphate | H | H | H | Cl | OMe |
| diphosphate | H | H | H | Cl | OEt |
| diphosphate | H | H | H | Cl | O-cyclopropyl |
| diphosphate | H | H | H | Cl | SH |
| diphosphate | H | H | H | Cl | SMe |
| diphosphate | H | H | H | Cl | SEt |
| diphosphate | H | H | H | Cl | S-cyclopropyl |
| triphosphate | H | H | H | Cl | NH₂ |
| triphosphate | H | H | H | Cl | NH-acetyl |
| triphosphate | H | H | H | Cl | NH-cyclopropyl |
| triphosphate | H | H | H | Cl | NH-methyl |
| triphosphate | H | H | H | Cl | NH-ethyl |
| triphosphate | H | H | H | Cl | OH |
| triphosphate | H | H | H | Cl | OMe |
| triphosphate | H | H | H | Cl | OEt |
| triphosphate | H | H | H | Cl | O-cyclopropyl |
| triphosphate | H | H | H | Cl | O-acetyl |
| triphosphate | H | H | H | Cl | SH |
| triphosphate | H | H | H | Cl | SMe |
| triphosphate | H | H | H | Cl | SEt |
| triphosphate | H | H | H | Cl | S-cyclopropyl |
| monophosphate | monophosphate | monophosphate | H | Cl | NH₂ |
| monophosphate | monophosphate | monophosphate | H | Cl | NH-cyclopropyl |
| monophosphate | monophosphate | monophosphate | H | Cl | OH |
| diphosphate | diphosphate | diphosphate | H | Cl | NH₂ |
| diphosphate | diphosphate | diphosphate | H | Cl | NH-cyclopropyl |
| diphosphate | diphosphate | diphosphate | H | Cl | OH |
| triphosphate | triphosphate | triphosphate | H | Cl | NH₂ |
| triphosphate | triphosphate | triphosphate | H | Cl | NH-cyclopropyl |
| triphosphate | triphosphate | triphosphate | H | Cl | OH |
| H | H | H | F | Cl | NH₂ |
| H | H | H | F | Cl | NH-cyclopropyl |
| H | H | H | F | Cl | OH |
| H | H | H | Cl | Cl | NH₂ |
| H | H | H | Cl | Cl | NH-cyclopropyl |
| H | H | H | Cl | Cl | OH |
| H | H | H | Br | Cl | NH₂ |
| H | H | H | Br | Cl | NH-cyclopropyl |
| H | H | H | Br | Cl | OH |
| H | H | H | NH₂ | Cl | NH₂ |
| H | H | H | NH₂ | Cl | NH-cyclopropyl |
| H | H | H | NH₂ | Cl | OH |
| H | H | H | SH | Cl | NH₂ |
| H | H | H | SH | Cl | NH-cyclopropyl |
| H | H | H | SH | Cl | OH |
| acetyl | H | H | H | Cl | NH₂ |
| acetyl | H | H | H | Cl | NH-cyclopropyl |
| acetyl | H | H | H | Cl | OH |
| acetyl | H | H | F | Cl | NH₂ |
| acetyl | H | H | F | Cl | NH-cyclopropyl |
| acetyl | H | H | F | Cl | OH |
| H | acetyl | acetyl | H | Cl | NH₂ |
| H | acetyl | acetyl | H | Cl | NH-cyclopropyl |
| H | acetyl | acetyl | H | Cl | OH |
| acetyl | acetyl | acetyl | H | Cl | NH₂ |
| acetyl | acetyl | acetyl | H | Cl | NH-cyclopropyl |
| acetyl | acetyl | acetyl | H | Cl | OH |
| monophosphate | acetyl | acetyl | H | Cl | NH₂ |
| monophosphate | acetyl | acetyl | H | Cl | NH-cyclopropyl |
| monophosphate | acetyl | acetyl | H | Cl | OH |
| diphosphate | acetyl | acetyl | H | Cl | NH₂ |
| diphosphate | acetyl | acetyl | H | Cl | NH-cyclopropyl |
| diphosphate | acetyl | acetyl | H | Cl | OH |
| triphosphate | acetyl | acetyl | H | Cl | NH₂ |
| triphosphate | acetyl | acetyl | H | Cl | NH-cyclopropyl |
| triphosphate | acetyl | acetyl | H | Cl | OH |
| H | H | H | H | Cl | NH₂ |
| H | H | H | H | Cl | NH-cyclopropyl |
| H | H | H | H | Cl | OH |
| H | H | H | H | Br | NH₂ |
| H | H | H | H | Br | NH-cyclopropyl |
| H | H | H | H | Br | OH |

Alternatively, the following nucleosides of Formula V are prepared, using the appropriate sugar and pyrimidine or purine bases.

$$\text{(V)}$$

wherein:

| R¹ | R² | R³ | X¹ | Y |
|---|---|---|---|---|
| H | H | H | H | H |
| H | H | H | H | NH₂ |
| H | H | H | H | NH-cyclopropyl |
| H | H | H | H | NH-methyl |
| H | H | H | H | NH-ethyl |
| H | H | H | H | NH-acetyl |

-continued

| R¹ | R² | R³ | X¹ | Y |
|---|---|---|---|---|
| H | H | H | H | OH |
| H | H | H | H | OMe |
| H | H | H | H | OEt |
| H | H | H | H | O-cyclopropyl |
| H | H | H | H | O-acetyl |
| H | H | H | H | SH |
| H | H | H | H | SMe |
| H | H | H | H | SEt |
| H | H | H | H | S-cyclopropyl |
| monophosphate | H | H | H | NH₂ |
| monophosphate | H | H | H | NH-acetyl |
| monophosphate | H | H | H | NH-cyclopropyl |
| monophosphate | H | H | H | NH-methyl |
| monophosphate | H | H | H | NH-ethyl |
| monophosphate | H | H | H | OH |
| monophosphate | H | H | H | O-acetyl |
| monophosphate | H | H | H | OMe |
| monophosphate | H | H | H | OEt |
| monophosphate | H | H | H | O-cyclopropyl |
| monophosphate | H | H | H | SH |
| monophosphate | H | H | H | SMe |
| monophosphate | H | H | H | SEt |
| monophosphate | H | H | H | S-cyclopropyl |
| diphosphate | H | H | H | NH₂ |
| diphosphate | H | H | H | NH-acetyl |
| diphosphate | H | H | H | NH-cyclopropyl |
| diphosphate | H | H | H | NH-methyl |
| diphosphate | H | H | H | NH-ethyl |
| diphosphate | H | H | H | OH |
| diphosphate | H | H | H | O-acetyl |
| diphosphate | H | H | H | OMe |
| diphosphate | H | H | H | OEt |
| diphosphate | H | H | H | O-cyclopropyl |
| diphosphate | H | H | H | SH |
| diphosphate | H | H | H | SMe |
| diphosphate | H | H | H | SEt |
| diphosphate | H | H | H | S-cyclopropyl |
| triphosphate | H | H | H | NH₂ |
| triphosphate | H | H | H | NH-acetyl |
| triphosphate | H | H | H | NH-cyclopropyl |
| triphosphate | H | H | H | NH-methyl |
| triphosphate | H | H | H | NH-ethyl |
| triphosphate | H | H | H | OH |
| triphosphate | H | H | H | OMe |
| triphosphate | H | H | H | OEt |
| triphosphate | H | H | H | O-cyclopropyl |
| triphosphate | H | H | H | O-acetyl |
| triphosphate | H | H | H | SH |
| triphosphate | H | H | H | SMe |
| triphosphate | H | H | H | SEt |
| triphosphate | H | H | H | S-cyclopropyl |
| monophosphate | monophosphate | H | H | NH₂ |
| monophosphate | monophosphate | H | H | NH-cyclopropyl |
| monophosphate | monophosphate | H | H | OH |
| diphosphate | diphosphate | diphosphate | H | NH₂ |
| diphosphate | diphosphate | diphosphate | H | NH-cyclopropyl |
| diphosphate | diphosphate | diphosphate | H | OH |
| triphosphate | triphosphate | triphosphate | H | NH₂ |
| triphosphate | triphosphate | triphosphate | H | NH-cyclopropyl |
| triphosphate | triphosphate | triphosphate | H | OH |
| H | H | H | F | NH₂ |
| H | H | H | F | NH-cyclopropyl |
| H | H | H | F | OH |
| H | H | H | Cl | NH₂ |
| H | H | H | Cl | NH-cyclopropyl |
| H | H | H | Cl | OH |
| H | H | H | Br | NH₂ |
| H | H | H | Br | NH-cyclopropyl |
| H | H | H | Br | OH |
| H | H | H | NH₂ | NH₂ |
| H | H | H | NH₂ | NH-cyclopropyl |
| H | H | H | NH₂ | OH |
| H | H | H | SH | NH₂ |
| H | H | H | SH | NH-cyclopropyl |
| H | H | H | SH | OH |
| acetyl | H | H | H | NH₂ |
| acetyl | H | H | H | NH-cyclopropyl |
| acetyl | H | H | H | OH |
| acetyl | H | H | F | NH₂ |
| acetyl | H | H | F | NH-cyclopropyl |
| acetyl | H | H | F | OH |
| H | acetyl | acetyl | H | NH₂ |
| H | acetyl | acetyl | H | NH-cyclopropyl |
| H | acetyl | acetyl | H | OH |
| acetyl | acetyl | acetyl | H | NH₂ |
| acetyl | acetyl | acetyl | H | NH-cyclopropyl |
| acetyl | acetyl | acetyl | H | OH |
| monophosphate | acetyl | acetyl | H | NH₂ |
| monophosphate | acetyl | acetyl | H | NH-cyclopropyl |
| monophosphate | acetyl | acetyl | H | OH |
| diphosphate | acetyl | acetyl | H | NH₂ |
| diphosphate | acetyl | acetyl | H | NH-cyclopropyl |
| diphosphate | acetyl | acetyl | H | OH |
| triphosphate | acetyl | acetyl | H | NH₂ |
| triphosphate | acetyl | acetyl | H | NH-cyclopropyl |
| triphosphate | acetyl | acetyl | H | OH |

Alternatively, the following nucleosides of Formula X are prepared, using the appropriate sugar and pyrimidine or purine bases.

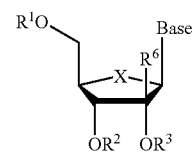

wherein:

| R¹ | R² | R³ | R⁶ | X | Base |
|---|---|---|---|---|---|
| H | H | H | CH₃ | O | 2,4-O-Diacetyluracil |
| H | H | H | CH₃ | O | Hypoxanthine |
| H | H | H | CH₃ | O | 2,4-O-Diacetylthymine |
| H | H | H | CH₃ | O | Thymine |
| H | H | H | CH₃ | O | Cytosine |
| H | H | H | CH₃ | O | 4-(N-mono-acetyl)cytosine |

-continued

| R¹ | R² | R³ | R⁶ | X | Base |
|---|---|---|---|---|---|
| H | H | H | CH₃ | O | 4-(N,N-diacetyl)cytosine |
| H | H | H | CH₃ | O | Uracil |
| H | H | H | CH₃ | O | 5-Fluorouracil |
| H | H | H | CH₃ | S | 2,4-O-Diacetyluraci |
| H | H | H | CH₃ | S | Hypoxanthine |
| H | H | H | CH₃ | S | 2,4-O-Diacetylthymine |
| H | H | H | CH₃ | S | Thymine |
| H | H | H | CH₃ | S | Cytosine |
| H | H | H | CH₃ | S | 4-(N-mono-acetyl)cytosine |
| H | H | H | CH₃ | S | 4-(N,N-diacetyl)cytosine |
| H | H | H | CH₃ | S | Uracil |
| H | H | H | CH₃ | S | 5-Fluorouracil |
| monophosphate | H | H | CH₃ | O | 2,4-O-Diacetyluracil |
| monophosphate | H | H | CH₃ | O | Hypoxanthine |
| monophosphate | H | H | CH₃ | O | 2,4-O-Diacetylthym |
| monophosphate | H | H | CH₃ | O | Thymine |
| monophosphate | H | H | CH₃ | O | Cytosine |
| monophosphate | H | H | CH₃ | O | 4-(N-mono-acetyl)cytosine |
| monophosphate | H | H | CH₃ | O | 4-(N,N-diacetyl)cytosine |
| monophosphate | H | H | CH₃ | O | Uracil |
| monophosphate | H | H | CH₃ | O | 5-Fluorouracil |
| monophosphate | H | H | CH₃ | S | 2,4-O-Diacetyluracil |
| monophosphate | H | H | CH₃ | S | Hypoxanthine |
| monophosphate | H | H | CH₃ | S | 2,4-O-Diacetylthym |
| monophosphate | H | H | CH₃ | S | Thymine |
| monophosphate | H | H | CH₃ | S | Cytosine |
| monophosphate | H | H | CH₃ | S | 4-(N-mono-acetyl)cytosine |
| monophosphate | H | H | CH₃ | S | 4-(N,N-diacetyl)cytosine |
| monophosphate | H | H | CH₃ | S | Uracil |
| monophosphate | H | H | CH₃ | S | 5-Fluorouracil |
| diphosphate | H | H | CH₃ | O | 2,4-O-Diacetyluracil |
| diphosphate | H | H | CH₃ | O | Hypoxanthine |
| diphosphate | H | H | CH₃ | O | 2,4-O-Diacetylthymine |
| diphosphate | H | H | CH₃ | O | Thymine |
| diphosphate | H | H | CH₃ | O | Cytosine |
| diphosphate | H | H | CH₃ | O | 4-(N-mono-acetyl)cytosine |
| diphosphate | H | H | CH₃ | O | 4-(N,N-diacetyl)cytosine |
| diphosphate | H | H | CH₃ | O | Uracil |
| diphosphate | H | H | CH₃ | O | 5-Fluorouracil |
| diphosphate | H | H | CH₃ | S | 2,4-O-Diacetyluracil |
| diphosphate | H | H | CH₃ | S | Hypoxanthine |
| diphosphate | H | H | CH₃ | S | 2,4-O-Diacetylthym |
| diphosphate | H | H | CH₃ | S | Thymine |
| diphosphate | H | H | CH₃ | S | Cytosine |
| triphosphate | H | H | CH₃ | O | 2,4-O-Diacetyluracil |
| triphosphate | H | H | CH₃ | O | Hypoxanthine |
| triphosphate | H | H | CH₃ | O | 2,4-O-Diacetylthymine |
| triphosphate | H | H | CH₃ | O | Thymine |
| triphosphate | H | H | CH₃ | O | Cytosine |
| triphosphate | H | H | CH₃ | O | 4-(N-mono-acetyl)cytosine |
| triphosphate | H | H | CH₃ | O | 4-(N,N-diacetyl)cytosine |
| triphosphate | H | H | CH₃ | O | Uracil |
| triphosphate | H | H | CH₃ | O | 5-Fluorouracil |

-continued

| R¹ | R² | R³ | R⁶ | X | Base |
|---|---|---|---|---|---|
| triphosphate | H | H | CH₃ | S | 2,4-O-Diacetyluracil |
| triphosphate | H | H | CH₃ | S | Hypoxanthine |
| triphosphate | H | H | CH₃ | S | 2,4-O-Diacetylthymine |
| triphosphate | H | H | CH₃ | S | Thymine |
| triphosphate | H | H | CH₃ | S | Cytosine |
| monophosphate | monophosphate | monophosphate | CF₃ | O | 2,4-O-Diacetyluracil |
| monophosphate | monophosphate | monophosphate | CF₃ | O | Hypoxanthine |
| monophosphate | monophosphate | monophosphate | CF₃ | O | 2,4-O-Diacetylthymine |
| monophosphate | monophosphate | monophosphate | CF₃ | O | Thymine |
| monophosphate | monophosphate | monophosphate | CF₃ | O | Cytosine |
| monophosphate | monophosphate | monophosphate | CF₃ | O | 4-(N-mono-acetyl)cytosine |
| monophosphate | monophosphate | monophosphate | CF₃ | O | 4-(N,N-diacetyl)cytosine |
| monophosphate | monophosphate | monophosphate | CF₃ | O | Uracil |
| monophosphate | monophosphate | monophosphate | CF₃ | O | 5-Fluorouracil |
| monophosphate | monophosphate | monophosphate | CF₃ | S | 2,4-O-Diacetyluracil |
| monophosphate | monophosphate | monophosphate | CF₃ | S | Hypoxanthine |
| monophosphate | monophosphate | monophosphate | CF₃ | S | 2,4-O-Diacetylthymine |
| monophosphate | monophosphate | monophosphate | CF₃ | S | Thymine |
| monophosphate | monophosphate | monophosphate | CF₃ | S | Cytosine |
| monophosphate | monophosphate | monophosphate | CF₃ | S | 4-(N-mono-acetyl)cytosine |
| monophosphate | monophosphate | monophosphate | CF₃ | S | 4-(N,N-diacetyl)cytosine |
| monophosphate | monophosphate | monophosphate | CF₃ | S | Uracil |
| monophosphate | monophosphate | monophosphate | CF₃ | S | 5-Fluorouracil |
| acetyl | acetyl | acetyl | CF₃ | O | 4-(N,N-diacetyl)cytosine |
| acetyl | acetyl | acetyl | CF₃ | S | 4-(N,N-diacetyl)cytosine |
| acetyl | acetyl | acetyl | 2-bromo-vinyl | O | 4-(N,N-diacetyl)cytosine |
| acetyl | acetyl | acetyl | 2-bromo-vinyl | S | 4-(N,N-diacetyl)cytosine |
| H | H | H | CH₃ | O | 2-(N,N-diacetyl)-guanine |
| H | H | H | CH₃ | O | 6-O-acetyl guanine |
| H | H | H | CH₃ | O | 8-fluoroguanine |
| H | H | H | CH₃ | O | guanine |
| H | H | H | CH₃ | O | 6-(N,N-diacetyl)-adenine |
| H | H | H | CH₃ | O | 2-fluoroadenine |
| H | H | H | CH₃ | O | 8-fluoroadenine |
| H | H | H | CH₃ | O | 2,8-difluoro-adenine |
| H | H | H | CH₃ | O | adenine |
| H | H | H | CH₃ | S | 2-(N,N-diacetyl)-guanine |
| H | H | H | CH₃ | S | 6-O-acetyl guanine |
| H | H | H | CH₃ | S | 8-fluoroguanine |
| H | H | H | CH₃ | S | guanine |
| H | H | H | CH₃ | S | 6-(N,N-diacetyl)-adenine |
| H | H | H | CH₃ | S | 2-fluoroadenine |
| H | H | H | CH₃ | S | 8-fluoroadenine |
| H | H | H | CH₃ | S | 2,8-difluoro-adenine |
| H | H | H | CH₃ | S | adenine |
| monophosphate | H | H | CH₃ | O | 2-(N,N-diacetyl)-guanine |
| monophosphate | H | H | CH₃ | O | 6-O-acetyl guanine |
| monophosphate | H | H | CH₃ | O | 8-fluoroguanine |
| monophosphate | H | H | CH₃ | O | guanine |
| monophosphate | H | H | CH₃ | O | 6-(N,N-diacetyl)-adenine |
| monophosphate | H | H | CH₃ | O | 2-fluoroadenine |
| monophosphate | H | H | CH₃ | O | 8-fluoroadenine |

-continued

| R¹ | R² | R³ | R⁶ | X | Base |
|---|---|---|---|---|---|
| monophosphate | H | H | CH₃ | O | 2,8-difluoro-adenine |
| monophosphate | H | H | CH₃ | O | adenine |
| monophosphate | H | H | CH₃ | S | 2-(N,N-diacetyl)-guanine |
| monophosphate | H | H | CH₃ | S | 6-O-acetyl guanine |
| monophosphate | H | H | CH₃ | S | 8-fluoroguanine |
| monophosphate | H | H | CH₃ | S | guanine |
| monophosphate | H | H | CH₃ | S | 6-(N,N-diacetyl)-adenine |
| monophosphate | H | H | CH₃ | S | 2-fluoroadenine |
| monophosphate | H | H | CH₃ | S | 8-fluoroadenine |
| monophosphate | H | H | CH₃ | S | 2,8-difluoro-adenine |
| monophosphate | H | H | CH₃ | S | adenine |
| diphosphate | H | H | CH₃ | O | 2-(N,N-diacetyl)-guanine |
| diphosphate | H | H | CH₃ | O | 6-O-acetyl guanine |
| diphosphate | H | H | CH₃ | O | 8-fluoroguanine |
| diphosphate | H | H | CH₃ | O | guanine |
| diphosphate | H | H | CH₃ | O | 6-(N,N-diacetyl)-adenine |
| diphosphate | H | H | CH₃ | O | 2-fluoroadenine |
| diphosphate | H | H | CH₃ | O | 8-fluoroadenine |
| diphosphate | H | H | CH₃ | O | 2,8-difluoro-adenine |
| diphosphate | H | H | CH₃ | O | adenine |
| diphosphate | H | H | CH₃ | S | 2-(N,N-diacetyl)-guanine |
| diphosphate | H | H | CH₃ | S | 6-O-acetyl guanine |
| diphosphate | H | H | CH₃ | S | 8-fluoroguanine |
| diphosphate | H | H | CH₃ | S | guanine |
| diphosphate | H | H | CH₃ | S | 6-(N,N-diacetyl)-adenine |
| diphosphate | H | H | CH₃ | S | 2-fluoroadenine |
| diphosphate | H | H | CH₃ | S | 8-fluoroadenine |
| diphosphate | H | H | CH₃ | S | 2,8-difluoro-adenine |
| diphosphate | H | H | CH₃ | S | adenine |
| triphosphate | H | H | CH₃ | O | 2-(N,N-diacetyl)-guanine |
| triphosphate | H | H | CH₃ | O | 6-O-acetyl guanine |
| triphosphate | H | H | CH₃ | O | 8-fluoroguanine |
| triphosphate | H | H | CH₃ | O | guanine |
| triphosphate | H | H | CH₃ | O | 6-(N,N-diacetyl)-adenine |
| triphosphate | H | H | CH₃ | O | 2-fluoroadenine |
| triphosphate | H | H | CH₃ | O | 8-fluoroadenine |
| triphosphate | H | H | CH₃ | O | 2,8-difluoro-adenine |
| triphosphate | H | H | CH₃ | O | 2-(N,N-diacetyl)-guanine |
| triphosphate | H | H | CH₃ | S | 6-O-acetyl guanine |
| triphosphate | H | H | CH₃ | S | 8-fluoroguanine |
| triphosphate | H | H | CH₃ | S | guanine |
| triphosphate | H | H | CH₃ | S | 6-(N,N-diacetyl)-adenine |
| triphosphate | H | H | CH₃ | S | 2-fluoroadenine |
| triphosphate | H | H | CH₃ | S | 8-fluoroadenine |
| triphosphate | H | H | CH₃ | S | 2,8-difluoro-adenine |
| triphosphate | H | H | CH₃ | S | adenine |
| monophosphate | monophosphate | monophosphate | CF₃ | O | 2-(N,N-diacetyl)-guanine |
| monophosphate | monophosphate | monophosphate | CF₃ | O | 6-O-acetyl guanine |
| monophosphate | monophosphate | monophosphate | CF₃ | O | 8-fluoroguanine |
| monophosphate | monophosphate | monophosphate | CF₃ | O | guanine |
| monophosphate | monophosphate | monophosphate | CF₃ | O | 6-(N,N-diacetyl)-adenine |
| monophosphate | monophosphate | monophosphate | CF₃ | O | 2-fluoroadenine |
| monophosphate | monophosphate | monophosphate | CF₃ | O | 8-fluoroadenine |

-continued

| R¹ | R² | R³ | R⁶ | X | Base |
|---|---|---|---|---|---|
| monophosphate | monophosphate | monophosphate | $CF_3$ | O | 2,8-difluoro-adenine |
| monophosphate | monophosphate | monophosphate | $CF_3$ | O | adenine |
| monophosphate | monophosphate | monophosphate | $CF_3$ | S | 2-(N,N-diacetyl)-guanine |
| monophosphate | monophosphate | monophosphate | $CF_3$ | S | 6-O-acetyl guanine |
| monophosphate | monophosphate | monophosphate | $CF_3$ | S | 8-fluoroguanine |
| monophosphate | monophosphate | monophosphate | $CF_3$ | S | guanine |
| monophosphate | monophosphate | monophosphate | $CF_3$ | S | 6-(N,N-diacetyl)-adenine |
| monophosphate | monophosphate | monophosphate | $CF_3$ | S | 2-fluoroadenine |
| monophosphate | monophosphate | monophosphate | $CF_3$ | S | 8-fluoroadenine |
| monophosphate | monophosphate | monophosphate | $CF_3$ | S | 2,8-difluoro-adenine |
| monophosphate | monophosphate | monophosphate | $CF_3$ | S | adenine |
| acetyl | acetyl | acetyl | $CF_3$ | O | guanine |
| acetyl | acetyl | acetyl | $CF_3$ | S | guanine |
| acetyl | acetyl | acetyl | 2-bromo-vinyl | O | guanine |
| acetyl | acetyl | acetyl | 2-bromo-vinyl | S | guanine |

Alternatively, the following nucleosides of Formula XI are prepared, using the appropriate sugar and pyrimidine or purine bases.

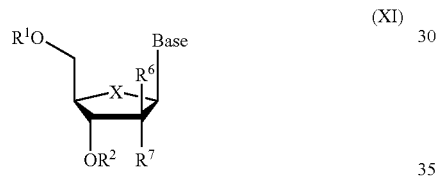

(XI)

wherein:

| R¹ | R² | R⁷ | R⁶ | X | Base |
|---|---|---|---|---|---|
| H | H | H | $CH_3$ | O | 2,4-O-Diacetyluracil |
| H | H | H | $CH_3$ | O | Hypoxanthine |
| H | H | H | $CH_3$ | O | 2,4-O-Diacetylthymine |
| H | H | H | $CH_3$ | O | Thymine |
| H | H | H | $CH_3$ | O | Cytosine |
| H | H | H | $CH_3$ | O | 4-(N-mono-acetyl)cytosine |
| H | H | H | $CH_3$ | O | 4-(N,N-diacetyl)cytosine |
| H | H | H | $CH_3$ | O | Uracil |
| H | H | H | $CH_3$ | O | 5-Fluorouracil |
| H | H | H | $CH_3$ | S | 2,4-O-Diacetyluracil |
| H | H | H | $CH_3$ | S | Hypoxanthine |
| H | H | H | $CH_3$ | S | 2,4-O-Diacetylthymine |
| H | H | H | $CH_3$ | S | Thymine |
| H | H | H | $CH_3$ | S | Cytosine |
| H | H | H | $CH_3$ | S | 4-(N-mono-acetyl)cytosin |
| H | H | H | $CH_3$ | S | 4-(N,N-diacetyl)cytosine |
| H | H | H | $CH_3$ | S | Uracil |
| H | H | H | $CH_3$ $CH_3$ | S | 5-Fluorouracil |
| monophosphate | H | H | $CH_3$ | O | 2,4-O-Diacetyluracil |
| monophosphate | H | H | $CH_3$ | O | Hypoxanthine |
| monophosphate | H | H | $CH_3$ | O | 2,4-O-Diacetylthymine |
| monophosphate | H | H | $CH_3$ | O | Thymine |
| monophosphate | H | H | $CH_3$ | O | Cytosine |
| monophosphate | H | H | $CH_3$ | O | 4-(N-mono-acetyl)cytosine |
| monophosphate | H | H | $CH_3$ | O | 4-(N,N-diacetyl)cytosine |
| monophosphate | H | H | $CH_3$ | O | Uracil |

-continued

| R¹ | R² | R⁷ | R⁶ | X | Base |
|---|---|---|---|---|---|
| monophosphate | H | H | CH₃ | O | 5-Fluorouracil |
| monophosphate | H | H | CH₃ | S | 2,4-O-Diacetyluracil |
| monophosphate | H | H | CH₃ | S | Hypoxanthine |
| monophosphate | H | H | CH₃ | S | 2,4-O-Diacetylthymine |
| monophosphate | H | H | CH₃ | S | Thymine |
| monophosphate | H | H | CH₃ | S | Cytosine |
| monophosphate | H | H | CH₃ | S | 4-(N-mono-acetyl)cytosine |
| monophosphate | H | H | CH₃ | S | 4-(N,N-diacetyl)cytosine |
| monophosphate | H | H | CH₃ | S | Uracil |
| monophosphate | H | H | CH₃ | S | 5-Fluorouracil |
| diphosphate | H | H | CH₃ | O | 2,4-O-Diacetylurac |
| diphosphate | H | H | CH₃ | O | Hypoxanthine |
| diphosphate | H | H | CH₃ | O | 2,4-O-Diacetylthymine |
| diphosphate | H | H | CH₃ | O | Thymine |
| diphosphate | H | H | CH₃ | O | Cytosine |
| diphosphate | H | H | CH₃ | O | 4-(N-mono-acetyl)cytosine |
| diphosphate | H | H | CH₃ | O | 4-(N,N-diacetyl)cytosine |
| diphosphate | H | H | CH₃ | O | Uracil |
| diphosphate | H | H | CH₃ | O | 5-Fluorouracil |
| diphosphate | H | H | CH₃ | S | 2,4-O-Diacetyluracil |
| diphosphate | H | H | CH₃ | S | Hypoxanthine |
| diphosphate | H | H | CH₃ | S | 2,4-O-Diacetylthym |
| diphosphate | H | H | CH₃ | S | Thymine |
| diphosphate | H | H | CH₃ | S | Cytosine |
| triphosphate | H | H | CH₃ | O | 2,4-O-Diacetyluracil |
| triphosphate | H | H | CH₃ | O | Hypoxanthine |
| triphosphate | H | H | CH₃ | O | 2,4-O-Diacetylthymine |
| triphosphate | H | H | CH₃ | O | Thymine |
| triphosphate | H | H | CH₃ | O | Cytosine |
| triphosphate | H | H | CH₃ | O | 4-(N-mono-acetyl)cytosine |
| triphosphate | H | H | CH₃ | O | 4-(N,N-diacetyl)cytos |
| triphosphate | H | H | CH₃ | O | Uracil |
| triphosphate | H | H | CH₃ | O | 5-Fluorouracil |
| triphosphate | H | H | CH₃ | S | 2,4-O-Diacetyluracil |
| triphosphate | H | H | CH₃ | S | Hypoxanthine |
| triphosphate | H | H | CH₃ | S | 2,4-O-Diacetyithym |
| triphosphate | H | H | CH₃ | S | Thymine |
| triphosphate | H | H | CH₃ | S | Cytosine |
| monophosphate | monophosphate | Br | CF₃ | O | 2,4-O-Diacetyluracil |
| monophosphate | monophosphate | Br | CF₃ | O | Hypoxanthine |
| monophosphate | monophosphate | Br | CF₃ | O | 2,4-O-Diacetylthymine |
| monophosphate | monophosphate | Br | CF₃ | O | Thymine |
| monophosphate | monophosphate | Br | CF₃ | O | Cytosine |
| monophosphate | monophosphate | Br | CF₃ | O | 4-(N-mono-acetyl)cytosine |
| monophosphate | monophosphate | Br | CF₃ | O | 4-(N,N-diacetyl)cytosine |
| monophosphate | monophosphate | Br | CF₃ | O | Uracil |
| monophosphate | monophosphate | Br | CF₃ | O | 5-Fluorouracil |
| monophosphate | monophosphate | Br | CF₃ | S | 2,4-O-Diacetyluracil |
| monophosphate | monophosphate | Br | CF₃ | S | Hypoxanthine |
| monophosphate | monophosphate | Br | CF₃ | S | 2,4-O-Diacetylthymine |
| monophosphate | monophosphate | Br | CF₃ | S | Thymine |
| monophosphate | monophosphate | Br | CF₃ | S | Cytosine |
| monophosphate | monophosphate | Br | CF₃ | S | 4-(N-mono-acetyl)cytosine |
| monophosphate | monophosphate | Br | CF₃ | S | 4-(N,N-diacetyl)cytos |
| monophosphate | monophosphate | Br | CF₃ | S | Uracil |
| monophosphate | monophosphate | Br | CF₃ | S | 5-Fluorouracil |
| acetyl | acetyl | NO2 | CF₃ | O | 4-(N,N-diacetyl)cytosine |
| acetyl | acetyl | NO2 | CF₃ | S | 4-(N,N-diacetyl)cytosine |
| acetyl | acetyl | NO2 | CF₃ | O | 4-(N,N-diacetyl)cytosine |
| acetyl | acetyl | NO2 | 2-bromo-vinyl | S | 4-(N,N-diacetyl)cytosine |

Alternatively, the following nucleosides of Formula XII are prepared, using the appropriate sugar and pyrimidine or purine bases.

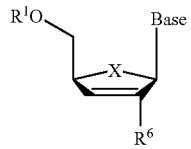

(XII)

wherein:

| $R^1$ | $R^6$ | X | Base |
|---|---|---|---|
| H | $CH_3$ | O | 2,4-O-Diacetyluracil |
| H | $CH_3$ | O | Hypoxanthine |
| H | $CH_3$ | O | 2,4-O-Diacetylthymine |
| H | $CH_3$ | O | Thymine |
| H | $CH_3$ | O | Cytosine |
| H | $CH_3$ | O | 4-(N-mono-acetyl)cytosine |
| H | $CH_3$ | O | 4-(N,N-diacetyl)cytosine |
| H | $CH_3$ | O | Uracil |
| H | $CH_3$ | O | 5-Fluorouracil |
| H | $CH_3$ | S | 2,4-O-Diacetyluracil |
| H | $CH_3$ | S | Hypoxanthine |
| H | $CH_3$ | S | 2,4-O-Diacetylthymine |
| H | $CH_3$ | S | Thymine |
| H | $CH_3$ | S | Cytosine |
| H | $CH_3$ | S | 4-(N-mono-acetyl)cytosine |
| H | $CH_3$ | S | 4-(N,N-diacetyl)cytosine |
| H | $CH_3$ | S | Uracil |
| H | $CH_3$ | S | 5-Fluorouracil |
| monophosphate | $CH_3$ | O | 2,4-O-Diacetyluracil |
| monophosphate | $CH_3$ | O | Hypoxanthine |
| monophosphate | $CH_3$ | O | 2,4-O-Diacetylthymine |
| monophosphate | $CH_3$ | O | Thymine |
| monophosphate | $CH_3$ | O | Cytosine |
| monophosphate | $CH_3$ | O | 4-(N-mono-acetyl)cytosine |
| monophosphate | $CH_3$ | O | 4-(N,N-diacetyl)cytosine |
| monophosphate | $CH_3$ | O | Uracil |
| monophosphate | $CH_3$ | O | 5-Fluorouracil |
| monophosphate | $CH_3$ | S | 2,4-O-Diacetyluracil |
| monophosphate | $CH_3$ | S | Hypoxanthine |
| monophosphate | $CH_3$ | S | 2,4-O-Diacetylthymine |
| monophosphate | $CH_3$ | S | Thymine |
| monophosphate | $CH_3$ | S | Cytosine |
| monophosphate | $CH_3$ | S | 4-(N-mono-acetyl)cytosine |
| monophosphate | $CH_3$ | S | 4-(N,N-diacetyl)cytosine |
| monophosphate | $CH_3$ | S | Uracil |
| monophosphate | $CH_3$ | S | 5-Fluorouracil |
| diphosphate | $CH_3$ | O | 2,4-O-Diacetyluracil |
| diphosphate | $CH_3$ | O | Hypoxanthine |
| diphosphate | $CH_3$ | O | 2,4-O-Diacetylthylnine |
| diphosphate | $CH_3$ | O | Thymine |
| diphosphate | $CH_3$ | O | Cytosine |
| diphosphate | $CH_3$ | O | 4-(N-mono-acetyl)cytosine |
| diphosphate | $CH_3$ | O | 4-(N,N-diacetyl)cytosine |
| diphosphate | $CH_3$ | O | Uracil |
| diphosphate | $CH_3$ | O | 5-Fluorouracil |
| diphosphate | $CH_3$ | S | 2,4-O-Diacetyluracil |
| diphosphate | $CH_3$ | S | Hypoxanthine |
| diphosphate | $CH_3$ | S | 2,4-O-Diacetylthymine |
| diphosphate | $CH_3$ | S | Thymine |
| diphosphate | $CH_3$ | S | Cytosine |
| triphosphate | $CH_3$ | O | 2,4-O-Diacetyluracil |
| triphosphate | $CH_3$ | O | Hypoxanthine |
| triphosphate | $CH_3$ | O | 2,4-O-Diacetylthymine |
| triphosphate | $CH_3$ | O | Thymine |
| triphosphate | $CH_3$ | O | Cytosine |
| triphosphate | $CH_3$ | O | 4-(N-mono-acetyl)cytosine |
| triphosphate | $CH_3$ | O | 4-(N,N-diacetyl)cytosine |
| triphosphate | $CH_3$ | O | Uracil |
| triphosphate | $CH_3$ | O | 5-Fluorouracil |
| triphosphate | $CH_3$ | S | 2,4-O-Diacetyluracil |
| triphosphate | $CH_3$ | S | Hypoxanthine |
| triphosphate | $CH_3$ | S | 2,4-O-Diacetylthymine |
| triphosphate | $CH_3$ | S | Thymine |
| triphosphate | $CH_3$ | S | Cytosine |
| monophosphate | $CF_3$ | O | 2,4-O-Diacetyluracil |
| monophosphate | $CF_3$ | O | Hypoxanthine |
| monophosphate | $CF_3$ | O | 2,4-O-Diacetylthymine |
| monophosphate | $CF_3$ | O | Thymine |
| monophosphate | $CF_3$ | O | Cytosine |
| monophosphate | $CF_3$ | O | 4-(N-mono-acetyl)cytosine |
| monophosphate | $CF_3$ | O | 4-(N,N-diacetyl)cytosine |
| monophosphate | $CF_3$ | O | Uracil |
| monophosphate | $CF_3$ | O | 5-Fluorouracil |
| monophosphate | $CF_3$ | S | 2,4-O-Diacetyluracil |
| monophosphate | $CF_3$ | S | Hypoxanthine |
| monophosphate | $CF_3$ | S | 2,4-O-Diacetylthymine |
| monophosphate | $CF_3$ | S | Thymine |
| monophosphate | $CF_3$ | S | Cytosine |
| monophosphate | $CF_3$ | S | 4-(N-mono-acetyl)cytosine |
| monophosphate | $CF_3$ | S | 4-(N,N-diacetyl)cytosine |
| monophosphate | $CF_3$ | S | Uracil |
| monophosphate | $CF_3$ | S | 5-Fluorouracil |
| acetyl | $CF_3$ | O | 4-(N,N-diacetyl)cytosine |
| acetyl | $CF_3$ | S | 4-(N,N-diacetyl)cytosine |
| acetyl | 2-bromo-vinyl | O | 4-(N,N-diacetyl)cytosine |
| acetyl | 2-bromo-vinyl | S | 4-(N,N-diacetyl)cytosine |

Alternatively, the following nucleosides of Formula XVII are prepared, using the appropriate sugar and pyrimidine or purine bases.

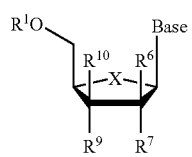

(XVII)

wherein:

| $R^1$ | $R^6$ | $R^7$ | X | Base | $R^9$ | $R^{10}$ |
|---|---|---|---|---|---|---|
| H | $CH_3$ | H | O | 2,4-O-Diacetyluracil | NHAc | Me |
| H | $CH_3$ | H | O | Hypoxanthine | NH2 | Me |
| H | $CH_3$ | H | O | 2,4-O-Diacetylthymine | NHAc | Me |
| H | $CH_3$ | H | O | Thymine | NH2 | Me |
| H | $CH_3$ | H | O | Cytosine | NH2 | Me |
| H | $CH_3$ | H | O | 4-(N-mono-acetyl)cytosine | NHAc | Me |
| H | $CH_3$ | H | O | 4-(N,N-diacetyl)cytosine | NHAc | Me |

-continued

| R¹ | R⁶ | R⁷ | X | Base | R⁹ | R¹⁰ |
|---|---|---|---|---|---|---|
| H | CH₃ | H | O | Uracil | NH2 | Me |
| H | CH₃ | H | O | 5-Fluorouracil | NH2 | Me |
| H | CH₃ | H | S | 2,4-O-Diacetyluracil | NHAc | Me |
| H | CH₃ | H | S | Hypoxanthine | NH2 | Me |
| H | CH₃ | H | S | 2,4-O-Diacetylthymine | NHAc | Me |
| H | CH₃ | H | S | Thymine | NH2 | Me |
| H | CH₃ | H | S | Cytosine | NH2 | Me |
| H | CH₃ | H | S | 4-(N-mono-acetyl)cytosine | NHAc | Me |
| H | CH₃ | H | S | 4-(N,N-diacetyl)cytosine | NHAc | Me |
| H | CH₃ | H | S | Uracil | NH2 | Me |
| H | CH₃ | H | S | 5-Fluorouracil | NH2 | Me |
| monophosphate | CH₃ | H | O | 2,4-O-Diacetyluracil | NHAc | Me |
| monophosphate | CH₃ | H | O | Hypoxanthine | NH2 | Me |
| monophosphate | CH₃ | H | O | 2,4-O-Diacetylthymine | NHAc | Me |
| monophosphate | CH₃ | H | O | Thymine | NH2 | Me |
| monophosphate | CH₃ | H | O | Cytosine | NH2 | Me |
| monophosphate | CH₃ | H | O | 4-(N-mono-acetyl)cytosine | NHAc | Me |
| monophosphate | CH₃ | H | O | 4-(N,N-diacetyl)cytosine | NHAc | Me |
| monophosphate | CH₃ | H | O | Uracil | NH2 | Me |
| monophosphate | CH₃ | H | O | 5-Fluorouracil | NH2 | Me |
| monophosphate | CH₃ | H | S | 2,4-O-Diacetyluracil | NHAc | Me |
| monophosphate | CH₃ | H | S | Hypoxanthine | NH2 | Me |
| monophosphate | CH₃ | H | S | 2,4-O-Diacetylthymine | NHAc | Me |
| monophosphate | CH₃ | H | S | Thymine | NH2 | Me |
| monophosphate | CH₃ | H | S | Cytosine | NH2 | Me |
| monophosphate | CH₃ | H | S | 4-(N-mono-acetyl)cytosine | NHAc | Me |
| monophosphate | CH₃ | H | S | 4-(N,N-diacetyl)cytosine | NHAc | Me |
| monophosphate | CH₃ | H | S | Uracil | NH2 | Me |
| monophosphate | CH₃ | H | S | 5-Fluorouracil | NH2 | Me |
| diphosphate | CH₃ | H | O | 2,4-O-Diacetyluracil | NHAc | Me |
| diphosphate | CH₃ | H | O | Hypoxanthine | NH2 | Me |
| diphosphate | CH₃ | H | O | 2,4-O-Diacetylthymine | NH2 | Me |
| diphosphate | CH₃ | H | O | Thymine | NH2 | Me |
| diphosphate | CH₃ | H | O | Cytosine | NH2 | Me |
| diphosphate | CH₃ | H | O | 4-(N-mono-acetyl)cytosine | NHAc | Me |
| diphosphate | CH₃ | H | O | 4-(N,N-diacetyl)cytos | NHAc | Me |
| diphosphate | CH₃ | H | O | Uracil | NH2 | Me |
| diphosphate | CH₃ | H | O | 5-Fluorouracil | NH2 | Me |
| diphosphate | CH₃ | H | S | 2,4-O-Diacetyluracil | NH2 | Me |
| diphosphate | CH₃ | H | S | Hypoxanthine | NH2 | Me |
| diphosphate | CH₃ | H | S | 2,4-O-Diacetylthymine | NHAc | Me |
| diphosphate | CH₃ | H | S | Thymine | NH2 | Me |
| diphosphate | CH₃ | H | S | Cytosine | NH2 | Me |
| triphosphate | CH₃ | H | O | 2,4-O-Diacetyluracil | NHAc | Me |
| triphosphate | CH₃ | H | O | Hypoxanthine | NHAc | Me |
| triphosphate | CH₃ | H | O | 2,4-O-Diacetylthymine | NHAc | Me |
| triphosphate | CH₃ | H | O | Thymine | NH2 | Me |
| triphosphate | CH₃ | H | O | Cytosine | NH2 | Me |
| triphosphate | CH₃ | H | O | 4-(N-mono-acetyl)cytosine | NHAc | Me |
| triphosphate | CH₃ | H | O | 4-(N,N-diacetyl)cytosine | NH2 | Me |
| triphosphate | CH₃ | H | O | Uracil | NH2 | Me |
| triphosphate | CH₃ | H | O | 5-Fluorouracil | NH2 | Me |
| triphosphate | CH₃ | H | S | 2,4-O-Diacetyluracil | NH2 | Me |
| triphosphate | CH₃ | H | S | Hypoxanthine | NH2 | Me |
| triphosphate | CH₃ | H | S | 2,4-O-Diacetylthymine | NH2 | Me |
| triphosphate | CH₃ | H | S | Thymine | NH2 | Me |
| triphosphate | CH₃ | H | S | Cytosine | NH2 | Me |
| monophosphate | CF₃ | H | O | 2,4-O-Diacetyluracil | NH2 | Me |
| monophosphate | CF₃ | H | O | Hypoxanthine | NH2 | Me |
| monophosphate | CF₃ | H | O | 2,4-O-Diacetylthymine | NH2 | Me |
| monophosphate | CF₃ | H | O | Thymine | NH2 | Me |
| monophosphate | CF₃ | H | O | Cytosine | NH2 | Me |
| monophosphate | CF₃ | H | O | 4-(N-mono-acetyl)cytosine | NH2 | Me |

-continued

| $R^1$ | $R^6$ | $R^7$ | X | Base | $R^9$ | $R^{10}$ |
|---|---|---|---|---|---|---|
| monophosphate | $CF_3$ | H | O | 4-(N,N-diacetyl)cytosine | $NH_2$ | Me |
| monophosphate | $CF_3$ | H | O | Uracil | $NH_2$ | Me |
| monophosphate | $CF_3$ | H | O | 5-Fluorouracil | $NH_2$ | Me |
| monophosphate | $CF_3$ | H | S | 2,4-O-Diacetyluracil | $NH_2$ | Me |
| monophosphate | $CF_3$ | H | S | Hypoxanthine | $NH_2$ | Me |
| monophosphate | $CF_3$ | H | S | 2,4-O-Diacetylthymine | $NH_2$ | Me |
| monophosphate | $CF_3$ | H | S | Thymine | $NH_2$ | Me |
| monophosphate | $CF_3$ | H | S | Cytosine | $NH_2$ | Me |
| monophosphate | $CF_3$ | H | S | 4-(N-mono-acetyl)cytosine | $NH_2$ | Me |
| monophosphate | $CF_3$ | H | S | 4-(N,N-diacetyl)cytosine | $NH_2$ | Me |
| monophosphate | $CF_3$ | H | S | Uracil | $NH_2$ | Me |
| monophosphate | $CF_3$ | H | S | 5-Fluorouracil | $NH_2$ | Me |
| acetyl | $CH_3$ | H | O | 4-(N,N-diacetyl)cytosine | H | Br |
| acetyl | $CH_3$ | H | S | 4-(N,N-diacetyl)cytosine | H | Br |
| acetyl | $CH_3$ | OH | O | 4-(N,N-diacetyl)cytosine | H | Br |
| acetyl | $CH_3$ | OH | S | 4-(N,N-diacetyl)cytosine | H | Br |

Example 3

Preparation of 3'-C-methylriboadenine

The title compound can be prepared according to a published procedure (R. F. Nutt, M. J. Dickinson, F. W. Holly, and E. Walton, "Branched-chain sugar nucleosides. III. 3'-C-methyladenine", *J. Org. Chem.* 1968, 33, 1789–1795) (Scheme 9).

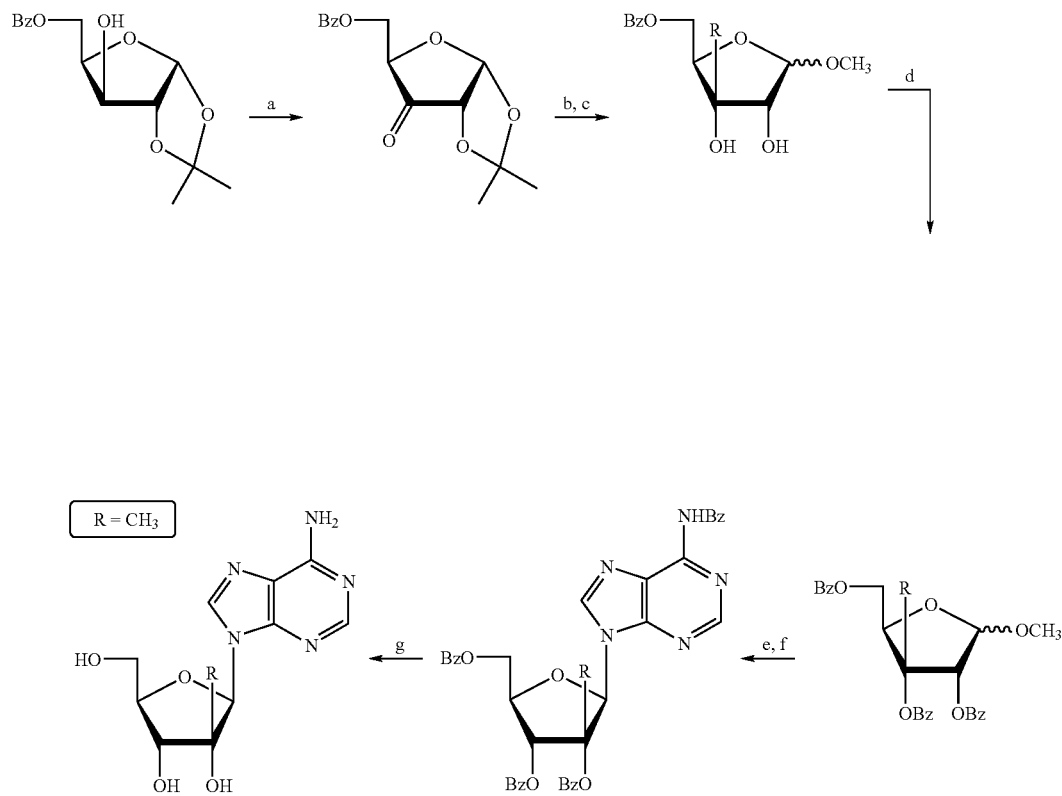

(a) RuO$_2$/NaIO$_4$; (b) MeMgI/TiCl$_4$; (c) HCl/MeOH/H$_2$O; (d) BzCl/pyridine; (e) AcBr, HBr/AcOH; (f) chloromercuri-6-benzamidopurine; (g) NH$_3$/MeOH.

In a similar manner, but using the appropriate sugar and pyrimidine or purine bases, the following nucleosides of Formula III are prepared.

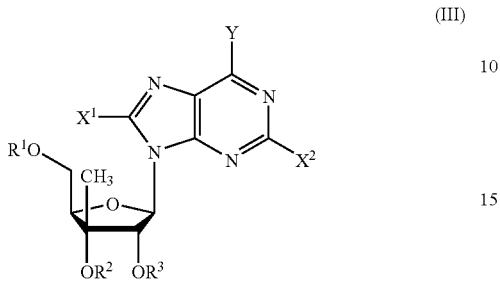

(III)

wherein:

| R$^1$ | R$^2$ | R$^3$ | X$^1$ | X$^2$ | Y |
|---|---|---|---|---|---|
| H | H | H | H | H | H |
| H | H | H | H | H | NH$_2$ |
| H | H | H | H | H | NH-cyclopropyl |
| H | H | H | H | H | NH-methyl |
| H | H | H | H | H | NH-ethyl |
| H | H | H | H | H | NH-acetyl |
| H | H | H | H | H | OH |
| H | H | H | H | H | OMe |
| H | H | H | H | H | OEt |
| H | H | H | H | H | O-cyclopropyl |
| H | H | H | H | H | O-acetyl |
| H | H | H | H | H | SH |
| H | H | H | H | H | SMe |
| H | H | H | H | H | SEt |
| H | H | H | H | H | S-cyclopropyl |
| H | H | H | H | H | F |
| H | H | H | H | H | Cl |
| H | H | H | H | H | Br |
| H | H | H | H | H | I |
| monophosphate | H | H | H | H | NH$_2$ |
| monophosphate | H | H | H | H | NH-acetyl |
| monophosphate | H | H | H | H | NH-cyclopropyl |
| monophosphate | H | H | H | H | NH-methyl |
| monophosphate | H | H | H | H | NH-ethyl |
| monophosphate | H | H | H | H | OH |
| monophosphate | H | H | H | H | O-acetyl |
| monophosphate | H | H | H | H | OMe |
| monophosphate | H | H | H | H | OEt |
| monophosphate | H | H | H | H | O-cyclopropyl |
| monophosphate | H | H | H | H | SH |
| monophosphate | H | H | H | H | SMe |
| monophosphate | H | H | H | H | SEt |
| monophosphate | H | H | H | H | 5-cyclopropyl |
| monophosphate | H | H | H | H | F |
| monophosphate | H | H | H | H | Cl |
| monophosphate | H | H | H | H | Br |
| monophosphate | H | H | H | H | I |
| diphosphate | H | H | H | H | NH$_2$ |
| diphosphate | H | H | H | H | NH-acetyl |
| diphosphate | H | H | H | H | NH-cyclopropyl |
| diphosphate | H | H | H | H | NH-methyl |
| diphosphate | H | H | H | H | NH-ethyl |
| diphosphate | H | H | H | H | OH |
| diphosphate | H | H | H | H | O-acetyl |
| diphosphate | H | H | H | H | OMe |
| diphosphate | H | H | H | H | OEt |
| diphosphate | H | H | H | H | O-cyclopropyl |
| diphosphate | H | H | H | H | SH |
| diphosphate | H | H | H | H | SMe |
| diphosphate | H | H | H | H | SEt |

-continued

| R¹ | R² | R³ | X¹ | X² | Y |
|---|---|---|---|---|---|
| diphosphate | H | H | H | H | S-cyclopropyl |
| diphosphate | H | H | H | H | F |
| diphosphate | H | H | H | H | Cl |
| diphosphate | H | H | H | H | Br |
| diphosphate | H | H | H | H | I |
| triphosphate | H | H | H | H | NH₂ |
| triphosphate | H | H | H | H | NH-acetyl |
| triphosphate | H | H | H | H | NH-cyclopropyl |
| triphosphate | H | H | H | H | NH-methyl |
| triphosphate | H | H | H | H | NH-ethyl |
| triphosphate | H | H | H | H | OH |
| triphosphate | H | H | H | H | OMe |
| triphosphate | H | H | H | H | OEt |
| triphosphate | H | H | H | H | O-cyclopropyl |
| triphosphate | H | H | H | H | O-acetyl |
| triphosphate | H | H | H | H | SH |
| triphosphate | H | H | H | H | SMe |
| triphosphate | H | H | H | H | SEt |
| triphosphate | H | H | H | H | S-cyclopropyl |
| triphosphate | H | H | H | H | F |
| triphosphate | H | H | H | H | Cl |
| triphosphate | H | H | H | H | Br |
| triphosphate | H | H | H | H | I |
| monophosphate | monophosphate | monophosphate | H | H | NH₂ |
| monophosphate | monophosphate | monophosphate | H | H | NH-cyclopropyl |
| monophosphate | monophosphate | monophosphate | H | H | OH |
| monophosphate | monophosphate | monophosphate | H | H | F |
| monophosphate | monophosphate | monophosphate | H | H | Cl |
| diphosphate | diphosphate | diphosphate | H | H | NH₂ |
| diphosphate | diphosphate | diphosphate | H | H | NH-cyclopropyl |
| diphosphate | diphosphate | diphosphate | H | H | OH |
| diphosphate | diphosphate | diphosphate | H | H | F |
| diphosphate | diphosphate | diphosphate | H | H | Cl |
| triphosphate | triphosphate | triphosphate | H | H | NH₂ |
| triphosphate | triphosphate | triphosphate | H | H | NH-cyclopropyl |
| triphosphate | triphosphate | triphosphate | H | H | OH |
| triphosphate | triphosphate | triphosphate | H | H | F |
| triphosphate | triphosphate | triphosphate | H | H | Cl |
| H | H | H | F | H | NH₂ |
| H | H | H | F | H | NH-cyclopropyl |
| H | H | H | F | H | OH |
| H | H | H | F | H | F |
| H | H | H | F | H | Cl |
| H | H | H | Cl | H | NH₂ |
| H | H | H | Cl | H | NH-cyclopropyl |
| H | H | H | Cl | H | OH |
| H | H | H | Cl | H | F |
| H | H | H | Cl | H | Cl |
| H | H | H | Br | H | NH₂ |
| H | H | H | Br | H | NH-cyclopropyl |
| H | H | H | Br | H | OH |
| H | H | H | Br | H | F |
| H | H | H | Br | H | Cl |
| H | H | H | NH₂ | H | NH₂ |
| H | H | H | NH₂ | H | NH-cyclopropyl |
| H | H | H | NH₂ | H | OH |
| H | H | H | NH₂ | H | F |
| H | H | H | NH₂ | H | Cl |
| H | H | H | SH | H | NH₂ |
| H | H | H | SH | H | NH-cyclopropyl |
| H | H | H | SH | H | OH |
| H | H | H | SH | H | F |
| H | H | H | SH | H | Cl |
| acetyl | H | H | H | H | NH₂ |
| acetyl | H | H | H | H | NH-cyclopropyl |
| acetyl | H | H | H | H | OH |
| acetyl | H | H | H | H | F |
| acetyl | H | H | H | H | Cl |
| acetyl | H | H | F | H | NH₂ |
| acetyl | H | H | F | H | NH-cyclopropyl |
| acetyl | H | H | F | H | OH |
| acetyl | H | H | F | H | F |
| acetyl | H | H | F | H | Cl |
| H | acetyl | acetyl | H | H | NH₂ |
| H | acetyl | acetyl | H | H | NH-cyclopropyl |
| H | acetyl | acetyl | H | H | OH |
| H | acetyl | acetyl | H | H | F |

-continued

| R¹ | R² | R³ | X¹ | X² | Y |
|---|---|---|---|---|---|
| H | acetyl | acetyl | H | H | Cl |
| acetyl | acetyl | acetyl | H | H | $NH_2$ |
| acetyl | acetyl | acetyl | H | H | NH-cyclopropyl |
| acetyl | acetyl | acetyl | H | H | OH |
| acetyl | acetyl | acetyl | H | H | F |
| acetyl | acetyl | acetyl | H | H | Cl |
| monophosphate | acetyl | acetyl | H | H | $NH_2$ |
| monophosphate | acetyl | acetyl | H | H | NH-cyclopropyl |
| monophosphate | acetyl | acetyl | H | H | OH |
| monophosphate | acetyl | acetyl | H | H | F |
| monophosphate | acetyl | acetyl | H | H | Cl |
| diphosphate | acetyl | acetyl | H | H | $NH_2$ |
| diphosphate | acetyl | acetyl | H | H | NH-cyclopropyl |
| diphosphate | acetyl | acetyl | H | H | OH |
| diphosphate | acetyl | acetyl | H | H | F |
| diphosphate | acetyl | acetyl | H | H | Cl |
| triphosphate | acetyl | acetyl | H | H | $NH_2$ |
| triphosphate | acetyl | acetyl | H | H | NH-cyclopropyl |
| triphosphate | acetyl | acetyl | H | H | OH |
| triphosphate | acetyl | acetyl | H | H | F |
| triphosphate | acetyl | acetyl | H | H | Cl |
| H | H | H | H | $NH_2$ | H |
| H | H | H | H | $NH_2$ | $NH_2$ |
| H | H | H | H | $NH_2$ | NH-cyclopropyl |
| H | H | H | H | $NH_2$ | NH-methyl |
| H | H | H | H | $NH_2$ | NH-ethyl |
| H | H | H | H | $NH_2$ | NH-acetyl |
| H | H | H | H | $NH_2$ | OH |
| H | H | H | H | $NH_2$ | OMe |
| H | H | H | H | $NH_2$ | OEt |
| H | H | H | H | $NH_2$ | O-cyclopropyl |
| H | H | H | H | $NH_2$ | O-acetyl |
| H | H | H | H | $NH_2$ | SH |
| H | H | H | H | $NH_2$ | SMe |
| H | H | H | H | $NH_2$ | SEt |
| H | H | H | H | $NH_2$ | S-cyclopropyl |
| H | H | H | H | $NH_2$ | F |
| H | H | H | H | $NH_2$ | Cl |
| H | H | H | H | $NH_2$ | Br |
| H | H | H | H | $NH_2$ | I |
| monophosphate | H | H | H | $NH_2$ | $NH_2$ |
| monophosphate | H | H | H | $NH_2$ | NH-acetyl |
| monophosphate | H | H | H | $NH_2$ | NH-cyclopropyl |
| monophosphate | H | H | H | $NH_2$ | NH-methyl |
| monophosphate | H | H | H | $NH_2$ | NH-ethyl |
| monophosphate | H | H | H | $NH_2$ | OH |
| monophosphate | H | H | H | $NH_2$ | O-acetyl |
| monophosphate | H | H | H | $NH_2$ | OMe |
| monophosphate | H | H | H | $NH_2$ | OEt |
| monophosphate | H | H | H | $NH_2$ | O-cyclopropyl |
| monophosphate | H | H | H | $NH_2$ | SH |
| monophosphate | H | H | H | $NH_2$ | SMe |
| monophosphate | H | H | H | $NH_2$ | SEt |
| monophosphate | H | H | H | $NH_2$ | 5-cyclopropyl |
| monophosphate | H | H | H | $NH_2$ | F |
| monophosphate | H | H | H | $NH_2$ | Cl |
| monophosphate | H | H | H | $NH_2$ | Br |
| monophosphate | H | H | H | $NH_2$ | I |
| diphosphate | H | H | H | $NH_2$ | $NH_2$ |
| diphosphate | H | H | H | $NH_2$ | NH-acetyl |
| diphosphate | H | H | H | $NH_2$ | NH-cyclopropyl |
| diphosphate | H | H | H | $NH_2$ | NH-methyl |
| diphosphate | H | H | H | $NH_2$ | NH-ethyl |
| diphosphate | H | H | H | $NH_2$ | OH |
| diphosphate | H | H | H | $NH_2$ | O-acetyl |
| diphosphate | H | H | H | $NH_2$ | OMe |
| diphosphate | H | H | H | $NH_2$ | OEt |
| diphosphate | H | H | H | $NH_2$ | O-cyclopropyl |
| diphosphate | H | H | H | $NH_2$ | SH |
| diphosphate | H | H | H | $NH_2$ | SMe |
| diphosphate | H | H | H | $NH_2$ | SEt |
| diphosphate | H | H | H | $NH_2$ | 5-cyclopropyl |
| diphosphate | H | H | H | $NH_2$ | F |
| diphosphate | H | H | H | $NH_2$ | Cl |
| diphosphate | H | H | H | $NH_2$ | Br |
| diphosphate | H | H | H | $NH_2$ | I |
| triphosphate | H | H | H | $NH_2$ | $NH_2$ |

-continued

| R¹ | R² | R³ | X¹ | X² | Y |
|---|---|---|---|---|---|
| triphosphate | H | H | H | NH₂ | NH-acetyl |
| triphosphate | H | H | H | NH₂ | NH-cyclopropyl |
| triphosphate | H | H | H | NH₂ | NH-methyl |
| triphosphate | H | H | H | NH₂ | NH-ethyl |
| triphosphate | H | H | H | NH₂ | OH |
| triphosphate | H | H | H | NH₂ | OMe |
| triphosphate | H | H | H | NH₂ | OEt |
| triphosphate | H | H | H | NH₂ | O-cyclopropyl |
| triphosphate | H | H | H | NH₂ | O-acetyl |
| triphosphate | H | H | H | NH₂ | SH |
| triphosphate | H | H | H | NH₂ | SMe |
| triphosphate | H | H | H | NH₂ | SEt |
| triphosphate | H | H | H | NH₂ | 5-cyclopropyl |
| triphosphate | H | H | H | NH₂ | F |
| triphosphate | H | H | H | NH₂ | Cl |
| triphosphate | H | H | H | NH₂ | Br |
| triphosphate | H | H | H | NH₂ | I |
| monophosphate | monophosphate | monophosphate | H | NH₂ | NH₂ |
| monophosphate | monophosphate | monophosphate | H | NH₂ | NH-cyclopropyl |
| monophosphate | monophosphate | monophosphate | H | NH₂ | OH |
| monophosphate | monophosphate | monophosphate | H | NH₂ | F |
| monophosphate | monophosphate | monophosphate | H | NH₂ | Cl |
| diphosphate | diphosphate | diphosphate | H | NH₂ | NH₂ |
| diphosphate | diphosphate | diphosphate | H | NH₂ | NIH-cyclopropyl |
| diphosphate | diphosphate | diphosphate | H | NH₂ | OH |
| diphosphate | diphosphate | diphosphate | H | NH₂ | F |
| diphosphate | diphosphate | diphosphate | H | NH₂ | Cl |
| triphosphate | triphosphate | triphosphate | H | NH₂ | NH₂ |
| triphosphate | triphosphate | triphosphate | H | NH₂ | NH-cyclopropyl |
| triphosphate | triphosphate | triphosphate | H | NH₂ | OH |
| triphosphate | triphosphate | triphosphate | H | NH₂ | F |
| triphosphate | triphosphate | triphosphate | H | NH₂ | Cl |
| H | H | H | F | NH₂ | NH₂ |
| H | H | H | F | NH₂ | NH-cyclopropyl |
| H | H | H | F | NH₂ | OH |
| H | H | H | F | NH₂ | F |
| H | H | H | F | NH₂ | Cl |
| H | H | H | Cl | NH₂ | NH₂ |
| H | H | H | Cl | NH₂ | NH-cyclopropyl |
| H | H | H | Cl | NH₂ | OH |
| H | H | H | Cl | NH₂ | F |
| H | H | H | Cl | NH₂ | Cl |
| H | H | H | Br | NH₂ | NH₂ |
| H | H | H | Br | NH₂ | NH-cyclopropyl |
| H | H | H | Br | NH₂ | OH |
| H | H | H | Br | NH₂ | F |
| H | H | H | Br | NH₂ | Cl |
| H | H | H | NH₂ | NH₂ | NH₂ |
| H | H | H | NH₂ | NH₂ | NH-cyclopropyl |
| H | H | H | NH₂ | NH₂ | OH |
| H | H | H | NH₂ | NH₂ | F |
| H | H | H | NH₂ | NH₂ | Cl |
| H | H | H | SH | NH₂ | NH₂ |
| H | H | H | SH | NH₂ | NH-cyclopropyl |
| H | H | H | SH | NH₂ | OH |
| H | H | H | SH | NH₂ | F |
| H | H | H | SH | NH₂ | Cl |
| acetyl | H | H | H | NH₂ | NH₂ |
| acetyl | H | H | H | NH₂ | NH-cyclopropyl |
| acetyl | H | H | H | NH₂ | OH |
| acetyl | H | H | H | NH₂ | F |
| acetyl | H | H | H | NH₂ | Cl |
| acetyl | H | H | F | NH₂ | NH₂ |
| acetyl | H | H | F | NH₂ | NH-cyclopropyl |
| acetyl | H | H | F | NH₂ | OH |
| acetyl | H | H | F | NH₂ | F |
| acetyl | H | H | F | NH₂ | Cl |
| H | acetyl | acetyl | H | NH₂ | NH₂ |
| H | acetyl | acetyl | H | NH₂ | NH-cyclopropyl |
| H | acetyl | acetyl | H | NH₂ | OH |
| H | acetyl | acetyl | H | NH₂ | F |
| H | acetyl | acetyl | H | NH₂ | Cl |
| acetyl | acetyl | acetyl | H | NH₂ | NH₂ |
| acetyl | acetyl | acetyl | H | NH₂ | NH-cyclopropyl |
| acetyl | acetyl | acetyl | H | NH₂ | OH |
| acetyl | acetyl | acetyl | H | NH₂ | F |
| acetyl | acetyl | acetyl | H | NH₂ | Cl |

-continued

| R¹ | R² | R³ | X¹ | X² | Y |
|---|---|---|---|---|---|
| monophosphate | acetyl | acetyl | H | NH₂ | NH₂ |
| monophosphate | acetyl | acetyl | H | NH₂ | NH-cyclopropyl |
| monophosphate | acetyl | acetyl | H | NH₂ | OH |
| monophosphate | acetyl | acetyl | H | NH₂ | F |
| monophosphate | acetyl | acetyl | H | NH₂ | Cl |
| diphosphate | acetyl | acetyl | H | NH₂ | NH₂ |
| diphosphate | acetyl | acetyl | H | NH₂ | NH-cyclopropyl |
| diphosphate | acetyl | acetyl | H | NH₂ | OH |
| diphosphate | acetyl | acetyl | H | NH₂ | F |
| diphosphate | acetyl | acetyl | H | NH₂ | Cl |
| triphosphate | acetyl | acetyl | H | NH₂ | NH₂ |
| triphosphate | acetyl | acetyl | H | NH₂ | NH-cyclopropyl |
| triphosphate | acetyl | acetyl | H | NH₂ | OH |
| triphosphate | acetyl | acetyl | H | NH₂ | F |
| triphosphate | acetyl | acetyl | H | NH₂ | Cl |
| H | H | H | H | Cl | H |
| H | H | H | H | Cl | H |
| H | H | H | H | Cl | NH₂ |
| H | H | H | H | Cl | NH-cyclopropyl |
| H | H | H | H | Cl | NH-methyl |
| H | H | H | H | Cl | NH-ethyl |
| H | H | H | H | Cl | NH-acetyl |
| H | H | H | H | Cl | OH |
| H | H | H | H | Cl | OMe |
| H | H | H | H | Cl | OEt |
| H | H | H | H | Cl | O-cyclopropyl |
| H | H | H | H | Cl | O-acetyl |
| H | H | H | H | Cl | SH |
| H | H | H | H | Cl | SMe |
| H | H | H | H | Cl | SEt |
| H | H | H | H | Cl | S-cyclopropyl |
| monophosphate | H | H | H | Cl | NH₂ |
| monophosphate | H | H | H | Cl | NH-acetyl |
| monophosphate | H | H | H | Cl | NH-cyclopropyl |
| monophosphate | H | H | H | Cl | NH-methyl |
| monophosphate | H | H | H | Cl | NH-ethyl |
| monophosphate | H | H | H | Cl | OH |
| monophosphate | H | H | H | Cl | O-acetyl |
| monophosphate | H | H | H | Cl | OMe |
| monophosphate | H | H | H | Cl | OEt |
| monophosphate | H | H | H | Cl | O-cyclopropyl |
| monophosphate | H | H | H | Cl | SH |
| monophosphate | H | H | H | Cl | SMe |
| monophosphate | H | H | H | Cl | SEt |
| monophosphate | H | H | H | Cl | S-cyclopropyl |
| diphosphate | H | H | H | Cl | NH₂ |
| diphosphate | H | H | H | Cl | NH-acetyl |
| diphosphate | H | H | H | Cl | NH-cyclopropyl |
| diphosphate | H | H | H | Cl | NH-methyl |
| diphosphate | H | H | H | Cl | NB-ethyl |
| diphosphate | H | H | H | Cl | OH |
| diphosphate | H | H | H | Cl | O-acetyl |
| diphosphate | H | H | H | Cl | OMe |
| diphosphate | H | H | H | Cl | OEt |
| diphosphate | H | H | H | Cl | O-cyclopropyl |
| diphosphate | H | H | H | Cl | SH |
| diphosphate | H | H | H | Cl | SMe |
| diphosphate | H | H | H | Cl | SEt |
| diphosphate | H | H | H | Cl | S-cyclopropyl |
| triphosphate | H | H | H | Cl | NH₂ |
| triphosphate | H | H | H | Cl | NH-acetyl |
| triphosphate | H | H | H | Cl | NH-cyclopropyl |
| triphosphate | H | H | H | Cl | NH-methyl |
| triphosphate | H | H | H | Cl | NH-ethyl |
| triphosphate | H | H | H | Cl | OH |
| triphosphate | H | H | H | Cl | OMe |
| triphosphate | H | H | H | Cl | OEt |
| triphosphate | H | H | H | Cl | O-cyclopropyl |
| triphosphate | H | H | H | Cl | O-acetyl |

-continued

| R¹ | R² | R³ | X¹ | X² | Y |
|---|---|---|---|---|---|
| triphosphate | H | H | H | Cl | SH |
| triphosphate | H | H | H | Cl | SMe |
| triphosphate | H | H | H | Cl | SEt |
| triphosphate | H | H | H | Cl | S-cyclopropyl |
| monophosphate | monophosphate | monophosphate | H | Cl | NH₂ |
| monophosphate | monophosphate | monophosphate | H | Cl | NH-cyclopropyl |
| monophosphate | monophosphate | monophosphate | H | Cl | OH |
| diphosphate | diphosphate | diphosphate | H | Cl | NH₂ |
| diphosphate | diphosphate | diphosphate | H | Cl | NH-cyclopropyl |
| diphosphate | diphosphate | diphosphate | H | Cl | OH |
| triphosphate | triphosphate | triphosphate | H | Cl | NH₂ |
| triphosphate | triphosphate | triphosphate | H | Cl | NH-cyclopropyl |
| triphosphate | triphosphate | triphosphate | H | Cl | OH |
| H | H | H | F | Cl | NH₂ |
| H | H | H | F | Cl | NH-cyclopropyl |
| H | H | H | F | Cl | OH |
| H | H | H | Cl | Cl | NH₂ |
| H | H | H | Cl | Cl | NH-cyclopropyl |
| H | H | H | Cl | Cl | OH |
| H | H | H | Br | Cl | NH₂ |
| H | H | H | Br | Cl | NH-cyclopropyl |
| H | H | H | Br | Cl | OH |
| H | H | H | NH₂ | Cl | NH₂ |
| H | H | H | NH₂ | Cl | NH-cyclopropyl |
| H | H | H | NH₂ | Cl | OH |
| H | H | H | SH | Cl | NH₂ |
| H | H | H | SH | Cl | NH-cyclopropyl |
| H | H | H | SH | Cl | OH |
| acetyl | H | H | H | Cl | NH₂ |
| acetyl | H | H | H | Cl | NH-cyclopropyl |
| acetyl | H | H | H | Cl | OH |
| acetyl | H | H | F | Cl | NH₂ |
| acetyl | H | H | F | Cl | NH-cyclopropyl |
| acetyl | H | H | F | Cl | OH |
| H | acetyl | acetyl | H | Cl | NH₂ |
| H | acetyl | acetyl | H | Cl | NH-cyclopropyl |
| H | acetyl | acetyl | H | Cl | OH |
| acetyl | acetyl | acetyl | H | Cl | NH₂ |
| acetyl | acetyl | acetyl | H | Cl | NH-cyclopropyl |
| acetyl | acetyl | acetyl | H | Cl | OH |
| monophosphate | acetyl | acetyl | H | Cl | NH₂ |
| monophosphate | acetyl | acetyl | H | Cl | NH-cyclopropyl |
| monophosphate | acetyl | acetyl | H | Cl | OH |
| diphosphate | acetyl | acetyl | H | Cl | NH₂ |
| diphosphate | acetyl | acetyl | H | Cl | NH-cyclopropyl |
| diphosphate | acetyl | acetyl | H | Cl | OH |
| triphosphate | acetyl | acetyl | H | Cl | NH₂ |
| triphosphate | acetyl | acetyl | H | Cl | NH-cyclopropyl |
| triphosphate | acetyl | acetyl | H | Cl | OH |
| H | H | H | H | Cl | NH₂ |
| H | H | H | H | Cl | NH-cyclopropyl |
| H | H | H | H | Cl | OH |
| H | H | H | H | Br | NH₂ |
| H | H | H | H | Br | NH-cyclopropyl |
| H | H | H | H | Br | OH |

Alternatively, the following nucleosides of Formula VI are prepared, using the appropriate sugar and pyrimidine or purine bases.

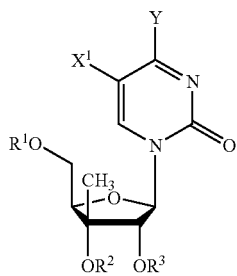

(VI)

wherein:

| $R^1$ | $R^2$ | $R^3$ | $X^1$ | Y |
|---|---|---|---|---|
| H | H | H | H | H |
| H | H | H | H | $NH_2$ |
| H | H | H | H | NH-cyclo-propyl |
| H | H | H | H | NH-methyl |
| H | H | H | H | NH-ethyl |
| H | H | H | H | NH-acetyl |
| H | H | H | H | OH |
| H | H | H | H | OMe |
| H | H | H | H | OEt |
| H | H | H | H | O-cyclopropyl |
| H | H | H | H | O-acetyl |
| H | H | H | H | SH |
| H | H | H | H | SMe |
| H | H | H | H | SEt |
| H | H | H | H | S-cyclopropyl |
| monophosphate | H | H | H | $NH_2$ |
| monophosphate | H | H | H | NH-acetyl |
| monophosphate | H | H | H | NH-cyclo-propyl |
| monophosphate | H | H | H | NH-methyl |
| monophosphate | H | H | H | NH-ethyl |
| monophosphate | H | H | H | OH |
| monophosphate | H | H | H | O-acetyl |
| monophosphate | H | H | H | OMe |
| monophosphate | H | H | H | OEt |
| monophosphate | H | H | H | O-cyclopropyl |
| monophosphate | H | H | H | SH |
| monophosphate | H | H | H | SMe |
| monophosphate | H | H | H | SEt |
| monophosphate | H | H | H | 5-cyclopropyl |
| diphosphate | H | H | H | $NH_2$ |
| diphosphate | H | H | H | NH-acetyl |
| diphosphate | H | H | H | NH-cyclo-propyl |
| diphosphate | H | H | H | NH-methyl |
| diphosphate | H | H | H | NH-ethyl |
| diphosphate | H | H | H | OH |
| diphosphate | H | H | H | O-acetyl |
| diphosphate | H | H | H | OMe |
| diphosphate | H | H | H | OEt |
| diphosphate | H | H | H | O-cyclopropyl |
| diphosphate | H | H | H | SH |
| diphosphate | H | H | H | SMe |
| diphosphate | H | H | H | SEt |
| diphosphate | H | H | H | 5-cyclopropyl |
| triphosphate | H | H | H | $NH_2$ |
| triphosphate | H | H | H | NH-acetyl |
| triphosphate | H | H | H | NH-cyclo-propyl |
| triphosphate | H | H | H | NH-methyl |
| triphosphate | H | H | H | NH-ethyl |
| triphosphate | H | H | H | OH |
| triphosphate | H | H | H | OMe |
| triphosphate | H | H | H | OEt |
| triphosphate | H | H | H | O-cyclopropyl |
| triphosphate | H | H | H | O-acetyl |
| triphosphate | H | H | H | SH |
| triphosphate | H | H | H | SMe |
| triphosphate | H | H | H | SEt |
| triphosphate | H | H | H | 5-cyclopropyl |
| monophosphate | monophosphate | monophosphate | H | $NH_2$ |
| monophosphate | monophosphate | monophosphate | H | NH-cyclo-propyl |
| monophosphate | monophosphate | monophosphate | H | OH |
| diphosphate | diphosphate | diphosphate | H | $NH_2$ |
| diphosphate | diphosphate | diphosphate | H | NH-cyclo-propyl |
| diphosphate | diphosphate | diphosphate | H | OH |
| triphosphate | triphosphate | triphosphate | H | $NH_2$ |
| triphosphate | triphosphate | triphosphate | H | NH-cyclo-propyl |
| triphosphate | triphosphate | triphosphate | H | OH |
| H | H | H | F | $NH_2$ |
| H | H | H | F | NH-cyclo-propyl |
| H | H | H | F | OH |
| H | H | H | Cl | $NH_2$ |
| H | H | H | Cl | NH-cyclo-propyl |
| H | H | H | Cl | OH |
| H | H | H | Br | $NH_2$ |
| H | H | H | Br | NH-cyclo-propyl |
| H | H | H | Br | OH |
| H | H | H | $NH_2$ | $NH_2$ |
| H | H | H | $NH_2$ | NH-cyclo-propyl |
| H | H | H | $NH_2$ | OH |
| H | H | H | SH | $NH_2$ |
| H | H | H | SH | NH-cyclo-propyl |
| H | H | H | SH | OH |
| acetyl | H | H | H | $NH_2$ |
| acetyl | H | H | H | NH-cyclo-propyl |
| acetyl | H | H | H | OH |
| acetyl | H | H | F | $NH_2$ |
| acetyl | H | H | F | NH-cyclo-propyl |
| acetyl | H | H | F | OH |
| H | acetyl | acetyl | H | $NH_2$ |
| H | acetyl | acetyl | H | NH-cyclo-propyl |
| H | acetyl | acetyl | H | OH |
| acetyl | acetyl | acetyl | H | $NH_2$ |
| acetyl | acetyl | acetyl | H | NH-cyclo-propyl |
| acetyl | acetyl | acetyl | H | OH |
| monophosphate | acetyl | acetyl | H | $NH_2$ |
| monophosphate | acetyl | acetyl | H | NH-cyclo-propyl |
| monophosphate | acetyl | acetyl | H | OH |
| diphosphate | acetyl | acetyl | H | $NH_2$ |
| diphosphate | acetyl | acetyl | H | NH-cyclo-propyl |
| diphosphate | acetyl | acetyl | H | OH |
| triphosphate | acetyl | acetyl | H | $NH_2$ |
| triphosphate | acetyl | acetyl | H | NH-cyclo-propyl |
| triphosphate | acetyl | acetyl | H | OH |

Alternatively, the following nucleosides of Formula XIII are prepared, using the appropriate sugar and pyrimidine or purine bases.

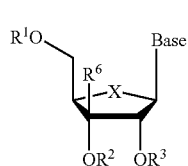

(XIII)

wherein:

| R¹ | R² | R³ | R⁶ | X | Base |
|---|---|---|---|---|---|
| H | H | H | CH₃ | O | 2,4-O-Diacetyluracil |
| H | H | H | CH₃ | O | Hypoxanthine |
| H | H | H | CH₃ | O | 2,4-O-Diacetylthymine |
| H | H | H | CH₃ | O | Thymine |
| H | H | H | CH₃ | O | Cytosine |
| H | H | H | CH₃ | O | 4-(N-monoacetyl)cytosine |
| H | H | H | CH₃ | O | 4-(N,N-diacetyl)cytosine |
| H | H | H | CH₃ | O | Uracil |
| H | H | H | CH₃ | O | 5-Fluorouracil |
| H | H | H | CH₃ | S | 2,4-O-Diacetyluraci |
| H | H | H | CH₃ | S | Hypoxanthine |
| H | H | H | CH₃ | S | 2,4-O-Diacetylthymine |
| H | H | H | CH₃ | S | Thymine |
| H | H | H | CH₃ | S | Cytosine |
| H | H | H | CH₃ | S | 4-(N-monoacetyl)cytosine |
| H | H | H | CH₃ | S | 4-(N,N-diacetyl)cytosine |
| H | H | H | CH₃ | S | Uracil |
| H | H | H | CH₃ | S | 5-Fluorouracil |
| monophosphate | H | H | CH₃ | O | 2,4-O-Diacetyluracil |
| monophosphate | H | H | CH₃ | O | Hypoxanthine |
| monophosphate | H | H | CH₃ | O | 2,4-O-Diacetylthym |
| monophosphate | H | H | CH₃ | O | Thymine |
| monophosphate | H | H | CH₃ | O | Cytosine |
| monophosphate | H | H | CH₃ | O | 4-(N-monoacetyl)cytosine |
| monophosphate | H | H | CH₃ | O | 4-(N,N-diacetyl)cytosine |
| monophosphate | H | H | CH₃ | O | Uracil |
| monophosphate | H | H | CH₃ | O | 5-Fluorouracil |
| monophosphate | H | H | CH₃ | S | 2,4-O-Diacetyluracil |
| monophosphate | H | H | CH₃ | S | Hypoxanthine |
| monophosphate | H | H | CH₃ | S | 2,4-O-Diacetylthym |
| monophosphate | H | H | CH₃ | S | Thymine |
| monophosphate | H | H | CH₃ | S | Cytosine |
| monophosphate | H | H | CH₃ | S | 4-(N-monoacetyl)cytosine |
| monophosphate | H | H | CH₃ | S | 4-(N,N-diacetyl)cytosine |
| monophosphate | H | H | CH₃ | S | Uracil |
| monophosphate | H | H | CH₃ | S | 5-Fluorouracil |
| diphosphate | H | H | CH₃ | O | 2,4-O-Diacetyluracil |
| diphosphate | H | H | CH₃ | O | Hypoxanthine |
| diphosphate | H | H | CH₃ | O | 2,4-O-Diacetylthymine |
| diphosphate | H | H | CH₃ | O | Thymine |
| diphosphate | H | H | CH₃ | O | Cytosme |
| diphosphate | H | H | CH₃ | O | 4-(N-monoacetyl)cytosine |
| diphosphate | H | H | CH₃ | O | 4-(N,N-diacetyl)cytosine |
| diphosphate | H | H | CH₃ | O | Uracil |
| diphosphate | H | H | CH₃ | O | 5-Fluorouracil |
| diphosphate | H | H | CH₃ | S | 2,4-O-Diacetyluracil |
| diphosphate | H | H | CH₃ | S | Hypoxanthine |
| diphosphate | H | H | CH₃ | S | 2,4-O-Diacetylthym |
| diphosphate | H | H | CH₃ | S | Thymine |
| diphosphate | H | H | CH₃ | S | Cytosine |
| triphosphate | H | H | CH₃ | O | 2,4-O-Diacetyluracil |
| triphosphate | H | H | CH₃ | O | Hypoxanthine |
| triphosphate | H | H | CH₃ | O | 2,4-O-Diacetylthymine |
| triphosphate | H | H | CH₃ | O | Thymine |
| triphosphate | H | H | CH₃ | O | Cytosine |
| triphosphate | H | H | CH₃ | O | 4-(N-monoacetyl)cytosine |
| triphosphate | H | H | CH₃ | O | 4-(N,N-diacetyl)cytosine |
| triphosphate | H | H | CH₃ | O | Uracil |
| triphosphate | H | H | CH₃ | O | 5-Fluorouracil |
| triphosphate | H | H | CH₃ | S | 2,4-O-Diacetyluracil |
| triphosphate | H | H | CH₃ | S | Hypoxanthine |
| triphosphate | H | H | CH₃ | S | 2,4-O-Diacetylthymine |
| triphosphate | H | H | CH₃ | S | Thymine |

-continued

| R¹ | R² | R³ | R⁶ | X | Base |
|---|---|---|---|---|---|
| triphosphate | H | H | CH₃ | S | Cytosine |
| monophosphate | monophosphate | monophosphate | CF₃ | O | 2,4-O-Diacetyluracil |
| monophosphate | monophosphate | monophosphate | CF₃ | O | Hypoxanthine |
| monophosphate | monophosphate | monophosphate | CF₃ | O | 2,4-O-Diacetylthymine |
| monophosphate | monophosphate | monophosphate | CF₃ | O | Thymine |
| monophosphate | monophosphate | monophosphate | CF₃ | O | Cytosine |
| monophosphate | monophosphate | monophosphate | CF₃ | O | 4-(N-monoacetyl)cytosine |
| monophosphate | monophosphate | monophosphate | CF₃ | O | 4-(N,N-diacetyl)cytosine |
| monophosphate | monophosphate | monophosphate | CF₃ | O | Uracil |
| monophosphate | monophosphate | monophosphate | CF₃ | O | 5-Fluorouracil |
| monophosphate | monophosphate | monophosphate | CF₃ | S | 2,4-O-Diacetyluracil |
| monophosphate | monophosphate | monophosphate | CF₃ | S | Hypoxanthine |
| monophosphate | monophosphate | monophosphate | CF₃ | S | 2,4-O-Diacetylthymine |
| monophosphate | monophosphate | monophosphate | CF₃ | S | Thymine |
| monophosphate | monophosphate | monophosphate | CF₃ | S | Cytosine |
| monophosphate | monophosphate | monophosphate | CF₃ | S | 4-(N-monoacetyl)cytosine |
| monophosphate | monophosphate | monophosphate | CF₃ | S | 4-(N,N-diacetyl)cytosine |
| monophosphate | monophosphate | monophosphate | CF₃ | S | Uracil |
| monophosphate | monophosphate | monophosphate | CF₃ | S | 5-Fluorouracil |
| acetyl | acetyl | acetyl | CF₃ | O | 4-(N,N-diacetyl)cytosine |
| acetyl | acetyl | acetyl | CF₃ | S | 4-(N,N-diacetyl)cytosine |
| acetyl | acetyl | acetyl | 2-bromovinyl | O | 4-(N,N-diacetyl)cytosine |
| acetyl | acetyl | acetyl | 2-bromovinyl | S | 4-(N,N-diacetyl)cytosine |
| H | H | H | CH₃ | O | 2-(N,N-diacetyl)guanine |
| H | H | H | CH₃ | O | 6-O-acetylguanine |
| H | H | H | CH₃ | O | 8-fluoroguanine |
| H | H | H | CH₃ | O | guanine |
| H | H | H | CH₃ | O | 6-(N,N-diacetyl)adenine |
| H | H | H | CH₃ | O | 2-fluoroadenine |
| H | H | H | CH₃ | O | 8-fluoroadenine |
| H | H | H | CH₃ | O | 2,8-difluoroadenine |
| H | H | H | CH₃ | O | adenine |
| H | H | H | CH₃ | S | 2-(N,N-diacetyl)guanine |
| H | H | H | CH₃ | S | 6-O-acetylguanine |
| H | H | H | CH₃ | S | 8-fluoroguanine |
| H | H | H | CH₃ | S | guanine |
| H | H | H | CH₃ | S | 6-(N,N-diacetyl)adenine |
| H | H | H | CH₃ | S | 2-fluoroadenine |
| H | H | H | CH₃ | S | 8-fluoroadenine |
| H | H | H | CH₃ | S | 2,8-difluoroadenine |
| H | H | H | CH₃ | S | adenine |
| monophosphate | H | H | CH₃ | O | 2-(N,N-diacetyl)guanine |
| monophosphate | H | H | CH₃ | O | 6-O-acetylguanine |
| monophosphate | H | H | CH₃ | O | 8-fluoroguanine |
| monophosphate | H | H | CH₃ | O | guanine |
| monophosphate | H | H | CiT3 | O | 6-(N,N-diacetyl)adenine |
| monophosphate | H | H | CH₃ | O | 2-fluoroadenine |
| monophosphate | H | H | CH₃ | O | 8-fluoroadenine |
| monophosphate | H | H | CH₃ | O | 2,8-difluoroadenine |
| monophosphate | H | H | CH₃ | O | adenine |
| monophosphate | H | H | CH₃ | S | 2-(N,N-diacetyl)guanine |
| monophosphate | H | H | CH₃ | S | 6-O-acetylguanine |
| monophosphate | H | H | CH₃ | S | 8-fluoroguanine |
| monophosphate | H | H | CH₃ | S | guanine |
| monophosphate | H | H | CH₃ | S | 6-(N,N-diacetyl)adenine |
| monophosphate | H | H | CH₃ | S | 2-fluoroadenine |
| monophosphate | H | H | CH₃ | S | 8-fluoroadenine |
| monophosphate | H | H | CH₃ | S | 2,8-difluoroadenine |
| monophosphate | H | H | CH₃ | S | adenine |
| diphosphate | H | H | CH₃ | O | 2-(N,N-diacetyl)guanine |
| diphosphate | H | H | CH₃ | O | 6-O-acetylguanine |
| diphosphate | H | H | CH₃ | O | 8-fluoroguanine |
| diphosphate | H | H | CH₃ | O | guanine |
| diphosphate | H | H | CH₃ | O | 6-(N,N-diacetyl)adenine |
| diphosphate | H | H | CH₃ | O | 2-fluoroadenine |
| diphosphate | H | H | CH₃ | O | 8-fluoroadenine |
| diphosphate | H | H | CH₃ | O | 2,8-difluoroadenine |
| diphosphate | H | H | CH₃ | O | adenine |
| diphosphate | H | H | CH₃ | S | 2-(N,N-diacetyl)guanine |
| diphosphate | H | H | CH₃ | S | 6-O-acetylguanine |
| diphosphate | H | H | CH₃ | S | 8-fluoroguanine |
| diphosphate | H | H | CH₃ | S | guanine |
| diphosphate | H | H | CH₃ | S | 6-(N,N-diacetyl)adenine |
| diphosphate | H | H | CH₃ | S | 2-fluoroadenine |
| diphosphate | H | H | CH₃ | S | 8-fluoroadenine |
| diphosphate | H | H | CH₃ | S | 2,8-difluoroadenine |
| diphosphate | H | H | CH₃ | S | adenine |

-continued

| R¹ | R² | R³ | R⁶ | X | Base |
|---|---|---|---|---|---|
| triphosphate | H | H | CH₃ | O | 2-(N,N-diacetyl)guanine |
| triphosphate | H | H | CH₃ | O | 6-O-acetylguanine |
| triphosphate | H | H | CH₃ | O | 8-fluoroguanine |
| triphosphate | H | H | CH₃ | O | guanine |
| triphosphate | H | H | CH₃ | O | 6-(N,N-diacetyl)adenine |
| triphosphate | H | H | CH₃ | O | 2-fluoroadenine |
| triphosphate | H | H | CH₃ | O | 8-fluoroadenine |
| triphosphate | H | H | CH₃ | O | 2,8-difluoroadenine |
| triphosphate | H | H | CH₃ | O | 2-(N,N-diacetyl)guanine |
| triphosphate | H | H | CH₃ | S | 6-O-acetylguanine |
| triphosphate | H | H | CH₃ | S | 8-fluoroguanine |
| triphosphate | H | H | CH₃ | S | guanine |
| triphosphate | H | H | CH₃ | S | 6-(N,N-diacetyl)adenine |
| triphosphate | H | H | CH₃ | S | 2-fluoroadenine |
| triphosphate | H | H | CH₃ | S | 8-fluoroadenine |
| triphosphate | H | H | CH₃ | S | 2,8-difluoroadenine |
| triphosphate | H | H | CH₃ | S | adenine |
| monophosphate | monophosphate | monophosphate | CF₃ | O | 2-(N,N-diacetyl)guanine |
| monophosphate | monophosphate | monophosphate | CF₃ | O | 6-O-acetylguanine |
| monophosphate | monophosphate | monophosphate | CF₃ | O | 8-fluoroguanine |
| monophosphate | monophosphate | monophosphate | CF₃ | O | guanine |
| monophosphate | monophosphate | monophosphate | CF₃ | O | 6-(N,N-diacetyl)adenine |
| monophosphate | monophosphate | monophosphate | CF₃ | O | 2-fluoroadenine |
| monophosphate | monophosphate | monophosphate | CF₃ | O | 8-fluoroadenine |
| monophosphate | monophosphate | monophosphate | CF₃ | O | 2,8-difluoroadenine |
| monophosphate | monophosphate | monophosphate | CF₃ | O | adenine |
| monophosphate | monophosphate | monophosphate | CF₃ | S | 2-(N,N-diacetyl)guanine |
| monophosphate | monophosphate | monophosphate | CF₃ | S | 6-O-acetylguanine |
| monophosphate | monophosphate | monophosphate | CF₃ | S | 8-fluoroguanine |
| monophosphate | monophosphate | monophosphate | CF₃ | S | guanine |
| monophosphate | monophosphate | monophosphate | CF₃ | S | 6-(N,N-diacetyl)adenine |
| monophosphate | monophosphate | monophosphate | CF₃ | S | 2-fluoroadenine |
| monophosphate | monophosphate | monophosphate | CF₃ | S | 8-fluoroadenine |
| monophosphate | monophosphate | monophosphate | CF₃ | S | 2,8-difluoroadenine |
| monophosphate | monophosphate | monophosphate | CF₃ | S | adenine |
| acetyl | acetyl | acetyl | CF₃ | O | guanine |
| acetyl | acetyl | acetyl | CF₃ | S | guanine |
| acetyl | acetyl | acetyl | 2-bromovinyl | O | guanine |
| acetyl | acetyl | acetyl | 2-bromovinyl | S | guanine |

Alternatively, the following nucleosides of Formula XIV are prepared, using the appropriate sugar and pyrimidine or purine bases.

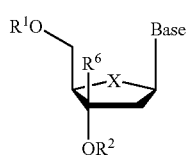

(XIV)

wherein:

| R¹ | R² | R⁶ | X | Base |
|---|---|---|---|---|
| H | H | CH₃ | O | 2,4-O-Diacetyluracil |
| H | H | CH₃ | O | Hypoxanthine |
| H | H | CH₃ | O | 2,4-O-Diacetylthymine |
| H | H | CH₃ | O | Thymine |
| H | H | CH₃ | O | Cytosine |
| H | H | CH₃ | O | 4-(N-mono-acetyl)cytosine |
| H | H | CH₃ | O | 4-(N,N-diacetyl)cytosine |
| H | H | CH₃ | O | Uracil |
| H | H | CH₃ | O | 5-Fluorouracil |
| H | H | CH₃ | S | 2,4-O-Diacetyluracil |
| H | H | CH₃ | S | Hypoxanthine |
| H | H | CH₃ | S | 2,4-O-Diacetylthymine |
| H | H | CH₃ | S | Thymine |
| H | H | CH₃ | S | Cytosine |
| H | H | CH₃ | S | 4-(N-mono-acetyl)cytosin |
| H | H | CH₃ | S | 4-(N,N-diacetyl)cytosine |
| H | H | CH₃ | S | Uracil |
| H | H | CH₃ | S | 5-Fluorouracil |
| monophosphate | H | CH₃ | O | 2,4-O-Diacetyluracil |
| monophosphate | H | CH₃ | O | Hypoxanthine |
| monophosphate | H | CH₃ | O | 2,4-O-Diacetylthym |
| monophosphate | H | CH₃ | O | Thymine |
| monophosphate | H | CH₃ | O | Cytosine |
| monophosphate | H | CH₃ | O | 4-(N-mono-acetyl)cytosine |
| monophosphate | H | CH₃ | O | 4-(N,N-diacetyl)cytos |
| monophosphate | H | CH₃ | O | Uracil |
| monophosphate | H | CH₃ | O | 5-Fluorouracil |
| monophosphate | H | CH₃ | S | 2,4-O-Diacetyluracil |
| monophosphate | H | CH₃ | S | Hypoxanthine |
| monophosphate | H | CH₃ | S | 2,4-O-Diacetylthym |
| monophosphate | H | CH₃ | S | Thymine |
| monophosphate | H | CH₃ | S | Cytosine |
| monophosphate | H | CH₃ | S | 4-(N-mono-acetyl)cytosine |
| monophosphate | H | CH₃ | S | 4-(N,N-diacetyl)cytosine |
| monophosphate | H | CH₃ | S | Uracil |
| monophosphate | H | CH₃ | S | 5-Fluorouracil |
| diphosphate | H | CH₃ | O | 2,4-O-Diacetyluracil |
| diphosphate | H | CH₃ | O | Hypoxanthine |
| diphosphate | H | CH₃ | O | 2,4-O-Diacetylthymine |
| diphosphate | H | CH₃ | O | Thymine |

-continued

| R¹ | R² | R⁶ | X | Base |
|---|---|---|---|---|
| diphosphate | H | CH₃ | O | Cytosine |
| diphosphate | H | CH₃ | O | 4-(N-mono-acetyl)cytosine |
| diphosphate | H | CH₃ | O | 4-(N,N-diacetyl)cytosine |
| diphosphate | H | CH₃ | O | Uracil |
| diphosphate | H | CH₃ | O | 5-Fluorouracil |
| diphosphate | H | CH₃ | S | 2,4-O-Diacetyluracil |
| diphosphate | H | CH₃ | S | Hypoxanthine |
| diphosphate | H | CH₃ | S | 2,4-O-Diacetylthymine |
| diphosphate | H | CH₃ | S | Thymine |
| diphosphate | H | CH₃ | S | Cytosine |
| triphosphate | H | CH₃ | O | 2,4-O-Diacetyluracil |
| triphosphate | H | CH₃ | O | Hypoxanthine |
| triphosphate | H | CH₃ | O | 2,4-O-Diacetylthymine |
| triphosphate | H | CH₃ | O | Thymine |
| triphosphate | H | CH₃ | O | Cytosine |
| triphosphate | H | CH₃ | O | 4-(N-mono-acetyl)cytosine |
| triphosphate | H | CH₃ | O | 4-(N,N-diacetyl)cytosine |
| triphosphate | H | CH₃ | O | Uracil |
| triphosphate | H | CH₃ | O | 5-Fluorouracil |
| triphosphate | H | CH₃ | S | 2,4-O-Diacetyluracil |
| triphosphate | H | CH₃ | S | Hypoxanthine |
| triphosphate | H | CH₃ | S | 2,4-O-Diacetylthymine |
| triphosphate | H | CH₃ | S | Thymine |
| triphosphate | H | CH₃ | S | Cytosine |
| monophosphate | monophosphate | CF₃ | O | 2,4-O-Diacetyluracil |
| monophosphate | monophosphate | CF₃ | O | Hypoxanthine |
| monophosphate | monophosphate | CF₃ | O | 2,4-O-Diacetylthymine |
| monophosphate | monophosphate | CF₃ | O | Thymine |
| monophosphate | monophosphate | CF₃ | O | Cytosine |
| monophosphate | monophosphate | CF₃ | O | 4-(N-mono-acetyl)cytosine |
| monophosphate | monophosphate | CF₃ | O | 4-(N,N-diacetyl)cytosine |
| monophosphate | monophosphate | CF₃ | O | Uracil |
| monophosphate | monophosphate | CF₃ | O | 5-Fluorouracil |
| monophosphate | monophosphate | CF₃ | S | 2,4-O-Diacetyluracil |
| monophosphate | monophosphate | CF₃ | S | Hypoxanthine |
| monophosphate | monophosphate | CF₃ | S | 2,4-O-Diacetylthymine |
| monophosphate | monophosphate | CF₃ | S | Thymine |
| monophosphate | monophosphate | CF₃ | S | Cytosine |
| monophosphate | monophosphate | CF₃ | S | 4-(N-mono-acetyl)cytosine |
| monophosphate | monophosphate | CF₃ | S | 4-(N,N-diacetyl)cytosine |
| monophosphate | monophosphate | CF₃ | S | Uracil |
| monophosphate | monophosphate | CF₃ | S | 5-Fluorouracil |
| acetyl | acetyl | CF₃ | O | 4-(N,N-diacetyl)cytosine |
| acetyl | acetyl | CF₃ | S | 4-(N,N-diacetyl)cytosine |
| acetyl | acetyl | 2-bromovinyl | O | 4-(N,N-diacetyl)cytosine |
| acetyl | acetyl | 2-bromovinyl | S | 4-(N,N-diacetyl)cytosine |

Alternatively, the following nucleosides of Formula XV are prepared, using the appropriate sugar and pyrimidine or purine bases.

(XV)

wherein:

| R¹ | R⁶ | X | Base |
|---|---|---|---|
| H | CH₃ | O | 2,4-O-Diacetyluracil |
| H | CH₃ | O | Hypoxanthine |
| H | CH₃ | O | 2,4-O-Diacetylthymine |
| H | CH₃ | O | Thymine |
| H | CH₃ | O | Cytosine |
| H | CH₃ | O | 4-(N-mono-acetyl)cytosine |
| H | CH₃ | O | 4-(N,N-diacetyl)cytosine |
| H | CH₃ | O | Uracil |
| H | CH₃ | O | 5-Fluorouracil |
| H | CH₃ | S | 2,4-O-Diacetyluracil |
| H | CH₃ | S | Hypoxanthine |
| H | CH₃ | S | 2,4-O-Diacetylthymine |
| H | CH₃ | S | Thymine |
| H | CH₃ | S | Cytosine |
| H | CH₃ | S | 4-(N-mono-acetyl)cytosine |
| H | CH₃ | S | 4-(N,N-diacetyl)cytosine |
| H | CH₃ | S | Uracil |
| H | CH₃ | S | 5-Fluorouracil |
| monophosphate | CH₃ | O | 2,4-O-Diacetyluracil |
| monophosphate | CH₃ | O | Hypoxanthine |
| monophosphate | CH₃ | O | 2,4-O-Diacetylthymine |
| monophosphate | CH₃ | O | Thymine |
| monophosphate | CH₃ | O | Cytosine |
| monophosphate | CH₃ | O | 4-(N-mono-acetyl)cytosine |
| monophosphate | CH₃ | O | 4-(N,N-diacetyl)cytosine |
| monophosphate | CH₃ | O | Uracil |
| monophosphate | CH₃ | O | 5-Fluorouracil |
| monophosphate | CH₃ | S | 2,4-O-Diacetyluracil |
| monophosphate | CH₃ | S | Hypoxanthine |
| monophosphate | CH₃ | S | 2,4-O-Diacetylthymine |
| monophosphate | CH₃ | S | Thymine |
| monophosphate | CH₃ | S | Cytosine |
| monophosphate | CH₃ | S | 4-(N-mono-acetyl)cytosine |
| monophosphate | CH₃ | S | Uracil |
| monophosphate | CH₃ | S | 5-Fluorouracil |
| diphosphate | CH₃ | O | 2,4-O-Diacetyluracil |
| diphosphate | CH₃ | O | Hypoxanthine |
| diphosphate | CH₃ | O | 2,4-O-Diacetylthymine |
| diphosphate | CH₃ | O | Thymine |
| diphosphate | CH₃ | O | Cytosine |
| diphosphate | CH₃ | O | 4-(N-mono-acetyl)cytosine |
| diphosphate | CH₃ | O | 4-(N,N-diacetyl)cytosine |
| diphosphate | CH₃ | O | Uracil |
| diphosphate | CH₃ | O | 5-Fluorouracil |
| diphosphate | CH₃ | S | 2,4-O-Diacetyluracil |
| diphosphate | CH₃ | S | Hypoxanthine |
| diphosphate | CH₃ | S | 2,4-O-Diacetylthymine |
| diphosphate | CH₃ | S | Thymine |
| diphosphate | CH₃ | S | Cytosine |
| triphosphate | CH₃ | O | 2,4-O-Diacetyluracil |
| triphosphate | CH₃ | O | Hypoxanthine |
| triphosphate | CH₃ | O | 2,4-O-Diacetylthymine |
| triphosphate | CH₃ | O | Thymine |
| triphosphate | CH₃ | O | Cytosine |
| triphosphate | CH₃ | O | 4-(N-mono-acetyl)cytosine |
| triphosphate | CH₃ | O | 4-(N,N-diacetyl)cytosine |
| triphosphate | CH₃ | O | Uracil |
| triphosphate | CH₃ | O | 5-Fluorouracil |
| triphosphate | CH₃ | S | 2,4-O-Diacetyluracil |
| triphosphate | CH₃ | S | Hypoxanthine |
| triphosphate | CH₃ | S | 2,4-O-Diacetylthymine |
| triphosphate | CH₃ | S | Thymine |

-continued

| R¹ | R⁶ | X | Base |
|---|---|---|---|
| triphosphate | CH₃ | S | Cytosine |
| monophosphate | CF₃ | O | 2,4-O-Diacetyluracil |
| monophosphate | CF₃ | O | Hypoxanthine |
| monophosphate | CF₃ | O | 2,4-O-Diacetylthymine |
| monophosphate | CF₃ | O | Thymine |
| monophosphate | CF₃ | O | Cytosine |
| monophosphate | CF₃ | O | 4-(N-mono-acetyl)cytosine |
| monophosphate | CF₃ | O | 4-(N,N-diacetyl)cytosine |
| monophosphate | CF₃ | O | Uracil |
| monophosphate | CF₃ | O | 5-Fluorouracil |
| monophosphate | CF₃ | S | 2,4-O-Diacetyluracil |
| monophosphate | CF₃ | S | Hypoxanthine |
| monophosphate | CF₃ | S | 2,4-O-Diacetylthymine |
| monophosphate | CF₃ | S | Thymine |
| monophosphate | CF₃ | S | Cytosine |
| monophosphate | CF₃ | S | 4-(N-mono-acetyl)cytosine |
| monophosphate | CF₃ | S | 4-(N,N-diacetyl)cytosine |
| monophosphate | CF₃ | S | Uracil |
| monophosphate | CF₃ | S | 5-Fluorouracil |
| acetyl | CF₃ | O | 4-(N,N-diacetyl)cytosine |
| acetyl | CF₃ | S | 4-(N,N-diacetyl)cytosine |
| acetyl | 2-bromo-vinyl | O | 4-(N,N-diacetyl)cytosine |
| acetyl | 2-bromo-vinyl | S | 4-(N,N-diacetyl)cytosine |

Alternatively, the following nucleosides of Formula XVIII are prepared, using the appropriate sugar and pyrimidine or purine bases.

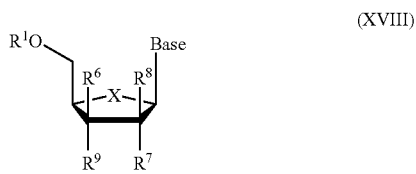

(XVIII)

wherein:

| R¹ | R⁶ | R⁷ | X | Base | R⁸ | R⁹ |
|---|---|---|---|---|---|---|
| H | CH₃ | OH | O | 2,4-O-Diacetyluracil | H | Me |
| H | CH₃ | OH | O | Hypoxanthine | H | Me |
| H | CH₃ | OH | O | 2,4-O-Diacetylthymine | H | Me |
| H | CH₃ | OH | O | Thymine | H | Me |
| H | CH₃ | OH | O | Cytosine | H | Me |
| H | CH₃ | OH | O | 4-(N-mono-acetyl)cystosine | H | Me |
| H | CH₃ | OH | O | 4-(N,N-diacetyl)cytosine | H | Me |
| H | CH₃ | OH | O | Uracil | H | Me |
| H | CH₃ | OH | O | 5-Fluorouracil | H | Me |
| H | CH₃ | OH | S | 2,4-O-Diacetyluracil | H | Me |
| H | CH₃ | OH | S | Hypoxanthine | H | Me |
| H | CH₃ | OH | S | 2,4-O-Diacetylthymine | H | Me |
| H | CH₃ | OH | S | Thymine | H | Me |
| H | CH₃ | OH | S | Cytosine | H | Me |
| H | CH₃ | OH | S | 4-(N-mono-acetyl)cytosine | H | Me |
| H | CH₃ | OH | S | 4-(N,N-diacetyl)cytosine | H | Me |
| H | CH₃ | OH | S | Uracil | H | Me |
| H | CH₃ | OH | S | 5-Fluorouracil | H | Me |
| monophosphate | CH₃ | OH | O | 2,4-O-Diacetyluracil | H | Me |
| monophosphate | CH₃ | OH | O | Hypoxanthine | H | Me |
| monophosphate | CH₃ | OH | O | 2,4-O-Diacetylthymine | H | Me |
| monophosphate | CH₃ | OH | O | Thymine | H | Me |
| monophosphate | CH₃ | OH | O | Cytosine | H | Me |
| monophosphate | CH₃ | OH | O | 4-(N-mono-acetyl)cytosine | H | Me |
| monophosphate | CH₃ | OH | O | 4-(N,N-diacetyl)cytosine | H | Me |
| monophosphate | CH₃ | OH | O | Uracil | H | Me |
| monophosphate | CH₃ | OH | O | 5-Fluorouracil | H | Me |
| monophosphate | CH₃ | OH | S | 2,4-O-Diacetyluracil | H | Me |
| monophosphate | CH₃ | OH | S | Hypoxanthine | H | Me |
| monophosphate | CH₃ | OH | S | 2,4-O-Diacetylthymine | H | Me |
| monophosphate | CH₃ | OH | S | Thymine | H | Me |
| monophosphate | CH₃ | OH | S | Cytosine | H | Me |
| monophosphate | CH₃ | OH | S | 4-(N-mono-acetyl)cytosine | H | Me |
| monophosphate | CH₃ | OH | S | 4-(N,N-diacetyl)cytosine | H | Me |
| monophosphate | CH₃ | OH | S | Uracil | H | Me |
| monophosphate | CH₃ | OH | S | 5-Fluorouracil | H | Me |
| diphosphate | CH₃ | OH | O | 2,4-O-Diacetyluracil | H | Me |
| diphosphate | CH₃ | OH | O | Hypoxanthine | H | Me |
| diphosphate | CH₃ | OH | O | 2,4-O-Diacetylthymine | H | Me |
| diphosphate | CH₃ | OH | O | Thymine | H | Me |
| diphosphate | CH₃ | OH | O | Cytosine | H | Me |
| diphosphate | CH₃ | OH | O | 4-(N-mono-acetyl)cytosine | H | Me |
| diphosphate | CH₃ | OH | O | 4-(N,N-diacetyl)cytosine | H | Me |
| diphosphate | CH₃ | OH | O | Uracil | H | Me |
| diphosphate | CH₃ | OH | O | 5-Fluorouracil | H | Me |
| diphosphate | CH₃ | OH | S | 2,4-O-Diacetyluracil | H | Me |
| diphosphate | CH₃ | OH | S | Hypoxanthine | H | Me |
| diphosphate | CH₃ | OH | S | 2,4-O-Diacetylthymine | H | Me |
| diphosphate | CH₃ | OH | S | Thymine | H | Me |
| diphosphate | CH₃ | OH | S | Cytosine | H | Me |
| triphosphate | CH₃ | OH | O | 2,4-O-Diacetyluracil | H | Me |
| triphosphate | CH₃ | OH | O | Hypoxanthine | H | Me |
| triphosphate | CH₃ | OH | O | 2,4-O-Diacetylthymine | H | Me |
| triphosphate | CH₃ | OH | O | Thymine | H | Me |
| triphosphate | CH₃ | OH | O | Cytosine | H | Me |
| triphosphate | CH₃ | OH | O | 4-(N-mono-acetyl)cytosine | H | Me |
| triphosphate | CH₃ | OH | O | 4-(N,N-diacetyl)cytosine | H | Me |
| triphosphate | CH₃ | OH | O | Uracil | H | Me |
| triphosphate | CH₃ | OH | O | 5-Fluorouracil | H | Me |
| triphosphate | CH₃ | OH | S | 2,4-O-Diacetyluracil | H | Me |
| triphosphate | CH₃ | OH | S | Hypoxanthine | H | Me |
| triphosphate | CH₃ | OH | S | 2,4-O-Diacetylthymine | H | Me |
| triphosphate | CH₃ | OH | S | Thymine | H | Me |
| triphosphate | CH₃ | OH | S | Cytosine | H | Me |
| monophosphate | CF₃ | OH | O | 2,4-O-Diacetyluracil | H | Me |
| monophosphate | CF₃ | OH | O | Hypoxanthine | H | Me |
| monophosphate | CF₃ | OH | O | 2,4-O-Diacetylthymine | H | Me |
| monophosphate | CF₃ | OH | O | Thymine | H | Me |
| monophosphate | CF₃ | OH | O | Cytosine | H | Me |
| monophosphate | CF₃ | OH | O | 4-(N-mono-acetyl)cytosine | H | Me |
| monophosphate | CF₃ | OH | O | 4-(N,N-diacetyl)cytosine | H | Me |
| monophosphate | CF₃ | OH | O | Uracil | H | Me |
| monophosphate | CF₃ | OH | O | 5-Fluorouracil | H | Me |
| monophosphate | CF₃ | OH | S | 2,4-O-Diacetyluracil | H | Me |
| monophosphate | CF₃ | OH | S | Hypoxanthine | H | Me |
| monophosphate | CF₃ | OH | S | 2,4-O-Diacetylthymine | H | Me |
| monophosphate | CF₃ | OH | S | Thymine | H | Me |
| monophosphate | CF₃ | OH | S | Cytosine | H | Me |
| monophosphate | CF₃ | OH | S | 4-(N-mono-acetyl)cytosine | H | Me |
| monophosphate | CF₃ | OH | S | 4-(N,N-diacetyl)cytosine | H | Me |
| monophosphate | CF₃ | OH | S | Uracil | H | Me |
| monophosphate | CF₃ | OH | S | 5-Fluorouracil | H | Me |
| acetyl | CH₃ | OH | O | 4-(N,N-diacetyl)cytosine | H | Br |
| acetyl | CH₃ | OH | S | 4-(N,N-diacetyl)cytosine | H | Br |

VII. Anti-Flavivirus or Pestivirus Activity

Compounds can exhibit anti-flavivirus or pestivirus activity by inhibiting flavivirus or pestivirus polymerase, by inhibiting other enzymes needed in the replication cycle, or by other pathways.

EXAMPLES

The test compounds were dissolved in DMSO at an initial concentration of 200 µM and then were serially diluted in culture medium.

Unless otherwise stated, baby hamster kidney (BHK-21) (ATCC CCL-10) and *Bos Taurus* (BT) (ATCC CRL 1390) cells were grown at 37° C. in a humidified $CO_2$ (5%) atmosphere. BHK-21 cells were passaged in Eagle MEM additioned of 2 mM L-glutamine, 10% fetal bovine serum (FBS, Gibco) and Earle's BSS adjusted to contain 1.5 g/L sodium bicarbonate and 0.1 mM non-essential amino acids. BT cells were passaged in Dulbecco's modified Eagle's medium with 4 mM L-glutamine and 10% horse serum (HS, Gibco), adjusted to contain 1.5 g/L sodium bicarbonate, 4.5 g/L glucose and 1.0 mM sodium pyruvate. The vaccine strain 17D (YFV-17D) (Stamaril®, Pasteur Merieux) and Bovine Viral Diarrhea virus (BVDV) (ATCC VR-534) were used to infect BHK and BT cells, respectively, in 75 $cm^2$ bottles. After a 3 day incubation period at 37° C., extensive cytopathic effect was observed. Cultures were freeze-thawed three times, cell debris were removed by centrifugation and the supernatant was aliquoted and stored at −70° C. YFV-17D and BVDV were titrated in BHK-21 and BT cells, respectively, that were grown to confluency in 24-well plates.

Example 4

Phosphorylation Assay of Nucleoside to Active Triphosphate

To determine the cellular metabolism of the compounds, HepG2 cells were obtained from the American Type Culture Collection (Rockville, Md.), and were grown in 225 $cm^2$ tissue culture flasks in minimal essential medium supplemented with non-essential amino acids, 1% penicillin-streptomycin. The medium was renewed every three days, and the cells were subcultured once a week. After detachment of the adherent monolayer with a 10 minute exposure to 30 mL of trypsin-EDTA and three consecutive washes with medium, confluent HepG2 cells were seeded at a density of $2.5 \times 10^6$ cells per well in a 6-well plate and exposed to 10 µM of [$^3$H] labeled active compound (500 dpm/pmol) for the specified time periods. The cells were maintained at 37° C. under a 5% $CO_2$ atmosphere. At the selected time points, the cells were washed three times with ice-cold phosphate-buffered saline (PBS). Intracellular active compound and its respective metabolites were extracted by incubating the cell pellet overnight at −20° C. with 60% methanol followed by extraction with an additional 20 µL of cold methanol for one hour in an ice bath. The extracts were then combined, dried under gentle filtered air flow and stored at −20° C. until HPLC analysis. The preliminary results of the HPLC analysis are tabulated in Table 1.

TABLE 1

| | [pmol/million cells] | | | |
|---|---|---|---|---|
| Time (h) | β-D-2'-CH$_3$-riboA-TP | β-D-2'-CH$_3$-riboU-TP | β-D-2'-CH$_3$-riboC-TP | β-D-2'-CH$_3$-riboG-TP |
| 2 | 33.1 | 0.40 | 2.24 | ND |
| 4 | 67.7 | 1.21 | 3.99 | ND |
| 8 | 147 | 1.57 | 9.76 | 2.85 |
| 24 | 427 | 6.39 | 34.9 | 0.91 |
| 30 | 456 | 7.18 | 36.2 | 3.22 |
| 48 | 288 | 9.42 | 56.4 | 6.26 |

Example 5

Bioavailability Assay in Cynomolgus Monkeys

Figure 3B:
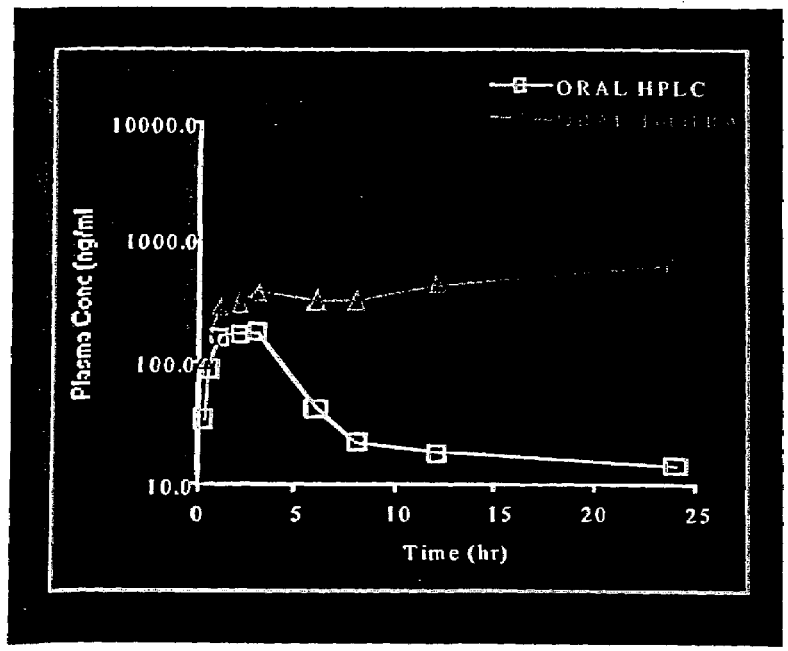

Within 1 week prior to the study initiation, the cynomolgus monkey was surgically implanted with a chronic venous catheter and subcutaneous venous access port (VAP) to facilitate blood collection and underwent a physical examination including hematology and serum chemistry evaluations and the body weight was recorded. Each monkey (six total), received approximately 250 uCi of $^3$H activity with each dose of active compound, namely β-D-2'-CH$_3$-riboG at a dose level of 10 mg/kg at a dose concentration of 5 mg/mL, either via an intravenous bolus (3 monkeys, IV), or via oral gavage (3 monkeys, PO). Each dosing syringe was weighed before dosing to gravimetrically determine the quantity of formulation administered. Urine samples were collected via pan catch at the designated intervals (approximately 18–0 hours pre-dose, 0–4, 4–8 and 8–12 hours post-dosage) and processed. Blood samples were collected as well (pre-dose, 0.25, 0.5, 1, 2, 3, 6, 8, 12 and 24 hours post-dosage) via the chronic venous catheter and VAP or from a peripheral vessel if the chronic venous catheter procedure should not be possible. The blood and urine samples were analyzed for the maximum concentration ($C_{max}$), time when the maximum concentration was achieved ($T_{max}$), area under the curve (AUC), half life of the dosage concentration ($T_{1/2}$), clearance (CL), steady state volume and distribution ($V_{SS}$) and bioavailability (F), which are tabulated in Tables 2 and 3, and graphically illustrated in FIGS. 2 and 3, respectively.

TABLE 2

Oral Bioavailability in Monkeys

| | Dose (mg) | AUC (ng/mL × h) | Norm AUC (ng/mL × h/mg) | Mean Norm AUC (ng/mL × h/mg) | F (%) |
|---|---|---|---|---|---|
| IV Monkey 1 | 46.44 | 13614 | 293.2 | | |
| IV Monkey 2 | 24.53 | 6581 | 268.3 | | |
| IV Monkey 3 | 20.72 | 6079 | 293.4 | 284.9 | |
| PO Monkey 1 | 29.04 | 758 | 26.1 | | |
| PO Monkey 2 | 30.93 | 898 | 29.0 | | |
| PO Monkey 3 | 30.04 | 1842 | 61.3 | 38.8 | 13.6 |

TABLE 3

Experimental Pharmacokinetics of β-D-2'-CH$_3$-riboG in Cynomolgus Monkeys

| | IV | PO |
|---|---|---|
| Dose/Route (mg/kg) | 10 | 10 |
| $C_{max}$ (ng/mL) | 6945.6 ± 1886.0 | 217.7 ± 132.1 |
| $T_{max}$ (hr) | 0.25 ± 0.00 | 2.00 ± 1.00 |
| AUC (ng/mL × hr) | 8758.0 ± 4212.9 | 1166.0 ± 589.6 |

TABLE 3-continued

Experimental Pharmacokinetics of β-D-2'-CH₃-riboG in Cynomolgus Monkeys

| | IV | PO |
|---|---|---|
| T½ (hr) | 7.9 ± 5.4 | 10.3 ± 4.1 |
| CL (L/hr/kg) | 1.28 ± 0.48 | |
| V$_{SS}$ (L/kg) | 2.09 ± 0.54 | |
| F (%) | | 13.8 |

Example 6

Bone Marrow Toxicity Assay

Human bone marrow cells were collected from normal healthy volunteers and the mononuclear population was separated by Ficoll-Hypaque gradient centrifugation as described previously by Sommadossi J-P, Carlisle R. "Toxicity of 3'-azido-3'-deoxythymidine and 9-(1,3-dihydroxy-2-propoxymethyl)guanine for normal human hematopoietic progenitor cells in vitro" Antimicrobial Agents and Chemotherapy 1987; 31:452–454; and Sommadossi J-P, Schinazi R F, Chu C K, Xie M-Y. "Comparison of cytotoxicity of the (−)- and (+)-enantiomer of 2',3'-dideoxy-3'-thiacytidine in normal human bone marrow progenitor cells" Biochemical Pharmacology 1992; 44:1921–1925. The culture assays for CFU-GM and BFU-E were performed using a bilayer soft agar or methylcellulose method. Drugs were diluted in tissue culture medium and filtered. After 14 to 18 days at 37° C. in a humidified atmosphere of 5% CO₂ in air, colonies of greater than 50 cells were counted using an inverted microscope. The results in Table 4 are presented as the percent inhibition of colony formation in the presence of drug compared to solvent control cultures.

TABLE 4

Human Bone Marrow Toxicity CFU-GM and BFU-E Clonogenic Assays

| | IC$_{50}$ in μM | |
|---|---|---|
| Treatment | CFU-GM | BFU-E |
| ribavirin | ~5 | ~1 |
| β-D-2'-CH₃-riboA | >100 | >100 |
| β-D-2'-CH₃-riboU | >100 | >100 |
| β-D-2'-CH₃-riboC | >10 | >10 |
| β-D-2'-CH₃-riboG | >10 | >100 |

Example 7

Mitochondria Toxicity Assay

HepG2 cells were cultured in 12-well plates as described above and exposed to various concentrations of drugs as taught by Pan-Zhou X-R, Cui L, Zhou X-J, Sommadossi J-P, Darley-Usmer VM. "Differential effects of antiretroviral nucleoside analogs on mitochondrial function in HepG2 cells" Antimicrob Agents Chemother 2000; 44:496–503. Lactic acid levels in the culture medium after 4 day drug exposure was measured using a Boehringer lactic acid assay kit. Lactic acid levels were normalized by cell number as measured by hemocytometer count. The preliminary results from this assay are tabulated in Table 5.

TABLE 5

Mitochondrial Toxicity Study (L-lactic acid assay)

| | Conc. (μM) | lactate (mg/10⁶ cell) | % of Control |
|---|---|---|---|
| Control | | 2.18 | |
| FIAU | 10 | 3.73 | 170.4 |
| β-D-2'-CH₃-riboC | 1 | 2.52 | 115.3 |
| | 10 | 2.36 | 107.9 |
| | 50 | 2.26 | 103.4 |
| | 100 | 2.21 | 101.2 |

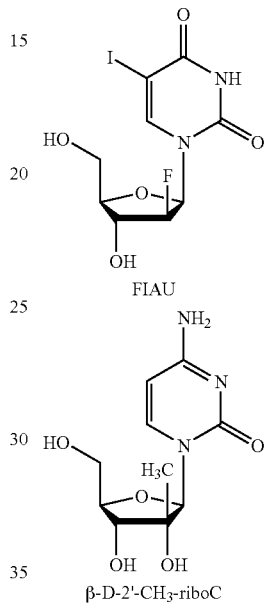

FIAU

β-D-2'-CH₃-riboC

Example 8

Cytotoxicity Assay

Cells were seeded at a rate of between 5×10³ and 5×10⁴/well into 96-well plates in growth medium overnight at 37° C. in a humidified CO₂ (5%) atmosphere. New growth medium containing serial dilutions of the drugs was then added. After incubation for 4 days, cultures were fixed in 50% TCA and stained with sulforhodamineB. The optical density was read at 550 nm. The cytotoxic concentration was expressed as the concentration required to reduce the cell number by 50% (CC$_{50}$). The data is tabulated in Table 6.

TABLE 6

MDBK versus Human Hepatoma

| | CC$_{50}$, μM | | |
|---|---|---|---|
| Compound | MDBK | Huh7 | HepG2 |
| β-D-2'-CH₃-riboA | 20 | 40 | 50–60 |
| β-D-2'-CH₃-riboU | >250 | >250 | >250 |
| β-D-2'-CH₃-riboC | 100 | >250 | 150 |
| β-D-2'-CH₃-riboG | 100 | >250 | >250 |
| Ribavirin | 5 | 25 | 150 |

Example 9

Cell Protection Assay (CPA)

The assay was performed essentially as described by Baginski, S. G.; Pevear, D. C.; Seipel, M.; Sun, S. C. C.; Benetatos, C. A.; Chunduru, S. K.; Rice, C. M. and M. S. Collett "Mechanism of action of a pestivirus antiviral compound" PNAS USA 2000, 97(14), 7981–7986. MDBK cells (ATCC) were seeded onto 96-well culture plates (4,000 cells per well) 24 hours before use. After infection with BVDV (strain NADL, ATCC) at a multiplicity of infection (MOI) of 0.02 plaque forming units (PFU) per cell, serial dilutions of test compounds were added to both infected and uninfected cells in a final concentration of 0.5% DMSO in growth medium. Each dilution was tested in quadruplicate. Cell densities and virus inocula were adjusted to ensure continuous cell growth throughout the experiment and to achieve more than 90% virus-induced cell destruction in the untreated controls after four days post-infection. After four days, plates were fixed with 50% TCA and stained with sulforhodamine B. The optical density of the wells was read in a microplate reader at 550 nm. The 50% effective concentration ($EC_{50}$) values were defined as the compound concentration that achieved 50% reduction of cytopathic effect of the virus. The results are tabulated in Table 7. FIGS. 4 and 5 provide a graphical illustration of the methodology used to arrive at the 50% effective concentration ($EC_{50}$) values for β-D-2'-$CH_3$-riboG and ribavirin. FIG. 6 compares the results of the CPA for β-D-2'-$CH_3$-riboG, β-D-2'-$CH_3$-riboC, β-D-2'-$CH_3$-riboU, β-D-2'-$CH_3$-riboA and ribavirin

TABLE 7

Cell Protection Assay

| | $EC_{50}$, μM | $CC_{50}$, μM |
|---|---|---|
| β-D-2'-$CH_3$-riboA | 2 | 20 |
| β-D-2'-$CH_3$-riboU | 20 | >250 |
| β-D-2'-$CH_3$-riboC | 2 | 100 |
| β-D-2'-$CH_3$-riboG | 4 | 100 |
| Ribavirin | >3 | 5 |

Example 10

Plaque Reduction Assay

For each compound the effective concentration was determined in duplicate 24-well plates by plaque reduction assays. Cell monolayers were infected with 100 PFU/well of virus. Then, serial dilutions of test compounds in MEM supplemented with 2% inactivated serum and 0.75% of methyl cellulose were added to the monolayers. Cultures were further incubated at 37° C. for 3 days, then fixed with 50% ethanol and 0.8% Crystal Violet, washed and air-dried. Then plaques were counted to determine the concentration to obtain 90% virus suppression and tabulated in Table 8. FIG. 7 is a graphical illustration of the results from the Plaque Reduction Assay. FIG. 8 is an image of BVDV plaque formation in the presence of increasing concentrations of β-D-2'-$CH_3$-riboU.

TABLE 8

Viral Suppression via Plaque Reduction Assay

| | $EC_{90}$, μM |
|---|---|
| β-D-2'-$CH_3$-riboA | <3 |
| β-D-2'-$CH_3$-riboU | <81 |
| β-D-2'-$CH_3$-riboC | <9 |
| β-D-2'-$CH_3$-riboG | <9 |

Example 11

Yield Reduction Assay

For each compound the concentration to obtain a 6-log reduction in viral load was determined in duplicate 24-well plates by yield reduction assays. The assay was performed as described by Baginski, S. G.; Pevear, D. C.; Seipel, M.; Sun, S. C. C.; Benetatos, C. A.; Chunduru, S. K.; Rice, C. M. and M. S. Collett "Mechanism of action of a pestivirus antiviral compound" PNAS USA 2000, 97(14), 7981–7986, with minor modifications. Briefly, MDBK cells were seeded onto 24-well plates (2×105 cells per well) 24 hours before infection with BVDV (NADL strain) at a multiplicity of infection (MOI) of 0.1 PFU per cell. Serial dilutions of test compounds were added to cells in a final concentration of 0.5% DMSO in growth medium. Each dilution was tested in triplicate. After three days, cell cultures (cell monolayers and supernatants) were lysed by three freeze-thaw cycles, and virus yield was quantified by plaque assay. Briefly, MDBK cells were seeded onto 6-well plates (5×105 cells per well) 24 h before use. Cells were inoculated with 0.2 mL of test lysates for 1 hour, washed and overlaid with 0.5% agarose in growth medium. After 3 days, cell monolayers were fixed with 3.5% formaldehyde and stained with 1% crystal violet (w/v in 50% ethanol) to visualize plaques. The plaques were counted to determine the concentration to obtain a 6-log reduction in viral load as tabulated in Table 9. FIG. 9 is a graphical illustration of the results from the Yield Reduction Assay. FIG. 8 is an image of BVDV yield reduction in the presence of increasing concentrations of β-D-2'-$CH_3$-riboC.

TABLE 9

Concentration to Obtain 6-log Reduction

| | Conc. for 6-log Reduction (μM) |
|---|---|
| β-D-2'-$CH_3$-riboU | 120 |
| β-D-2'-$CH_3$-riboG | 20 |
| β-D-2'-$CH_3$-riboC | 20 |
| β-D-2'-$CH_3$-riboA | 9 |

Example 12

Comparative Cytotoxicity

Table 10 summarizes the cytotoxicity of two compounds of this invention, β-D-1'-$CH_3$-riboA and β-D-2'-$CH_3$-riboA, in comparison to RBV ("ribavirin"), in various cell systems.

TABLE 10

| | Comparative Cytotoxicity* ($CC_{50}$) | | | |
| --- | --- | --- | --- | --- |
| | BD | BHK | VERO | MT-4 |
| β-D-1'-$CH_3$-riboA | >100 | 200 | >100 | 18 |
| β-D-2'-$CH_3$-riboA | 75 | 22 | 22 | 6.6 |
| RBV | ND | 50 | 11 | ND |

*Compound concentration (μM) required to reduce the viability of cells by 50%.

The chemical structures for β-D-1'-$CH_3$-riboA and β-D-2'-$CH_3$-riboA are as follows:

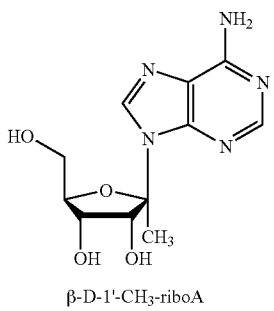

β-D-1'-$CH_3$-riboA

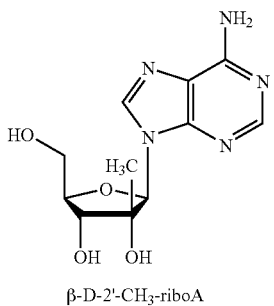

β-D-2'-$CH_3$-riboA

Table 11 summarizes the antiviral activity of β-D-1'-$CH_3$-riboA and β-D-2'-$CH_3$-riboA against several viruses within the flavivirus and pestivirus genuses.

TABLE 11

| | Comparative Antiviral Activity* ($EC_{50}$) | | | | |
| --- | --- | --- | --- | --- | --- |
| | BVDV | YFV | PICO | VSV | HIV-1 |
| β-D-1'-$CH_3$-riboA | 10 | 7.0 | 51 | >100 | >18 |
| β-D-2'-$CH_3$-riboA | 0.1 | 0.2 | 5.0 | >100 | >6.6 |
| RBV | ND | 30 | >30 | ND | ND |

*Compound concentration (μM) required to reduce the plaque number by 50%. The following virus-cell system were used: BVDC-BT, YFV-BHK, PICO (Cosxackie B1 and Polio Sabin)/VSV - Vero.

Table 12 summarizes the antiviral activity and toxicity of β-D-2'-methyl-riboG, β-D-2'-methyl-riboC and β-D-2'-methyl-riboU, against a couple of viruses within the flavivirus and pestivirus genuses.

TABLE 12

| | Comparative Antiviral Activity* ($EC_{50}$) | | | |
| --- | --- | --- | --- | --- |
| | BVDV | | YFV | |
| | $EC_{50}$* | $CC_{50}$** | $EC_{50}$* | $CC_{50}$** |
| β-D-2'-$CH_3$-riboG | 2 | >100 | 1.2 | 20 |
| β-D-2'-$CH_3$-riboC | 3.7 | >100 | 70 | >100 |
| β-D-2'-$CH_3$-riboU | 20 | >100 | 33 | >100 |

*Compound concentration (μM) required to reduce the plaque number by 50%. The following virus-cell system were used: BVDC-BT and YFV-BHK.
*Compound concentration (μM) required to reduce the viability of cells by 50%.

The chemical structures for β-D-2'-$CH_3$-riboG, β-D-2'-$CH_3$-riboC and β-D-2'-$CH_3$-riboU are as follows:

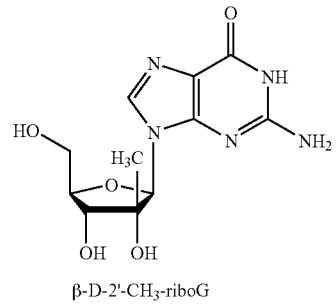

β-D-2'-$CH_3$-riboG

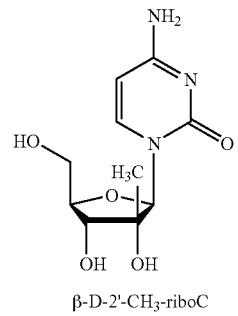

β-D-2'-$CH_3$-riboC

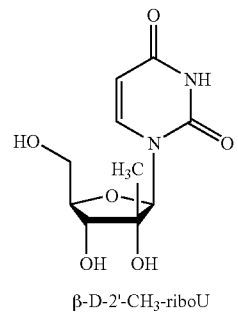

β-D-2'-$CH_3$-riboU

Table 13 summarizes the anti-viral activity of several compounds of this invention against BVDV in three different assays.

TABLE 13

| | for BVDV | | | | |
|---|---|---|---|---|---|
| | Cell Protection (EC$_{50}$, μM) | Plaque Reduction (EC$_{90}$, μM) | Yield Reduction | | Cytotoxicity Huh7 cells (EC$_{50}$, μM) |
| Compound | | | EC$_{90}$, μM | 6 log$_{10}$ reduction (μM) | |
| β-D-2'-CH$_3$-riboA | 2 | <3 | <2 | 9 | 50 |
| β-D-2'-CH$_3$-riboT | >250 | ND | ND | ND | >250 |
| β-D-2'-CH$_3$-riboU | 20 | <81 | 24 | 120 | >250 |
| β-D-2'-CH$_3$-riboC | 2 | <9 | <4 | 20 | >250 |
| β-D-2'-CH$_3$-riboG | 4 | <9 | 3 | 20 | >250 |
| β-D-2'-CH$_3$-riboI | 45 | ND | ND | ND | >250 |
| Ribavirin | >3 | >200 | >20 | toxic | 20 |

This invention has been described with reference to its preferred embodiments. Variations and modifications of the invention, will be obvious to those skilled in the art from the foregoing detailed description of the invention.

The invention claimed is:

1. A method for the treatment of a flavivirus or pestivirus infection in a host, comprising administering to said host an anti-virally effective amount of a compound of Formula XVII:

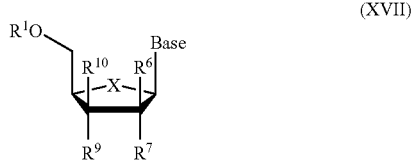

(XVII)

or a pharmaceutically acceptable salt or ester thereof, wherein:

Base is a pyrrolopyrimidine;

R$^1$ and R$^2$ are independently H; phosphate; a stabilized phosphate prodrug; acyl; alkyl; sulfonate ester; benzyl, wherein the phenyl group is optionally substituted with one or more moieties selected from the group consisting of hydroxyl, amino, alkylamino, arylamino, alkoxy, aryloxy, nitro, cyano, sulfonic acid, sulfate, phosphonic acid, phosphate, or phosphonate, either unprotected, or protected as necessary; a lipid; an amino acid; a carbohydrate; a peptide; a cholesterol; or other pharmaceutically acceptable leaving group which when administered in vivo provides a compound wherein R$^1$ and R$^2$ are independently H or phosphate;

R$^6$ is alkyl, azido, cyano, alkenyl, alkynyl, Br-vinyl, —C(O)O(alkyl), —, —O(acyl), —O(alkyl), —O(alkenyl), chloro, bromo, fluoro, iodo, NO$_2$, NH$_2$, —NH(lower alkyl), —NH(acyl), —N(lower alkyl)$_2$, or —N(acyl)$_2$;

R$^7$ and R$^8$ are independently OR$^2$, hydroxy, alkyl, azido, cyano, alkenyl, alkynyl, Br-vinyl, —C(O)O(alkyl), —O(acyl), O(alkyl), —O(alkenyl), chlorine, bromine, iodine, NO$_2$, NH$_2$, —NH(lower alkyl), —NH(acyl), —N(lower alkyl)$_2$, or —N(acyl)$_2$;

R$^{10}$ is H, alkyl, chlorine, bromine or iodine;

and

X is O, S, SO$_2$ or CH$_2$.

2. The method of claim 1 for the treatment of a flavivirus or pestivirus infection in a host, comprising administering an anti-virally effective amount of a compound of Formula X or XI:

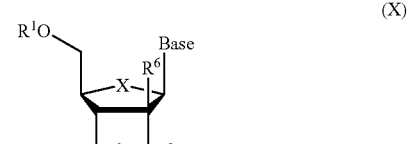

(X)

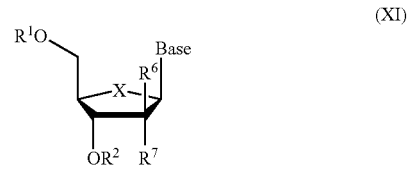

(XI)

or a pharmaceutically acceptable salt or ester thereof, wherein:

Base is a pyrrolopyrimidine;

R$^1$, R$^2$ and R$^3$ are independently H; phosphate or a stabilized phosphate prodrug; acyl; alkyl; sulfonate ester; or benzyl, wherein the phenyl group is optionally substituted; a lipid; an amino acid; a carbohydrate; a peptide; cholesterol; or other pharmaceutically acceptable leaving group which when administered in vivo provides a compound wherein R$^1$, R$^2$ and R$^3$ are independently H or phosphate;

R$^6$ is alkyl, azido, cyano, alkenyl, alkynyl, Br-vinyl, —C(O)O(alkyl), —O(acyl), —O(alkyl), O(alkenyl), chloro, bromo, fluoro, iodo, NO$_2$, NH$_2$, —NH(lower alkyl), —NH(acyl), —N(lower alkyl)$_2$, or —N(acyl)$_2$;

R$^7$ is OR$^3$, hydroxy, alkyl, azido, cyano, alkenyl, alkynyl, Br-vinyl, —C(O)O(alkyl), —O(acyl), —O(alkyl), —O(alkenyl), chlorine, bromine, iodine, NO$_2$, NH$_2$, —NH(lower alkyl), —NH(acyl), —N(lower alkyl)$_2$, or —N(acyl)$_2$; and X is O, S, SO$_2$ or CH$_2$.

3. The method of claim 1 for the treatment of a flavivirus or pestivirus infection in a host, wherein, in the compound of Formula XVII:

R$^{10}$ is H, alkyl, chlorine, bromine or iodine;

R$^7$ and R$^8$ are independently OR$^2$, alkyl, alkenyl, alkynyl, Br-vinyl, O-alkenyl, chlorine, bromine, iodine, NO$_2$, NH$_2$, —NH(lower alkyl), —NH(acyl), —N(lower alkyl)$_2$, or —N(acyl)$_2$;

R$^6$ is alkyl, chlorine, bromine or iodine;

and

X is O, S, SO$_2$ or CH$_2$.

4. The method of claim 1 wherein R$^1$ is hydrogen or phosphate.

5. The method of claim 1 wherein R$^2$ is hydrogen, acyl or alkyl.

6. The method of claim 1 wherein R$^6$ is alkyl.

7. The method of claim 1 wherein R$^7$ and R$^9$ are independently selected from OR$^2$ or hydroxy.

8. The method of claim 1 wherein R$^7$ is hydroxy.

9. The method of claim 1 wherein R$^9$ is hydroxy.

10. The method of claim 1 wherein R$^7$ and R$^9$ are hydroxy.

11. The method of claim 1 wherein R$^{10}$ is hydrogen.

12. The method of claim 1 wherein X is O.

13. The method of claim 1 wherein $R^1$ is hydrogen or phosphate;
$R^2$ is hydrogen, acyl or alkyl;
$R^6$ is alkyl;
$R^7$ and $R^8$ are independently $OR^2$ or hydroxy
$R^{10}$ is hydrogen; and
X is O.

14. The method of claim 1 for the treatment of a flavivirus or pestivirus infection in a host, comprising administering an antivirally effective amount of a compound of the structure:

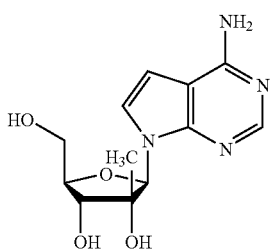

or a pharmaceutically acceptable salt or ester thereof.

15. The method of claim 1, wherein the method comprises administering the compound or a pharmaceutically acceptable salt or ester thereof in combination or alternation with a second anti-flavivirus or anti-pestivirus agent.

16. The method of any one of claims 15, wherein the second anti-flavivirus or anti-pestivirus agent is selected from the group consisting of consisting of interferon, ribavirin, a protease inhibitor, a thiazolidine derivative, a polymerase inhibitor, and a helicase inhibitor.

17. The method of claim 16, wherein the second anti-flavivirus or anti-pestivirus agent is interferon.

18. The method of claim 16, wherein the second anti-flavivirus or anti-pestivirus agent is a protease inhibitor.

19. The method of claim 16, wherein the second anti-flavivirus or anti-pestivirus agent is ribavirin.

20. The method of claim 1, wherein the compound is in the form of a dosage unit.

21. The method of claim 20, wherein the dosage unit contains 50 to 1000 mg of said compound.

22. The method of claim 20, wherein said dosage unit is a tablet or capsule.

23. The method of claim 1, wherein the host is a human.

24. The method of claim 1, wherein the compound is in substantially pure form.

25. The method of claim 1, wherein the compound is at least 90% by weight of the β-D-isomer.

26. The method of claims 1, wherein the compound is at least 95% by weight of the β-D-isomer.

27. The method of claim 1, wherein the flavivirus or pestivirus is a Dengue virus.

28. The method of claim 1, wherein the flavivirus or pestivirus is a West Nile virus.

29. The method of claim 1, wherein the flavivirus or pestivirus is a yellow fever virus.

30. The method of claims 1, wherein the flavivirus or pestivirus is a bovine viral diarrhea virus (BVDV).

31. The method of claim 1 wherein:
$R^1$ is hydrogen;
$R^6$ is methyl;
$R^7$ and $R^9$ are independently hydroxy;
$R^{10}$ is hydrogen; and
X is O.

* * * * *